United States Patent [19]
Suzuki et al.

[11] Patent Number: 6,015,789
[45] Date of Patent: Jan. 18, 2000

[54] COMBINED USE OF GNRH AGONIST AND ANTAGONIST

[75] Inventors: Nobuhiro Suzuki; Shuichi Furuya, both of Tsukuba, Japan

[73] Assignee: Takeda Chemical Industries, Ltd., Osaka, Japan

[21] Appl. No.: 08/894,317

[22] PCT Filed: Apr. 25, 1997

[86] PCT No.: PCT/JP97/01459

§ 371 Date: Aug. 14, 1997

§ 102(e) Date: Aug. 14, 1997

[87] PCT Pub. No.: WO97/40846

PCT Pub. Date: Nov. 6, 1997

[30] Foreign Application Priority Data

Apr. 30, 1996 [JP] Japan .................................. 8-109790
May 31, 1996 [JP] Japan .................................. 8-138873

[51] Int. Cl.[7] ................. A61K 38/09; A61K 31/505; A61K 31/44
[52] U.S. Cl. ..................... 514/15; 514/256; 514/258; 514/301; 514/317; 514/330; 514/329
[58] Field of Search .............. 514/12, 256, 258, 514/329, 301, 317, 330

[56] References Cited

FOREIGN PATENT DOCUMENTS

95/28405  10/1995  WIPO .
96/24597  8/1996  WIPO .
WO 97/40846  11/1997  WIPO .

OTHER PUBLICATIONS

Th. Reissmann et al., "Development and applications of luteinizing hormone–releasing hormone antagonists in the treatment of infertility: an overview", Human Reproduction, vol. 10, No. 8, pp. 1974–1981, 1995.

J. Pinski et al., "Blockade of the LH response induced by the agonist D–Trp–6–LHRH in rats by a highly potent LH–RH antagonist SB–75", The Prostate, vol. 20, No. 3, pp. 213–224, 1992.

G. Emons et al., "The use of luteinizing hormone releasing hormone agonists and antagonists in gynaecological cancers", Human Reproduction Update, vol. 9, No. 7, pp. 1364–1379, 1994.

*Primary Examiner*—F. T. Moezie
*Attorney, Agent, or Firm*—Wenderoth, Lind & Ponack, L.L.P.

[57] ABSTRACT

The present invention relates to a pharmaceutical luteinizing hormone releasing hormone agonist in combination with a luteinizing hormone releasing hormone antagonist. By using a luteinizing hormone releasing hormone agonist and a luteinizing hormone releasing hormone antagonist in combination, the transient exacerbation with elevation of serum testosterone and estrogen owing to the pituitary-gonadotropic action (acute action) manifested immediately following an initial dose of the luteinizing hormone releasing hormone agonist can be successfully obviated.

22 Claims, No Drawings

COMBINED USE OF GNRH AGONIST AND ANTAGONIST

This application is a §371 application of PCT/JP97/01459, filed Apr. 25, 1997.

TECHNICAL FIELD

1. Background of the Invention

The present invention relates to a pharmaceutical comprising a compound having luteinizing hormone releasing hormone activity in combination with a nonpeptide compound having luteinizing hormone releasing hormone antagonizing activity.

2. Background Art

Superactive peptide analogs of luteinizing hormone releasing hormone (hereinafter referred to sometimes as LH-RH) which is one of the hormones originating from the hypothalamus [Schally, A. V. et al., J. Biological Chemistry, 246, 7230–7236, 1971 and Burgus, R. et al., Proc. Natl. Acad. Sci. USA, 69, 278–282, 1972] are superagonists or agonists of LH-RH receptors and, if administered repeatedly, suppress the production and release of luteinizing hormone releasing hormone in the hypophysis to weaken the responsiveness of the testes and ovaries to luteinizing hormone releasing hormone and consequently reduce the secretion of testosterone and estrogen. It is, therefore, known that these compounds exhibit antitumor activity in cancers dependent on such hormones, for example carcinoma of the prostate, and actually they have been put to use clinically. These compounds are also used broadly as therapeutic drugs for endometriosis, hystereoma, and precocious puberty.

Reports are available on the combined use of a peptide LH-RH (super)agonist and a peptide LH-RH antagonist but there has been no report about the use of a nonpeptide LH-RH antagonist in combination with an LH-RH superagonist or agonist.

Since the above-mentioned peptide hormone analogs are either superagonists or agonists, they have been found to cause a transient exacervation (flare) of illness with elevation of serum testosterone and estrogen as the result of a pituitary-gonadotropic action (acute action) manifested immediately following initial dosing. In fact, it takes about 2–3 weeks for such a peptide superagonist or agonist to show a steady effect and, therefore, establishment of a prophylactic modality for preventing the progression and exacerbation of illness during this intervening period is a major goal of research.

Furthermore, in order that the action of such a peptide or nonpeptide (super)agonist may be amplified, the advent of a nonpeptide LH-RH antagonist compound that may be administered orally is being awaited.

3. Disclosure of Invention

The inventors of the present invention, taking into account the fact that thieno[2,3-b]pyridine derivatives and thieno[2,3-d]pyrimidine derivatives, both of which have excellent LH-RH antagonizing activity, can be administered orally and speculating that said superagonists or agonists might be safely administered if their effect be carefully modulated by controlling the dosage and administration interval, did much research and have completed the present invention.

SUMMARY OF THE INVENTION

The present invention relates to:
(1) a pharmaceutical comprising a compound having luteinizing hormone releasing hormone activity in combination with a nonpeptide compound having luteinizing hormone releasing hormone antagonizing activity, (2) the pharmaceutical according to (1), wherein the compound having luteinizing hormone releasing hormone activity is a peptide compound, (3) the pharmaceutical according to (2), wherein the peptide compound is a natural hormone or an analog thereof, (4) the pharmaceutical according to (2), wherein the peptide compound is a polypeptide of the formula:

$$(Pyr)Glu\text{-}R_1\text{-}Trp\text{-}Ser\text{-}R_2\text{-}R_3\text{-}R_4\text{-}Arg\text{-}Pro\text{-}R_5 \qquad (I)$$

wherein $R_1$ is His, Tyr, Trp or p-$NH_2$—Phe; $R_2$ is Tyr or Phe; $R_3$ is Gly or a D-amino acid residue which may optionally be substituted; $R_4$ is Leu, Ile, or Nle; $R_5$ is a group of the formula: Gly-NH—$R_6$ wherein $R_6$ is a hydrogen or an optionally substituted alkyl group, or a group of the formula: NH—$R_6'$ wherein $R_6'$ is a hydrogen, an alkyl group which may optionally be substituted with amino or hydroxy or ureido, (5) the pharmaceutical according to (2), wherein the peptide compound is a compound selected from the group consisting of leuprorelin, gohadorelin, buserelin, triptorelin, goserelin, nafarelin, histrelin, deslorelin, meterelin, and recirelin, (6) the pharmaceutical according to (1), wherein the compound having luteinizing hormone releasing hormone activity is in a controlled release dosage form, (7) the pharmaceutical according to (6), wherein the controlled release dosage form is microcapsules, (8) the pharmaceutical according to (6), wherein the controlled release dosage form is a transnasal drug delivery system or an implant, (9) the pharmaceutical according to (1), wherein the nonpeptide compound is a condensed cyclic compound containing at least a condensed bicyclic structure of an optionally substituted homo or hetero 5- to 7-membered ring with an optionally substituted homo or hetero 5- to 7-membered ring, or a salt thereof,

(10) the pharmaceutical according to (9), wherein the condensed cyclic compound is represented by the formula:

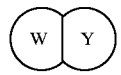

wherein ring W stands for an optionally substituted homo or hetero 5- to 7-membered cyclic group, and ring Y stands for an optionally substituted homo or hetero 5- to 7-membered cyclic group,

(11) the pharmaceutical according to (10), wherein ring W is a group represented by the formula:

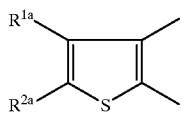

wherein each of $R^{1a}$ and $R^{2a}$ stand for a hydrogen atom or a group bonded through a carbon atom, a nitrogen atom, an oxygen atom or a sulfur atom,

(12) the pharmaceutical according to (10), wherein ring W is a group represented by the formula:

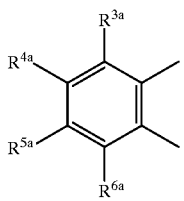

wherein each of $R^{3a}$, $R^{4a}$, $R^{5a}$ and $R^{6a}$ stand for a hydrogen atom or a group bonded through a carbon atom, a nitrogen atom, an oxygen atom or a sulfur atom,

(13) the pharmaceutical according to (10), wherein ring Y is any one of the groups represented by the formulas:

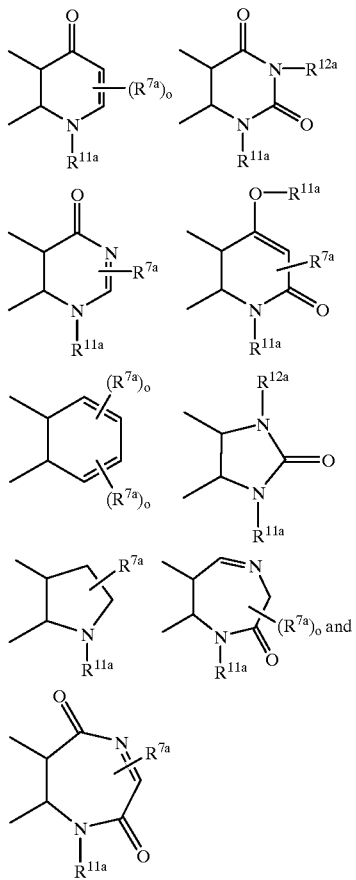

wherein $R^{7a}$ independently stands for a hydrogen atom or a group bonded through a carbon atom, a nitrogen atom, an oxygen atom or a sulfur atom; $R^{11a}$ and $R^{12a}$ independently stand for a hydrogen atom or an optionally substituted hydrocarbon residue; and o denotes an integer of 1 to 2,

(14) the pharmaceutical according to (10), wherein ring Y is a group represented by the formula:

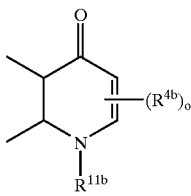

wherein $R^{4b}$ independently stands for a hydrogen atom or a group bonded through a carbon atom, a nitrogen atom, an oxygen atom or a sulfur atom; $R^{11b}$ stands for an optionally substituted hydrocarbon residue; and o denotes an integer of 1 to 2; or a group represented by the formula:

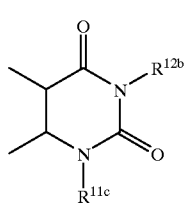

wherein each of $R^{11c}$ and $R^{12b}$ independently stand for a hydrogen atom or an optionally substituted hydrocarbon residue,

(15) the pharmaceutical according to (9), wherein the condensed cyclic compound is a compound of the formula:

(X)

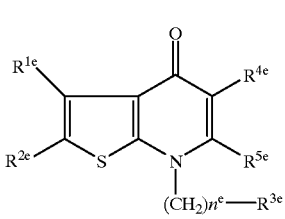

wherein
$R^{1e}$ and $R^{2e}$ are independently a hydrogen atom or a group bonded through a carbon atom, a nitrogen atom, an oxygen atom or a sulfur atom,
$R^{3e}$ is an optionally substituted homo- or hetero-cyclic ring,
$R^{4e}$ is a hydrogen atom, a group bonded through a carbon atom, a nitrogen atom, an oxygen atom or a sulfur atom or an optionally substituted heterocyclic group,
$R^{5e}$ is a hydrogen atom or a group bonded through a carbon atom,
n is an integer of 0 to 3;

a compound of the formula:

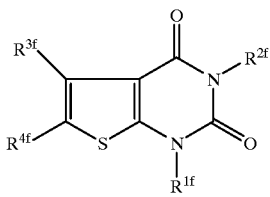

(XX)

wherein $R^{1f}$ is (1) a hydrogen atom, (2) a group bonded through a carbon atom or (3) a group of the formula:

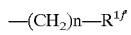

—$(CH_2)n$—$R^{1f'}$ wherein
$R^{1f'}$ is a group bonded through a carbon atom or an optionally substituted homo- or hetero-cyclic group and n is an integer of 0 to 3,
$R^{2f}$ is a hydrogen atom or a group bonded through a carbon atom,
$R^{3f}$ and $R^{4f}$ are independently a group bonded through a carbon atom; or a compound of the formula:

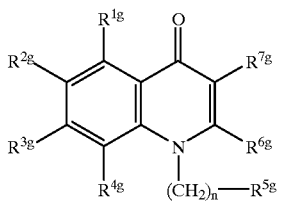

(XXX)

wherein $R^{1g}$, $R^{2g}$, $R^{3g}$, $R^{4g}$, $R^{6g}$ and $R^{7g}$ independently stand for a hydrogen atom or a group bonded through a carbon atom, a nitrogen atom, an oxygen atom or a sulfur atom, $R^{5g}$ is a group bonded through a carbon atom or an optionally substituted homo- or heterocyclic ring, n is an integer of 0 to 3, with the proviso that all of the groups $R^{2g}$, $R^{3g}$, $R^{4g}$, $R^{6g}$ and $R^{7g}$ are not a hydrogen atom simultaneously,

(16) the pharmaceutical according to (9), wherein the condensed cyclic compound is a compound represented by the formula:

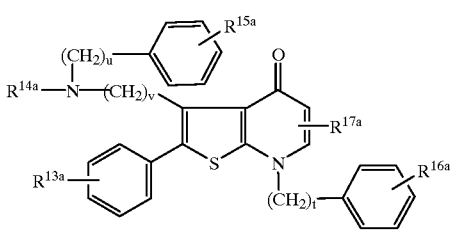

wherein $R^{13a}$ stands for 1 to 5 substituents and independently stands for a hydrogen atom, an alkyl group, an alkoxy group, a halogen atom or an alkanoylamino group; $R^{14a}$ stands for a hydrogen atom or an alkyl group; $R^{15a}$ stands for 1 to 5 substituents and independently stands for a hydrogen atom, a halogen atom, an alkyl group, an alkoxy group or an alkylthio group; $R^{16a}$ stands for 1 to 5 substituents and independently stands for a hydrogen atom, an alkyl group, a halogen atom or an alkoxy group; $R^{17a}$ stands for one or two substituents and independently stands for an optionally esterified or amidated carboxyl group, an alkylcarbonyl group, an arylcarbonyl group or an optionally substituted alkyl group; and each of v, t and u denote an integer of 0 to 3,

(17) the pharmaceutical according to (9), wherein the condensed cyclic compound is a compound represented by the formula:

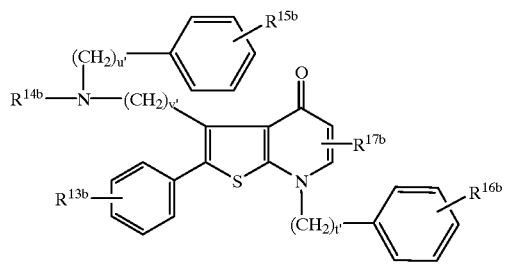

wherein $R^{13b}$ stands for 1 to 3 substituents and independently stands for a hydrogen atom, a $C_{1-6}$ alkoxy group or a $C_{1-8}$ alkanoylamino group, $R^{14b}$ stands for a hydrogen atom or a $C_{1-6}$ alkyl group, $R^{15b}$ stands for 1 to 3 substituents and independently stands for a hydrogen atom or a halogen atom, $R^{16b}$ stands for 1 to 3 substituents and independently stands for a hydrogen atom, a halogen atom or a $C_{1-6}$ alkoxy group, $R^{17b}$ stands for 1 to 2 substituents and independently stands for a carboxyl group which may optionally be esterified or amidated or a $C_{1-6}$ alkylcarbonyl group, and each of v', t' and u' denote an integer of 1 to 3,

(18) the pharmaceutical according to (1), wherein the nonpeptide compound having luteinizing hormone releasing hormone antagonizing activity is 4,7-dihydro-3-(N-methyl-N-benzylaminomethyl)-7-(2-methoxybenzyl)-2-(4-methoxyphenyl)-4-oxo-thieno[2,3-b]pyridine-5-carboxylic acid ethyl ester or its salt,

(19) the pharmaceutical according to (1), wherein the nonpeptide compound having luteinizing hormone releasing hormone antagonizing activity is 2-(4-acetylaminophenyl)-4,7-dihydro-3-(N-methyl-N-benzylaminomethyl)-7-(2-methoxybenzyl)-4-oxo-thieno[2,3-b]pyridine-5-carboxylic acid ethyl ester or its salt,

(20) the pharmaceutical according to (1), wherein the nonpeptide compound having luteinizing hormone releasing hormone antagonizing activity is 5-n-butyryl-4,7-dihydro-3-(N-methyl-N-benzylaminomethyl)-7-(2-fluorobenzyl)-2-(4-methoxyphenyl)-4-oxo-thieno[2,3-b]pyridine or its salt,

(21) the pharmaceutical according to (1), wherein the nonpeptide compound having luteinizing hormone releasing hormone antagonizing activity is 5-benzoyl-4,7-dihydro-3-(N-methyl-N-benzylaminomethyl)-7-(2-fluorobenzyl)-2-(4-methoxyphenyl)-4-oxo-thieno[2,3-b]pyridine or its salt,

(22) the pharmaceutical according to (1), wherein the nonpeptide compound having luteinizing hormone releasing hormone antagonizing activity is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine or its salt,

(23) the pharmaceutical according to (1), wherein the nonpeptide compound having luteinizing hormone releasing hormone antagonizing activity is 7-(2,6-difluorobenzyl)-4,7-dihydro-3-(N-methyl-N-benzylaminomethyl)-5-isobutyryl-2-(4-propionylaminophenyl)-4-oxo-thieno[2,3-b]pyridine or its salt,

(24) the pharmaceutical according to (1), wherein the nonpeptide compound having luteinizing hormone releasing hormone antagonizing activity is 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine or its salt,

(25) the pharmaceutical according to (1), wherein the nonpeptide compound having luteinizing hormone releasing hormone antagonizing activity is 3-(N-benzyl-N-methylaminomethyl)-4,7-dihydro-2-(4-allyloxyphenyl)-5-isobutyryl-7-(2,6-difluorobenzyl)-4-oxothieno[2,3-b]pyridine or its salt,

(26) the pharmaceutical according to (1), wherein the nonpeptide compound having luteinizing hormone releasing hormone antagonizing activity is isopropyl [3-(N-benzyl-N-methylaminomethyl)-2-(4-isobutyrylaminophenyl)-4-oxo-7-(2,6-difluorobenzyl)thieno[2,3-b]pyridine-5-carboxylate] or its salt,

(27) the pharmaceutical according to (1), wherein the nonpeptide compound having luteinizing hormone releasing hormone antagonizing activity is isopropyl [3-(N-benzyl-N-methylaminomethyl)-2-(4-isobutyrylaminophenyl)-4-oxo-7-(2,6-difluorobenzyl)-6-methylthieno[2,3-b]pyridine-5-carboxylate] or its salt,

(28) the pharmaceutical according to (1), wherein the nonpeptide compound having luteinizing hormone releasing hormone antagonizing activity is isopropyl [3-(N-benzyl-N-methylaminomethyl)-2-(4-allyloxyphenyl)-4-oxo-6-methyl-7-(2,6-difluorobenzyl)thieno[2,3b]pyridine-5-carboxylate] or its salt,

(29) a pharmaceutical kit for prevention or treatment of sex hormone-dependent diseases which comprises a compound having luteinizing hormone releasing hormone activity in combination with a nonpeptide compound having luteinizing hormone releasing hormone antagonizing activity,

(30) the pharmaceutical kit according to (29), comprising a compound having luteinizing hormone releasing hormone activity in a non-oral dosage form in combination with a nonpeptide compound having luteinizing hormone releasing hormone antagonizing activity in an oral dosage form,

(31) use of a nonpeptide compound having luteinizing hormone releasing hormone antagonizing activity for reducing the flare phenomenon following administration of a compound having luteinizing hormone releasing hormone activity, and

(32) use of a nonpeptide compound having luteinizing hormone releasing hormone antagonizing activity for amplifying the action of a compound having luteinizing hormone releasing hormone activity, and

(33) a method for preventing or treating a sex hormone-dependent disease in a mammal, which comprises administering to said mammal a compound having luteinizing hormone releasing hormone activity in combination with a nonpeptide compound having luteinizing hormone releasing hormone antagonizing activity.

DETAILED DESCRIPTION OF THE INVENTION

Best Mode for Carrying Out the Invention

The compound having LH-RH activity may be each of a peptide compound or a nonpeptide compound, including any and all compounds having such activity.

The peptide compound having LH-RH activity includes the natural hormone, i.e. a polypeptide of the following formula (I) wherein $R_1$=His, $R_2$=Tyr, $R_3$=Gly, $R_4$=Leu, $R_5$=Gly—$NH_2$ and its analogs, and polypeptides of the formula (I):

(Pyr)Glu-$R_1$-Trp-Ser-$R_2$-$R_3$-$R_4$-Arg-Pro-$R_5$ (I), wherein $R_1$ represents His, Tyr, Trp, or p-$NH_2$—Phe; $R_2$ represents Tyr or Phe; $R_3$ represents Gly or a D-amino acid residue which may be substituted; $R_4$ represents Leu, Ile, or Nle; $R_5$ represents a group of the formula: Gly-NH—$R_6$, wherein $R_6$ represents hydrogen or an optionally substituted alkyl, or a group of the formula: NH—$R_6'$ wherein $R_6'$ represents (1) hydrogen, (2) alkyl group which may optionally be substituted with amino or hydroxy, or (3) ureido (—NH—CO—$NH_2$), and their analogs.

Referring to the above formula (I), the D-amino acid residue of $R_3$ includes α-D-amino acids containing 11 carbon atoms at the maximum, e.g. D-Leu, Ile, Nle, Val, Nval, Abu, Phe, Phg, Ser, Thr, Met, Ala, Trp which may optionally have 1 to 3 suitable substituents e.g. a $C_{1-4}$ alkyl group such as methyl or t-butyl, a $C_{1-4}$ alkoxy group such as t-butoxy, a $C_{1-4}$ alkoxy-carbonyl group such as t-butoxycarbonyl, a $C_{6-10}$ aryl group such as 2-naphthyl, indolyl group or imidazolyl group which may optionally be substituted with $C_{1-4}$ alkyl, $C_{6-10}$ aryl or $C_{6-10}$ aryl-$C_{1-4}$ alkyl such as indole-3-yl, 2-methylindolyl, benzylimidazole-2-yl, etc. The substituent for the optionally substituted alkyl of $R_6$ includes hydroxy and amino. The alkyl group of the alkyl which may optionally be substituted with amino or hydroxy includes $C_{1-4}$ alkyl, preferably $C_{1-3}$ alkyl. The $C_{1-4}$ alkyl includes methyl, ethyl, propyl, isopropyl, butyl, isobutyl, sec-butyl, and tert-butyl. The number of substituents is 1 to 3, preferably 1 or 2, and more preferably 1. The salts with acid (inorganic acid or organic acid) and metal complex compounds of peptide (I) can also be used in the same manner as peptide (I).

Preferred examples of the peptide compound having LH-RH activity are polypeptides of the formula:

(Pyr)Glu-$R_1$-Trp-Ser-$R_2$-$R_3'$-$R_4$-Arg-Pro-$R_5'$ (I'), wherein $R_1$ represents His, Tyr, Trp, or p-$NH_2$—Phe, $R_2$ represents Tyr or Phe; $R_3'$ represents Gly or a D-amino acid residue, $R_4$ represents Leu, Ile, or Nle; $R_5'$ represents Gly-NH—$R_6''$, wherein $R_6''$ represents hydrogen or $C_{1-3}$ alkyl group which may optionally be substituted with hydroxy, or NH—$R_6''$ wherein $R_6''$ is as defined above, and salts thereof [U.S. Pat. No. 3,853,837, U.S. Pat. No. 4,008,209, U.S. Pat. No. 3,972,859, BP 1423083; Proceedings of the National Academy of Sciences of the United States of America, 78, 6509–6512, 1981].

Referring to the above formula (I'), the D-amino acid residue of $R_3'$ includes α-D-amino acids containing 11 carbon atoms at the maximum, e.g. D-Leu, Ile, Nle, Val, Nval, Abu, Phe, Phg, Ser, Thr, Met, Ala, Trp, which may optionally have 1 to 2 suitable substituents, e.g. $C_{1-4}$ alkyl group such as t-butyl, $C_{1-4}$ alkoxy group such as t-butoxy, $C_{1-4}$ alkoxy-carbonyl group such as t-butoxycarbonyl, etc. The $C_{1-3}$ alkyl group of the $C_{1-3}$ alkyl which may optionally be substituted with hydroxy for $R_{6''}$ includes methyl, ethyl, propyl, isopropyl, etc. The number of substituents (hydroxy) is 1 or 2, preferably 1. The salts with acid (inorganic acid or organic acid and metal complex compounds of peptide (I') can also be used in the same manner as said peptide (I').

Whenever the amino acids, peptides, and protective groups relating to the polypeptides of formulas (I) and (I') are expressed by abbreviations in the following description, it should be understood that the abbreviations adopted by IUPAC-IUB Commission on Biochemical Nomenclature or those in common use in the art are used. It should also be understood that where any amino acid may exist as optical isomers, the L-configuration is meant unless otherwise indicated. Examples of the abbreviations are mentioned below.

Abu: aminobutyric acid
Ala: alanine
Gly: glycine
His: histidine
Ile: isoleucine
Leu: leucine
Met: methionine
Nle: norleucine
Nval: norvaline
Phe: phenylalanine
Phg: phenylglycine
Pro: proline
(Pyr)Glu: pyroglutamic acid
Ser: serine
Thr: threonine
Trp: tryptophan
Tyr: tyrosine
Val: valine Throughout this specification, referring to the above formulas (I) and (I'), the generic name of the polypeptide in which $R_1$=His, $R_2$=Tyr, $R_3$=D-Leu, $R_4$=Leu, and $R_5$=NHCH$_2$—CH$_3$ is leuprorelin.

The peptide compound having LH-RH activity in the present invention includes leuprorelin, a polypeptide of the formula (I) mentioned above, wherein $R_1$ is His, $R_2$ is Tyr, $R_3$ is D-Ala, $R_4$ is Leu, and $R_5$ is NHCH$_2$—CH$_3$, gonadrelin:

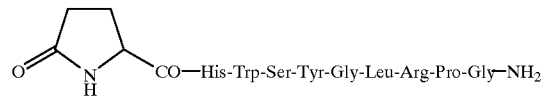

(German Patent No. 2213737),
buserelin:

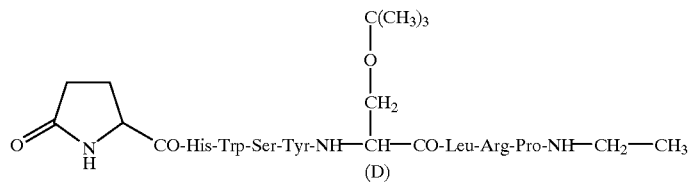

(U.S. Pat. No. 4,024,248, German Patent No. 2438352, JP-A 41359/1976), triptorelin:

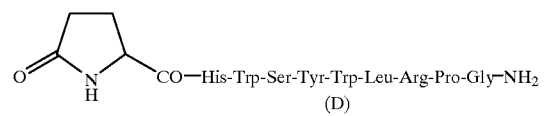

(U.S. Pat. No. 4,010,125, JP-A 31073/1977), goserelin:

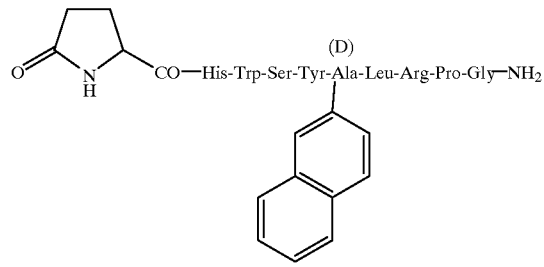

(U.S. Pat. No. 4,100,274, JP-A 136172/1977), nafarelin:

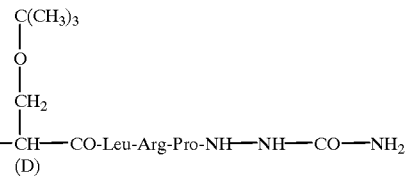

(U.S. Pat. No. 4,234,571, JP-A 164663/1980, JP-A 264498/1988, JP-A 25794/1989), histrelin:

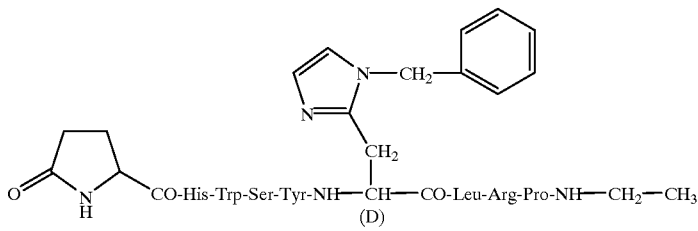
(D)

deslorelin:

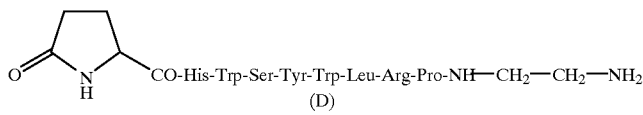
(D)

(U.S. Pat. No. 4,569,967, U.S. Pat. No. 4,218,439), meterelin:

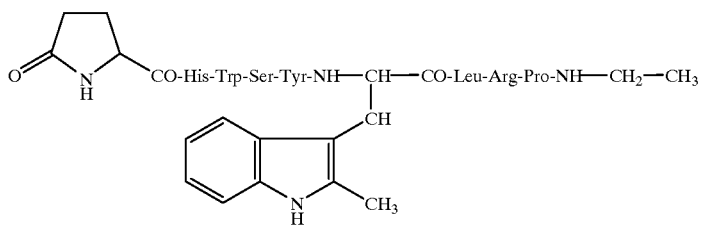

(PCT WO 9118916), and
lecirelin:

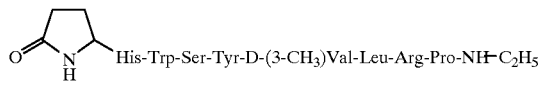

(Belgian Patent No. 897455, JP-A 59654/1984).
Leuprorelin is preferable.

In the above-mentioned peptide compound, the amino acid corresponding to $R_3$ of the general formula (I) mentioned above is D-configuration.

The nonpeptide compound having luteinizing hormone releasing hormone activity includes for example, morphinan derivatives (JP-A 271275/1986).

As the compound having LH-RH antagonizing activity, a condensed cyclic compound containing at least a condensed bicyclic structure of an optionally substituted homo or hetero 5- to 7-membered ring together with an optionally substituted homo or hetero 5- to 7-membered ring, or a salt thereof can be used.

In the above condensed bicyclic compound, W ring denotes an optionally substituted homo or hetero 5- to 7-membered ring.

Examples of the homocyclic group in the optionally substituted homocyclic groups of W ring include 5- to 7-membered cyclic hydrocarbon groups consisting of carbon atoms, for example, phenylene; $C_{5-7}$ cycloalkylene, e.g. cyclopropylene, cyclobutylene, cyclopentylene, cyclohexene and cycloheptylene; and $C_{5-7}$ cycloalkenylene, e.g. cyclopropenylene, cyclobutenylene, cyclopentenylene, cyclohexenylene and cycloheptenylene.

Examples of the substituent which the homocyclic groups may have, are preferably a group bonded through a carbon atom, a nitrogen atom, an oxygen atom or a sulfur atom for $R^{1a}$, $R^{21}$, $R^{31}$, $R^{41}$, $R^{5a}$, $R^{6a}$ or $R^{4b}$, and includes (1) $C_{1-15}$ alkyl (and among others $C_{1-6}$ alkyl being preferable), e.g. methyl, ethyl, n-propyl, iso-propyl, n-butyl, iso-butyl, sec-butyl, t-butyl, pentyl, hexyl, heptyl, octyl, nonyl, decyl, undecyl, dodecyl, tridecyl, tetradecyl, pentadecyl, etc. which may optionally be substituted by 1 to 3 halogen, (2) $C_{3-10}$ cycloalkyl, e.g. cyclopropyl, cyclobutyl, cyclopentyl, cyclohexyl, cycloheptyl, cyclooctyl, cyclononyl, etc., (3) $C_{2-10}$ alkenyl, e.g. vinyl, allyl, isopentenyl, 1-butenyl, 2-butenyl, 3-butenyl, butadienyl, 2-methylallyl, hexatrienyl, 3-octenyl, etc., (4) $C_{2-10}$ alkynyl, e.g. ethynyl, 2-propinyl, propargyl, 3-hexynyl, etc., (5) $C_{6-10}$ aryl, e.g. phenyl, naphthyl, (6) $C_{7-19}$ aralkyl, e.g. phenyl-$C_{1-6}$ alkyl such as benzyl, phenethyl, and phenylpropyl, benzhydryl, trityl etc., (7) nitro, (8) hydroxyl, (9) mercapto, (10) oxo, (11) thioxo, (12) cyano, (13) carbamoyl, (14) carboxyl, (15) $C_{1-5}$ alkoxy-carbonyl (e.g. methoxycarbonyl and ethoxycarbonyl), (16) sulfo, (17) halogen, (18) $C_{1-6}$ alkoxy, e.g. methoxy, ethoxy, butoxy, etc., (19) $C_{6-10}$ aryloxy, e.g. phenoxy, (20) $C_{1-6}$ acyloxy, e.g. $C_{1-6}$ alkanoyloxy such as acetoxy, propionyloxy, (21) $C_{1-6}$ alkylthio, e.g. methylthio, ethylthio, n-propylthio, isopropylthio, n-butylthio, t-butylthio, (22) $C_{6-10}$ arylthio, e.g. phenylthio, (23) $C_{1-6}$ alkylsulfinyl, e.g. methylsulfinyl and ethylsulfinyl, (24) $C_{6-10}$ arylsulfinyl, e.g. phenylsulfinyl, (25) $C_{1-6}$ alkylsulfonyl, e.g. methylsulfonyl and ethylsulfonyl, (26) $C_{6-10}$ arylsulfonyl, e.g. phenylsulfonyl, (27) amino, (28) $C_{1-6}$ acylamino, e.g. $C_{1-6}$ alkanoylamino such as acetylamino and propylamino, (29) mono- or di-$C_{1-4}$ alkylamino, e.g. methylamino, ethylamino, n-propylamino, isopropylamino, n-butylamino, dimethylamino and diethylamino, (30) $C_{3-8}$ cycloalkylamino, e.g. cyclopropylamino, cyclobutylamino, cyclopentylamino and cyclohexylamino, (31) $C_{6-10}$ arylamino, e.g. anilino, (32) $C_{1-6}$ alkanoyl, e.g. formyl, acetyl and hexanoyl, (33) $C_{1-6}$ alkanoyl-oxy, e.g. acetyloxy, propionyloxy, (34) $C_{6-10}$ arylcarbonyl, e.g. benzoyl, and (35) 5- to 6-membered heterocyclic groups containing, besides carbon atom, 1 to 4 hetero-atoms selected from oxygen, sulfur and nitrogen, e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl. The number of substituents ranges from 1 to 6, preferably from 1 to 3, more preferably from 1 to 2. As the hetero 5- to 7-membered ring of W ring, it is exemplified by a 5- to 7-membered heterocyclic ring which may have one or more, preferably one to two, of a nitrogen atom, a sulfur atom or an oxygen atom. The preferable examples of W ring include homo or hetero 5- to 6-membered ring. As the preferable examples of the 5- to 7-membered homo or heterocyclic ring of the W ring, mention is made of the following rings:

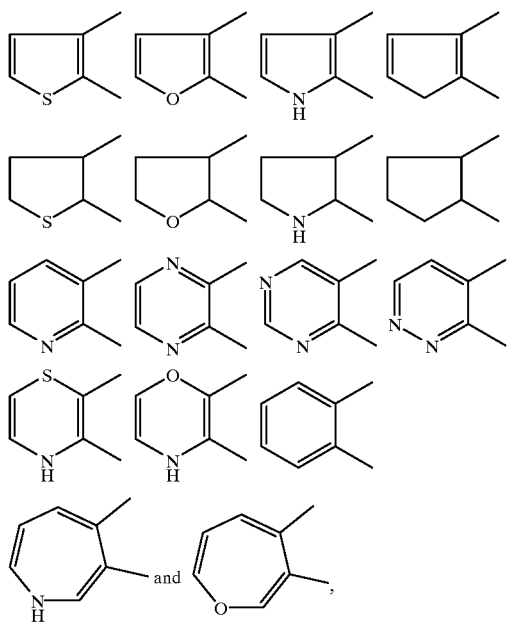

Among these, more preferable examples include:

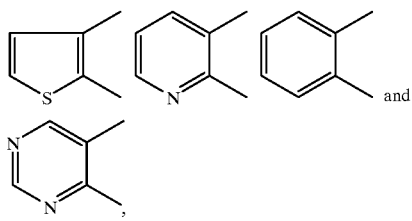

Among these, further more preferable examples include:

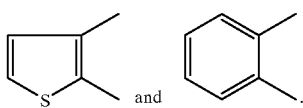

As the W ring, most preferable examples include a group of the formula:

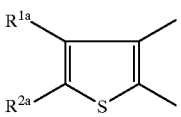

wherein each of $R^{1a}$ and $R^{2a}$ stand for a hydrogen atom or a group bonded through a carbon atom, a nitrogen atom, an oxygen atom or a sulfur atom, or a group of the formula:

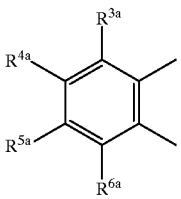

wherein each $R^{3a}$, $R^{4a}$, $R^{5a}$ and $R^{6a}$ stand for a hydrogen atom or a group bonded through a carbon atom, a nitrogen atom, an oxygen atom or a sulfur atom.

As the homo or hetero 5- to 7-membered ring of Y ring in the above condensed bicyclic structure, it is exemplified by 5- to 7-membered homo or heterocyclic ring which may have one or more, preferably one to two, of a nitrogen atom, a sulfur atom or an oxygen atom. Examples of the homo or hetero 5- to 7-membered ring for Y ring include the same kinds of groups as those mentioned above for W ring. Especially the homo or hetero 5- to 7-membered ring which may optionally be substituted by oxo is preferable. The preferable examples include homo or hetero 5- to 6-membered ring, more preferable 6-membered ring. As the preferable examples of the 5- to 7-membered homo or heterocyclic ring of the Y ring, mention is made of the following rings:

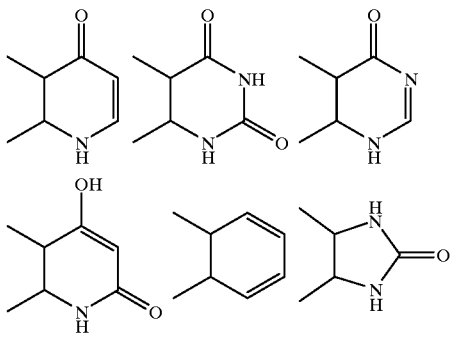

-continued

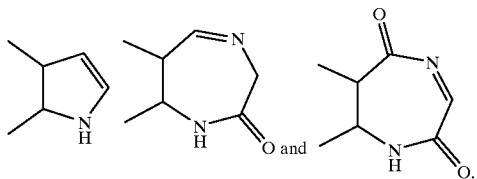

Among these, more preferable examples include the following groups:

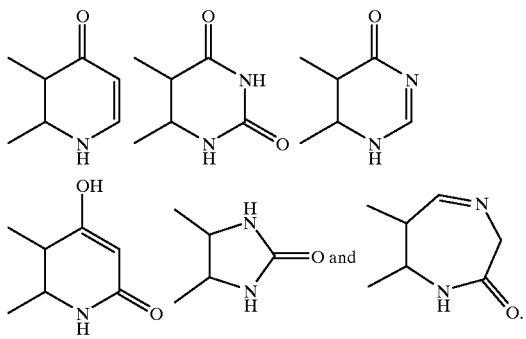

Further preferable examples include the following groups:

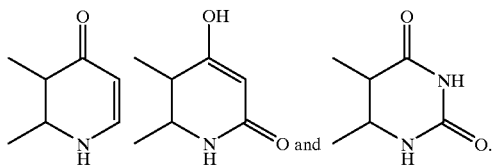

Most preferable examples of the Y ring include the following structure:

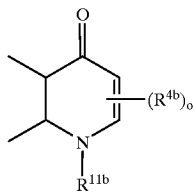

wherein $R^{4b}$ independently stands for a hydrogen atom or a group bonded through a carbon atom, a nitrogen atom, an oxygen atom or a sulfur atom; $R^{11b}$ stands for an optionally substituted hydrocarbon group; and o denotes an integer of 1 to 2; or a group represented by the formula:

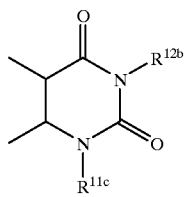

wherein $R^{11c}$ and $R^{12b}$ independently stand for a hydrogen atom or an optionally substituted hydrocarbon group.

The group bonded through a carbon atom for $R^{1a}$, $R^{2a}$, $R^{3a}$, $R^{4a}$, $R^{5a}$, $R^{6a}$ or $R^{4b}$ includes, for example, (1) a hydrocarbon residue, (2) an acyl group, (3) a carbamoyl group, and (4) a heterocyclic group which bonds through carbon atom of the heterocyclic group. Each of these groups may optionally be substituted. Furthermore, as the group bonded through a carbon atom, (5) an optionally esterified or amidated carboxyl group, (6) a cyano group and (7) an amidino group are mentioned.

The hydrocarbon residue in the optionally substituted hydrocarbon residue of the group bonded through a carbon atom for $R^{1a}$, $R^{2a}$, $R^{3a}$, $R^{4a}$, $R^{5a}$, $R^{6a}$ or $R^{4b}$, or hydrocarbon group for $R^{11b}$, $R^{12b}$ or $R^{11c}$ includes a $C_{1-20}$ hydrocarbon. As examples of the $C_{1-20}$ hydrocarbon residue, mention is made of (1) $C_{1-15}$ alkyl, e.g. methyl, ethyl, n-propyl, isopropyl, n-butyl, isobutyl, sec-butyl, t-butyl, pentyl, hexyl, heptyl, octyl, nonyl, decyl, undecyl, dodecyl, tridecyl, tetradecyl, pendadecyl, etc, and among others, with $C_{1-10}$ alkyl or $C_{1-6}$ alkyl being preferable; (2) $C_{3-10}$ cycloalkyl, e.g. cyclopropyl, cyclobutyl, cyclopentyl, cyclohexyl, cycloheptyl, cyclooctyl, cyclononyl, etc, and among others, with $C_{3-6}$ cycloalkyl being preferable; or $C_{7-20}$ bicycloalkyl, e.g. bicyclo[2,2,1]heptyl, bicyclo[2,2,2]octyl, bicyclo[3,2,1]octyl, bicyclo[3,2,1]nonyl, bicyclo[4,2,1]nonyl, bicyclo[4,3,1]decyl; (3) $C_{2-10}$ alkenyl, e.g. vinyl, allyl, isopropenyl, 1-butenyl, 2-butenyl, 3-butenyl, 2-methylallyl, butadienyl, hexatrienyl, 3-octenyl, etc, and among others, with $C_{2-6}$ alkenyl being preferable, (4) $C_{2-10}$ alkynyl, e.g. ethynyl, 2-propynyl, isopropynyl, butynyl, t-butynyl, 3-hexynyl, etc, and among others, with $C_{2-6}$ alkynyl being preferable; (5) $C_{3-10}$ cycloalkenyl, e.g. cyclopropenyl, cyclopentenyl, cyclohexenyl, etc, among others, with $C_{3-6}$ cycloalkenyl being preferable; (6) $C_{6-14}$ aryl, e.g. phenyl, 1- or 2-naphthyl, anthryl, phenanthryl, acenaphthyl, etc., among others, with phenyl and naphthyl being preferable; and (7) $C_{7-20}$ aralkyl, e.g. phenyl-$C_{1-6}$ alkyl such as benzyl, phenethyl or phenylpropyl, benzhydryl, trityl, etc, and among others, with phenyl-$C_{1-6}$ alkyl such as benzyl or phenethyl being preferable.

The substituents which said hydrocarbon residue may optionally have include (1) halogen, (2) nitro, (3) nitroso, (4) cyano, (5) a hydroxyl group which may optionally be substituted by (i) $C_{1-6}$ alkyl, which may optionally be substituted by 1 to 3 substituents selected from hydroxyl, $C_{1-6}$ alkoxy, $C_{1-3}$ alkoxy-$C_{1-3}$ alkoxy, $C_{1-3}$ alkylthio, hydroxy-$C_{1-3}$ alkoxy, $C_{1-6}$ alkyl-carbonyl, carboxyl, carbamoyl, $C_{1-6}$ alkyl-carbamoyl, 5 to 8 membered nitrogen-containing heterocyclic group, $C_{6-10}$ aryl, $C_{7-13}$ aralkyl, nitro, and halogen, (ii) $C_{1-4}$ acyl, (iii) $C_{7-20}$ aralkyl which may optionally be substituted by 1 to 3 substituents selected from halogen, $C_{1-3}$ alkoxy, $C_{1-6}$ alkyl, $C_{6-14}$ aryl, $C_{7-13}$ aralkyl and nitro, (iv) $C_{6-14}$ aryl which may optionally be substituted by 1 to 3 substituents selected from $C_{1-6}$ alkyl, $C_{6-14}$ aryl, $C_{7-13}$ aralkyl, $C_{1-3}$ alkoxy-$C_{1-6}$ alkoxy, nitro and halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkyl-amino, (ix) $C_{2-6}$ alkenyl-amino, (x) $C_{1-3}$ alkoxy-carbonyl, (xi) $C_{1-6}$ alkyl-carbonyl, (xii) $C_{3-6}$ cycloalkyl-oxycarbonyl, (xiii) $C_{6-14}$ aryl-carbonyl, (xiv) $C_{7-20}$ aralkyl-carbonyl, (xv) $C_{6-14}$ aryl-oxycarbonyl, (xvi) trifluorosulfonyl, (xvii) pyranyl, (xviii) furanyl or (xix) tri($C_{1-4}$ alkyl)silyl, e.g. trimethylsilyl, triethylsilyl, (6) a group of the formula: $—S(O)_f—R^{31}$, wherein f is an integer of 0 to 2, $R^{31}$ represents a hydrogen atom or a hydrocarbon residue which may optionally be substituted or an amino group which may optionally be substituted with mono- or di-$C_{1-4}$ alkyl, (the hydrocarbon residue has the same meaning as defined above, among others, $C_{1-20}$ alkyl especially $C_{1-6}$ alkyl, $C_{6-14}$ aryl, $C_{7-20}$ aralkyl are preferable, and as examples of the substituent to the hydrocarbon residue, mention is made of 1 to 3 substituents selected from halogen, nitro, cyano, hydroxy, oxo, thioxo, carboxyl, cyano-$C_{6-14}$ aryl, halogeno-$C_{6-14}$ aryl, etc), (7) an optionally substituted amino group, which is represented by the formula: —$NR^{32}R^{33}$, wherein $R^{32}$ and $R^{33}$ independently are (i) hydrogen, (ii) $C_{1-6}$ alkyl, (iii) $C_{1-6}$ acyl, (iv) a carbamoyl group which may optionally be substituted with mono- or di-$C_{1-4}$ alkyl, $C_{1-4}$ alkylthio or $C_{6-4}$ aryl, (v) $C_{6-14}$ aryl, (vi) $C_{1-4}$ alkylthio, (vii) $C_{1-4}$ alkyl-sulfonyl, (viii) $C_{1-4}$ alkyl-sulfinyl or (ix) a cyclic amino group or a nitrogen-containing heterocyclic group which is mentioned below, (8) a group of the formula: —CO—$R^{34}$ wherein $R^{34}$ denotes (i) hydrogen, (ii) hydroxy, (iii) $C_{1-10}$ alkyl, (iv) $C_{1-6}$ alkoxy which may be substituted with $C_{6-14}$ aryl which may optionally be substituted with 1 to 3 halogens, nitro, $C_{6-14}$ aryl, (v) $C_{3-6}$ cycloalkyl, (vi) $C_{6-14}$ aryl, (vii) $C_{6-14}$ aryloxy, (viii) $C_{7-20}$ aralkyl, (ix) $C_{7-20}$ aralkyloxy, (x) an optionally substituted amino group as defined in (7) above, (xi) an optionally susbstituted aminooxy group represented by the formula: —O—$NR^{32}R^{33}$, wherein $R^{32}$ and $R^{33}$ have the same meaning as defined above, (xii) 5- to 8-membered heterocyclic group, or (xiii) 5- to 8-membered heterocyclic-oxy group, (9) a 3- to 9-membered heterocyclic group containing 1 to 4 heteroatom(s) selected from oxygen (O), sulfur (S) and nitrogen (N) as ring members, the heterocyclic group being optionally substituted, for example, by (i) halogen, (ii) $C_{1-4}$ alkyl, (iii) $C_{1-3}$ alkoxy, (iv) $C_{1-4}$ alkylthio or (v) phenoxy which may optionally be substituted by 1 to 3 halogens, (10) sulfo, (11) $C_{6-14}$ aryl, e.g. phenyl, naphthyl, anthryl, acenaphthyl, etc, which may optionally be substituted with 1 to 4 substituents selected from (a) hydroxyl, (b) amino, (c) mono- or di-$C_{1-6}$ alkylamino, e.g. methylamino, ethylamino, propylamino, dimethylamino, diethylamino, etc, (d) $C_{1-6}$ alkoxy, (e) halogen or (f) cyano, (12) $C_{3-7}$ cycloalkyl, (13) $C_{1-6}$ alkylenedioxy, e.g. methylenedioxy, ethylenedioxy, propylenedioxy, 2,2-dimethylenedioxy, etc, (14) oxo, (15) thioxo, (16) $C_{1-5}$ alkyl, (17) $C_{2-10}$ alkynyl, (18) $C_{3-10}$ cycloalkyl, (19) $C_{2-10}$ alkenyl, e.g. vinyl, allyl, isopropenyl, 1-butenyl, 2-butenyl, butadienyl, hexatrienyl, etc., (among others, $C_{2-6}$ alkenyl is preferable), (20) $C_{5-7}$ cycloalkenyl, (21) $C_{7-20}$ aralkyl, (22) amidino, (23) azido, (24) —B(OH)$_2$, (25) epoxy(—O—), (26) phosphono, (27) a group of the formula: —A—$R^{35}$, wherein A is a spacer group and $R^{35}$ denotes a $C_{1-10}$ alkyl group, (28) phthaloyl, (29) hexamethylenetetraamino, (30) indanyl and (31) phthalimido.

As the spacer group shown by the symbol "A", mention is made of, for example, chemical bond, $C_{1-4}$ alkylene (e.g. methylene, ethylene), $C_{2-6}$ alkenylene (e.g. vinylene, butadienylene); a group of the formula: —(CH$_2$)m'NR$^{38}$— in which m' is an integer of 0 to 3 and R is hydrogen or $C_{1-6}$ alkyl e.g. methyl, ethyl, n-propyl, isopropyl, n-butyl, isobutyl, sec-butyl, t-butyl, pentyl, isopentyl, neopentyl, hexyl, etc; a group of the formula: —CO—; a group of the formula: —CONR$^{38'}$— in which R$^{38'}$ is hydrogen; $C_{1-6}$ alkyl (examples are the same ones as described above); $C_{3-7}$ cycloalkanediyl e.g. cyclopropylene, cyclobutylene, cyclopentylene, cyclohexylene, cycloheptylene, etc.; $C_{6-14}$ arylene e.g. phenylene, naphthylene; or a heterocyclic group (examples are mentioned below a)); a group of the formula: —S(O)m"+, wherein m" is an integer of 0 to 2; —O—; a group of the formula —NR$^{38'}$S(O)m"'— in which m"' is an integer of 0 to 2, R$^{38'}$ is of the same meaning as defined above.

The substituents on the hydrocarbon residue may further have 1 to 3 substituents. Such substituents includes (1) hydroxy, (2) amino, (3) mono- or di-$C_{1-4}$ alkyl-amino, e.g. methylamino, ethylamino, propylamino, dimethylamino, diethylamino, etc, (4) $C_{1-4}$ alkoxy, (5) $C_{1-6}$ alkyl which may optionally be substituted with 1 to 3 halogens, (6) $C_{6-14}$ aryl which may optionally be substituted with 1 to 3 substituents selected from halogen and cyano, (7) $C_{7-13}$ aralkyl, (8) $C_{1-6}$ alkoxy-carbonyl, (9) 5- to 8-membered heterocyclic group, (10) $C_{1-10}$ acyl, (11) carboxyl, (12) $C_{1-6}$ alkoxy-carbonyl, (13) $C_{6-14}$ aryl-carbonyl, (14) $C_{1-6}$ alkylendioxy, (15) sulfamoyl, (16) carbamoyl, (17) $C_{1-4}$ alkylthio, (18) $C_{1-4}$ alkylsulfinyl, (19) $C_{1-4}$ alkylsulfonyl, (20) halogen, (21) nitro, (22) mercapto and (23) cyano. The number of the substituents is more preferably 1 to 2.

When the above hydrocarbon residue is cycloalkyl, cycloalkenyl, alkynyl, aryl or aralkyl, each of the group may have one to three of $C_{1-6}$ alkyl, as a substituent. The $C_{1-6}$ alkyl group may further substituted by one to three substituents selected from hydroxy, oxo, $C_{1-3}$ alkoxy, $C_{1-3}$ acyl, $C_{1-3}$ alkylthio, halogen and carbamoyl.

When the hydrocarbon residue is cycloalkyl, cycloalkenyl, alkynyl, aryl or aralkyl, as examples of $C_{1-6}$ alkyl which may optionally have, mention is made of (1) formyl (i.e. methyl is substituted by oxo), (2) carboxyl (i.e. methyl is substituted by oxo and hydroxy), (3) $C_{1-6}$ alkoxy-carbonyl (i.e. methyl is substituted by oxo and alkoxy, $C_{1-6}$ alkoxycarbonyl such as e.g. methoxycarbonyl, ethoxycarbonyl, t-butoxycarbonyl), (4) hydroxy-$C_{1-6}$ alkyl, e.g. hydroxymethyl, hydroxyethyl, hydroxypropyl, hydroxybutyl, (5) $C_{1-3}$ alkoxy-$C_{1-6}$ alkyl, e.g. methoxymethyl, ethoxymethyl, ethoxybutyl, propoxymethyl, propoxyhexyl.

In the above optionally substituted hydrocarbon residue, the number of the substituent(s) is preferably 1 to 6, more preferably 1 to 5, still more preferably 1 to 3 and most preferably 1 to 2. The number of the substituent(s) which is substituted on the substituent is preferably 1 to 3, more preferably 1 or 2.

As the acyl group in the optionally substituted acyl group in the group bonded through a carbon atom for $R^{1a}$, $R^{2a}$, $R^{3a}$, $R^{4a}$, $R^{5a}$, $R^{6a}$, $R^{4b}$, mention is made of an acyl group of hydrocarbon-carbonyl or hydrocarbon-oxy-carbonyl, which is derived from $C_{1-24}$ aliphatic carboxylic acid.

Further examples of the acyl group include formyl, $C_{1-10}$ alkyl-carbonyl, e.g. acetyl, propionyl, butyryl, isobutyryl, valeryl, isovaleryl, pivaloyl, hexanoyl, heptanoyl, octanoyl; $C_{1-13}$ alkoxy-carbonyl; $C_{6-14}$ aryl-carbonyl, e.g. benzoyl, naphthylcarbonyl, anthracenylcarbonyl; $C_{6-14}$ aryloxycarbonyl, e.g. phenoxycarbonyl; $C_{7-20}$ aralkyl-carbonyl, e.g. benzylcarbonyl; $C_{7-19}$ aralkyloxy-carbonyl, e.g. benzyloxycarbonyl; $C_{3-10}$ cycloalkyl-carbonyl, e.g. cyclopropylcarbonyl, cyclobutylcarbonyl, cyclopentylcarbonyl, cyclohexylcarbonyl; $C_{2-6}$ alkenylcarbonyl, e.g. vinylcarbonyl, butenylcarbonyl, butadienylcarbonyl, hexatrienylcarbonyl. Among others, $C_{1-10}$ alkyl-carbonyl or $C_{1-13}$ alkoxy-carbonyl is preferable. As substituents on the acyl group, mention is made of the same substituents on the optionally substituted hydrocarbon residue as mentioned above.

Among acyl group as mentioned above, as the $C_{1-13}$ alkoxy in $C_{1-13}$ alkoxy-carbonyl, examples are straight-chain or branched C-$_{1-13}$ alkoxy. As straight-chain alkoxy, it is preferable $C_{1-9}$ straight-chain alkoxy, e.g. methoxy, ethoxy, propoxy, butoxy, pentoxy, neopentyloxy, hexyloxy, octyloxy. As the branched alkoxy group, mention is made of $C_{3-13}$ branched alkoxy groups, e.g. isopropoxy, isobutoxy, sec-butoxy, tert-butoxy, isopentoxy, sec-pentyloxy, tert-pentyloxy, 3-pentyloxy, isohexyloxy, sec-hexyloxy, terthexyloxy, isooctyloxy, sec-octyloxy, tert-octyloxy, cyclopentyloxy, cyclopropyloxy, cyclobutyloxy, cycloheptyloxy, 2-indanyloxy, 4-piperidinyloxy, tetrahydro-4H-pyran-4-yloxy. As the branched alkoxy group, among them, $C_{3-7}$ branched alkoxy groups are preferable.

Examples of the optionally substituted carbamoyl group for the group bonded through a carbon atom for $R^{1a}$, $R^{2a}$, $R^{3a}$, $R^{4a}$, $R^{5a}$, $R^{6a}$ or $R^{4b}$ include a carbamoyl group which may optionally be substituted by an optionally substituted $C_{1-20}$ hydrocarbon residue or a cyclic amino group. As an optionally substituted $C_{1-20}$ hydrocarbon residue, mention is made of those described hereinbefore. The substituents on the carbamoyl group are the same as those on the hydrocarbon residue. Concrete examples of the substituted carbamoyl include mono- or di-$C_{1-15}$ alkyl-carbamoyl, e.g. methylcarbamoyl, ethylcarbamoyl, hexylcarbamoyl, dimethylcarbamoyl, methylethylcarbamoyl.

As the heterocyclic group in the optionally substituted heterocyclic group which bonds with the constitutive carbon atom for the group bonded through a carbon atom for $R^{1a}$, $R^{2a}$, $R^{3a}$, $R^{4a}$, $R^{5a}$, $R^{6a}$ or $R^{4b}$, mention are made of 3 to 9, preferably 5 to 8, membered heterocyclic groups which have 1 to 4 hetero atoms selected from an oxygen atom, sulfur atom and nitrogen atom besides carbon atom; and condensed hetero-bi- or tri-cyclic groups composed of the above heterocyclic group and other ring groups.

Examples of the heterocyclic groups include (1) 5-membered cyclic groups containing, besides the carbon atom, 1 to 4 hetero-atoms selected from an oxygen atom, sulfur atom and nitrogen atom, such as 2- or 3-thienyl, 2- or 3-furyl, 2- or 3-pyrrolyl, 3- or 4-pyrrolinyl, 2-, 4- or 5-oxazolyl, 2-, 4- or 5-thiazolyl, 3-, 4- or 5-pyrazolyl, 2- or 3-pyrrolidinyl, 2-, 4- or 5-imidazolyl, 2-imidazolinyl, 3-, 4- or 5-isoxazolyl, 3-, 4- or 5-isothiazolyl, 3- or 5-(1,2,4-oxadiazolyl), 2-, 5- or 6-(1,3,4-oxadiazolyl), 3- or 4-furazanyl, 3- or 5-(1,2,4-thiadiazolyl), 4- or 5-(1,2,3-thiadiazolyl), 3- or 4-(1,2,5-thiadiazolyl), 2- or 5-(1,2,3-triazolyl), 3- or 5-(1,2,4-triazolyl), and 5-(1H- or 2H-tetrazolyl); (2) 6-membered cyclic groups containing, besides, carbon atom, 1 to 4 hetero-atoms selected from an oxygen atom, sulfur atom and nitrogen atom, as exemplified by 2-, 3- or 4-pyridyl, 2-, 4- or 5-pyrimidinyl, 2- or 3-thiomorpholinyl, 2- or 3-morpholinyl, 2- or 4-triazinyl, 2- or 3-piperazinyl, 2- 3- or 4-piperidinyl, 2- or 3-pyranyl, 2- or 3-thiopyranyl, 2- or 3-(1,4-oxadinyl), 2- or 3-(1,4-thiazinyl), 1- or 4-(1,3-thiazinyl), 3- or 6-triazinyl, 3- or 4-pyridazinyl and 2- or 3-pyrazinyl; (3) condensed bicyclic or tricyclic groups containing, besides carbon atom, 1 to 4 hetero-atoms selected from oxygen atom, sulfur atom and nitrogen atom, as exemplified by benzofuranyl, isobenzofuranyl, benzothiazolyl, 1,2-benzoisothiazolyl, benzo[b]thienyl, -benzoxazolyl, 1H-benzotriazolyl, 1,2-benzoisoxazolyl, tetrazolo[1,5-b]pyridazinyl, triazolo[4,5b]pyridazinyl, benzoimidazolyl, quinolyl, isoquinolyl, cinnolinyl, phthaladinyl, quinazolinyl, quinoxalinyl, indolidinyl, indolyl, isoindolyl, 1H-indazolyl, quinolizinyl, 1,8-naphthylidinyl, purinyl, pteridinyl, dibenzofuranyl, carbazolyl, α-carbolinyl, β-carbolinyl, γ-carbolinyl, acridinyl, phenoxazinyl, phenanthridinyl, chromanyl, benzoxadinyl, phenazinyl, phenothiazinyl, phenoxathiinyl, phenoxazinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo(1,2-b)pyridazinyl, imidazo[1,2-a]pyrimidinyl, 1,2,4-triazolo[4,3-a]pyridyl, 1,2,4-triazolo[4,3-b]pyridazinyl. The heterocyclic group may be a hydrogen additive form.

Examples of the substituents, which the heterocyclic group which bonds with the constitutive carbon atom may have include (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{7-11}$ aralkyl, (7) $C_{6-14}$ aryl, (8) $C_{1-6}$ alkoxy, (9) $C_{6-14}$ aryloxy, e.g. phenoxy, (10) $C_{1-6}$ alkanoyl, e.g. formyl, acetyl, propionyl, n-butyryl and isobutyryl, (11) $C_{6-14}$ arylcarbonyl, e.g. benzoyl, (12) $C_{1-6}$ alkanoyloxy, e.g. formyloxy, acetyloxy, propionyloxy, n-butyryloxy and isobutyryloxy, (13) $C_{6-14}$ aryl-carbonyloxy, e.g. benzoyloxy, (14) carboxyl, (15) $C_{1-6}$ alkoxy-carbonyl, e.g. methoxycarbonyl, ethoxycarbonyl, n-propoxycarbonyl, isopropoxycarbonyl, n-butoxycarbonyl, isobutoxycarbonyl and tert-butoxycarbonyl, (16) carbamoyl, (17) N-mono-$C_{1-4}$ alkylcarbamoyl, e.g. N-methylcarbamoyl, N-ethylcarbamoyl, N-propylcarbamoyl, N-isopropylcarbamoyl and N-butylcarbamoyl, (18) N,N-di-$C_{1-4}$ alkyl-carbamoyl, e.g. N,N-dimethylcarbamoyl, N,N-diethylcarbamoyl, N,N-dipropylcarbamoyl and N,N-dibutylcarbamoyl, (19) cyclic aminocarbonyl, e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl, (20) halogen, (21) mono-, di- or tri-halogeno-$C_{1-4}$ alkyl, e.g. chloromethyl, dichloromethyl, trifluoromethyl and trifluoroethyl, (22) oxo, (23) amidino, (24) imino, (25) amino, (26) mono- or di-$C_{1-4}$ alkylamino, e.g. methylamino, ethylamino, propylamino, isopropylamino, butylamino, dimethylamino, diethylamino, dipropylamino, diisopropylamino and dibutylamino, (27) 3- to 6-membered cyclic amino group containing, besides the carbon atom and one nitrogen atom, 1 to 3 hetero-atoms selected from oxygen atom, sulfur atom and nitrogen atom, e.g. aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl and N-ethylpiperazinyl, (28) $C_{1-6}$ alkanoylamino, e.g. formamido, acetamido, trifluoroacetamido, propionylamido, butyrylamido and isobutyrylamido, (29) benzamido, (30) carbamoylamino, (31) N—$C_{1-4}$ alkylcarbamoylamino, e.g. N-methylcarbamoylamino, N-ethylcarbamoylamino, N-propylcarbamoylamino, N-isopropylcarbamoylamino and N-butylcarbamoylamino, (32) N,N-di-$C_{1-4}$ alkylcarbamoylamino, e.g. N,N-dimethylcarbamoylamino, N,N-diethylcarbamoylamino, N,N-dipropylcarbamoylamino and N,N-dibutylcarbamoylamino, (33) $C_{1-3}$ alkylenedioxy, e.g. methylenedioxy and ethylenedioxy, (34) —B(OH)$_2$, (35) hydroxyl, (36) epoxy (—O—), (37) nitro, (38) cyano, (39) mercapto, (40) sulfo, (41) sulfino, (42) phosphono, (43) sulfamoyl, (44) $C_{1-6}$ alkylsulfamoyl, e.g. N-methylsulfamoyl, N-ethylsulfamoyl, N-propylsulfamoyl, N-isopropylsulfamoyl and N-butyl-sulfamoyl, (45) di-$C_{1-6}$ alkylsulfamoyl, e.g. N,N-dimethylsulfamoyl, N,N-diethylsulfamoyl, N,N-dipropylsulfamoyl and N,N-dibutylsulfamoyl, (46) $C_{1-6}$ alkylthio, e.g. methylthio, ethylthio, propylthio, isopropylthio, n-butylthio, sec-butylthio and tert-butylthio, (47) phenylthio, (48) $C_{1-6}$ alkylsulfinyl, e.g. methylsulfinyl, ethylsulfinyl, propylsulfinyl and butylsulfinyl), (49) phenylsulfinyl, (50) $C_{1-6}$ alkylsulfonyl, e.g. methylsulfonyl, ethylsulfonyl, propylsulfonyl and butylsulfonyl, and (51) $C_{6-14}$ arylsulfonyl, e.g. phenylsulfonyl. The number of the substituents ranges from 1 to 6, preferably 1 to 3.

The optionally esterified carboxyl group for the group bonded through a carbon atom for $R^{1a}$, $R^{2a}$, $R^{3a}$, $R^{4a}$, $R^{5a}$, $R^{6a}$ or $R^{4b}$ includes a group of the formula: —COO—$R^{21}$, wherein $R^{21}$ is a hydrogen atom, a hydrocarbon residue or a heterocyclic group. Each of these hydrocarbon residue and heterocyclic group may optionally be substituted. The hydrocarbon group or a substituent thereof is of the same meaning as defined in $C_{1-20}$ hydrocarbon group as mentioned above. The heterocyclic group or a substituent thereof is of the same meaning as defined in a) hereinafter.

The optionally amidated carboxyl group includes a group of the formula; $-CO-NR^{22}R^{23}$, wherein $R^{22}$ is a hydrogen atom, a hydrocarbon residue, a heterocyclic group or a group bonded through a sulfur atom. $R^{23}$ represents a hydrogen atom or a hydrocarbon residue. $R^{22}$ and $R^{23}$ may form a 5 to 8 membered cyclic amino group together with the adjacent nitrogen atom or may form a nitrogen-containing heterocyclic group together with the adjacent nitrogen atom. Each of these hydrocarbon residue, heterocyclic group, cyclic amino group, nitrogen-containing heterocyclic group may optionally be substituted. The hydrocarbon group for $R^{22}$ or $R^{23}$ includes above-mentioned $C_{1-20}$ hydrocarbon group. The heterocyclic group includes those of a) as mentioned below. The group bonded through a sulfur atom is defined below. The optionally amidated carboxyl group may have 1 to 3 substituents as those of the substituents on the hydrocarbon residue mentioned below.

Examples of the group bonded through a nitrogen atom include (1) nitro, (2) a group of the formula: $-NR^{24}R^{25}$, wherein $R^{24}$ represents a hydrogen atom, a hydrocarbon group, a hydrocarbon-oxy group, an acyl group, hydroxyl, a heterocyclic group, condensed homo-bicyclic group or a group of the formula: $-SO_p-R^{26}$, wherein p denotes an integer of 0 to 2, and $R^{26}$ represents a hydrocarbon group, $R^{25}$ represents a hydrogen or a hydrocarbon group, and the group $-NR^{24}R^{25}$ may form a cyclic amino group or a nitrogen-containing heterocyclic group. Each of these hydrocarbon group, hydrocarbon-oxy group, acyl group, hydroxy, heterocyclic group and cyclic amino group may optionally be substituted. As the hydrocarbon group or the hydrocarbon group in the hydrocarbon-oxy group for $R^{24}$, $R^{25}$ or $R^{26}$, and the acyl group for $R^{24}$ or $R^{25}$ include the same ones as defined for $R^{1a}$, $R^{2a}$, $R^{3a}$, $R^{4a}$, $R^{5a}$, $R^{6a}$ or $R^{4b}$ as mentioned above. Examples of the heterocyclic group, condensed homo-bicyclic group, cyclic amino group or nitrogen-containing heterocyclic group includes those of a), d), b) or c) as mentioned below. The group bonded through a nitrogen atom may have 1 to 3 substituents as those of the substituents on the hydrocarbon group mentioned above.

Examples of the group bonded through an oxygen atom include a group of the formula: $-O-R^{27}$, wherein $R^{27}$ is a hydrogen atom, a hydrocarbon group, an acyl group or a heterocyclic group. Each of these hydrocarbon residue, acyl group and heterocyclic group may optionally be substituted. The hydrocarbon group, acyl group or their substituents include same ones defined for $R^{1a}$, $R^{2a}$, $R^{3a}$, $R^{4a}$, $R^{5a}$, $R^{6a}$ or $R^{4b}$ as mentioned above. The heterocyclic group or a substituent thereof is of the same meaning as defined in a) hereinafter.

Examples of the group bonded through a sulfur atom include a group of the formula: $-S(O)_{te}-R^{28}$, wherein $R^{28}$ is a hydrogen atom, a hydrocarbon group or a heterocyclic group, and te denotes an integer of 0 to 2. Each of these hydrocarbon residue and heterocyclic group may be optionally substituted.

The hydrocarbon group or a substituent thereof include same ones defined for $R^{1a}$, $R^{2a}$, $R^{3a}$, $R^{4a}$, $R^{5a}$, $R^{6a}$ or $R^{4b}$ as mentioned above. The heterocyclic group or a substituent thereof is defined in a) hereinafter.

In the present application;
a) examples of the above-mentioned optionally substituted heterocyclic groups include 3- to 9-membered cyclic groups preferably 5 to 8-membered cyclic groups, or the condensed hetero- bi- or tri-cyclic group containing, besides carbon atom, 1 to 4 hetero-atoms such as oxygen atom, sulfur atom and nitrogen atom. Examples of (1) 5-membered cyclic groups containing, besides carbon atom, 1 to 4 hetero-atoms selected from oxygen atom, sulfur atom and nitrogen atom include thienyl, furyl, pyrrolyl, pyrrolidinyl, pyrrolinyl, oxazolyl, thiazolyl, pyrazolyl, pyrazolidinyl, pyrazolinyl, imidazolyl, imidazolinyl, imidazolidinyl, isoxazolyl, isothiazolyl, 1,2,4-oxadiazolyl, 1,3,4-oxadiazolyl, furazanyl, 1,2,4-thiadiazolyl, 1,2,3-thiadiazolyl, 1,2,5-thiadiazolyl, 1,2,3-triazolyl, 1,2,4-triazolyl, triazolidinyl, and 1H- or 2H-tetrazolyl; (2) 6-membered cyclic groups containing, besides, carbon atom, 1 to 4 hetero-atoms selected from oxygen atom, sulfur atom or nitrogen atom include pyridyl, pyrimidinyl, thiomorpholinyl, morpholinyl, triazinyl, piperidinyl, piperidyl, pyranyl, thiopyranyl, 1,4-oxadinyl, 1,4-thiazinyl, 1,3-thiazinyl, piperadinyl, pyridazinyl and pyrazinyl; (3) condensed hetero bicyclic or tricyclic groups containing, besides carbon atom, 1 to 4 hetero-atoms selected from oxygen atom, sulfur atom and nitrogen atom include benzofuranyl, isobenzofuranyl, benzothiazolyl, 1,2-benzoisothiazolyl, benzo[b]thienyl, benzoxazolyl, 1H-benzotriazolyl, 1,2-benzoisoxazolyl, tetrazolo[1,5-b]pyridazinyl, triazolo[4,5-b]pyridazinyl, benzoimidazolyl, quinolyl, isoquinolyl, cinnolinyl, phthaladinyl, quinazolinyl, quinoxalinyl, indolidinyl, indolyl, isoindolyl, 1H-indazolyl, quinolizinyl, 1,8-naphthylidinyl, purinyl, pteridinyl, dibenzofuranyl, carbazolyl, α-carbolinyl, β-carbolinyl, γ-carbolinyl, acridinyl, phenoxazinyl, phenanthridinyl, chromanyl, benzoxadinyl, phenazinyl, phenothiazinyl, phenoxathiinyl, phenoxazinyl, thianthrenyl, phenanthridinyl, phenanthrolinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl; (4) 3-membered heterocyclic group such as oxiranyl, aziridinyl; and (5) 4-membered heterocyclic group such as azetidinyl. The heterocyclic group may be a hydrogen additive form.

Examples of the substituents, which the heterocyclic group may have include (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{7-11}$ aralkyl, (7) $C_{6-14}$ aryl, (8) $C_{1-6}$ alkoxy, (9) $C_{6-14}$ aryloxy, e.g. phenoxy, (10) $C_{1-6}$ alkanoyl, e.g. formyl, acetyl, propionyl, n-butyryl and isobutyryl, (11) $C_{6-14}$ arylcarbonyl, e.g. benzoyl, (12) $C_{1-6}$ alkanoyloxy, e.g. formyloxy, acetyloxy, propionyloxy, n-butyryloxy and isobutyryloxy, (13) $C_{6-14}$ aryl-carbonyloxy, e.g. benzoyloxy, (14) carboxyl, (15) $C_{1-6}$ alkoxy-carbonyl, e.g. methoxycarbonyl, ethoxycarbonyl, n-propoxycarbonyl, isopropoxycarbonyl, n-butoxycarbonyl, isobutoxycarbonyl and tert-butoxycarbonyl, (16) carbamoyl, (17) N-mono-$C_{1-4}$ alkylcarbamoyl, e.g. N-methylcarbamoyl, N-ethylcarbamoyl, N-propylcarbamoyl, N-isopropylcarbamoyl and N-butylcarbamoyl, (18) N,N-di-$C_{1-4}$ alkyl-carbamoyl, e.g. N,N-dimethylcarbamoyl, N,N-diethylcarbamoyl, N,N-dipropylcarbamoyl and N,N-dibutylcarbamoyl, (19) cyclic aminocarbonyl, e.g.

1-aziridinylcarbonyl, 1-azetidinylcarbonyl, 1-pyrrolidinylcarbonyl, 1-piperidinylcarbonyl, N-methylpiperazinylcarbonyl and morpholinocarbonyl, (20) halogen, (21) mono-, di- or tri-halogeno-$C_{1-4}$ alkyl, e.g. chloromethyl, dichloromethyl, trifluoromethyl and trifluoroethyl, (22) oxo, (23) amidino, (24) imino, (25) amino, (26) mono- or di-$C_{1-4}$ alkylamino, e.g. methylamino, ethylamino, propylamino, isopropylamino, butylamino, dimethylamino, diethylamino, dipropylamino, diisopropylamino and dibutylamino, (27) 3- to 6-membered cyclic amino group containing, besides the carbon atom and one nitrogen atom, 1 to 3 hetero-atoms selected from oxygen atom, sulfur atom and nitrogen atom, e.g. aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl and N-ethylpiperazinyl, (28) $C_{1-6}$ alkanoylamino, e.g. formamido, acetamido, trifluoroacetamido, propionylamido, butyrylamido and isobutyrylamido, (29) benzamido, (30) carbamoylamino, (31) N—$C_{1-4}$ alkylcarbamoylamino, e.g. N-methylcarbamoylamino, N-ethylcarbamoylamino, N-propylcarbamoylamino, N-isopropylcarbamoylamino and N-butylcarbamoylamino, (32) N,N-di-$C_{1-4}$ alkylcarbamoylamino, e.g. N,N-dimethylcarbamoylamino, N,N-diethylcarbamoylamino, N,N-dipropylcarbamoylamino and N,N-dibutylcarbamoylamino, (33) $C_{1-3}$ alkylenedioxy, e.g. methylenedioxy and ethylenedioxy, (34) —B(OH)$_2$, (35) hydroxyl, (36) epoxy (—O—), (37) nitro, (38) cyano, (39) mercapto, (40) sulfo, (41) sulfino, (42) phosphono, (43) sulfamoyl, (44) $C_{1-6}$ alkylsulfamoyl, e.g. N-methylsulfamoyl, N-ethylsulfamoyl, N-propylsulfamoyl, N-isopropylsulfamoyl and N-butylsulfamoyl, (45) di-$C_{1-6}$ alkylsulfamoyl, e.g. N,N-dimethylsulfamoyl, N,N-diethylsulfamoyl, N,N-dipropylsulfamoyl and N,N-dibutylsulfamoyl, (46) $C_{1-6}$ alkylthio, e.g. methylthio, ethylthio, propylthio, isopropylthio, n-butylthio, sec-butylthio and tert-butylthio, (47) phenylthio, (48) $C_{1-6}$ alkylsulfinyl, e.g. methylsulfinyl, ethylsulfinyl, propylsulfinyl and butylsulfinyl), (49) phenylsulfinyl, (50) $C_{1-6}$ alkylsulfonyl, e.g. methylsulfonyl, ethylsulfonyl, propylsulfonyl and butylsulfonyl, and (51) $C_{6-14}$ arylsulfonyl, e.g. phenylsulfonyl. The number of the substituents ranges from 1 to 6, preferably 1 to 3, more preferably 1 to 2.

b) As examples of the cyclic amino groups containing nitrogen atom, 3 to 8-membered cyclic amino group are preferable, and aziridinyl, azetidinyl, pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, azepinyl, hexamethyleneamino, oxazolidino, morpholino, thiazolidino, thiomorpholino, phthalimido are mentioned. As more preferable cyclic amino groups, mention is made of 5 to 6-membered ring such as pyrrolidinyl, pyrazolinyl, pyrazolyl, piperidinyl, piperazinyl, morpholino and thiomorpholino.

c) The nitrogen-containing heterocyclic groups are preferably 5 to 7-membered heterocyclic groups and condensed bicyclic group. The nitrogen-containing heterocyclic groups and condensed bicyclic group are exemplified by pyrrolyl, pyrazolyl, thiazolyl, isothiazolyl, oxazolyl, isoxazolyl, imidazolyl, triazolyl, tetrazolyl, furazanyl, pyridyl, pyrimidinyl, pyridazinyl, oxadiazolyl, morpholinyl, thiomorpholinyl, pyrrolidinyl, pyrrolinyl, pyrazolidinyl, pyrazolinyl, imidazolidinyl, imidazolinyl, 1,2,3-triazinyl, 1,2,3-triazolidinyl, piperidinyl, piperazinyl, hexamethyleneaminyl, oxazolidinyl, thiazolidinyl, indolyl, indazolyl, purinyl, quinolyl. The heterocyclic group includes hydrogen additive forms. As more preferable heterocyclic groups, mention is made of 5 to 6 membered heterocyclic groups. In particular, pyrrolidinyl, pyrazolinyl, pyrazolyl, piperidinyl, piperazinyl, morpholinyl and thiomorpholinyl are preferable.

The cyclic amino groups and the nitrogen-containing heterocyclic group may have 1 to 3 substituents. The examples of the substituents includes (1) $C_{1-6}$ alkyl, (2) $C_{6-14}$ aryl, (3) $C_{7-13}$ aralkyl, (4) $C_{1-6}$ alkyl-carbonyl, (5) $C_{6-14}$ aryl-carbonyl, (6) $C_{1-6}$ alkoxy-carbonyl. As the preferable substituent, mention is made of $C_{1-6}$ alkyl, more preferably $C_{1-3}$ alkyl.

d) As examples of the homo bicyclic group, mention is made of indenyl and indenyl.

e) As the examples of halogen, mention is made of fluorine, chlorine, bromine, iodine.

f) As examples of the $C_{1-6}$ alkyl, mention is made of methyl, ethyl, n-propyl, isopropyl, n-butyl, isobutyl, s-butyl, t-butyl, pentyl, isopentyl, neopentyl, hexyl. The $C_{1-4}$ alkyl is exemplified by methyl, ethyl, n-propyl, isopropyl, n-butyl, isobutyl, sec-butyl, t-butyl. The $C_{1-3}$ alkyl is exemplified by methyl, ethyl, n-propyl, isopropyl.

g) As examples of the $C_{2-10}$ alkenyl, mention is made of vinyl, allyl, propenyl, 2-methylallyl, isopropenyl, 2-butenyl, 3-butenyl, butadienyl, hexatrienyl, 3-octenyl. Examples of the $C_{2-6}$ alkenyl are vinyl, allyl, propenyl, isopropenyl, butenyl and hexatrienyl. Examples of the $C_{2-4}$ alkenyl are vinyl, allyl, isopropenyl and butenyl.

h) As example of the $C_{2-10}$ alkynyl, mention is made of ethynyl, 1-propynyl, 2-propynyl, propargyl, and 3-hexynyl. The $C_{2-6}$ alkynyl and the $C_{2-4}$ alkynyl are exemplified by ethynyl, 1-propynyl, 2-propynyl.

i) The $C_{3-10}$ cycloalkyl is exemplified by cyclopropyl, cyclobutyl, cyclopentyl, cyclohexyl, cycloheptyl, cyclooctyl, cyclononyl. The $C_{3-8}$ cycloalkyl is exemplified by cyclopropyl, cyclobutyl, cyclopentyl, cyclohexyl, cycloheptyl, cyclooctyl. The $C_{3-7}$ cycloalkyl is exemplified by cyclopropyl, cyclobutyl, cyclopentyl, cyclohexyl, cycloheptyl. The $C_{3-6}$ cycloalkyl is exemplified by cyclopropyl, cyclobutyl, cyclopentyl, cyclohexyl.

j) Examples of the $C_{3-7}$ cycloalkenyl are cyclopropenyl, cyclobutenyl, cyclopentenyl, cyclohexenyl, and examples of the $C_{5-7}$ cycloalkenyl are cyclopentenyl, cyclohexenyl.

k) The $C_{6-14}$ aryl is exemplified by phenyl, naphthyl, anthryl, phenanthryl, acenaphthyl, anthracenyl. Examples of the $C_{6-10}$ aryl are phenyl and naphthyl. Especially phenyl is most preferable.

l) The $C_{7-20}$ aralkyl and the $C_{7-19}$ aralkyl are exemplified by benzyl, phenethyl, benzhydryl, trithyl. The $C_{7-15}$ aralkyl and the $C_{7-13}$ aralkyl are phenyl-$C_{1-6}$ alkyl such as benzyl, phenethyl; benzhydryl. Examples of the $C_{7-11}$ aralkyl and the $C_{7-10}$ aralkyl are phenyl-$C_{1-5}$ alkyl and phenyl-$C_{1-4}$ alkyl such as benzyl, α-methylbenzyl and phenethyl.

m) The $C_{1-6}$ alkoxy is exemplified by methoxy, ethoxy, propoxy, isopropoxy, n-butoxy, isobutoxy, s-butoxy, t-butoxy, pentyloxy, isopentyloxy, neopentyloxy, hexyloxy, and the $C_{1-4}$ alkoxy is exemplified by methoxy, ethoxy, propoxy, isopropoxy, n-butoxy, isobutoxy, s-butoxy, t-butoxy. The $C_{1-3}$ alkoxy is exemplified by methoxy, ethoxy, propoxy, isopropoxy.

n) The $C_{1-6}$ acyl is exemplified by a $C_{1-6}$ alkanoyl group of the formula: —CO—$R^{36}$, wherein $R^{36}$ is hydrogen or $C_{1-5}$ alkyl (e.g. methyl, ethyl, propyl, isopropyl, n-butyl, isobutyl, s-butyl, t-butyl, pentyl).

The $C_{1-4}$ acyl is exemplified by a $C_{1-4}$ alkanoyl group of the formula: —CO—$R^{37}$, wherein $R^{37}$ is hydrogen, $C_{1-3}$ alkyl such as methyl, ethyl, propyl, isopropyl.

o) The $C_{1-8}$ alkanoyl-is exemplified by formyl, acetyl, propionyl, butyryl, isobutyryl, valeryl, isovaleryl, octanoyl.

Examples of the compound employed in the present invention include 4-oxothieno[2,3-b]pyridine derivatives of the formula (X):

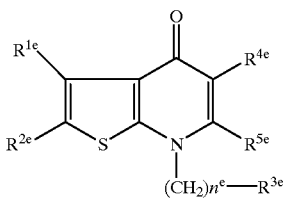

(X)

wherein
$R^{1e}$ and $R^{2e}$ are independently a hydrogen atom, a group bonded through a carbon atom, a nitrogen atom, an oxygen atom or a sulfur atom,
$R^{3e}$ is an optionally substituted homo- or hetero-cyclic group,
$R^{4e}$ is a hydrogen atom, a group bonded through a carbon atom, a nitrogen atom, an oxygen atom or a sulfur atom or an optionally substituted heterocyclic group,
$R^{5e}$ is a hydrogen atom or a group bonded through a carbon atom, n is an integer of 0 to 3;
2,4(1H,3H)-dioxothieno[2,3-d]pyrimidine derivatives of the formula (XX):

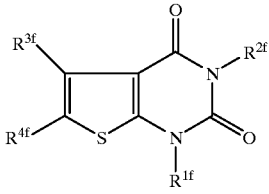

(XX)

wherein $R^{1f}$ is (1) a hydrogen atom, (2) a group bonded through a carbon atom or (3) a group of the formula:

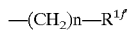

—(CH$_2$)n—$R^{1f}$ wherein
$R^{1f}$ is a group bonded through a carbon atom or an optionally substituted homo- or hetero-cyclic group and n is an integer of 0 to 3,
$R^{2f}$ is a hydrogen atom or a group bonded through a carbon atom, $R^{3f}$ and $R^{4f}$ are independently a group bonded through a carbon atom; or quinoline derivatives of the formula (XXX):

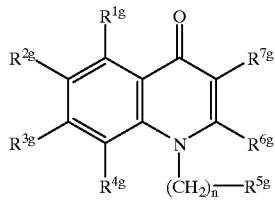

(XXX)

wherein each $R^{1g}$, $R^{2g}$, $R^{3g}$, $R^{4g}$, $R^{6g}$ and $R^{7g}$ are a hydrogen atom or a group bonded through a carbon atom, a nitrogen atom, an oxygen atom or a sulfur atom, $R^{5g}$ is a group bonded through a carbon atom or an optionally substituted homo- or hetero-cyclic group, and n is an integer of 0 to 3, with the proviso that $R^{1g}$, $R^{2g}$, $R^{3g}$, $R^{4g}$, $R^{6g}$ and $R^{7g}$ are not simultaneously a hydrogen atom. The group bonded through a carbon atom, a nitrogen atom, an oxygen atom or a sulfur atom and the optionally substituted homo- or hetero-cyclic group in the formula (X), (XX), or (XXX) have the same meanings as defined above.

In the compound of the formula (X), preferable examples include a compound of the formula (XI):

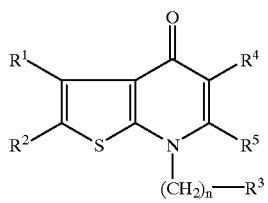

(XI)

wherein
$R^1$ and $R^2$ are each independently hydrogen or a group bonded through a carbon atom, a nitrogen atom, an oxygen atom or a sulfur atom;
$R^3$ is an optionally substituted homo- or hetero-cyclic group;
$R^4$ is (1) hydrogen, (2) formyl, (3) cyano, (4) a lower alkyl group substituted by a group bonded through a sulfur atom, an optionally substituted hydroxyl group, or an optionally substituted hydrocarbon residue, (5) a carbonyl group substituted with an optionally substituted hydrocarbon residue, or (6) an optionally esterified or amidated carboxyl group;
$R^5$ is hydrogen or a group bonded through a carbon atom;
n is an integer of 0 to 3;
$R^1$, $R^2$, $R^3$ and $R^5$ are of the same meanings as $R^{1e}$, $R^{2e}$, $R^{3e}$ and $R^{5e}$ as mentioned above.

Examples of the groups bonded through sulfur atom, shown by $R^4$, include mercapto, each optionally substituted $C_{1-6}$ alkylthio, $C_{1-6}$ alkylsulfinyl, cycloalkylthio, $C_{6-14}$ arylthio, $C_{7-11}$ aralkylthio and heterocyclic thio groups. The $C_{1-6}$ alkyl, $C_{3-7}$ cycloalkyl, $C_{6-14}$ aryl, $C_{7-11}$ aralkyl and heterocyclic groups, in the said optionally substituted $C_{1-6}$ alkylthio, $C_{1-6}$ alkylsulfinyl, $C_{3-7}$ cycloalkylthio, $C_{6-14}$ arylthio, $C_{7-11}$ aralkylthio and heterocyclic thio groups, are of the same meaning as defined above f), i), k) and a).

The substituents, which these groups may have, are of the same meaning as that of the substituents which the above-mentioned optionally substituted groups bonded through a nitrogen atom may have.

As the esterified carboxyl group shown by $R^4$, mention is made of, for example, $C_{1-6}$ alkyloxycarbonyl, $C_{3-7}$-- cycloalkyloxycarbonyl, $C_{6-14}$ aryloxycarbonyl, $C_{7-11}$ aralkyloxycarbonyl and oxycarbonyl substituted by heterocyclic group, and these $C_{1-6}$ alkyl, $C_{3-7}$ cycloalkyl, $C_{6-14}$ aryl, $C_{7-11}$ aralkyl and heterocyclic group are of the same meaning as defined in above f), i), k), and a).

Examples of the amidated carboxyl groups shown by $R^4$ include "a group bonded through a nitrogen atom"—carbonyl group, wherein the group bonded through a nitrogen atom has the same meaning as defined above.

As the lower alkyl in the substituted lower alkyl shown by $R^4$, mentioned is made of, for example, $C_{1-6}$ alkyl such as methyl, ethyl, propyl, i-propyl, butyl, i-butyl, s-butyl, pentyl, hexyl and the like.

The optionally substituted hydrocarbon residue in the lower alkyl group substituted with an optionally substituted hydrocarbon residue of $R^4$ has the same meaning as defined above.

As substituents in the optionally substituted hydroxyl, use is made of, for example, $C_{1-6}$ alkyl (e.g. methyl, ethyl, n-propyl, i-propyl, n-butyl and tert-butyl) optionally having 1 to 4 substituents selected from halogen (e.g. chlorine, bromine and fluorine), $C_{6-10}$ aryl (e.g. phenyl and naphthyl), $C_{7-12}$ aralkyl (e.g. phenyl-$C_{1-6}$ alkyl such as benzyl and phenylethyl) and nitro; $C_{6-10}$ aryl (e.g. phenyl and naphthyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. phenyl-$C_{1-6}$ alkyl such as benzyl, phenethyl) and nitro; $C_{7-12}$ aralkyl (e.g. phenyl-$C_{1-6}$ alkyl such as benzyl, phenylethyl and naphthyl-$C_{1-2}$ alkyl such as naphthylmethyl) optionally having 1 to 4 substituents selected from halogen, (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. phenyl-$C_{1-6}$ alkyl such as benzyl and phenethyl) and nitro; $C_{1-6}$ alkyl-carbonyl (e.g. acetyl and propionyl) optionally having 1 to 3 substituents selected from formyl, halogen (e.g. chlorine, bromine and fluorine), $C_{1-6}$ alkyl (e.g. methyl, ethyl and n-propyl), $C_{6-10}$ aryl (e.g. phenyl and naphthyl), $C_{712}$ aralkyl (e.g. phenyl-$C_{1-6}$ alkyl such as benzyl and phenylethyl) and nitro; $C_{6-10}$ aryloxy-carbonyl (e.g. phenyloxycarbonyl and naphthyloxycarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. phenyl-$C_{1-6}$ alkyl such as benzyl and phenylethyl) and nitro; $C_{6-10}$ aryl-carbonyl (e.g. benzoyl and naphthylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. phenyl-$C_{1-6}$ alkyl such as benzyl and phenylethyl) and nitro; $C_{7-12}$ aralkyl-carbonyl (e.g. benzylcarbonyl and phenethylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. phenyl-$C_{1-6}$ alkyl such as benzyl and phenethyl) and nitro; and pyranyl, furanyl or tri ($C_{1-4}$ alkyl) silyl (e.g. trimethylsilyl and triethylsilyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. phenyl-$C_{1-6}$ alkyl such as benzyl and phenethyl) and nitro. The group bonded through a sulfur atom is as the--same meaning as defined in above $R^{1a}$, $R^{2a}$, $R^{3a}$, $R^{4a}$, $R^{5a}$ or $R^{6a}$.

As the hydrocarbon residue in the carbonyl group substituted by the hydrocarbon residue, shown by $R^4$, mention is made of, for example, saturated or unsaturated hydrocarbon residues having up to 25 carbon atoms. Examples of them include alkyl (e.g. $C_{1-8}$ alkyl such as methyl, ethyl, propyl, isopropyl, butyl, isobutyl, sec-butyl, t-butyl, pentyl, isopentyl, hexyl and heptyl), cycloalkyl (e.g. $C_{3-6}$ cycloalkyl such as cyclopropyl, cyclobutyl, cyclopentyl and cyclohexyl), alkoxyalkyl (e.g. $C_{1-3}$ alkoxy-$C_{1-6}$ alkyl such as methoxymethyl, ethoxymethyl, ethoxybutyl and propoxyhexyl), alkenyl (e.g. $C_{2-6}$ alkenyl such as vinyl, butenyl, butadienyl and hexatrienyl), aryl (e.g. $C_{6-14}$ aryl such as phenyl, naphthyl and anthracenyl) and aralkyl (e.g. $C_{7-20}$ aralkyl such as phenyl-$C_{1-6}$ alkyl such as benzyl; benzhydryl and trityl). As the substituents, mention is made of the same substituents on the above group bonded through a carbon atom.

Either one of $R^1$ and $R^2$ (desirably $R^1$) is preferably (1) a group of the formula:

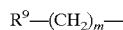

$$R^9-(CH_2)_m-$$

wherein $R^9$ is halogen, hydroxy, cyano, an optionally substituted heterocyclic group or a group bonded through a nitrogen atom which may optionally be substituted, and m is an integer of 0 to 3, or (2) an optionally substituted $C_{6-14}$ aryl group, and the other one (desirably $R^2$) being a group represented by the general formula:

$$R^{10}-A-$$

wherein $R^{10}$ is an optionally substituted $C_{6-14}$ aryl group, an optionally substituted $C_{1-6}$ alkyl group, $C_{6-14}$ aryl-carbonyl group, $C_{7-11}$ aralkyl-carbonyl group or halogen and A is spacer group. The halogen shown by $R^4$ is of the same meaning as above-mentioned e). The optionally substituted heterocyclic group is of the same meaning as above-mentioned a).

The optionally substituted group bonded through nitrogen atom, shown by the above-mentioned $R^9$, is of the same meaning as described above. The optionally substituted group bonded through a nitrogen atom is preferably a mono- or di-substituted amino group. The substituent of the amino group includes (1) $C_{7-11}$ aralkyl which may optionally be substituted by 1 to 3 substituents selected from (i) sulfamoyl, (ii) $C_{1-6}$ alkoxy, (iii) $C_{1-6}$ alkylthio, (iv) halogen, (v) nitro, (vi) $C_{6-14}$ aryl which may optionally be substituted by 1 to 3 cyanos, (vii) $C_{1-6}$ alkyl which may optionally be substituted by 1 to 3 halogens, (viii) hydroxy, and (ix) $C_{1-6}$ alkoxy-carbonyl, (2) $C_{6-14}$ aryl, (3) $C_{1-6}$ alkyl which may optionally be substituted by 1 to 3 substituents selected from (i) heterocyclic group which may optionally be substituted by 1 to 3 $C_{1-6}$ alkyls, (ii) amino, (iii) hydroxy, (iv) oxo, (V) $C_{1-6}$ alkoxy, (vi) carbamoyl which may optionally be substituted by 1 to 2 substituents selected from $C_{1-6}$ alkyl and $C_{6-14}$ aryl, and (vii) nitro, (4) $C_{1-6}$ alkyl-carbonyl, (5) $C_{2-10}$ alkenyl which may optionally be substituted by $C_{6-14}$ aryl, or (6) heterocyclic group. The optionally substituted group bonded through a nitrogen atom is especially preferably a group of the formula: $-NR^{39}R^{40}$ wherein $R^{39}$ is a $C_{1-6}$ alkyl group and $R^{40}$ is a $C_{7-11}$ aralkyl group.

In $R^{10}$ the $C_{6-14}$ aryl group in the optionally substituted $C_{6-14}$ aryl group or $C_{6-14}$ aryl-carbonyl group is of the same meaning as defined in above k), and the $C_{1-6}$ alkyl group in the optionally substituted $C_{1-6}$ alkyl group is of the same meaning as defined in above f). The $C_{7-11}$ aralkyl group in the $C_{7-11}$ aralkyl-carbonyl group is of the same meaning as defined in above 1), and the halogen is of the same meaning as defined in above e).

Examples of the substituents in optionally substituted $C_{6-14}$ aryl group shown by the above-mentioned $R^{10}$ include (1) halogen, (2) $C_{1-6}$ alkoxy which may optionally be substituted by 1 to 3 substituents selected from halogen, $C_{1-6}$ alkyl-carbonyl, $C_{2-10}$ alkenyl and $C_{3-7}$ cycloalkyl, (3) $C_{1-6}$ alkoxy-carbonyl, (4) nitro, (5) $C_{1-6}$ alkoxy-$C_{1-6}$ alkoxy, (6) mono- or di-$C_{1-6}$ alkyl-carbonyl, (7) amino which may optionally be substituted by 1 to 2 substituents selected from (i) $C_{2-10}$ alkenyl which may optionally be substituted by 1 to 3 $C_{1-6}$ alkyl-carbonyl groups, (ii) $C_{3-7}$ cycloalkyl which may optionally be substituted by 1 to 3 hydroxy groups, (iii) $C_{1-6}$ alkyl which may optionally be substituted by 1 to 3 substitituents selected from oxo, hydroxy, and $C_{1-6}$ alkyl-carbonyl, (iv) $C_{1-6}$ alkyl-carbonyl which may optionally be substituted by 1 to 3 substituents selected from halogen and $C_{1-6}$ alkoxy, (v) formyl, (vi) carbamoyl which may optionally be substituted by 1 to 2 substituents selected from (a) $C_{1-6}$ alkyl, (b) $C_{1-6}$ alkylthio, (c) $C_{6-14}$ aryl and (d) $C_{1-6}$ alkoxy which may optionally be substituted by 1 to 3 halogens, (vii) $C_{6-14}$ aryl-carbonyl, (viii) $C_{1-6}$ alkyl-sulfinyl, (ix) $C_{1-6}$ alkoxy-carbonyl, (x) heterocyclic group-carbonyl and (xi) $C_{1-6}$ alkoxy, (8) hydroxy, (9) $C_{1-6}$ alkoxy-carbonyl which may optionally be substituted by 1 to 3 nitro groups, (10) $C_{7-11}$ aralkyl, (11) $C_{2-10}$ alkenyl which may optionally be substituted by 1 to 3 substituents selected from $C_{6-14}$ aryl, hydroxy, $C_{1-6}$ alkoxy, and $C_{1-6}$ alkyl, (12) cyclic amino, (13) $C_{2-10}$ alkenyloxy which may optionally be substituted by $C_{1-6}$ alkyl or (14) $C_{1-6}$ alkyl which may optionally be substituted by 1 to 3 $C_{2-10}$ alkenyl groups. The number of substituents ranges from 1 to 5, preferably 1 to 3.

As the spacer group shown by the symbol "A", mention is made of those as defined above, e.g. a chemical bond or methylene.

$R^3$ is preferably a group of the formula:

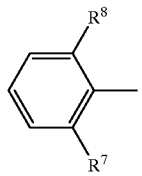

wherein $R^7$ is hydrogen, halogen or a group bonded through a carbon, nitrogen, oxygen or sulfur atom, and $R^8$ is hydrogen, halogen, nitro, cyano or an optionally substituted aliphatic hydrocarbon residue which may optionally be substituted with a group bonded through a carbon, oxygen,. nitrogen or sulfur atom.

The above-mentioned optionally substituted groups bonded through a carbon, nitrogen, oxygen or sulfur atom, shown by $R^7$ are of the same meaning as defined above.

Examples of the optionally substituted aliphatic hydrocarbon residue, in the aliphatic hydrocarbon residue which may optionally be substituted by a group bonded through an oxygen, nitrogen or sulfur atom shown by the above-mentioned $R^8$, include $C_{1-15}$ alkyl (e.g. methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl and pentadecyl), $C_{3-8}$ cycloalkyl (e.g. cyclopropyl, cyclobutyl, cyclopentyl and cyclohexyl), $C_{2-10}$ alkenyl (e.g. vinyl, allyl, 2-methylallyl, 2-butenyl, 3-butenyl and 3-octenyl), $C_{2-10}$ alkynyl (e.g. ethynyl, 2-propynyl and 3-hexynyl) and $C_{1-6}$ alkoxy (e.g. methoxy, ethoxy, propoxy and butoxy). Examples of the substituents, which the said hydrocarbon group may have, include nitro, hydroxyl, oxo, thioxo, cyano, carbamoyl, carboxyl, $C_{1-4}$ alkoxy-carbonyl (e.g. methoxycarbonyl and ethoxycarbonyl), sulfo, halogen (fluorine, chlorine, bromine and iodine), $C_{1-4}$ alkoxy (e.g. methoxy, ethoxy, propoxy, isopropoxy, butoxy, isobutoxy, s-butoxy and t-butoxy), $C_{1-4}$ alkylthio (e.g. methylthio, ethylthio, n-propylthio, isopropylthio, n-butylthio and t-butylthio), amino, $C_{1-6}$ alkanoylamino (e.g. acetylamino and propionylamino), mono- or di-$C_{1-4}$ alkylamino (e.g. methylamino, ethylamino, n-propylamino, isopropylamino, n-butylamino, dimethylamino and diethylamino), $C_{1-4}$ alkanoyl (e.g. formyl, acetyl and propionyl), 5- or 6-membered heterocyclic groups containing, besides carbon atom, 1 to 4 hetero-atoms selected from oxygen, sulfur and nitrogen, as exemplified by 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl, which may optionally have 1 to 4 substituents selected from (a) halogen (e.g. fluorine, chlorine, bromine and iodine) and (b) $C_{1-4}$ alkyl (e.g. methyl, ethyl, propyl and isopropyl), and $C_{1-6}$ haloalkyl (e.g. difluoromethyl, trifluoromethyl, trifluoroethyl and trichloroethyl). Number of the substituents ranges from 1 to 4, preferably 1 to 3.

$R^7$ or $R^8$ is preferably (1) $C_{1-6}$ alkoxy, (2) $C_{1-6}$ alkyl which may optionally be substituted by 1 to 3 halogens, (3) $C_{1-6}$ alkyl-carbonyloxy, (4) $C_{1-6}$ alkylthio, (5) $C_{6-14}$ aryl which may optionally be substituted by 1 to 3 cyano and $C_{1-6}$ alkoxy-carbonyl, (6) halogen, or (7) $C_{7-11}$ aralkyl which may optionally be substituted by 1 to 3 halogens.

$R^4$ is preferably halogen, cyano, an optionally substituted hydrocarbon group, an optionally substituted hydrocarbon-oxy group, carbonyl group which is substituted by an optionally substituted hydrocarbon group, sulfonyl which is substituted by an optionally substituted hydrocarbon group, sulfonyl-oxy group which is substituted by an optionally substituted hydrocarbon group, a mono- or di-substituted amino group, a mono- or di-substituted amino-carbonyl group or a heterocyclic group.

The hydrocarbon group or the hydrocarbon group of the hydrocarbon-oxy group and the substituent thereof has the same meaning as defined in above $R^{1a}$, $R^{2a}$, $R^{3a}$, $R^{4a}$, $R^{5a}$, $R^{6a}$ or $R^{4b}$. The heterocyclic group has the same meaning as defined in above a). As the substituent of the amino group, mention is made of the same ones as defined for the substituent of the group bonded through a nitrogen atom for $R^{1a}$, $R^{2a}$, $R^{3a}$, $R^{4a}$, $R^{5a}$ or $R^{6a}$.

$R^4$ is more preferably (1) $C_{1-6}$ alkyl which may optionally be substituted by 1 to 3 substituents selected from (i) hydroxy, (ii) $C_{1-6}$ alkyl-carbonyloxy, (iii) $C_{1-6}$ alkylthio, (iv) $C_{6-14}$ aryl which may optionally be substituted by 1 to 3 halogens, (V) $C_{3-7}$ cycloalkyl, (vi) $C_{1-6}$ alkyl-carbonyl, (vii) $C_{1-6}$ alkylsulfinyl, and (viii) $C_{6-14}$ aryl-carbonyloxy, (2) $C_{1-6}$ alkoxy-carbonyl, (3) $C_{6-14}$ aryl-carbonyl which may optionally be substituted by 1 to 3 halogens, "amino which has 1 to 2 $C_{1-6}$ alkyl", $C_{1-6}$ alkoxy, $C_{1-6}$ alkylthio, $C_{1-6}$ alkyl or $C_{6-14}$ aryloxy, (4) $C_{1-6}$ alkyl-carbonyl, (5) formyl, (6) heterocyclic group-carbonyl, (7) amino-carbonyl which may optionally be substituted by 1 to 2 substituents selected from (i) $C_{7-11}$ aralkyl-heterocyclic group, (ii) heterocyclic group, (iii) $C_{1-6}$ alkyl which may optionally be substituted by 1 to 3 amino groups which may optionally have 1 or 2 $C_{1-6}$ alkyl, and (iv) heterocyclic group- $C_{1-6}$ alkyl, (8) $C_{1-6}$ alkoxy which may optionally be substituted by $C_{1-6}$ alkoxy-carbonyl or amino-carbonyl, (9) cyano, (10) $C_{3-7}$ cycloalkyl-carbonyl, (11) heterocyclic group, (12)

amino which may optionally be substituted by 1 or 2 $C_{1-6}$ alkyl-carbonyl groups, (13) $C_{1-6}$ alkyl-carbonyloxy, (14) hydroxy, (15) $C_{1-6}$ alkylsulfonyloxy, (16) $C_{1-6}$ alkylthio, (17) $C_{1-6}$ alkylsulfinyl or (18) $C_{1-6}$ alkylsulfonyl.

$R^5$ is preferably a hydrogen atom or a $C_{1-6}$ alkyl group.

The compound (XI) is preferably a compound represented by the formula:

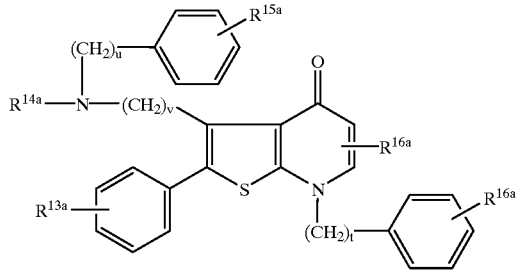

wherein $R^{13a}$ stands for 1 to 5 substituents and independently stand for a hydrogen atom, a $C_{1-6}$ alkyl group, a $C_{1-6}$ alkoxy group, a halogen atom or a $C_{1-8}$ alkanoylamino group; R stands for a hydrogen atom or a $C_{1-6}$ alkyl group; $R^{15a}$ stands for 1 to 5 substituents and independently stand for a hydrogen atom, a halogen atom, a $C_{1-6}$ alkyl group, a $C_{1-6}$ alkoxy group or a $C_{1-6}$ alkylthio group; $R^{16a}$ stands for 1 to 5 substituents and independently stand for a hydrogen atom, a $C_{1-6}$ alkyl group, a halogen atom or a $C_{1-6}$ alkoxy group; $R^{17a}$ stands for one or two substituents and independently stands for an optionally esterified or amidated carboxyl group, a $C_{1-6}$ alkylcarbonyl group, a $C_{6-14}$ arylcarbonyl group or an optionally substituted $C_{1-6}$ alkyl group; and each v, t and u denote an integer of 0 to 3.

The preferable substituent of $C_{1-6}$ alkyl group for $R^{17a}$ includes (i) hydroxy, (ii) $C_{1-6}$ alkyl-carbonyloxy, (iii) $C_{1-6}$ alkylthio, (iv) $C_{6-14}$ aryl which may optionally be substituted by 1 to 3 halogens, (V) $C_{3-7}$ cycloalkyl, (vi) $C_{1-6}$ alkyl-carbonyl, (vii) $C_{1-6}$ alkylsulfinyl or (viii) $C_{6-14}$ arylcarbonyloxy. Number of substituent is preferably 1 to 3.

The above-mentioned $C_{1-6}$ alkyl group or $C_{1-6}$ alkyl group of $C_{1-6}$ alkylthio group, $C_{1-6}$ alkyl-carbonyl group or $C_{1-6}$ alkyl-carbonyloxy group has the same meaning as defined in above f). The above-mentioned $C_{1-6}$ alkoxy group has the same meaning as defined in above m). The above-mentioned halogen has the same meaning as defined in above e). The $C_{1-8}$ alkanoyl group in the $C_{1-6}$ alkanoylamino group has the same meaning as defined in above o). The $C_{6-14}$ aryl group has the same meaning as defined in above k). The optionally esterified or amidated carboxyl group has the same meaning as that defined for above-mentioned $R^{1a}$, $R^{2a}$, $R^{3a}$, $R^{4a}$, $R^{5a}$, $R^{6a}$ or $R^{4b}$. Also the compound (XI) is preferably a compound represented by the formula:

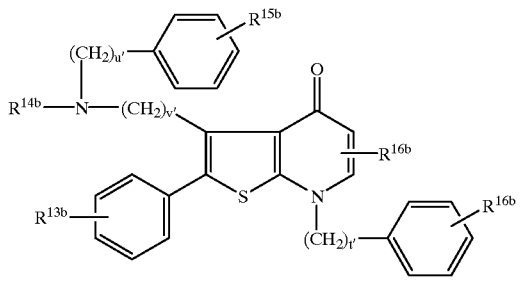

wherein $R^{13b}$ stands for 1 to 3 substituents and independently stand for hydrogen atom, a $C_{1-6}$ alkoxy group or $C_{1-8}$ alkanoylamino group, $R^{14b}$ stands for hydrogen atom or a $C_{1-6}$ alkyl group, $R^{15b}$ stands for 1 to 3 substituents and independently stand for a hydrogen atom or a halogen atom, $R^{16b}$ stands for 1 to 3 substituents and independently stand for a hydrogen atom, a halogen atom or a $C_{1-6}$ alkoxy group, $R^{17b}$ stands for 1 to 2 substituents and independently stand for a carboxyl group which may optionally be esterified or amidated or a $C_{1-6}$ alkylcarbonyl group, and each v', t' and u' denote an integer of 0 to 3. The above-mentioned $C_{1-6}$ alkoxy group, the $C_{1-8}$ alkanoyl group in the $C_{1-8}$ alkanoylamino group, $C_{1-6}$ alkyl group or the $C_{1-6}$ alkyl group in the $C_{1-6}$ alkylcarbonyl group or halogen has the same meaning as defined in above m), o), f), or e) respectively. The optionally esterified or amidated carboxyl group has the same meaning as that defined for above-mentioned $R^{1a}$, $R^{2a}$, $R^{3a}$, $R^{4a}$, $R^{5a}$, $R^{6a}$ or $R^{4b}$. $R^{17a}$ or $R^{17b}$ is preferably bonded at 5-position of the thieno[2,3-b]pyridine skeleton.

Especially preferable examples of the compound (XI) include 4,7-dihydro-3-(N-methyl-N-benzylaminomethyl)-7-(2-methoxybenzyl)-2-(4-methoxyphenyl)-4-oxo-thieno[2,3-b]pyridine-5-carboxylic acid ethyl ester or its salt, 2-(4-acetylaminophenyl)-4,7-dihydro-3-(N-methyl-N-benzylaminomethyl)-7-(2-methoxybenzyl)-4-oxo-thieno[2,3-b]pyridine-5-carboxylic acid ethyl ester or its salt, 5-n-butyryl-4,7-dihydro-3-(N-methyl-N-benzylamino-methyl)-7-(2-fluorobenzyl)-2-(4-methoxyphenyl)-4-oxo-thieno[2,3-b]pyridine or its salt, 5-benzoyl-4,7-dihydro-3-(N-methyl-N-benzylaminomethyl)-7-(2-fluorobenzyl)-2-(4-methoxyphenyl)-4-oxo-thieno-[2,3-b]pyridine or its salt, 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine or its salt. 7-(2,6-difluorobenzyl)-4,7-dihydro-3-(N-methyl-N-benzylaminomethyl)-5-isobutyryl-2-(4-propionylamino-phenyl)-4-oxo-thieno[2,3-b]pyridine or its salt, and 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine or its salt.

In the compound of the formula (X), a preferable examples include also a compound of the formula (XII):

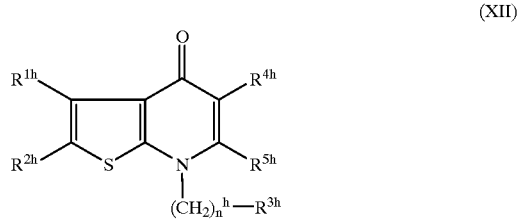

(XII)

wherein each of $R^{1h}$ and $R^{2h}$ are hydrogen or a group bonded through a carbon atom, a nitrogen atom, an oxygen atom or a sulfur atom, $R^{3h}$ is an optionally substituted homo- or hetero-cyclic group, $R^{4h}$ is an optionally substituted heterocyclic group or a group bonded through a hetero atom, $R^{5h}$ s hydrogen or a group bonded through a carbon atom, n is an integer of 0 to 3.

$R^{1h}$, $R^{2h}$, $R^{3h}$ and $R^{5h}$ are of the same meanings as each of $R^{1e}$, $R^{2e}$, $R^{3e}$ and $R^{5e}$.

The optionally substituted heterocyclic group of $R^{4h}$ is of the same meanings as in $R^{4e}$.

Examples of the group bonded through a hetero atom of $R^{4h}$ includes a group bonded through a nitrogen atom, a group bonded through an oxygen atom and a group bonded through a sulfur atom. Those groups are the same as those defined in $R^{4e}$.

In the compound (XII), preferred examples of $R^{1h}$ are a group bonded through a carbon atom or a group bonded through a nitrogen atom. As the group bonded through a carbon atom, mention is made of an optionally substituted $C_{1-20}$ hydrocarbon residue. Among them an optionally substituted $C_{1-10}$ alkyl group is preferable. Further an optionally substituted $C_{1-6}$ alkyl group is especially preferable. The $C_{1-6}$ alkyl has the same meaning as defined in above f). As substituents in the optionally substituted $C_{1-20}$ hydrocarbon residue of $R^{1h}$, mention is made of (1) halogen, (2) nitro, (3) cyano, (4) an optionally substituted amino, (5) an optionally substituted hydroxyl group, (6) a group of the formula: —S(O)$t^h$—$R^{6h}$, wherein $t^h$ denotes an integer of 0 to 2, and $R^{6h}$ is a hydrogen atom or an optionally substituted hydrocarbon residue.

A more preferable example of $R^{1h}$ is substituted aminoalkyl such as N,N-disubstituted amino-$C_{1-6}$ alkyl. The most preferable example of $R^{1h}$ is N-aralkyl-N-alkylaminoalkyl, especially N—$C_{7-11}$ aralkyl-N—$C_{1-6}$ alkylamino-$C_{1-6}$ alkyl.

As the preferable example of $R^{2h}$, mention is made of a group bonded through a carbon atom, especially an optionally substituted $C_{1-20}$ hydrocarbon residue, more especially an optionally substituted $C_{6-14}$ aryl group. The $C_{6-14}$ aryl group has the same meaning as defined in above k). As the preferable examples of the substituents for the optionally substituted $C_{1-20}$ hydrocarbon group of $R^2h$, mention is made of (1) an optionally substituted amino, (2) an optionally substituted hydroxyl group, (3) an optionally substituted carbamoyl group, (4) an optionally substituted carboxyl group, (5) an optionally substituted $C_{2-10}$ alkenyl group, (6) $C_{1-6}$ acyl group or (7) nitro. The $C_{2-10}$ alkenyl group and $C_{1-6}$ acyl group have the same meaning as defined in above g) and n) respectively.

The preferable substituents in the optionally substituted $C_{6-14}$ aryl, include (1) a $C_{1-6}$ alkoxy group, (2) a $C_{1-6}$ alkylcarbonyl group, (3) a $C_{1-6}$ alkylaminocarbonyl group, (4) an optionally substituted $C_{2-1}$O alkenyl, whose preferable substituent includes $C_{1-6}$ alkylcarbonyl or $C_{1-6}$ alkylaminocarbonyl, or (5) an optionally substituted amino, whose preferable substituent includes a $C_{1-6}$ alkyl group, a $C_{1-8}$ alkanoyl group, $C_{1-6}$ alkyl group which is substituted by hydroxy. Especially, a $C_{1-8}$ alkanoylamino group or a $C_{1-6}$ alkoxy group is more preferable.

As the preferable group of $R^{2h}$, mention is made of a $C_{6-14}$ aryl group which may optionally be substituted with a group selected from the group consisting of (i) nitro, (ii) $C_{1-6}$ alkoxy and (iii) amino which may optionally be substituted with $C_{1-8}$ alkanoyl.

The above-mentioned $C_{1-6}$ alkoxy has the same meaning as defined in above m). The $C_{1-6}$ alkyl or the $C_{1-6}$ alkyl of the $C_{1-6}$ alkylcarbonyl or $C_{1-6}$ alkylaminocarbonyl has the same meaning as defined in above f). The $C_{2-10}$ alkenyl, $C_{1-8}$ alkanoyl and $C_{1-8}$ alkanoyl of $C_{1-8}$ alkanoylamino have the same meanings as defined in above g) and o) respectively.

As the preferable example of $R^{3h}$, mention is made of an optionally substituted homo-cyclic group. The optionally substituted homo-cyclic group is the same as that defined in W ring. More preferably, an optionally substituted $C_{6-14}$ aryl group are mentioned. The $C_{6-14}$ aryl group has the same meaning as defined in above k).

The substituents in the optionally substituted homo-cyclic group, mention is made of (1) halogen, (2) nitro, (3) an optionally substituted hydroxyl group, (4) a group of the formula: —S(O)$t^h$—$R^{6h}$, wherein $t^h$ denotes an integer of 0 to 2, and $R^{6h}$ is a hydrogen atom or an optionally substituted $C_{1-20}$ hydrocarbon residue.

As more preferable group of $R^{3h}$, mention is made of an $C_{6-14}$ aryl group substituted by one or two halogens. As the aryl group, phenyl is most preferable. The most preferable group of $R^{3h}$ is a phenyl group substituted by fluorine.

As the preferable example of $R^{4h}$, mention is made of an optionally substituted heterocyclic group, optionally substituted amino group, optionally substituted hydroxyl group and optionally substituted mercapto group.

As the preferable example of the heterocyclic group in the optionally substituted heterocyclic group of $R^{4h}$, mention is made of an optionally substituted 3- to 8-membered heterocyclic group, especially an optionally substituted 5- to 8-membered heterocyclic group having at least one nitrogen atom in a ring, and more preferably 5- to 6-membered heterocyclic group having at least one nitrogen atom in a ring. The heterocyclic group has the same meaning as defined in above a). As the preferred examples of the heterocyclic group, mention is made of oxazolyl, isoxazolyl, thiazolyl, imidazolyl, triazolyl, oxoimidazolyl, thiazinyl. Among others, isoxazoly is most preferred.

Preferred examples of the substituent to the heterocyclic group are (1) halogen, (2) nitro, (3) an optionally substituted hydroxyl group, (4) a group of the formula: —S(O)$m^h$—$R^{6h}$, wherein $m^h$ denotes an integer of 0 to 2, and $R^{6h}$ is a hydrogen atom or an optionally substituted $C_{1-20}$ hydrocarbon residue, (5) an optionally substituted amino, or (6) a $C_{1-10}$ hydrocarbon residue.

Preferred examples of the substituents on the optionally substituted amino group, the optionally substituted hydroxyl group or the optionally substituted mercapto group of $R^{4h}$ are (1) $C_{1-10}$ hydrocarbon residue which may optionally be substituted by $C_{1-6}$ alkoxy-carbonyl or carbamoyl, (2) $C_{1-6}$ acyl group, or (3) a group of the formula: —S(O)$t^h$—$R^{6h'}$, wherein $t^h$ denotes an integer of 0 to 2, and $R^{6h}$ is a hydrogen atom or an optionally substituted $C_{1-20}$ hydrocarbon residue. The $C_{1-6}$ alkoxy of the $C_{1-6}$ alkoxycarbonyl group and the $C_{1-6}$ acyl has the same meaning as defined in above m) and n).

Preferably $R^{4h}$ is (1) a 5- or 6-membered heterocyclic group which has one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxycarbonyl or carbamoyl, (ii) $C_{1-8}$ alkanoyl and (iii) $C_{1-6}$ alkylsulfonyl, (3) a group of the formula: —S(O)$t^h$—$R^{6h'}$, wherein $t^h$ is an integer of 0 to 2 and $R^{6h'}$ is $C_{1-6}$ alkyl, or (4) an amino group which may optionally be substituted with $C_{1-8}$ alkanoyl. The 5- or 6-membered heterocyclic group bonded through a carbon atom is the same as that defined in above $R^{1a}$, $R^{2a}$, $R^{3a}$, $R^{4a}$, $R^{5a}$, $R^{6a}$ or $R^{4b}$. Also, the $C_{1-6}$ alkoxy of $C_{1-6}$ alkoxy-carbonyl, $C_{1-6}$ alkyl or $C_{1-6}$ alkyl of $C_{1-6}$ alkylsulfonyl, or $C_{1-8}$ alkanoyl has the same meaning as defined in above m), f), or O).

As the group $R^{5h}$, a hydrogen atom or an optionally substituted hydrocarbon residue is preferable, especially, a hydrogen atom or $C_{1-20}$ hydrocarbon atom is more preferable. Among others, hydrogen atom or $C_{1-6}$ alkyl is more preferable. Hydrogen atom is most preferable. The $C_{1-6}$ alkyl has the same meaning as defined in above f).

More preferable examples of the compound (XII) include a compound of the formula (XII), wherein $R^{1h}$ is an $C_{1-6}$ alkyl group which may optionally be substituted with halogen or $N$—$C_{7-13}$ aralkyl-$N$—$C_{1-6}$ alkylamino, $R^{2h}$ is a $C_{6-14}$ aryl group which may optionally be substituted with a group selected from the group consisting of (i) nitro, (ii) $C_{1-6}$ alkoxy and (iii) amino which may optionally be substituted with $C_{1-8}$ alkanoyl, $R^{3h}$ is a mono- or di-halogeno-$C_{6-14}$ aryl group, $R^{4h}$ is (1) a 5- or 6- membered heterocyclic group which has at least one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxy-carbonyl or carbamoyl, (ii) $C_{1-8}$ alkanoyl and (iii) $C_{1-6}$ alkylsulfonyl, (3) a group of the formula: —S(O)$t^h$—$R^{6h'}$, wherein $t^h$ is an integer of 0 to 2 and $R^{6h'}$ is $C_{1-6}$ alkyl, or (4) an amino group which may optionally be substituted with $C_{1-8}$ alkanoyl, $R^{5h}$ is a hydrogen atom. The halogen; $C_{7-13}$ aralkyl of $N$—$C_{7-13}$ aralkyl-$N$—$C_{1-6}$ alkylamino; $C_{1-6}$ alkyl or $C_{1-6}$ alkyl of $N$—$C_{7-13}$ aralkyl-$N$—$C_{1-6}$ alkylamino or $C_{1-6}$ alkylsulfonyl; $C_{1-6}$ alkoxy or $C_{1-6}$ alkoxy of $C_{1-6}$ alkoxycarbonyl; $C_{1-8}$ alkanoyl; $C_{6-14}$ aryl or $C_{6-14}$ aryl of mono- or di-halogeno $C_{6-14}$ aryl has the same meaning as defined in above e), 1), f), m), o) or k) respectively.

Moreover, 5- or 6-membered heterocyclic group bonded through a carbon atom is the same as that defined in above $R^{1a}$, $R^{2a}$, $R^{3a}$, $R^{4a}$, $R^{5a}$, $R^{6a}$ or $R^{4b}$.

In the formula (XII), $n^h$ is preferably 1.

In the compound of the formula (X), preferable examples include a compound of the formula (XIII):

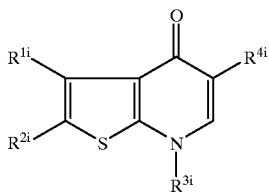

(XIII)

wherein $R^{1i}$ stands for a group represented by the formula:

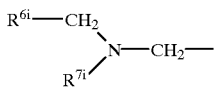

wherein $R^{6i}$ stands for (1) phenyl group which may optionally be substituted with 1 to 3 substituents selected from fluorine, bromine, sulfamoyl, methylthio and nitro, (2) 2- or 3-pyridyl group, (3) 3-indolyl group optionally substituted with methyl, (4) propyl group or (5) butylcarbamoyl group, and $R^{7i}$ stands for methyl group; or hexamethylenetetraaminomethyl group, $R^{2i}$ stands for phenyl group substituted with methoxycarbonylvinyl, ethoxycarbonylvinyl, carboxyvinyl, benzoylvinyl, acetylvinyl, propionylvinyl, isobutyrylamino, propionylamino, 3-oxobutylamino, 3-oxopentylamino, 2-hydroxycyclohexylamino, trifluoroacetylamino, 2-hydroxypropylamino, 2-hydroxybutylamino, 2-hydroxyisobutylamino, N-ethyl-N-trifluoroacetylamino, methylamino, ethylamino, propylamino, butylamino, isobutylamino, diethylamino, 1-pyrrolidinylamino, ethanesulfonamide or acetonyloxy, $R^{3i}$ stands for 2-fluorobenzyl group or 2,6-difluorobenzyl group, and $R^{4i}$ stands for (1) acyl group or (2) a $C_{1-6}$ alkyl group which may optionally be substituted with 1 to 3 substituents selected from hydroxy and alkylcarbonyloxy, or salts thereof.

Preferable examples of the group shown by $R^{1i}$ in the compound (XIII) of this invention include N-methyl-N-benzylaminomethyl.

The number of substituents in $R^{2i}$ and $R^{4i}$ in the compound (XIII) of this invention ranges from 1 to 6, preferably 1 to 3, more preferably 1 to 2.

Preferable examples of the group shown by $R^{2i}$ in the compound (XIII) of this invention include phenyl group substituted with groups represented by the formula $R^{10i}$—$R^{9i}$—, wherein $R^{9i}$ stands for vinylene group and $R^{10i}$ stands for $C_{1-6}$ alkoxy-carbonyl such as methoxycarbonyl, ethoxycarbonyl; carboxyl; benzoyl; $C_{1-8}$ alkanoyl such as acetyl or propionyl; groups represented by the formula $R^{11i}$—NH—, wherein $R^{11i}$ stands for 3-oxobutyl, 3-oxopentyl or 2-hydroxycyclohexyl; or groups represented by the formula $R^{12i}$—O—, wherein $R^{12i}$ stands for acetonyl.

Preferable examples of acyl shown by $R^{4i}$ in the compound (XIII) of this invention include groups represented by the formula —CO—$R^{8i}$, wherein —$R^{8i}$ stands for an optionally substituted hydrocarbon residue or an optionally substituted heterocyclic group.

Examples of the hydrocarbon residue are those as defined in the above $R^{1a}$, $R^{2a}$, $R^{3a}$, $R^{4a}$, $R^{5a}$ or $R^{6a}$.

Examples of substituents of the hydrocarbon residue include nitro, hydroxy, oxo, thioxo, cyano, sulfo, carbamoyl, carboxyl, halogen (e.g. fluorine, chlorine, bromine, iodine), $C_{1-6}$ alkoxy (e.g. methoxy, ethoxy, propoxy, isopropoxy and butoxy), $C_{1-3}$ alkoxy-$C_{1-6}$ alkoxy, amino, mono- or di-$C_{1-6}$ alkylamino (e.g. methylamino, ethylamino, propylamino, dimethylamino and diethylamino), $C_{1-6}$ alkyl-carbonyl, $C_{1-6}$ alkyl-carbonyloxy (e.g. acetoxy and ethylcarbonyloxy), $C_{1-6}$ alkyl-thio, $C_{1-6}$ alkyl-sulfonyl, $C_{1-6}$ alkyl-sulfinyl, benzoyl, phenoxy, $C_{1-6}$ alkylenedioxy and heterocyclic groups. The number of substituents ranges from 1 to 6, preferably 1 to 3, more preferably 1 to 2.

Examples of the heterocyclic groups are those as defined in the above a).

Examples of substituents of the heterocyclic groups include $C_{1-6}$ alkyl (e.g. methyl, ethyl, propyl, isopropyl, butyl, isobutyl, sec-butyl and tert-butyl), $C_{2-6}$ alkenyl (e.g. vinyl, 1-methylvinyl, 1-propenyl and allyl), $C_{2-6}$ alkynyl (e.g. ethynyl, 1-propynyl and propargyl), $C_{3-6}$ cycloalkyl (e.g. cyclopropyl, cyclobutyl, cyclopentyl and cyclohexyl), $C_{5-7}$ cycloalkenyl (e.g. cyclopentenyl and cyclohexenyl), $C_{7-11}$ aralkyl (e.g. phenyl-$C_{1-5}$ alkyl such as benzyl, α-methylbenzyl and phenethyl), $C_{6-14}$ aryl (e.g. phenyl and naphthyl), $C_{1-6}$ alkoxy (e.g. methoxy, ethoxy, propoxy, iso-propoxy, n-butoxy, isobutoxy, sec-butoxy and tert-butoxy), $C_{6-14}$ aryloxy (e.g. phenoxy), $C_{1-6}$ alkanoyl (e.g. formyl, acetyl, propionyl, n-butyryl and iso-butyryl), $C_{6-14}$ aryl-carbonyl (e.g. benzoyl), $C_{1-6}$ alkanoyloxy (e.g. formyloxy, acetyloxy, propionyloxy, n-butyryloxy and iso-butyryloxy), carboxyl, $C_{1-6}$ alkoxy-carbonyl (e.g. methoxycarbonyl, ethoxycarbonyl, n-propoxycarbonyl, isopropoxycarbonyl, n-butoxycarbonyl, isobutoxycarbonyl and tert-butoxycarbonyl), carbamoyl group, halogen (fluorine, chlorine, bromine, iodine), oxo, amino, mono- or di-$C_{1-4}$ alkylamino (e.g. methylamino, ethylamino, propylamino, isopropylamino, butylamino, dimethylamino, diethylamino, dipropylamino, diisopropylamino and dibutylamino), $C_{1-6}$ alkanoylamino (e.g. formamido, acetamido, trifluoroacetamido, propionylamido, butyrylamido and isobutyrylamido), carbamoylamino, N—$C_{1-4}$ alkyl carbamoylamino (e.g. N-methylcarbamoylamino, N-ethylcarbamoylamino, N-propylcarbamoylamino, N-isopropylcarbamoylamino and N-butylcarbamoylamino), nitro, cyano, mercapto, sulfo, sulfino, phosphono, sulfamoyl, $C_{1-6}$ alkylsulfamoyl (e.g. N-methylsulfamoyl, N-ethylsulfamoyl, N-propylsulfamoyl, N-isopropylsulfamoyl and N-butylsulfamoyl), di-$C_{1-6}$ alkylsulfamoyl (e.g. N,N-dimethylsulfamoyl, N,N-diethylsulfamoyl, N,N-dipropylsulfamoyl and N,N-dibutylsulfamoyl), $C_{1-6}$ alkylthio (e.g. methylthio, ethylthio, propylthio, isopropylthio, n-butylthio, sec-butylthio and tert-butylthio), $C_{1-6}$ alkylsulfinyl (e.g. methylsulfinyl, ethylsulfinyl, propylsulfinyl and butylsulfinyl) and $C_{1-6}$ alkylsulfonyl (e.g. methylsulfonyl, ethylsulfonyl, propylsulfonyl and butylsulfonyl). The number of substituents ranges from 1 to 6, preferably 1 to 3, more preferably 1 to 2.

Preferable examples of the hydrocarbon residue shown by $R^{8i}$ in the above-mentioned —CO—$R^{8i}$ include optionally substituted $C_{6-14}$ aryl group and optionally substituted $C_{1-6}$ alkyl group.

Preferable examples of substituents in the optionally substituted $C_{6-14}$ aryl group include $C_{1-6}$ alkyl, $C_{1-6}$ alkoxy, $C_{1-6}$ alkoxy-$C_{1-6}$ alkoxy, $C_{1-6}$ alkylenedioxy, phenoxy, hydroxyl, $C_{1-6}$ alkylcarbonyloxy, mono- or di-$C_{1-6}$ alkylamino and $C_{1-6}$ alkylthio.

Examples of substituents in the optionally substituted $C_{1-6}$ alkyl groups include hydroxy, halogen, nitro, cyano, $C_{1-6}$ alkoxycarbonyl, $C_{1-6}$ alkoxy or a group represented by the formula —S(O)$p^i$—$R^{7i}$, wherein $p^i$ denotes an integer of 0 to 2, $R^{7i}$ stands for $C_{1-6}$ alkyl, and $C_{1-6}$ alkylenedioxy.

Preferable examples of the heterocyclic groups shown by $R^{8i}$ include thienyl, furyl, pyrrolyl, pyridyl, pyrimidinyl, thiazolyl, imidazolyl, triazolyl, isoxazolyl, isothiazolyl, morpholinyl, oxoimidazonyl, pyrrolidinyl, piperidinyl and thiazinyl. Especially, thienyl is preferable.

Preferable examples of substituents of the said heterocyclic groups include $C_{1-6}$ alkyl, $C_{1-6}$ alkoxy, carboxyl, $C_{1-6}$ alkoxy-carbonyl, carbamoyl group, halogen, oxo, amino, mono- or di-$C_{1-4}$ alkylamino, nitro, cyano, mercapto, sulfo, sulfino, phosphono, sulfamoyl and $C_{1-6}$ alkylthio.

More preferable examples of the group —CO—$R^{8i}$ include (1) benzoyl group substituted with $C_{1-6}$ alkoxy, $C_{1-6}$ alkoxy-$C_{1-6}$ alkoxy, $C_{1-6}$ alkylenedioxy, phenoxy, hydroxy, $C_{1-6}$ alkylcarbonyloxy, mono- or di-$C_{1-6}$ alkylamino, or $C_{1-6}$ alkylthio, (2) $C_{1-6}$ alkylcarbonyl group substituted with $C_{1-3}$ alkylenedioxy or (3) thienylcarbonyl group.

Preferable examples of $C_{1-6}$ alkyl groups, shown by $R^{4i}$, optionally substituted with hydroxyl or $C_{1-6}$ alkylcarbonyloxy include $C_{1-6}$ alkyl groups substituted with hydroxy or acetyloxy, and, further, 2-hydroxyisobutyl and 2-acetoxyisobutyl are preferable.

In the above definitions, as $C_{1-3}$ alkylenedioxy group, mention is made of, for example, methylenedioxy, ethylenedioxy and propylenedioxy.

As $C_{1-6}$ alkyl group in the above definitions, mention is made of, methyl, ethyl, n-propyl, isopropyl, n-butyl, isobutyl, sec-butyl, tert-butyl, pentyl, isopentyl and hexyl. Among them, $C_{1-3}$ alkyl groups are more preferable.

As $C_{1-6}$ alkoxy group in the above definitions, mention is made of methoxy, ethoxy, propoxy, isopropoxy, butoxy, isobutoxy, sec-butoxy, tert-butoxy, pentyloxy, isopentyloxy, neopentyloxy and hexyloxy. Among them, $C_{1-3}$ alkoxy groups are preferable.

In the compound of the formula (X), preferable examples include a compound of the formula (XIV):

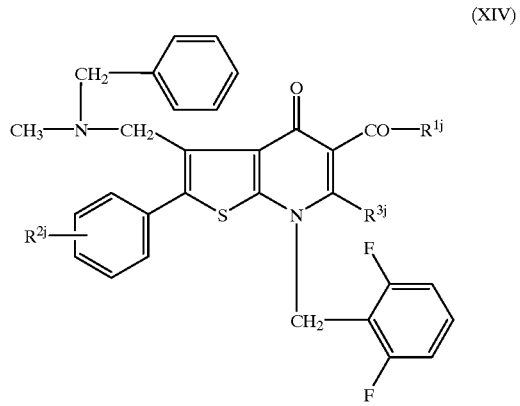

(XIV)

wherein $R^{1j}$ stands for a group of the formula —X—$R^{4j}$, wherein (1) in the case of X is O, $R^{4j}$ is an optionally substituted branched alkyl group, an optionally substituted cycloalkyl group or an optionally substituted 6-membered heterocyclic group which has one or more (preferably 1 or 2) oxygen atoms, (2) in the case of X is S, $R^{4j}$ is an optionally substituted alkyl group, an optionally substituted cycloalkyl group or an optionally substituted 6-membered heterocyclic group which has one or more (preferably 1 or 2) oxygen atoms, or a hydroxyl group, $R^{2j}$ stands for a $C_{1-8}$ alkanoylamino group, $R^{3j}$ is a hydrogen atom or an alkyl group, or a salt thereof.

In the above formula, preferable examples of the branched alkyl group in the optionally substituted branched alkyl group shown by $R^{1j}$ include $C_{3-13}$ branched alkyl groups (e.g. isopropyl, sec-butyl, tert-butyl, isopentyl, sec-pentyl, tert-pentyl, 3-pentyl, isohexyl, sec-hexyl, tert-hexyl, isooctyl, sec-octyl, tert-octyl. As the branched alkyl group, among them, $C_{3-7}$ branched alkyl groups are preferable, and isopropyl, sec-butyl, 3-pentyl or 2,4-dimethyl-3-pentyl are especially preferable.

The branched alkyl group may optionally have substituents, as exemplified by $C_{1-4}$ alkyl, halogen, amino, mono- or di-$C_{1-4}$ alkylamino, $C_{1-4}$ alkoxy and $C_{3-7}$ cycloalkyl. Among them, $C_{1-4}$ alkyl and halogen are preferable. As the $C_{1-4}$ alkyl or $C_{1-4}$ alkyl in mono- or di-$C_{1-4}$ alkylamino, mention is made of, for example, methyl, ethyl, propyl, isopropyl, n-butyl, isobutyl, s-butyl and t-butyl. Among them, $C_{1-2}$ alkyl is preferable. As the halogen, mention is made of fluorine, chlorine, bromine and iodine. Among them, fluorine and chlorine are preferable. Examples of the $C_{1-4}$ alkoxy include methoxy, ethoxy, propoxy, isopropoxy, butoxy and isobutoxy. Among them, methoxy and ethoxy are preferable. Examples of the $C_{3-7}$ cycloalkyl include cyclopropyl, cyclobutyl, cyclopentyl and cyclohexyl. Among them, cyclohexyl is preferable. The number of these substituents ranges from 1 to 3, preferably 1 or 2.

Specific examples of the optionally substituted branched alkyl groups include isopropyl, sec-butyl, tert-butyl, isopentyl, sec-pentyl, tert-pentyl, 3-pentyl, isohexyl, sec-hexyl, tert-hexyl, isooctyl, sec-octyl, tert-octyl, 1,3-difluoro-2-propyl.

As the cycloalkyl group of an optionally substituted cycloalkyl group, $C_{3-10}$ cycloalkyl is preferable. Examples of the $C_{3-10}$ cycloalkyl include cyclopropyl, cyclobutyl, cyclopentyl, cyclohexyl, cycloheptyl and cycloctyl. Among them, $C_{3-7}$ cycloalkyl is more preferable. The cycloalkyl group may form bicyclic condensed ring, as exemplified by indanyl.

Examples of the substituents of the cycloalkyl group include (1) halogen, (2) $C_{1-6}$ alkoxy, (3) $C_{1-6}$ alkyl, (4) $C_{3-7}$ cycloalkyl, (5) $C_{1-6}$ alkylthio, (6) amino, (7) mono- or di-$C_{1-6}$ alkylamino, (8) nitro, (9) hydroxyl, (10) oxo, (11) carbamoyl, (12) cyano, (13) mercapto and (14) sulfo.

The number of these substituents ranges from 1 to 6, preferably 1 to 3, more preferably 1 to 2.

The preferable substituent is halogen, nitro or amino.

Examples of the optionally substituted cycloalkyl group include 2,6-dimethyl-1-cyclohexyl, 3,5-dimethyl-1-cyclohexyl, amino-l-cyclohexyl.

The above-mentioned halogen, $C_{1-6}$ alkoxy, and $C_{1-6}$ alkyl are of the same as defined in above e), m) and f) respectively.

Examples of the mono-alkylamino include mono-$C_{1-4}$ alkylamino such as N-methylamino, N-ethylamino, N-propylamino, N-n-butylamino, and N-isobutylamino. As the di-alkylamino, di-$C_{1-4}$ alkylamino such as N,N-dimethylamino, N,N-diethylamino, and N,N-dipropylamino are preferable.

As the alkylthio, $C_{1-4}$ alkylthio such as methylthio, ethylthio, n-propylthio, isopropylthio, n-butylthio and isobutylthio are preferable. Examples of the 6-membered heterocyclic group which has one or more oxygen atoms in the optionally substituted 6-membered heterocyclic group which has one or more oxygen atoms include pyranyl, tetrahydropyranyl, dioxanyl, oxadinyl, and isoxadinyl. The heterocyclic group may be a hydrogen additive form. Examples of the substituent of the 6-membered heterocyclic group which has one or more oxygen atoms include (1) $C_{1-6}$ alkyl (e.g. methyl, ethyl, propyl, isopropyl, n-butyl, isobutyl, sec-butyl, tert-butyl, etc.), (2) $C_{1-6}$ alkoxy (e.g. methoxy, ethoxy, propoxy, iso-propoxy, n-butoxy, isobutoxy, sec-butoxy, tert-butoxy, etc.), (3) carbamoyl, (4) halogen (e.g. fluorine, chlorine, bromine and iodine), (5) oxo, (6) hydroxy, (7) amino, (8) mono- or di-$C_{1-4}$ alkylamino (e.g. methylamino, ethylamino, propylamino, isopropylamino, butylamino, dimethylamino, diethylamino, dipropylamino, diisopropylamino, dibutylamino), (9) nitro, (10) cyano, (11) mercapto, (12) sulfo, (13) sulfino, (14) $C_{1-6}$ alkylthio (e.g. methylthio, ethylthio, propylthio, isopropylthio, n-butylthio, sec-butylthio, tert-butylthio).

The number of substituents ranges from 1 to 6, preferably 1 to 3, more preferably 1 to 2.

As the substituent on the heterocyclic group, halogen, nitro, amino, mono- or di-$C_{1-4}$ alkylamino, oxo, hydroxy, $C_{1-6}$ alkyl (preferably $C_{1-4}$ alkyl), $C_{1-6}$ alkoxy (preferably $C_{1-4}$ alkoxy), $C_{1-6}$ alkylthio (preferably $C_{1-4}$ alkylthio) are preferable.

Preferable example of $R^{1j}$ is a group of the formula —X—$R^{5j}$, wherein X is O, $R^{5j}$ is (1) a $C_{3-13}$ branched alkyl group (preferably $C_{3-7}$ branched alkyl group) which may optionally be substituted by $C_{1-4}$ alkyl or halogen or (2) a 6-membered heterocyclic group which has one or more oxygen atoms, and which may optionally be substituted by halogen, $C_{1-4}$ alkoxy, $C_{1-4}$ alkyl or $C_{1-4}$ alkylthio.

Further, isopropoxy, sec-butoxy, 3-pentyloxy or 2,4-diemthyl-3-pentyloxy is especially preferable.

In the above formula, examples of the $C_{1-8}$ alkanoylamino group shown by $R^{2j}$ include formylamino, acetylamino, propionylamino, butyrylamino, isobutyrylamino and octanoylamino. As the alkanoylamino group shown by $R^{2j}$, $C_{3-5}$ alkanoylamino is preferable, isobutyrylamino being especially preferable.

$R^{2j}$ is preferably substituted by one or two substituents on the phenyl group, and, more preferably substituted at the 4-position of the phenyl group by one substituent.

In the above formula, the alkyl of $R^{3j}$ include $C_{1-6}$ alkyl as defined in above f).

$R^{3j}$ is preferably hydrogen atom.

The compound of the formula (X), preferable examples include a compound of the formula (XV):

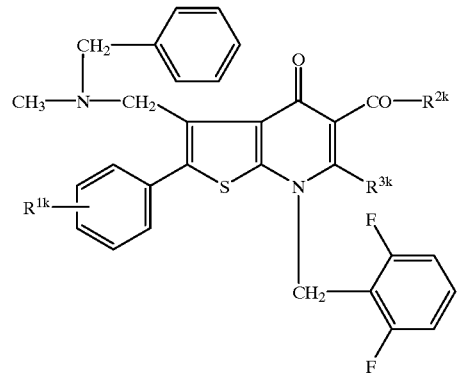

(XV)

wherein $R^{1k}$ stands for an alkoxy group substituted with a group selected from (i) halogen, (ii) cycloalkyl and (iii) alkenyl optionally substituted with alkyl, and $R^{2k}$ stands for alkyl group, aryl group or a group of the formula —X—$R^{4k}$, wherein $R^{4k}$ is an optionally substituted alkyl group or an optionally substituted cycloalkyl group; X is O or S, $R^{3k}$ stands for a hydrogen atom or an alkyl group, or a salt thereof.

In the above formula, as the alkoxy group in the substituted alkoxy group with a group selected from (i) halogen, (ii) cycloalkyl and (iii) alkenyl optionally substituted with alkyl, $C_{1-6}$ alkoxy group is preferable, as exemplified by methoxy, ethoxy, propoxy, isopropoxy, butoxy, isobutoxy, sec-butoxy, tert-butoxy, pentoxy and hexyloxy. Among them, $C_{1-3}$ alkoxy group is preferable, and methoxy is especially preferable.

In $R^{1k}$ of the above formula, as the substituent halogen on the alkoxy group, fluorine, chlorine, bromine and iodine are mentioned. Among them, fluorine is preferable. As the substituent cycloalkyl on the alkoxy group, $C_{3-10}$ cycloalkyl is preferable, which is exemplified by cyclopropyl, cyclobutyl, cyclopentyl, cyclohexyl, cycloheptyl, cyclooctyl and cyclononyl. Among them, $C_{3-6}$ cycloalkyl is preferable, and cyclopropyl is especially preferable. As the alkenyl group optionally substituted with alkyl on the alkoxy group, $C_{2-10}$ alkenyl is preferable, which is exemplified by vinyl, allyl, 1-butenyl, 2-butenyl butadienyl, isopropenyl, hexatrienyl and 3-octenyl. Among them, $C_{2-6}$ alkenyl group is preferable, and $C_{2-4}$ alkenyl group is especially preferable. As the alkyl in the alkenyl group optionally substituted with alkyl, $C_{1-3}$ alkyl is preferable, which is exemplified by methyl, ethyl propyl and isopropyl, methyl being especially preferable. Preferable examples of the alkenyl group substituted with alkyl include 2-methyl allyl.

As $R^{1k}$, a $C_{1-3}$ alkoxy group substituted with a group selected from (i) halogen, (ii) $C_{3-10}$ cycloalkyl and (iii) $C_{2-10}$ alkenyl is preferable, and, further, vinyl-$C_{1-3}$ alkoxy is preferable, allyloxy being especially preferable.

The number of substituents in $R^{1k}$ is preferably 1 to 3, especially 1 to 2.

As the alkyl group shown by $R^{2k}$, $C_{1-6}$ alkyl group is preferable, exemplified by methyl, ethyl, n-propyl, isopropyl, butyl, isobutyl, sec-butyl, tert-butyl, pentyl and hexyl. Among them, $C_{1-3}$ alkyl is preferable, especially $C_3$ alkyl group (n-propyl, isopropyl) being preferable.

As the aryl group shown by $R^{2k}$, $C_{6-14}$ aryl group is preferable, exemplified by phenyl, naphthyl, anthryl, phenanthryl, acenaphthyl and anthracenyl.

As the alkyl group in optionally substituted alkyl group shown by $R^{4k}$, straight-chain or branched $C_{1-9}$ alkyl group is preferable, exemplified by methyl, ethyl, propyl, isopropyl, butyl, isobutyl, sec-butyl, tert-butyl, pentyl, isopentyl, sec-pentyl, tert-pentyl, 3-pentyl, neopentyl, hexyl, isohexyl, sec-hexyl, tert-hexyl, octyl, isooctyl, sec-octyl and tert-octyl. Among them, $C_{3-7}$ alkyl group is preferable, $C_3$ alkyl group (n-propoxy, isopropoxy) being especially preferable.

As substituent in the optionally substituted alkyl group shown by $R^{4k}$, mention is made of halogen, nitro, amino, alkoxy, alkyl and cycloalkyl. The halogen is exemplified by fluorine, chlorine, bromine and iodine. Among them, fluorine and chlorine are preferable. As alkoxy, $C_{1-4}$ alkoxy is preferable, exemplified by methoxy, ethoxy, propoxy, isopropoxy, butoxy, isobutoxy, sec-butoxy and tert-butoxy. Among them, methoxy is especially preferable. As the alkyl, $C_{1-4}$ alkyl is preferable, exemplified by methyl, ethyl, n-propyl, isopropyl, butyl, isobutyl, sec-butyl and tert-butyl. Among them, methyl is especially preferable. As cycloalkyl, $C_{3-8}$ cycloalkyl is preferable, exemplified by cyclopropyl, cyclopentyl, cyclohexyl, cycloheptyl and cyclooctyl.

As cycloalkyl of the optionally substituted cycloalkyl group for $R^{4k}$, $C_{3-10}$ cycloalkyl is preferable, exemplified by cyclopropyl, cyclobutyl, cyclopentyl, cyclohexyl, cycloheptyl, and cyclooctyl. Among them $C_{3-7}$ cycloalkyl is preferable. The cycloalkyl group may form bicyclic condensed ring, exemplified by indanyl.

Examples of the cycloalkyl group include (1) halogen, (2) alkoxy, (3) alkyl, (4) cycloalkyl, (5) alkylthio, (6) amino, (7) mono- or di-alkylamino, (8) nitro, (9) hydroxy, (10) oxo, (11) carbamoyl, (12) cyano, (13) mercapto, (14) sulfo.

The number of substituents is from 1 to 6, preferably 1 to 3, more preferably 1 to 2.

The preferable substitution on the cycloalkyl is halogen, nitro or amino.

The halogen, alkoxy, alkyl and cycloalkyl mentioned above have the same meaning as those defined in above $R^{4k}$. The above-mentioned mono- or di-alkylamino and alkylthio group have the same meanings as those defined in above $R^{4j}$.

As $R^{1k}$, $C_{1-4}$ alkoxy group substituted by $C_{2-6}$ alkenyl is preferable. Especially vinyl-$C_{1-3}$ alkoxy or allyloxy is preferable.

As $R^{2k}$, (1) $C_{1-3}$ alkyl, (2) $C_{6-14}$ aryl group or (3) $C_{3-7}$ alkoxy group optionally substituted with halogen, $C_{1-3}$ alkyl or $C_{1-3}$ alkoxy is preferable. Among them, isopropyl, phenyl, isopropoxy, sec-butoxy, 3-pentyloxy or 2,4-dimethyl-3-pentyloxy are especially preferable.

The number of substituents in the group shown by $R^{2k}$ is preferably 1 to 3, especially 1 or 2.

Preferably $R^{2k}$ is substituted by one or two substituents on the phenyl group and especially substituted at the 4-position of the phenyl group by one substituent. As alkyl group of $R^{3k}$, $C_{1-6}$ alkyl is mentioned. The alkyl has the same meaning as defined in above f).

Preferable $R^{3k}$ is a hydrogen atom.

In the compound of the formula (XX), a preferable example includes a compound of the formula (XXI):

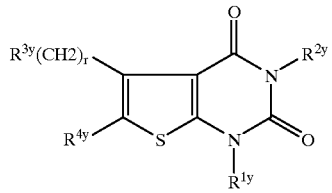

(XXI)

wherein $R^{1y}$ is hydrogen, an alkyl group or a group of the formula:

$$Q—(CH_2)p^y—$$

in which

Q is (1) an aryl group which may optionally be substituted by 1 to 3 substituents selected from (i) halogen, (ii) nitro, (iii) cyano, (iv) amino, (v) an optionally substituted carboxyl, (vi) alkylenedioxy and (vii) a group of the formula: —$A^y$—$R^{5y}$ in which $A^y$ is a chemical bond or a spacer group and $R^{5y}$ is an alkyl group, (2) an optionally substituted cycloalkyl group or (3) an optionally substituted heterocyclic group, and $p^y$ is an integer of 0 to 3;

$R^{2y}$ is hydrogen, an alkyl group which may optionally be substituted by alkoxy, an optionally substituted aryl group, an optionally substituted aralkyl group or an optionally substituted cycloalkyl group;

$R^{3y}$ is an optionally substituted amino group; r is an integer of 0 to 3; and $R^{4y}$ is an optionally substituted aryl group; or a salt thereof.

In the formula (XXI), as the alkyl group shown by $R^{1y}$, $R^{5y}$ and alkyl which may be substituted by alkoxy shown by $R^{2y}$, mention is made of, for example, $C_{1-6}$ alkyl (e.g. methyl, ethyl, propyl, isopropyl, butyl, sec-butyl, t-butyl, pentyl, hexyl). Among these, alkyl group having one to three carbon atoms is preferable.

As the aryl group shown by Q or in the optionally substituted aryl group shown by $R^{2y}$ and $R^{4y}$, mention is made of, for example, mono cyclic- or condensed polycyclic-aromatic hydrocarbon residues. Preferable example of them includes $C_{6-14}$ aryl such as phenyl, naphthyl, anthryl, phenanthryl, acenaphthylenyl and the like. Among these, $C_{6-10}$ aryl such as phenyl, 1-naphthyl and 2-naphthyl are more preferable.

The number of substituents on the aryl group is one to three. Examples of the substituents on the aryl group shown by $R^{2y}$ and $R^{4y}$ include (1) $C_{1-6}$ alkyl (e.g. methyl, ethyl, n-propyl, isopropyl, n-butyl, isobutyl, pentyl, hexyl. The alkyl may optionally be substituted by $C_{1-6}$ alkyl-carbonyl or $C_{1-6}$ alkoxy-carbonyl), (2) an optionally substituted $C_{2-6}$ alkenyl group (e.g. vinyl, allyl, 1-butenyl, 2-butenyl), which may optionally be substituted by one to three of $C_{1-6}$ acyl or $C_{1-6}$ alkoxy-carbonyl, (3) $C_{2-6}$ alkynyl (e.g. ethynyl, propargyl, 2-butynyl, 5-hexynyl), (4) $C_{3-7}$ cycloalkyl (e.g. cyclopropyl, cyclobutyl, cyclopentyl, cyclohexyl), (5) $C_{6-14}$ aryl (e.g. phenyl, naphthyl) which may optionally be substituted by one to three substituents selected from (i) halogen, (ii) $C_{1-6}$ alkyl, (iii) $C_{1-6}$ alkoxy which may be further substituted by $C_{1-6}$ alkoxy, (iv) nitro, (v) cyano, (vi) a group of the formula —$S(O)n^y$—$R^{6y}$ wherein $n^y$ is an integer of 0 to 2 and $R^{6y}$ shows $C_{1-6}$ alkyl or amino, (vii) amino, (viii) $C_{1-6}$ acyl, (ix) carbamoyl, (x) carboxy and (xi)

hydroxy, (6) heterocyclic group, for example, 5- to 6-membered aromatic heterocyclic group having 1 to 4 hetero atoms selected from a nitrogen atom, an oxygen atom and a sulfur atom (e.g. furyl, thienyl, pyrrolyl, thiazolyl, imidazolyl, pyrazolyl, pyridyl), or 3- to 9-membered non-aromatic heterocyclic group having 1 to 4 hetero atoms selected from a nitrogen atom, an oxygen atom and a sulfur atom (e.g. oxiranyl, azetidinyl, oxetanyl, thietanil, pyrrolidinyl, tetrahydrofuryl, thioranyl, piperidinyl, tetrahydropyranyl, morpholinyl, thiomorpholinyl, piperazinyl), these heterocyclic group may optionally be substituted by one to three substituents selected from (i) halogen, (ii) $C_{1-6}$ alkyl, (iii) amino, (iv) $C_{1-6}$ acyl, (v) carbamoyl, (vi) carboxy, (vii) nitro, (viii) hydroxy, (ix) $C_{1-6}$ alkoxy and (x) a group of the formula: —S(O)n$^y$—R$^{6y}$ in which n$^y$ is an integer of 0 to 2 and R$^{6y}$ is $C_{1-6}$ alkyl group, (7) $C_{7-13}$ aralkyl (e.g. benzyl, phenethyl, benzhydryl) which may be substituted by one to three halogens, (8) an optionally substituted amino group such as a group of the formula:

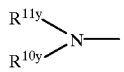

wherein R$^{11y}$ denotes hydrogen; $C_{1-6}$ alkyl which may optionally be substituted by 1 to 3 hydroxy groups; acyl (e.g. $C_{1-6}$ alkyl-carbonyl, formyl; $C_{6-14}$ arylcarbonyl) which may optionally be substituted by one to three substituents selected from halogen-and $C_{1-6}$ alkoxy; an optionally substituted alkoxy group as mentioned below; $C_{3-7}$ cycloalkyl which may optionally be substituted by one to three hydroxy groups; a group of the formula: —S(O)n$^y$—R$^{6y}$ in which n$^y$ is an integer of 0 to 2 and R$^{6y}$ is $C_{1-6}$ alkyl group and R$^{12y}$ denotes hydrogen or $C_{1-6}$ alkyl, (9) a group of the formula:

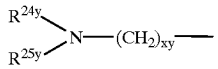

wherein R$^{24y}$ is hydrogen, $C_{1-6}$ alkyl group or $C_{6-14}$ aryl group, R$^{25y}$ is hydrogen or $C_{1-6}$ alkyl group and R$^{24y}$ and R$^{25y}$ may form an optionally substituted 5 to 7-membered cyclic amino group-containing the adjacent nitrogen atom and x$^y$ is an integer of 0 to 3, (10) amidino, (11) acyl (e.g. $C_{1-8}$ alkanoyl such as formyl, acetyl, propionyl, butyryl, octanoyl; $C_{1-8}$ alkoxy-carbonyl such as methoxycarbony, ethoxycarbonyl, propoxycarbonyl, butoxycarbonyl; $C_{6-14}$ aryl-carbonyl such as benzoyl; $C_{8-11}$ aralkylcarbonyl such as benzylcarbonyl; $C_{7-12}$ aralkyloxy-carbonyl (e.g. phenyl-$C_{1-6}$ alkyloxy-carbonyl) such as benzyloxycarbonyl) which may optionally be substituted by one to three substituents (e.g. halogen $C_{1-6}$, alkylthio, $C_{1-6}$ alkoxy, oxo, hydroxy), (12) an optionally substituted carbamoyl group, e.g. carbamoyl, N-monosubstituted carbamoyl {e.g. N-($C_{1-6}$ alkyl)carbamoyl such as methylcarbamoyl, ethylcarbamoyl, propylcarbamoyl, isopropylcarbamoyly, N,N-disubstituted carbamoyl [e.g. N,N-di($C_{1-6}$ alkyl)carbamoyl such as dimethylcarbamoyl, diethylcarbamoyl, N-ethyl-N-methylcarbamoyl, N-propyl-N-methylcarbamoyl}, (13) sulfamoyl, (14) N-monosubstituted sulfamoyl {e.g. N-($C_{1-6}$ alkyl)sulfamoyl such as methylsulfamoyl, ethylsulfamoyl, propylsulfamoyl}, (15) N,N-disubstituted sulfamoyl {e.g. N,N-di($C_{1-6}$ alkyl)sulfamoyl such as dimethylsulfamoyl, diethylsulfamoyl}, (16) carboxy, (17) $C_{1-3}$ alkoxy-carbonyl (e.g. methoxycarbonyl, ethoxycarbonyl, propoxycarbonyl), (18) hydroxyl, (19) an optionally substituted alkoxy group, e.g. $C_{1-6}$ alkoxy (e.g. methoxy, ethoxy, propoxy, isopropoxy, butoxy, isobutoxy, sec-butoxy, t-butoxy, pentyloxy, hexyloxy) which may have one to three substituents (e.g. $C_{1-6}$ alkanoyl which is the same as above o), $C_{1-3}$ alkyl, halogen, $C_{1-3}$ alkylthio, $C_{1-3}$ alkoxy, $C_{3-7}$ cycloalkyl which are the same as above f), m), i); oxo, hydroxy), (20) $C_{2-4}$ alkenyloxy (e.g. vinyloxy, allyloxy), (21) $C_{3-7}$ cycloalkyloxy (e.g. cyclopropyloxy, cyclopentyloxy, cyclohexyloxy), (22) $C_{7-13}$ aralkyloxy (e.g. phenyl-$C_{1-3}$ alkyloxy such as benzyloxy; benzhydryloxy), (23) $C_{6-14}$ aryloxy (e.g. phenyloxy, naphthyloxy), (24) mercapto, (25) $C_{7-13}$ aralkylthio (e.g. phenyl-$C_{1-3}$ alkylthio such as benzylthio; benzhydrylthio), (26) $C_{6-14}$ arylthio (e.g. phenylthio, naphthylthio), (27) a group of the formula: —S(O)n$^y$—R$^{6y}$ in which n$^y$ is an integer of 0 to 2 and R$^{6y}$ is $C_{1-6}$ alkyl group (e.g. methylthio, ethylthio, propylthio, methylsulfinyl, ethylsulfinyl, propylsulfinyl, methylsulfonyl, ethylsulfonyl, propylsulfonyl), (28) $C_{1-3}$ alkylenedioxy (e.g. methylenedioxy, ethylenedioxy, propylenedioxy), (29) sulfo, (30) cyano, (31) azido, (32) nitro, (33) nitroso, (34) halogen (e.g. fulorine, chlorine, bromine iodine), and the like.

As the cycloalkyl in the optionally substituted cycloalkyl shown by Q of R$^{1y}$ and R$^{2y}$, mention is made of, for example, $C_{3-10}$ cycloalkyl and $C_{3-10}$ bicycloalkyl. The preferable examples of them include cyclopropyl, cyclobutyl, cyclopentyl, cyclohexyl, cycloheptyl, cyclooctyl, bicyclo[2,2,1]heptyl, bicyclo[2,2,2]octyl, bicyclo[3,2,1]octyl, bicyclo[3,2,1]nonyl, bicyclo[4,2,1]nonyl, bicyclo[4,3,1]decyl. Among these, cyclopentyl and cyclohexyl are more preferable. The substituents are of the same meaning as those defined in the substituents which aryl, shown by R$^{2y}$ and R$^{4y}$, may have. Preferred examples of the substituents are $C_{1-6}$ alkyl, $C_{1-6}$ alkoxy or halogen. The number of substituents is preferably 1 to 3.

As the heterocyclic group in the optionally substituted heterocyclic group shown by Q of R$^{1y}$, mention is made of, for example, 5- to 13-membered aromatic heterocyclic group having one to four hetero atom(s) selected from an oxygen atom, a sulfur atom and a nitrogen atom; or saturated or unsaturated non-aromatic heterocyclic group.

Examples of the aromatic heterocyclic group include an aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl), an aromatic condensed heterocyclic group {e.g. benzofuranyl, isobenzofuranyl, benzo[b]thienyl, indolyl, isoindolyl, 1H-indazolyl, benzoimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2-4-tiazolo[4,3-a]pyridyl, 1,2,4-triazolo[4,3-b]pyridazinyl}. Examples of the non-aromatic heterocyclic group include oxylanyl, azetizinyl, oxethanyl, thiethanyl, pyrrolidinyl, tetrahydrofuranyl, thiolanyl, piperidyl, tetrahydropyranyl, morpholinyl, thiomorpholinyl, piperazinyl. Among these, furyl, thienyl, thiazolyl, imidazolyl, pyrazolyl, pyridyl, pyrimidyl, benzofuryl, indolyl and quinolyl are preferable.

The heterocyclic group may have one or more substituents, preferably one to three substituents. The substituents are of the same meaning as defined in the optionally substituted aryl shown by $R^{2y}$ and $R^{4y}$. Preferred examples of the substituents are halogen, $C_{1-6}$ alkyl, $C_{1-6}$ alkylthio or $C_{1-6}$ alkoxy.

As the halogen, as the substituent of the aryl shown by Q, mention is made of fluorine, chlorine, bromine, iodine.

As the optionally substituted carboxyl of the aryl group shown by Q, mention is made of carboxyl, $C_{1-6}$ alkyloxycarbonyl, $C_{3-7}$ cycloalkyloxycarbonyl, $C_{6-14}$ aryloxycarbonyl, $C_{7-20}$ aralkyloxycarbonyl and oxycarbonyl substituted by heterocyclic group. The $C_{1-6}$ alkyl, $C_{3-7}$ cycloalkyl, $C_{6-14}$ aryl, $C_{7-20}$ aralkyl and heterocyclic groups are of the same meaning as defined above f), i), k), l), and a).

As the alkylenedioxy as the substituent of aryl group shown by Q, mention is made of, for example, $C_{1-6}$ alkylenedioxy. Examples of the alkylenedioxy includes methylenedioxy, ethylenedioxy, propylenedioxy, 2,2-dimethylmetylenedioxy.

As the spacer group shown by the symbol "$A^y$", mention is made of, for example, $C_{1-4}$ alkylene (e.g. methylene, ethylene), $C_{2-6}$ alkenylene (e.g. vinylene, butadienylene); a group of the formula: —$(CH_2)_cNR^{26y}$— in which c is 0 to 3, $R^{26y}$ is hydrogen, $C_{1-6}$ alkyl (e.g. above f)); a group of the formula: —CO—; a group of the formula: —$CONR^{27y}$— in which $R^{27y}$ is hydrogen, $C_{1-6}$ alkyl (Examples of the alkyl are made of those mentioned above f)), $C_{3-7}$ cycloalkyl (Examples of the cycloalkyl are made of those mentioned above i)), $C_{6-14}$ aryl (Examples of the aryl are made of those mentioned above k)), a heterocyclic group (Examples of the heterocyclic group are made of those mentioned above a)); a group of the formula: —$S(O)m^y$— wherein $m^y$ is an integer of 0 to 2; —O—; a group of the formula: —$NR^{27y}S(O)Z^y$— wherein $Z^y$ is an integer of 0 to 2, $R^{27y}$ is of the same meaning as defined in the above.

As the alkoxy which may be the substituent of the alkyl group shown by $R^{2y}$, mention is made of $C_{1-6}$ alkoxy. The $C_{1-6}$ alkoxy is of the same meaning as defined in above m).

As the aralkyl in the optionally substituted aralkyl shown by $R^{2y}$, mention is made of, for example, $C_{6-14}$ aryl-$C_{1-6}$ alkyl. The aryl is of the same meaning as defined in $R^2$. Examples of the alkyl include $C_{1-6}$ alkyl such as methyl, ethyl, propyl, butyl, pentyl, hexyl. The substituents on the aralkyl shown by $R^{2y}$ are of the same meaning as defined in the substituents which $C_{6-14}$ aryl group shown by $R^{2y}$ and $R^{4y}$ may have.

As the optionally substituted amino group shown by $R^{3y}$, mention is made of, for example, (1) a group of the formula:

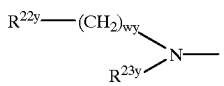

wherein $R^{22y}$ is a $C_{1-6}$ alkyl, $C_{3-7}$ cycloalkyl, $C_{6-14}$ aryl or heterocyclic group and these groups may optionally be substituted, $w^y$ is an integer of 0 to 3, $R^{23y}$ is hydrogen or an optionally substituted $C_{1-6}$ alkyl, or (2) hexamethylenetetraamino. The above-mentioned $C_{1-6}$ alkyl, $C_{3-7}$ cycloalkyl, $C_{6-14}$ aryl and heterocyclic groups in the above $R^{22y}$ and $R^{23y}$ are of the same meaning as defined in f), i), k), a). The substituents on these groups are of the same meaning as defined in the substitution on ary group shown by $R^{2y}$ and $R^{4y}$ as mentioned above.

As the preferable spacer group represented by $A^y$ in the definition of the substituents on the aryl group of Q in $R^{1y}$, mention is made of —O— or —$S(O)m^y$— in which $m^y$ is an integer of 0 to 2.

As preferred examples of the above group $R^{1y}$, mention is made of the group of the formula: Q—$(CH_2)p^y$— wherein Q and $p^y$ has the same meaning as defined above.

As preferred examples of the above group $R^{1y}$, mention is made of hydrogen or a group of the formula: —$(CH_2)_pQ'$ wherein Q' denotes a $C_{6-14}$ aryl group which may optionally be substituted by halogen, nitro, cyano, amino or a group of the formula: —$A^{y'}$—$R^{5y'}$, wherein $A^{y'}$ denotes —O— or —S— and $R^{5y'}$ denotes $C_{1-6}$ alkyl, and $p^y$ has the same meaning as defined above.

As more preferred examples of the above group $R^{1y}$, mention is made of a group of the formula:

Q—$(CH_2)p^y$— in which Q is a $C_{6-14}$ aryl group which may optionally be substituted by one to three substituents selected from (i) halogen and (ii) a group of the formula: —$A^y$—$R^{5y}$ in which $A^y$ is —O— or —$S(O)m^y$— in which $m^y$ is an integer of 0 to 2 and $R^5$ is $C_{1-6}$ alkyl group; and $p^y$ is an integer of 0 to 3.

As still more preferable examples of the group $R^{1y}$, mention is made of $C_{6-14}$ aryl-methyl which may optionally be substituted by 1 to 3 substituents selected from halogen and a group —$A^{y''}$—$R^{5y''}$ wherein $A^{y''}$ is —O— or —S— and $R^{5y''}$ is $C_{1-6}$ alkyl.

As especially preferable example of the group $R^{1y}$, mention is made of the group Q'''—$(CH_2)p^y$— wherein Q''' is a $C_{6-14}$ aryl group which may optionally be substituted by 1 to 3 halogens and $p^y$ is an integer of 0 to 3.

As preferred examples of the group $R^{2y}$, mention is made of (1) a $C_{1-6}$ alkyl group which may optionally be substituted by 1 to 3 $C_{1-6}$ alkoxy groups, (2) a $C_{6-14}$ aryl group which may optionally be substituted by one to three substituents selected from (i) amino, (ii) $C_{1-6}$ acyl, (iii) carbamoyl, (iv) carboxy, (v) nitro, (vi) hydroxy, (vii) $C_{1-6}$ alkoxy group which may optionally be substituted by 1 to 3 $C_{1-6}$ alkoxy groups, (viii) halogen and (ix) a group of the formula: —$S(O)n^y$—$R^{6y}$ in which $n^y$ is an integer of 0 to 2 and $R^{6y}$ is $C_{1-6}$ alkyl group, (3) a $C_{7-20}$ aralkyl group which may optionally be substituted by 1 to 3 halogens or (4) $C_{3-10}$ cycloalkyl group.

As more preferred examples of the group $R^{2y}$, mention is made of (1) $C_{1-6}$ alkyl which may optionally be substituted by 1 to 3 $C_{1-3}$ alkoxy groups, (2) $C_{6-14}$ aryl which may optionally be substituted by one to three substituents selected from amino, $C_{1-6}$ acyl, carbomoyl, carboxyl, nitro, hydroxy, $C_{1-3}$ alkoxy, sulfo, halogen and a group of the formula: —$S(O)n^y$—$R^{6y}$ wherein $n^y$ is an integer of 0 to 2 and $R^{6y}$ is $C_{1-3}$ alkyl, or (3) $C_{3-10}$ cycloalkyl.

As further more preferred examples of the group $R^{2y}$, mention is made of (1) a $C_{1-6}$ alkyl group which may optionally be substituted by 1 to 3 $C_{1-3}$ alkoxy groups, (2) a $C_{6-14}$ aryl group which may optionally be substituted by one to three substituents selected from (i) hydroxy, (ii) $C_{1-3}$ alkoxy group which may optionally be substituted by 1 to 3 $C_{1-3}$ alkoxy groups, (iii) halogen and (iv) a group of the formula: —$S(O)n^y$—$R^{6y}$ in which $n^y$ is an integer of 0 to 2 and $R^{6y}$ is a $C_{1-3}$ alkyl group, (3) $C_{7-20}$ aralkyl group or (4) a $C_{3-7}$ cycloalkyl group.

As more preferable examples of the group $R^{2y}$, mention is made of (1) $C_{1-6}$ alkyl which may optionally be substituted by 1 to 3 $C_{1-3}$ alkoxy groups, (2) $C_{6-14}$ aryl which may optionally be substituted by one to three substituents selected from $C_{1-3}$ alkoxy and a group of the formula:

—S(O)n$^y$—R$^{6y}$ wherein n$^y$ is an integer of 0 to 2 and R$^{6y}$ is C$_{1-3}$ alkyl, or (3) C$_{3-7}$ cycloalkyl.

As the most preferred examples of the group R$^{2y}$, mention is made of a C$_{6-14}$ aryl group which may optionally be substituted by one to three substituents selected from (1) a C$_{1-3}$ alkoxy group which may optionally be substituted by 1 to 3 C$_{1-3}$ alkoxy group, (2) halogen and (3) a group of the formula: —S(O)n$^y$—R$^{6y}$ in which n$^y$ is an integer of 0 to 2 and R$^{6y}$ is a C$_{1-3}$ alkyl group.

As preferred examples of the above group R$^{3y}$, mention is made of hexamethylenetetraamino or a substituted amino group of the formula:

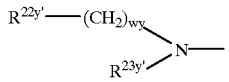

wherein R$^{22y'}$ is (1) a C$_{6-14}$ aryl group which may optionally be substituted by one to three substituents selected from (i) amino, (ii) C$_{1-6}$ acyl, (iii) carbamoyl, (iv) carboxy, (v) nitro, (vi) hydroxy, (vii) C$_{1-6}$ alkoxy group which may optionally be substituted by 1 to 3 C$_{1-6}$ alkoxy groups, (viii) halogen, (ix) C$_{1-6}$ alkyl and (x) a group of the formula: —S(O)n$^y$—R$^{6y}$ in which n$^y$ is an integer of 0 to 2 and R$^{6y}$ is C$_{1-6}$ alkyl group, (2) heterocyclic group which may optionally be substituted by one to three substituents selected from (i) amino, (ii) C$_{1-6}$ acyl, (iii) carbamoyl, (iv) carboxy, (v) nitro, (vi) hydroxy, (vii) C$_{1-6}$ alkoxy, (viii) halogen, (ix) C$_{1-6}$ alkyl and (x) a group of the formula: —S(O)n$^y$—R$^{6y}$ in which n$^y$ is an integer of 0 to 2 and R$^{6y}$ is C$_{1-6}$ alkyl group, (3) a C$_{7-20}$ aralkyl group which may optionally be substituted by 1 to 3 halogens, (4) a group of the formula:

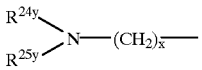

wherein R$^{24y}$ is hydrogen, a C$_{1-6}$ alkyl group or a C$_{6-14}$ aryl group, R$^{25y}$ is hydrogen or a C$_{1-6}$ alkyl group and R$^{24y}$ and R$^{25y}$ may form an optionally substituted 5 to 7 membered cyclic amino group together with the adjacent nitrogen atom and x is an integer of 0 to 3 or (5) a C$_{1-6}$ alkyl group which may optionally be substituted by 1 to 3 C$_{1-6}$ alkylthios, w$^y$ is an integer of 0 to 3; and R$^{23y'}$ is hydrogen or a C$_{1-6}$ alkyl group.

As more preferred examples of the above group R$^{3y}$, mention is made of hexamethylenetetraamino or a group of the formula:

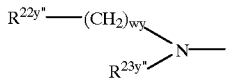

wherein R$^{22y''}$ denotes (1) C$_{1-6}$ alkyl, (2) phenyl which may optionally be substituted by one to three substituents selected from halogen, nitro, C$_{1-6}$ alkyl and a group of the formula: —S(O)n$^y$—R$^{6y}$ wherein n$^y$ is an integer of 0 to 2 and R$^{6y}$ is a C$_{1-6}$ alkyl group or an amino group, (3) a heterocyclic group which may optionally be substituted by one to three substituents selected from halogen and C$_{1-6}$ alkyl and (4) N-mono-substituted C$_{1-6}$ alkylcarbamoyl, w$^y$ is an integer of 0 to 3; R$^{23y''}$ denotes hydrogen or C$_{1-6}$ alkyl.

As more preferred examples of the above R$^{3y}$, mention is made of a substituted amino group of the formula:

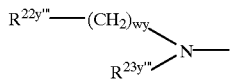

wherein R$^{22y'''}$ is (1) C$_{6-14}$ aryl group which may optionally be substituted by 1 to 3 C$_{1-6}$ alkylthio groups, (2) heterocyclic group, (3) a group of the formula:

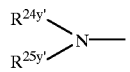

wherein R$^{24y'}$ is hydrogen or C$_{1-6}$ alkyl and R$^{25y'}$ is hydrogen or C$_{1-6}$ alkyl and R$^{24y'}$ and R$^{25y'}$ may form a 5 to 7 membered cyclic amino group together with the adjacent nitrogen atom or (4) a C$_{1-6}$ alkyl group which may optionally be substituted by 1 to 3 C$_{1-6}$ alkylthio groups, w$^y$ is an integer of 0 to 3; and R$^{23y'''}$ is hydrogen or a C$_{1-6}$ alkyl group.

As preferred examples of the above group R$^{3y}$, mention is made of a group of the formula:

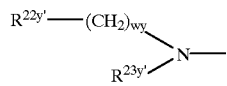

wherein R$^{22y'}$ is phenyl or pyridyl, these groups being unsubstituted or substituted by a group of the formula: —S(O)n$^y$—R$^{6y}$ in which n$^y$ is an integer of 0 to 2 and R$^{6y}$ is a C$_{1-6}$ alkyl group, w$^y$ is an integer of 0 to 3. R$^{23y'}$ is hydrogen or a C$_{1-6}$ alkyl group.

As preferred examples of the group R$^{4y}$, mention is made of the aryl group which may optionally be substituted by one to three substituents selected from (1) an optionally substituted amino group, (2) C$_{1-6}$ acyl, (3) an optionally substituted carbamoyl group, (4) carboxy, (5) nitro, (6) hydroxy, (7) an optionally substituted C$_{1-6}$ alkoxy group and (8) an optionally substituted C$_{2-10}$ alkenyl group.

As more preferred examples of the above group R$^{4y}$, mention is made of the C$_{6-14}$ aryl group which may optionally be substituted by one to three substituents selected from (1) a group of the formula:

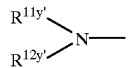

wherein R$^{11y'}$ is (i) hydrogen, (ii) C$_{1-6}$ alkyl, (iii) an optionally substituted C$_{1-6}$ alkoxy group, (iv) an optionally substituted C$_{1-6}$ acyl group or (v) a group of the formula: —S(O)n$^y$—R$^{6y}$ in which n$^y$ is an integer of 0 to 2 and R$^{6y}$ is a C$_{1-6}$ alkyl group and R$^{12y'}$ is hydrogen or a C$_{1-6}$ alkyl group, (2) C$_{1-6}$ acyl, (3) carbamoyl, (4) N-mono or di-C$_{1-6}$ alkylcarbamoyl, (5) nitro, (6) C$_{1-6}$ alkoxy which may optionally be substituted by one to three substituents selected from C$_{1-6}$ alkoxy, C$_{1-8}$ alkanoyl, oxo, hydroxy, C$_{3-7}$ cycloalkyl and halogen, (7) C$_{2-10}$ alkenyl which may optionally be substituted by 1 to 3 substituents selected from C$_{1-6}$ alkoxycarbonyl and C$_{1-6}$ alkylcarbonyl and (8) C$_{2-10}$ alkenyloxy.

Further preferred examples of the above group R$^{4y}$, mention is made of the C$_{6-14}$ aryl group which may optionally be substituted by one to three of (1) a group of the formula:

wherein $R^{11y''}$ is (i) hydrogen, (ii) $C_{1-6}$ alkyl, (iii) $C_{1-6}$ alkoxy which may optionally be substituted by 1 to 3 substituents selected from halogen and $C_{1-6}$ alkoxy, (iv) formyl, (v) $C_{1-8}$ alkanoyl which may optionally be substituted by 1 to 3 substituents selected from halogen and $C_{1-6}$ alkoxy, (vi) benzoyl or (vii) a group of the formula: —S(O)$n^y$—$R^{6y}$ in which $n^y$ is an integer of 0 to 2 and $R^{6y}$ is a $C_{1-6}$ alkyl group and $R^{12y''}$ is hydrogen or $C_{1-6}$ alkyl, (2) $C_{1-6}$ alkoxy which may optionally be substituted by 1 to 3 substituents selected from $C_{1-6}$ alkoxy, $C_{1-8}$ alkanoyl and $C_{3-7}$ cycloalkyl, (3) N-mono or di-$C_{1-6}$ alkylcarbamoyl, (4) nitro (5) $C_{2-10}$ alkenyl which may optionally be substituted by 1 to 3 substituents selected from $C_{1-6}$ alkoxycarbonyl and $C_{1-6}$ alkylcarbonyl or (6) $C_{2-10}$ alkenyloxy.

Further preferred examples of the aryl group in the above optionally substituted aryl $R^{4y}$, mention is made of phenyl. As the preferred examples of the substituents on the aryl group shown by $R^{4y}$, mention is made of amino, $C_{1-6}$ acyl, carbamoyl, N-monosubstituted $C_{1-6}$ alkylcarbamoyl, carboxyl, nitro, hydroxy, $C_{1-3}$ alkoxy which may optionally be substituted by 1 to 3 $C_{1-3}$ alkoxys, a group of the formula:

(wherein $R^{31y}$ denotes $C_{1-6}$ alkyl; $C_{1-3}$ alkoxy which may optionally be substituted by 1 to 3 $C_{1-3}$ alkoxy groups; or formyl, $R^{32y}$ denotes hydrogen or $C_{1-6}$ alkyl), or $C_2$-alkenyl which may optionally be substituted by 1 to 3 substituents selected from $C_{1-6}$ alkoxy-carbonyl and $C_{1-6}$ alkyl-carbonyl.

As more preferred examples of the substituents on the aryl group shown by $R^{4y}$, mention is made of amino; $C_{1-6}$ acyl; N-monosubstituted $C_{1-6}$ alkylcarbamoyl; nitro; $C_{1-3}$ alkoxy which may optionally be substituted by 1 to 3 $C_{1-3}$ alkoxy groups; a group of the formula;

(wherein $R^{33y}$ denotes $C_{1-6}$ alkyl, $C_{1-3}$ acyl which may optionally be substituted by 1 to 3 $C_{1-3}$ alkoxy groups; $C_{1-3}$ alkoxy which may optionally be substituted by 1 to 3 $C_{1-4}$ acyl groups; benzoyl; or formyl, $R^{34y}$ denotes hydrogen or $C_{1-6}$ alkyl), $C_{2-4}$ alkenyl which may optionally be substituted by 1 to 3 substituents selected from $C_{1-3}$ alkoxy-carbonyl and $C_{1-3}$ alkyl-carbonyl.

In the above each groups, the number of the substituents is preferably 1 to 3. r is preferably 1. $p^y$ is preferably 1, and $w^y$ is preferably 1.

As the 5 to 7 membered cyclic amino group, mention is made of pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneamino, oxazolidino, morpholino, thiazolidino or thiomorpholino. As more preferable cyclic amino group, mention is made of pyrolidinyl, pyrazolinyl, pyrazolyl, piperidinyl, piperazinyl, morpholino and thiomorpholino.

The cyclic amino group may be substituted. The examples of the substituents includes $C_{1-6}$ alkyl, $C_{6-14}$ aryl, $C_{7-10}$ aralkyl, benzhydryl, $C_{1-6}$ alkyl-carbonyl, $C_{6-14}$ aryl-carbonyl, $C_{1-6}$ alkoxy-carbonyl. As the preferable substituent, mention is made of $C_{1-6}$ alkyl, preferably $C_{1-3}$ alkyl.

As the preferable alkyl in the above definition, mention is made of, for example, $C_{1-6}$ alkyl. Examples of the alkyl includes methyl, ethyl, propyl, isopropyl, butyl, isobutyl, sec-butyl, t-butyl, pentyl, isopentyl, neopentyl and hexyl. Among these, alkyl having one to three carbon atoms is preferable.

As the acyl, mention is made of $C_{1-6}$ acyl and the examples of the acyl are for example $C_{1-6}$ alkanoyl, $C_{6-14}$ aryl-carbonyl, $C_{7-20}$ aralkyl-carbonyl and $C_{7-20}$ aralkyloxy-carbonyl which are mentioned above o), k) and l).

As the preferable acyl and alkanoyl in the above definition, mention is made of $C_{1-6}$ alkyl-carbonyl, and alkyl is of the same meaning as defined above f).

As the preferable alkoxy in the above definition, mention is made of $C_{1-6}$ alkoxy, and examples of the alkoxy includes methoxy, ethoxy, propoxy, isopropoxy, butoxy, isobutoxy, sec-butoxy, t-butoxy, pentyloxy, isopentyloxy, neopentyloxy, hexyloxy. Among these, alkoxy having 1 to 3 carbon atoms is preferable.

As the preferable alkenyl in the above definition, mention is made of $C_{2-10}$ alkenyl more preferable $C_{2-4}$ alkenyl. Examples of the alkenyl includes vinyl, allyl, 1-butenyl, 2-butenyl.

As the preferable aryl in the above definition, mention is made of $C_{6-14}$ aryl. Examples of the aryl includes phenyl, naphthyl.

As the preferable aralkyl in the above definition, mention is made of $C_{7-20}$ aralkyl more preferable $C_{7-10}$ aralkyl. Examples of the aralkyl includes phenyl-$C_{1-4}$ alkyl such as benzyl, phenethyl.

As the halogen, mention is made of fluorine, chlorine, bromine, iodine.

In the compound of the formula (XXX), preferable examples include a compound of the formula (XXXI):

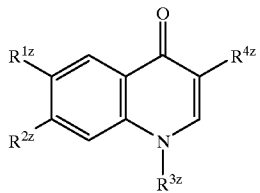

(XXXI)

wherein $R^{1z}$ is a group of the formula:

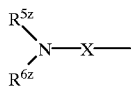

in which $R^{5z}$ is an aralkyl group, $R^{6z}$ is an alkyl group, X is an alkylene group, or an alkyl group which may optionally be substituted by halogen, $R^{2z}$ is an acylaminoaryl group, $R^{3z}$ is a halogenoaralkyl group, $R^{4z}$ is a carboxyl group which may optionally be esterified or amidated, or a salt thereof.

As the aralkyl group of $R^{5z}$ in $R^{1z}$, $C_{7-19}$ aralkyl is preferable, and the $C_{7-19}$ aralkyl is exemplified by phenyl- $C_{1-4}$ alkyl such as benzyl, phenethyl; biphenylmethyl, benzhydryl. In particular, benzyl is most preferable.

As the alkyl groups of $R^{6z}$, a $C_{1-6}$ alkyl group is preferable, and the $C_{1-6}$ alkyl group is exemplified by methyl, ethyl, n-propyl, isopropyl, n-butyl, isobutyl, s-butyl, t-butyl, n-pentyl, isopentyl, neopentyl, hexyl. Among them, $C_{1-3}$ alkyl is preferable.

As the alkylene group of X in $R^{1z}$, $C_{1-6}$ alkylene is preferable, and $C_{1-6}$ alkylene is exemplified by methylene, ethylene, trimethylene, tetramethylene, pentamethylene, hexamethylene. Among them, $C_{1-3}$ alkylene is more preferable.

As the alkyl group in the alkyl group which may optionally be substituted by halogen of $R^{1z}$, it is exemplified by those mentioned above f) as $C_{1-6}$ alkyl. As the halogen, mention is made of fluorine, chlorine, bromine and iodine. The number of substituents is 1 to 3. As the preferred alkyl group which has halogen, mention is made of bromomethyl.

As the acylaminoaryl of $R^{2z}$, $C_{1-6}$ acylamino-$C_{6-14}$ aryl group is preferable. As examples of the $C_{1-6}$ acyl, mention is made of $C_{1-6}$ alkanoyl such as formyl, acetyl, propionyl, butyryl, isobutyryl, valeryl, isovaleryl. As examples of the $C_{6-14}$ aryl, mention is made of phenyl, naphthyl, anthryl.

As the halogenoaralkyl of $R^{3z}$, halogeno-$C_{7-19}$ aralkyl is preferable. As the halogen in the halogenoaralkyl, mention is made of fluorine, chlorine, bromine and iodine. The number of halogens is 1 to 3. As examples of aralkyl in the halogenoaralkyl, mention is made of benzyl, phenethyl, benzhydryl, in particular, benzyl is most preferable.

As the esterified carboxyl of $R^{4z}$, $C_{1-6}$ alkyloxy-carbonyl is preferable, and examples of $C_{1-6}$ alkyl in the $C_{1-6}$ alkyloxy-carbonyl are methyl, ethyl, n-propyl, isopropyl, n-butyl, isobutyl, s-butyl, t-butyl, n-pentyl, isopentyl, neopentyl, n-hexyl. Among them, ethoxycarbonyl is most preferable.

The amidated carboxyl of $R^{4z}$ is exemplified by carbamoyl, N—$C_{1-4}$ alkyl-carbamoyl such as methylcarbamoyl, and isopropylcarbamoyl, 2-pyridylcarbamoyl, N—$C_{7-11}$ aralkyl-carbonyl such as benzylcarbamoyl.

As the more preferable groups in the compound (XXXI), $R^{1z}$ is N-benzyl-N-methylaminomethyl, $R^{2z}$ is propionylaminophenyl or isobutyrylaminophenyl, $R^{3z}$ is difluorobenzyl, and $R^{4z}$ is ethoxycarbonyl.

The compounds (X) to (XV), (XX), (XXI), (XXX) and (XXXI) and their salts which are employed in the present invention can be produced easily by per se known methods, as exemplified by the following production methods.

Production Method 1

In accordance with the method disclosed by K. Gewald, E. Schinke and H. Bøttcher, Chem. Ber., 99, 94–100 (1966), an adequate ketone or aldehyde having an active methylene (i) is allowed to react with a cyanoacetic acid ester derivative and sulfur to convert into a 2-aminothiophene derivative (ii). More specifically, in the case of using ketone ($R^{1'}\neq H$), a ketone (i) is subjected to heating under reflux together with a cyanoacetic acid ester derivative, in the presence of acetic acid and ammonium acetate, in a proper solvent such as toluene to give an alkylidene cyanoacetic acid ester derivative, which is then heated in an adequate solvent, for example, ethanol in the presence of sulfur and a base to afford a 2-aminothiophene derivative (ii). And, in the case of using aldehyde ($R^{1'}=H$), an aldehyde is heated in a proper solvent, for example, N,N-dimethylformamide, in the presence of a cyanoacetic acid ester derivative, sulfur and a base to give a 2-aminothiophene derivative (ii). The compound (ii) thus obtained is heated, in accordance with the method disclosed by Kuwata et al. (cf. German Patent 2,435,025), with diethyl ethoxymethylenemalonate to give an adduct (iii). The adduct is stirred in a solvent, which does not give undesirable effect on the reaction, e.g. alcohols such as ethanol and methanol, in the presence of a base, e.g. alkali metal hydroxide such as potassium hydroxide and sodium hydroxide, at a temperature ranging from about 10 to 70° C. to give carboxylic acid (iv). Then, the carboxylic acid (iv) thus obtained is subjected to ring-closure reaction by heating in polyphosphoric acid ester (PPE) to give a thieno[2,3-b] pyridine derivative (v). The compound (v) is stirred in a solvent, which does not give undesirable effect on the reaction, e.g. amides such as N,N-dimethylformamide and N,N-dimethylacetamide, in the presence of a halogenated aralkyl derivative and a base, e.g. an organic base such as pyridine and triethylamine, at a temperature ranging from about 10 to 100° C. to give a 4,7-dihydro-4-oxothieno[2,3-b]pyridine-5-carboxylic acid ester derivative shown by the formula (XIa). Then, the compound (XIa) is stirred together with N-bromosuccinimide (NBS) in a solvent, which does not give undesirable effect on the reaction, e.g. halogenated hydrocarbons such as carbon tetrachloride and chloroform, in the presence of α,α'-azobisisobutyronitrile (AIBN), at a temperature ranging from about 30 to 100° C. to give a compound (XIb). Upon necessity, the halogen atom in the compound (XIb) is converted to alkylsulfonyloxy, arylsulfonyloxy. The compound (XIb) is stirred together with various amines (H-$R^9$) in a solvent, which does not give undesirable effect on the reaction, e.g. amides such as N,N-dimethylformamide and N,N-dimethylacetamide, nitrile such as acetonitrile and alcohols such as ethanol, in the presence of a base at a temperatures ranging from about 10 to 100° C. to give the compound (XI') in the free form, and then the compound is treated with HCl—EtOH to produce the compound (XI). The Production Method 1 described above is shown in Scheme 1:

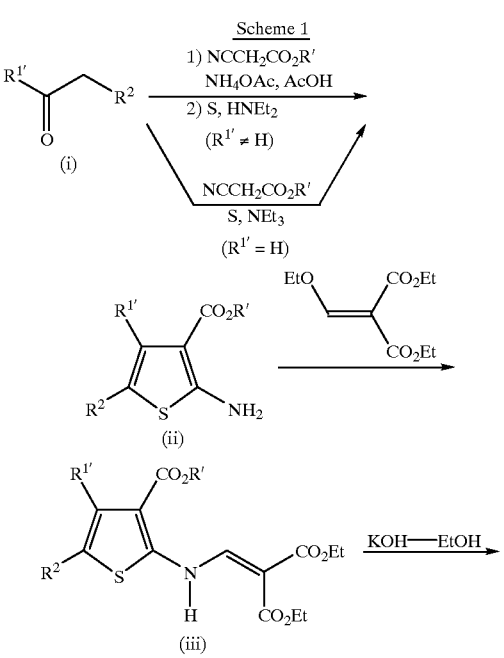

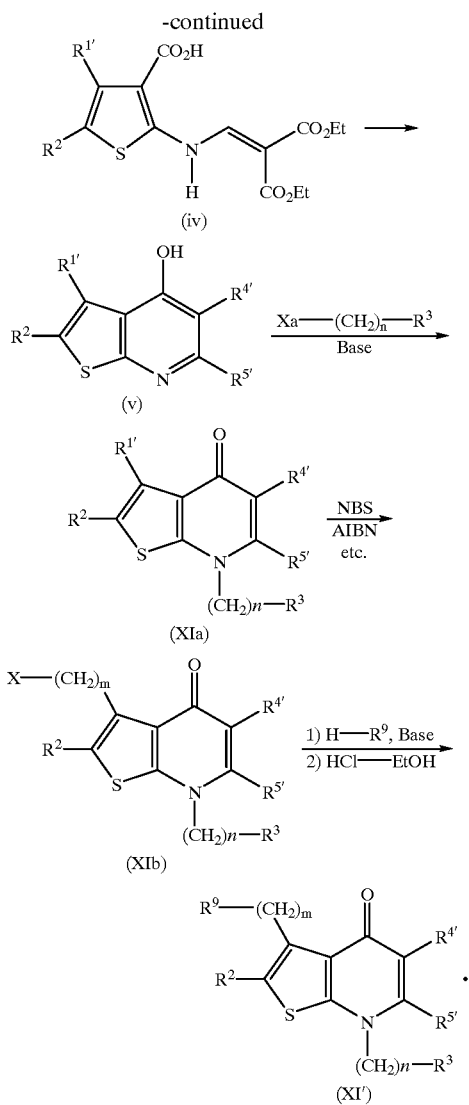

(iv)

(v)

(XIa)

(XIb)

(XI')

wherein $R^{1'}$ is hydrogen or an optionally substituted alkyl group, R' is an alkyl group, X is a leaving group, Xa is halogen, and $R^2$, $R^3$, $R^9$ and n are of the same meaning as defined above. $R^{4'}$ denotes ethoxycarbonyl. $R^{5'}$ denotes a hydrogen atom. m denotes an integer of 0 to 6.

The alkyl group shown by $R^{1'}$ and R' is of the same meaning as defined above f).

As the leaving group shown by X, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen (e.g. iodine, bromine chlorine), $C_{1-8}$ alkanoyloxy (e.g. acetoxy), $C_{1-6}$ alkylsulfonyloxy (e.g. methanesulfonyloxy), $C_{1-6}$ alkyl-$C_{6-14}$ arylsulfonyloxy (e.g. p-toluenesulfonyloxy), $C_{6-14}$ arylsulfonyloxy (e.g. benzenesulfonyloxy).

The halogen shown by Xa is fluorine, iodine, chlorine, iodine. Among these, bromine is more preferable.

Production Method 2

In the substantially same manner as in Production Method 1, a 2-aminothiophene derivative (vi) whose 5-position is unsubstituted, which can be synthesized by the method disclosed by Karl Gewald (K. Gewald, Chem. Ber., 98, 3571–3577 (1965); K. Gewald and E. Schinke, Chem. Ber., 99, 2712–2715 (1966)) is allowed to react with diethyl ethoxymethylene malonate under heating, in accordance with the method disclosed by Kuwata et al. German Patent 2,435,025, to give an adduct (vii). The adduct is stirred at temperature ranging from about 10 to 60° C. in a solvent, which does not affect adversely on the reaction, e.g. alcohols such as ethanol and methanol, in the presence of a suitable base, e.g. alkali metal hydroxide such as potassium hydroxide and sodium hydroxide, to give carboxylic acid (viii). The compound (viii) is subjected to various electrophilic substitution reactions and, depending on cases, to a suitable change of functional groups to introduce the substituent shown by $R^{2''}$, which is then subjected to ring-closure reaction under heating in polyphosphoric acid ester (PPE) to give a thieno[2,3-b]pyridine derivative (ix). As the electrophilic substitution reaction, mention is made of, for example, nitration (fuming nitric acid-concentrated sulfuric acid, sodium nitrate-concentrated sulfuric acid), acylation (acid chloride-aluminum chloride), formylation (phosphorus oxychloride-N,N-dimethylformamide or N-methylformanilide) and halogenation such as bromination (N-bromosuccinimide, bromine-pyridine). The compound (ix) is then processed in the substantially the same manner as in Production Method 1 to produce compounds (XIa'), (XIb') and (XI'). The Production Method 2 is shown in Scheme 2:

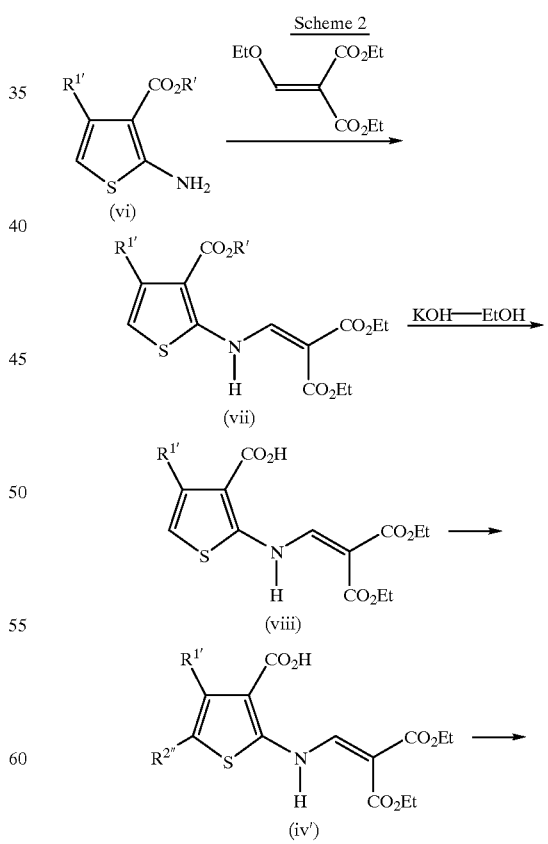

Scheme 2

(vi)

(vii)

(viii)

(iv')

-continued

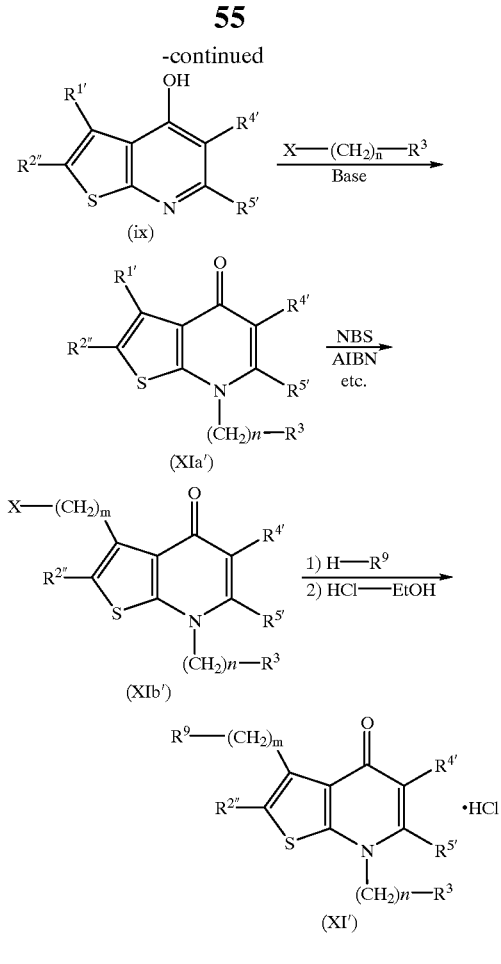

wherein each symbol has the same meaning as defined above.

Production Method 3

An alantonic acid derivative (x) is stirred at a temperature ranging from about 30 to 110° C. together with an equivalent or an excess amount of a compound of the formula: (CCl$_3$O)$_2$CO relative to the compound (x) in a solvent which does not adversely affect on the reaction (e.g. ethers such as tetrahydrofuran and 1,4-dioxane) to give an isatoic acid anhydride derivative (xi). Then, a halogenated aralkyl derivative shown by the formula (xii) is stirred at a temperature ranging from about 40 to 130° C. in a solvent, which does not affect adversely on the reaction, (ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide), in the presence of a base (e.g. alkali metal carbonate such as potassium carbonate, alkali metal hydride such as sodium hydride and potassium hydride, and alkali metal alkoxide such as potassium-butoxide), to give a substituted aralkyl derivative (xiii). The aralkyl derivative (xiii) is allowed to react with an equivalent or a little excess amount (e.g. about 1.1 to 1.5 equivalent) of a β-keto-acid ester derivative (xiv) relative to the compound (xiii) at a temperature ranging from 40 to 110° C. in a solvent, which does not affect adversely on the reaction, e.g. ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide, in the presence of a base (e.g. alkali metal carbonate such as potassium carbonate, alkali metal hydride such as sodium hydride and potassium hydride, and alkali metal alkoxide such as potassium-butoxide) to give the compound (Va). The foregoing Production Method 3 is shown in Scheme 3:

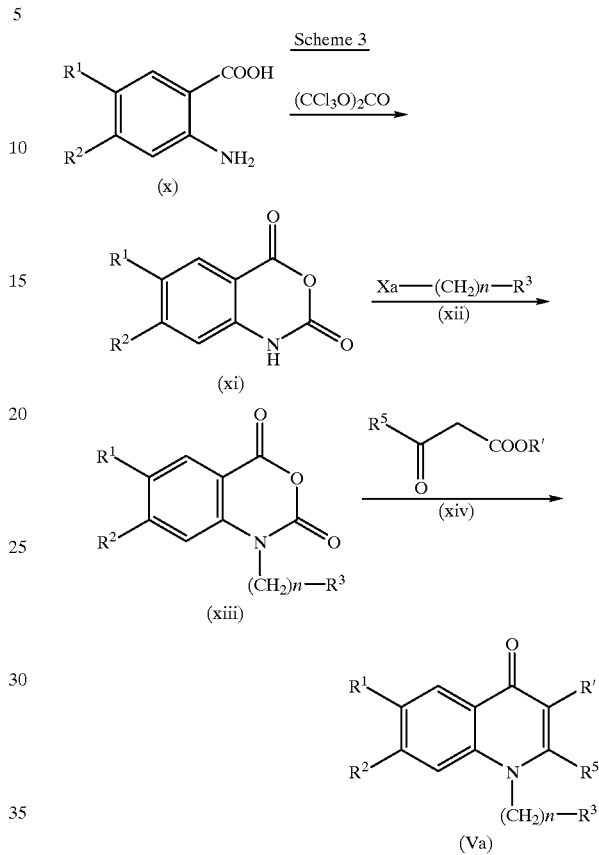

wherein each symbol is of the same meaning as defined above.

Production Method 4

A pyridine derivative (xv) is stirred, together with equivalent or an excess amount of the compound of the formula: (CCl$_3$O)$_2$CO relative to the compound (xv), in a solvent, which does not affect adversely on the reaction, (e.g. ethers such as tetrahydrofuran and 1,4-dioxane), at a temperature ranging from about 30 to 110° C. to give an acid anhydride derivative (xvi). Then, the halogenated aralkyl derivative shown by (xii) is stirred in a solvent, which does not affect adversely on the reaction, (e.g. ethers such as tetrahydrofuran and 1,4-dioxane, aromatic hydrocarbons such as benzene and toluene, amides such as N,N-dimethylformamide and N,N-dimethylacetamide, and alkyl sulfoxides such as dimethyl sulfoxide), at a temperature ranging from about 40 to 130° C. in the presence of a base (e.g. alkali metal carbonate such as potassium carbonate, alkali metal hydride such as sodium hydride and potassium hydride, and alkali metal alkoxide such as potassium butoxide) to give a substituted aralkyl derivative (xvii). The aralkyl derivative (xvii) is allowed to react with equivalent or a little excess amount (e.g. 1.1 to 1.5 equivalent) of a β-keto-acid ester derivative (xiv) in a solvent, which does not affect adversely on the reaction, (e.g. ethers such as tetrahydrofuran and 1,4-dioxane, aromatic hydrocarbons such as benzene and toluene, amides such as N,N-dimethylformamide and N,N-dimethylacetamide, and alkyl sulfoxides such as dimethyl sulfoxide), in the presence of a base (e.g. alkali metal carbonate such as potassium carbonate, alkali metal hydride such as sodium hydride and potassium hydride and alkali metal alkoxide such as potassium-butoxide), at a temperature ranging from about 40 to 110° C., to give the compound (Vb). The foregoing Production Method 4 is shown by Scheme 4:

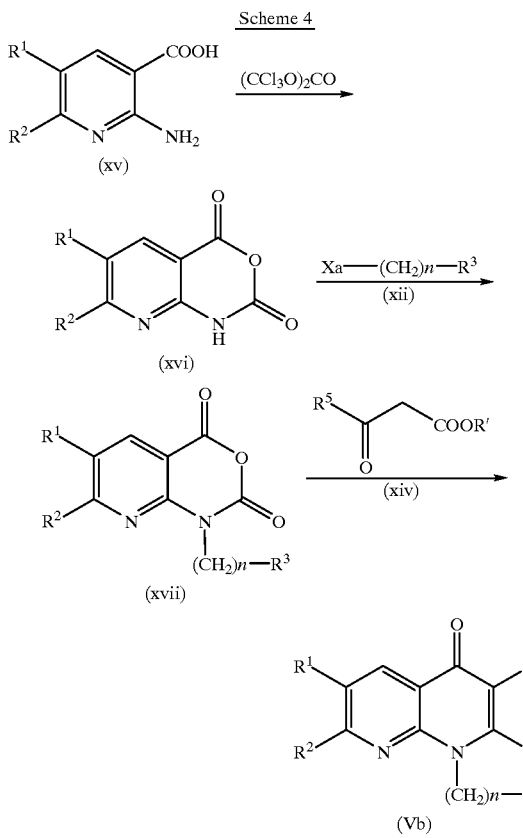

wherein each symbol is of the same meaning as defined above.

Production Method 5

In a suitable solvent, which does not affect adversely on the reaction, (e.g. ethers such as tetrahydrofuran, ethyl ether and dioxane), 4,7-dihydro-4-oxothieno[2,3-b]pyridine-5-carboxylic acid ester derivative (va) is stirred together with a suitable reducing agent (e.g. lithium aluminum hydride) at a temperature ranging from about 0 to 80° C. to give a 4,7-dihydro-4-oxothieno[2,3-b]pyridine derivative shown by the formula (XIc). The derivative obtained is stirred, together with a suitable oxidizing agent (e.g. manganese dioxide), in a suitable solvent (e.g. dichloromethane or chloroform) at a temperature ranging from about 10 to 80° C. to give a 5-formyl derivative. The derivative (XId) thus produced is stirred, together with a Grignard's reagent ($R^{25d}$MgXa), at a temperature ranging from about 0 to 80° C. in a solvent, which does not affect adversely on the reaction, (e.g. ethers such as tetrahydrofuran and ethyl ether) to give a corresponding secondary alcohol derivative (XIe). The compound (XIe) is stirred, together with a suitable oxidizing agent (e.g. metal oxide such as manganese dioxide), in a suitable solvent (e.g. halogenated hydrocarbons such as dichloromethane and chloroform) at a temperature ranging from about 10 to 80° C. to give a 5-carbonyl derivative (XIf). The foregoing Production Method 5 is shown in Scheme 5:

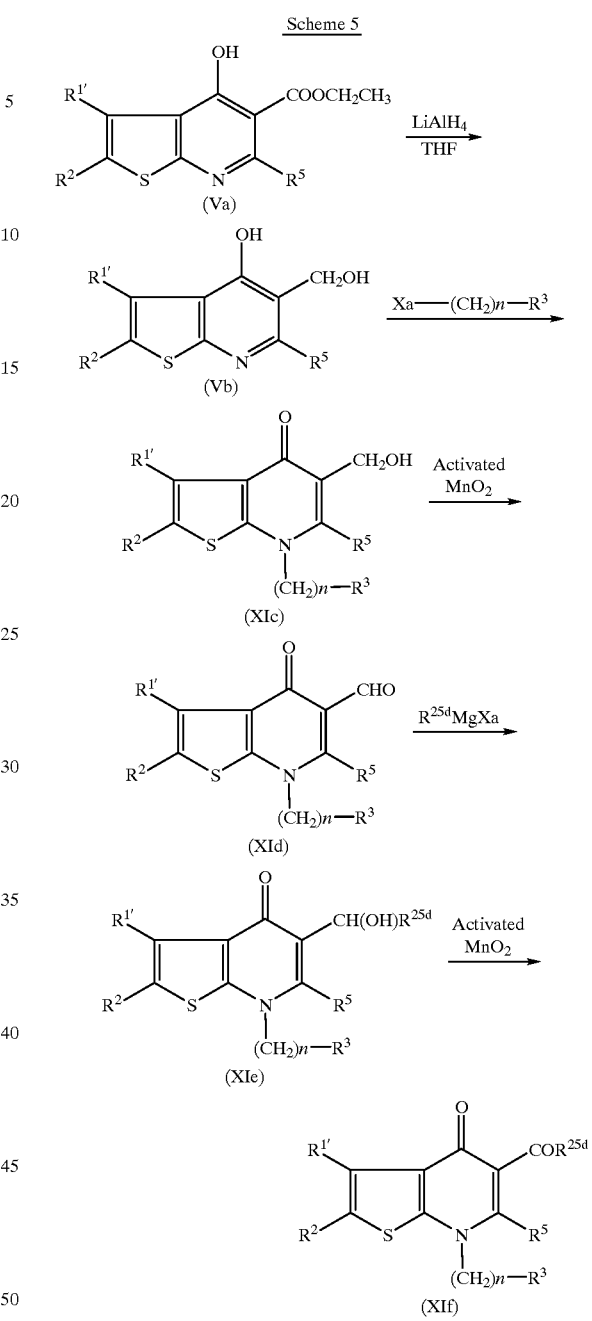

wherein $R^{25d}$ is hydrocarbon residue, and other symbols are of the same meaning as defined above.

The hydrocarbon residue shown by the above $R^{25d}$ is of the same meaning as the hydrocarbon residue in the carbonyl group substituted with hydrocarbon residue shown by the above-described $R^4$.

Production Method 6

4,7-Dihydro-4-oxothieno[2,3-b]pyridine-5-carboxylic acid ester derivative (XIa') is stirred at a temperature ranging from about 10 to 100° C., together with an aluminum amide derivative previously produced from a proper aluminum reagent [(e.g. trimethyl aluminum and diisobutyl aluminum hydride (DIBAL)] and amine in a suitable solvent, which does not affect adversely on the reaction, (e.g. halogenated hydrocarbons such as dichloromethane and ethers such as tetrahydrofuran, ethyl ether and dioxane), to give a 4,7- dihydro-4-oxothieno[2,3-b]pyridine-5-carboxylic acid amide derivative (XIa"). The said derivative (XIa") is stirred, together with a Grignard's reagent, in a proper solvent, which does not affect adversely on the reaction, (e.g. tetrahydrofuran and ethyl ether) at a temperature ranging from about −78° C. to 80° C. to give a corresponding ketone derivative (XIf). The foregoing Production Method 6 is shown in Scheme 6:

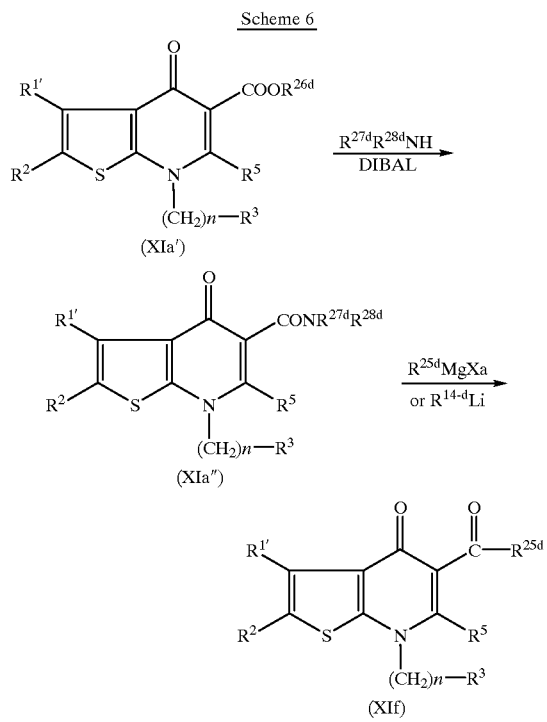

wherein $R^{26d}$ is $C_{1-6}$ alkyl or $C_{6-14}$ aryl; $R^{27d}$ and $R^{28d}$ are each hydrogen or hydrocarbon residue; and other symbols are of the same meaning as defined above.

The alkyl and aryl shown by the above $R^{26d}$ are of the same meaning as defined above f) or k).

The hydrocarbon residue shown by the above $R^{27d}$ and $R^{28d}$ has the same meaning as the hydrocarbon residue in the carbonyl group substituted with hydrocarbon residue shown by the above $R^4$.

Production Method 7

In a proper solvent, which does not affect adversely on the reaction, e.g. halogenated hydrocarbons such as dichloromethane; ethers such as tetrahydrofuran, ethyl ether and dioxane; and pyridine, a 4,7-dihydro-5-hydroxymethyl-4-oxothieno[2,3-b]pyridine derivative (XIc) is stirred together with a suitable halogenating reagent (e.g. thionyl chloride and methanesulfonyl chloride) at a temperature ranging from about 0 to 100° C. to give a 4,7-dihydro-5-halomethyl-4-oxothieno[2,3-b]pyridine derivative (XIg). The derivative (XIg) is stirred, together with a suitable nucleophilic reagent, in a proper solvent, which does not affect adversely on the reaction, e.g. ethers such as tetrahydrofuran and ethyl ether; and amides such as dimethylformamide, to give a corresponding 5-substituted derivative (XIh). The above Production Method 7 is shown in Scheme 7:

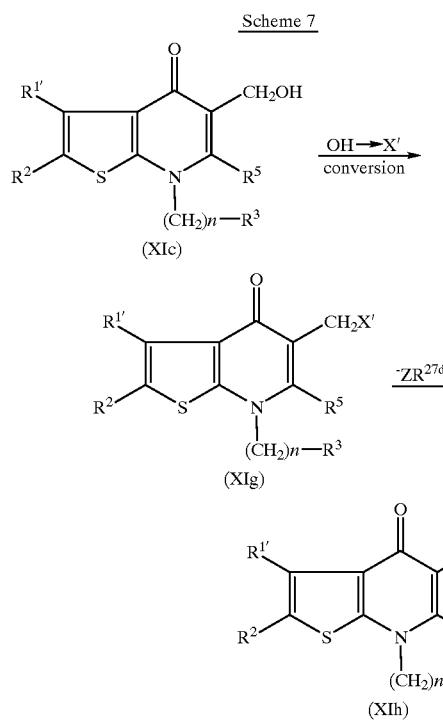

wherein X' is a leaving group, Z is an oxygen atom, a sulfur atom, a group of the formula: —NH or a nitrogen atom substituted with hydrocarbon residue, and other symbols are of the same meaning as defined above.

As the leaving group shown by the above X', mention is made of, for example, groups readily susceptible to substitution reaction by a nucleophilic reagent, e.g. the hydrocarbon residue having a hetero-atom with negative electric charge (e.g. oxygen atom, sulfur atom and nitrogen atom) shown by the above $^-ZR^{27d}$. More specifically, for example, halogen (e.g. chlorine, bromine, iodine), $C_{7-20}$ aralkyloxy (e.g. acetoxy), $C_{1-6}$ alkylsulfonyloxy (e.g. methanesulfonyloxy) and $C_{1-6}$ alkyl-$C_{6-14}$ aryl sulfonyloxy (e.g. p-toluenesulfonyloxy) are mentioned.

The hydrocarbon residue in the nitrogen atom substituted with hydrocarbon residue mentioned above has the same meaning as defined in reference to the hydrocarbon residue in the carbonyl group substituted with hydrocarbon residue shown by the above-mentioned $R^4$.

Production Method 8

In a proper solvent, which does not affect adversely on the reaction, e.g. ethers such as tetrahydrofuran, ethyl ether and dioxane; and pyridine, 4,7-dihydro-5-formy-4-oxothieno[2,3-b]pyridine derivative (XId) is stirred together with a suitable Wittig reagent at a temperature ranging from about 0 to 100° C. to give a derivative (XIi). The said derivative (XIi) is stirred at a temperature ranging from about 10 to 100° C. together with a suitable reducing reagent, e.g. hydrogenation using, in hydrogen streams, a catalyst (e.g. palladium-carbon catalyst), in a proper solvent, which does not affect adversely on the reaction (e.g. alcohols such as ethyl alcohol, esters such as acetic acid ethyl ester, ethers such as tetrahydrofuran, ethyl ether and dimethylformamide) to give a corresponding 5-substituted derivative (XIj). The above production method 8 is shown in Scheme 8:

Scheme 8

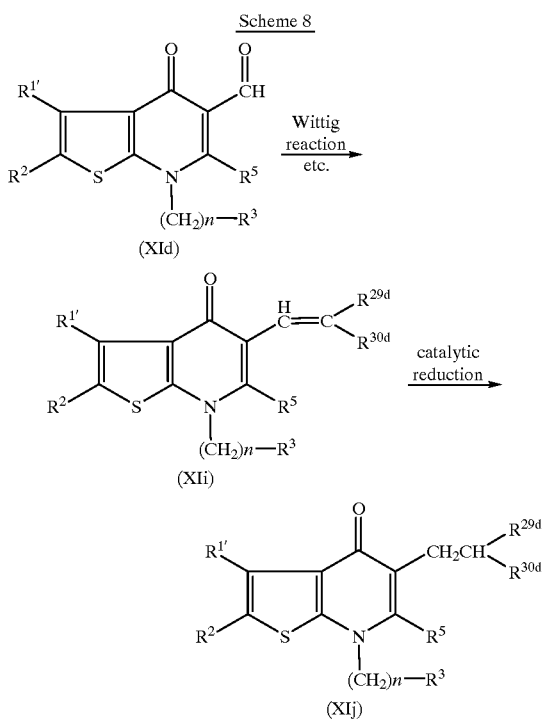

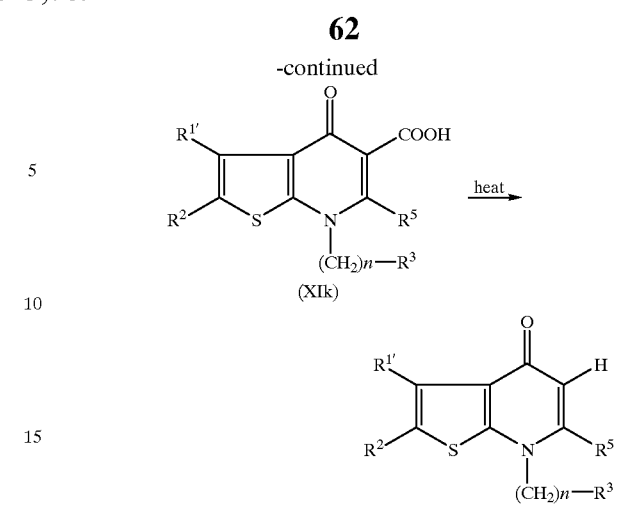

wherein each symbol is of the same meaning as defined above.

Production Method 10

Starting from the 2-aminothiophene derivative (ii), the urea derivative (II) is produced by, for example, the following method A or B.

1. Method A: The 2-aminothiophene derivative (ii) produced by the method described in Production Method 1 or a salt thereof is allowed to react with an isocyanate derivative. The isocyanate derivative is exemplified by derivatives represented by the formula, $R^{2f}$—NCO (wherein $R^{2f}$ is of the same meaning as defined above). The reaction of the compound (ii) or a salt thereof with the isocyanate derivative is conducted in an solvent which does not adversely affect on the reaction (e.g. tetrahydrofuran, pyridine, dioxane, benzene, dichloromethane, 1,2-dichloroethane, toluene, xylene) at a temperature ranging from about 15 to about 130° C. The isocyanate derivative is employed in an amount of about 1 to 5 equivalents, preferably about 1.1 to 2.5 equivalents, relative to 1 equivalent of the compound (ii). The reaction time ranges from several hours to several days, preferably from about 15 minutes -to about two days.

wherein $R^{29d}$ and $R^{30d}$ are each hydrogen or hydrocarbon residue, and other symbols are of the same meaning as defined above.

The hydrocarbon residue shown by the above-mentioned $R^{29d}$ and $R^{30d}$ has the same meaning as the hydrocarbon residue in the carbonyl group substituted with the hydrocarbon residue shown by the above-mentioned $R^4$.

Production Method 9

In a proper solvent, which does not affect adversely on the reaction, e.g. ethers such as tetrahydrofuran and dioxane; and alcohols such as ethyl alcohol, 4,7-dihydro-4-oxothieno [2,3-b]pyridine-5-carboxylic acid ester derivative (XIf') is subjected to hydrolysis under stirring at a temperature ranging from about 10 to 100° C. by adding an acid (e.g. inorganic acid such as hydrochloric acid) or an alkaline aqueous solution (e.g. 1–4N aqueous solution of alkali metal hydroxide such as sodium hydroxide, potassium hydroxide and lithium hydroxide). The resulting 5-carboxylic acid derivative (XIk) is heated at a temperature ranging from about 50 to 200° C. in a proper solvent, which does not affect adversely on the reaction, to give a corresponding decarboxylated derivative (XIn). The foregoing production method 9 is shown by Scheme 9:

2. Method B: Amine, e.g. a compound represented by the formula $R^{2f}$—$NH_2$ wherein $R^{2f}$ is of the same meaning as defined above, is subjected to addition reaction to an isocyanate derivative produced by allowing a 2-aminothiophene derivative (ii) or a salt thereof to react with phosgene or an equivalent compound thereof, e.g. diphosgene such as bis(trichloromethyl)carbonate, triphosgene such as trichloromethylchloroformate. The reaction of the compound (ii) or a salt thereof with phosgene or an equivalent compound thereof is conducted in a solvent which does not affect adversely on the reaction (e.g. dioxane, tetrahydrofuran, benzene, toluene, xylene, 1,2-dichloroethane, chloroform) at a temperature ranging from about 40 to 120° C. Phosgene or an equivalent compound thereof is employed in an amount ranging from about 0.5 to 2 equivalents, preferably from about 0.9 to 1.1 equivalent. The reaction time ranges from several minutes to several days, preferably from about 15 minutes to about two days. The addition reaction of amine is conducted in a solvent which does not affect adversely on the reaction (e.g. pyridine, tetrahydrofuran, dioxane, benzene, dichloromethane, 1,2-dichloroethane, toluene, xylene) at a temperature ranging from about 15 to 130° C. Amine is employed in an amount ranging from about 1 to 5 equivalents, preferably from about 1.1 to 3 equivalents.

Scheme 9

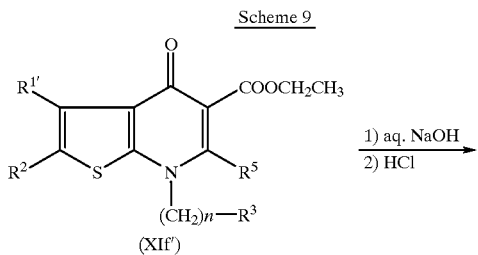

The reaction time ranges from several minutes to several days, preferably from about 15 minutes to about two days.

The compound (xv) or a salt thereof thus produced is processed with a base to cause ring-closure reaction to thereby produce a thieno [2,3-d] pyrimidine derivative (xvi). The ring-closure reaction is conducted in a solvent which does not affect adversely on the reaction. The solvent is exemplified by alcohols such as methanol, ethanol or propanol, and ethers such as dioxane or tetrahydrofuran.

As the base, use is made of, for example, an alkali metal alkoxide such as sodium methylate, sodium ethylate or sodium isopropoxide, and an alkali metal hydride such as sodium hydride.

The amount of the base to be employed ranges from 1 to 5 equivalents, preferably from about 1.5 to 3 equivalents, relative to 1 equivalent of the compound (xv).

The reaction temperature ranges from about 10° C. to the boiling point of the solvent then employed, preferably from about 25° C. to the boiling point of the solvent then employed.

The reaction time ranges from several minutes to several days, preferably from about 10 minutes to two days.

The compound (xvi) and a halogenated aralkyl derivative are stirred, in the presence of a base (e.g. an organic base such as pyridine or triethylamine), in a solvent which does not affect adversely on the reaction (e.g. amides such as dimethylformamide or dimethylacetamide), at about 10 to 100° C., to produce a 2,4-dioxothieno[2,3-d]pyrimidine derivative (IIa). Subsequently, the said compound (IIa) is stirred together with N-bromosuccinimide (NBS) in a solvent which does not affect adversely on the reaction (e.g. halogenated hydrocarbons such as carbon tetrachloride or chloroform), in the presence of α, α'-azobisisobutyronitrile, to thereby produce the compound (IIb). Further, the said compound is stirred together with various amines, in the presence of a base, in a solvent which does not affect adversely on the reaction (e.g. amides such as dimethylformamide or dimethylacetamide, nitriles such as acetonitrile, alcohols such as ethanol), at a temperature ranging from about 10 to 100° C., to thereby produce the compound (II). When necessary, the said compound is made into a corresponding salt with a suitable acid (e.g. hydrochloric acid or oxalic acid).

The foregoing Production Method 10 is shown by Scheme 10:

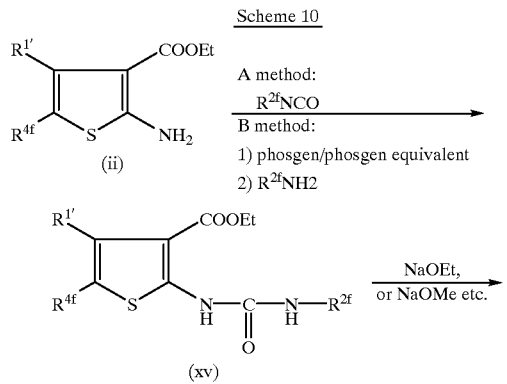

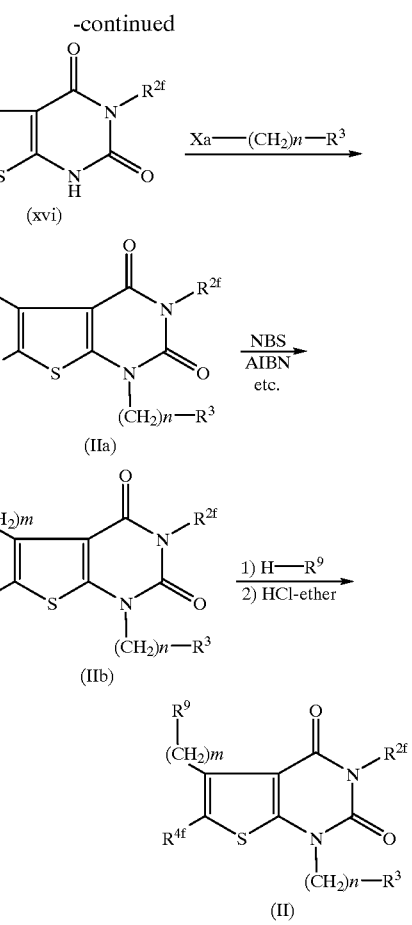

wherein each symbol is of the same meaning as defined above.

Production Method 11

The amino group of a 2-aminothiophene derivative (xvii) is protected (e.g. Boc), which is stirred, in accordance with the method of German Patent, 2155403 (1972), or the method of JP-B 73-01664 (1973) together with a halogenated acyl derivative, in the presence of a base, in a solvent which does not affect adversely on the reaction (e.g. amides such as dimethylformamide or dimethylacetamide) at a temperature ranging from about 0 to 100° C. to give a derivative (xviii), which is stirred together with a suitable salt (e.g. lithium iodide) in a suitable solvent (e.g. acetone or methyl ethyl ketone) to give a derivative (xix), which is subjected to substitution reaction with a suitable amine (e.g. ammonia) to give a derivative (xx), which is stirred in a solvent which does not affect adversely on the reaction (e.g. toluene, dimethylformamide, dimethylacetamide, methanol or ethanol), when necessary in the presence of a suitable catalyst (e.g. sodium ethoxide or toluenesulfonic acid) at a temperature ranging from about 30 to 120° C., to cause dehydrocyclization to thereby produce a derivative (VIIa). The said compound is stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at a temperature ranging from about 10 to 100° C. to give a 2-oxothieno [2,3-e] azepine derivative (viib). Subsequently, the said compound (VIIb) is stirred together with N-bromosuccinimide (NBS) in a solvent (e.g. halogenated hydrocarbons including carbon tetrachloride and chloroform), in the presence of α,α'-azobisisobutyronitrile, at a temperature ranging from about 30 to 100° C., to give a compound (VIIc). The said compound is stirred with various amines in the presence of a base, in a solvent which does not affect adversely on the reaction (e.g. amides including dimethylformamide and dimethylacetamide, nitriles including acetonitrile, and alcohols including ethanol) at a temperature ranging from about 10 to 100° C. to give a compound (VIId). When necessary, the said compound is made into a corresponding salt with a suitable acid (e.g. hydrochloric acid or oxalic acid). The foregoing Production Method 11 is shown in Scheme 11:

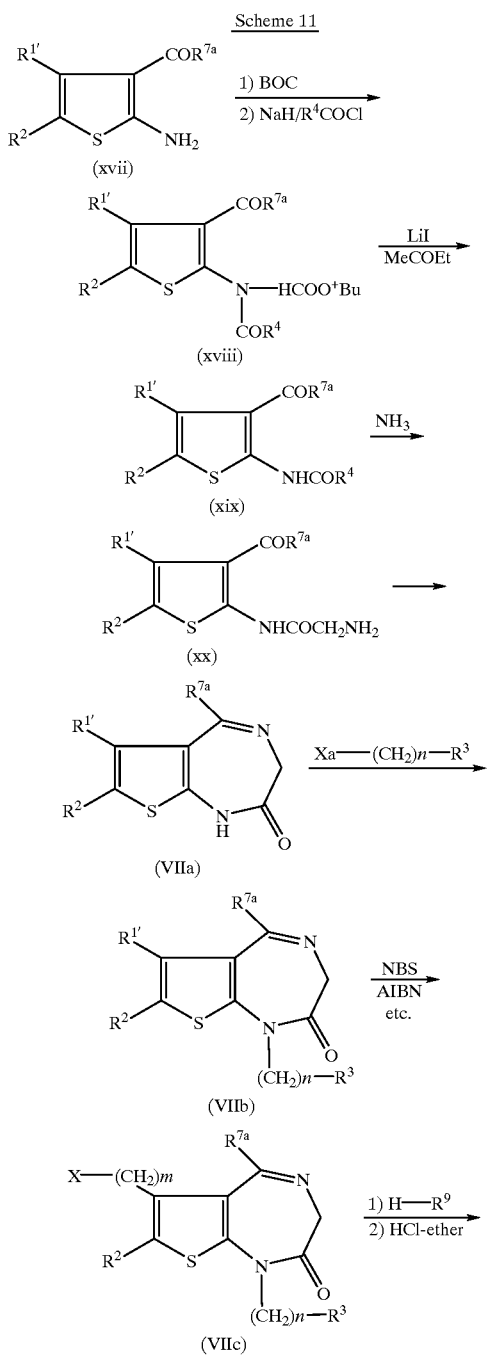

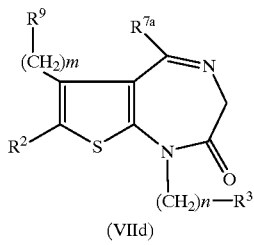

wherein each symbol is of the same meaning as defined above.

Production Method 12

The amino group of a 2-aminothiophene derivative (ii) producible by the method described in Production Method 1 is protected (e.g. Boc), which is stirred together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at a temperature ranging from about 10 to 100° C., to give a derivative (xxi), which is subjected to alkali hydrolysis with a suitable alkali (e.g. sodium hydroxide) in a suitable solvent (e.g. methanol, tetrahydrofuran), and, the derivative thus produced is stirred together with diphenylphosphorylazide (DPPA) in a solvent which does not affect adversely on the reaction (e.g. toluene, tetrahydrofuran, dimethylformamide, dimethylacetamide, ethanol) at a temperature ranging from about 0 to 100° C., and the resultant is converted into a carbamic acid ester derivative (xxii) with a suitable alcohol (e.g. ethanol). The said derivative is stirred, in the presence of a base (e.g. sodium ethoxide), in a solvent which does not affect adversely on the reaction (e.g. dimethylformamide, dimethylacetamide), at a temperature ranging from about 0 to 100° C. to give a 2-oxothieno[2,3-d] imidazol derivative (VIIe). The said compound is stirred together with a halogenated alkyl derivative, in the presence of a base, in a solvent which does not affect adversely on the reaction (e.g. amides including dimethylformamide, dimethylacetamide), at a temperature ranging from about 0 to 100° C. to give a compound (VIIf). Subsequently, the said compound (VIIf) is stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile, at a temperature ranging from about 30 to 100° C. to give a compound (VIIg). The said compound is further stirred, together with various amine, in the presence of a base, in a solvent which does not affect adversely on the reaction (e.g. amides including dimethylformamide and dimethylacetamide, nitriles including acetonitrile, alcohols including ethanol), at a temperature ranging from about 10 to 100° C. to produce a compound (VIIh). The said compound, when necessary, is converted into a corresponding salt with a suitable acid (e.g. hydrochloric acid, oxalic acid). The foregoing Production Method 12 is shown in Scheme 12:

Scheme 12

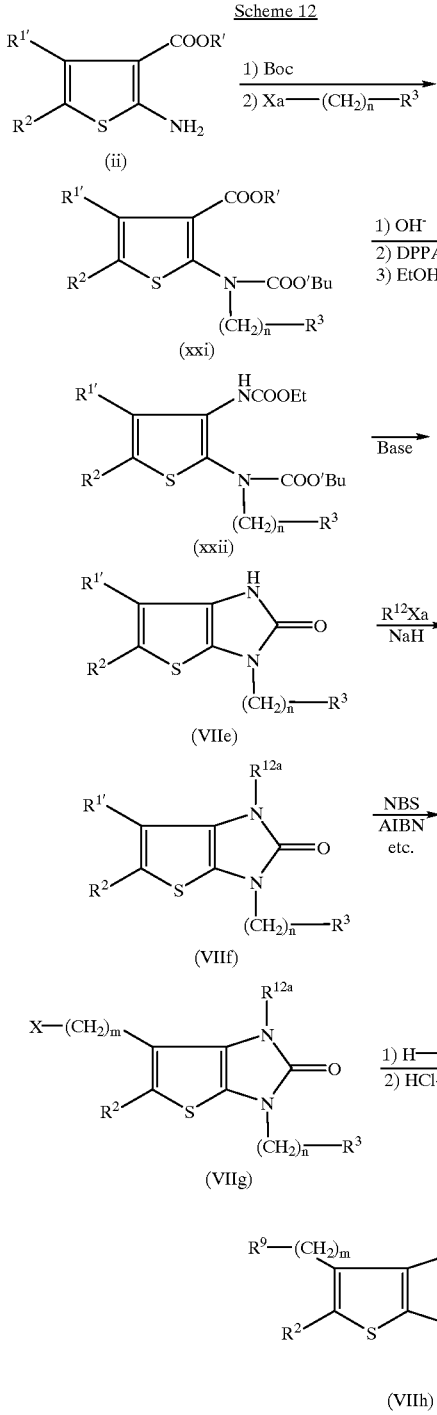

wherein each symbol is of the same meaning as defined above.

Production Method 13

Starting from a 2-aminothiophene derivative (ii) producible by the method described in Production Method 1 or a salt thereof, 4,5-dihydro-7-hydroxy-5-oxothieno [3,2-b] pyridine-6-carboxylic acid ethyl derivative (VIIj) is produced by the method of J. M. Barker et al. (J. Chem. Res. (M), 1980, 113; J. Chem. Res. (s), 6(1980)). More specifically, the 2-aminothiophene derivative (ii) or a salt thereof is allowed to react with malonic acid ester to give the compound (xxiii), which is stirred, in the presence of a suitable base (e.g. sodium hydride), in a solvent which does not affect adversely on the reaction (e.g. amides including dimethylformamide (DMF) and dimethyl acetamide), at a temperature ranging from about 10 to 100° C. to give the derivative (VIIj). The said derivative (VIIj) is stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethyl acetamide), at a temperature ranging from about 10 to 100° C. to give a derivative (VIIk), and, the said derivative is stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile (AIBN), at a temperature ranging from about 30 to 100° C. to give the compound (VIIm). Further, the said compound was stirred, together with various amines, in the presence of a base, in a solvent which does not affect adversely on the reaction (e.g. amides including dimethylformamide and dimethyl acetamide, nitrites including acetonitrile, alcohols including ethanol), at a temperature ranging from about 10 to 100° C. to produce the compound (VIIn). When necessary, the said compound is made into a corresponding salt with a suitable acid (e.g. hydrochloric acid, oxalic acid). The foregoing Production Method 13 is shown in Scheme 13:

Scheme 13

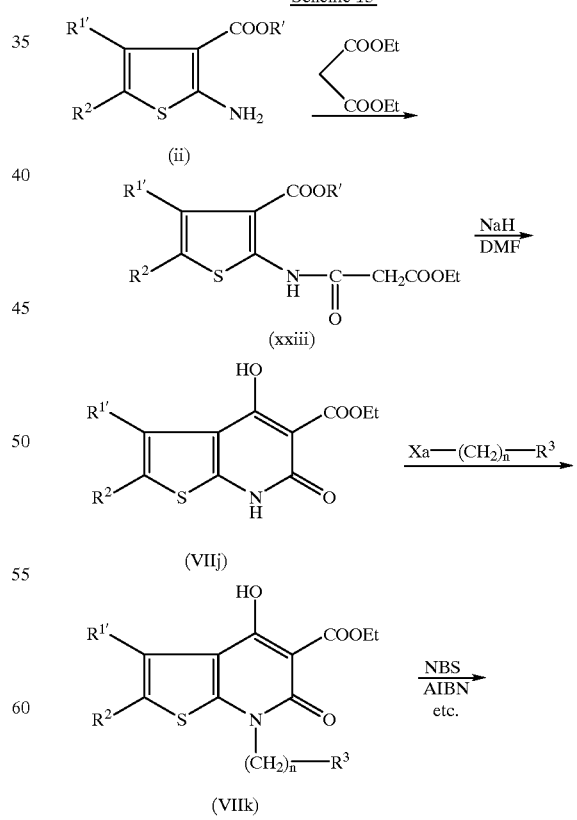

-continued

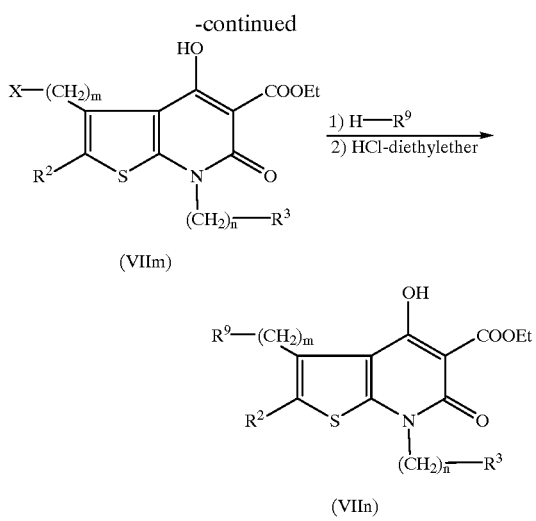

(VIIm)

(VIIn)

wherein each symbol is of the same meaning as defined above.

Production Method 14

In a suitable solvent which does not affect adversely on the reaction (e.g. halogenated hydrocarbons including dichloromethane, and ethers including tetrahydrofuran, ethyl ether and dioxane), the 1,4-dihydro-4-oxoquinoline-3-carboxylic acid ester derivative (Va') is stirred, together with an aluminum amide derivative produced from a suitable aluminum reagent, e.g. trimethyl aluminum, triethyl aluminum or diisobutyl aluminum hydride (DIBAL), and amines, at a temperature ranging from about 10 to 100° C. to give a 1,4-dihydro-4-oxoquinoline-3-carboxylic acid amide derivative (Va"). The said derivative is stirred, together with a Grignard reagent ($R^{14d}$ MgXa), in a suitable solvent (e.g. tetrahydrofuran and ethyl ether) at a temperature ranging from 0 to 80° C. to give a corresponding ketone derivative (Vc). The above Production Method 14 is shown in Scheme 14:

-continued

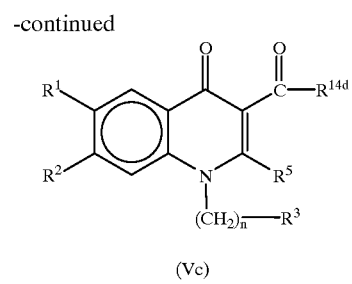

(Vc)

wherein $R^{26d}$ is $C_{1-6}$ alkyl or $C_{6-14}$aryl, $R^{27d}$ and $R^{28d}$ are each hydrogen or hydrocarbon residue, and other symbols are of the same meaning as defined in the foregoing.

The $C_{1-6}$ alkyl and $C_{6-14}$ aryl shown by the above-mentioned $R^{26d}$ is of the same meaning as defined in above f) and k).

The hydrocarbon residues shown by the above-mentioned $R^{27d}$ and $R^{28d}$ are of the same meaning as the hydrocarbon residue in the optionally substituted carbonyl group with a hydrocarbon residue shown by the above-mentioned R'.

Production Method 15

In a suitable solvent which does not affect adversely on the reaction (e.g. halogenated hydrocarbons including dichloromethane, and ethers including tetrahydrofuran, ethyl ether and dioxane), 1,4-dihydro-4-oxopyrido [2,3-b] pyridine-3-carboxylic acid ester derivative (Vd) is stirred, together with an aluminum amide derivative produced from a suitable aluminum reagent [e.g. trimethyl aluminum, triethyl aluminum and diisobutyl aluminum hydride (DIBAL)] and amines, at a temperature ranging from about 10 to 100° C. to give a 1,4-dihydro-4-oxopyrido[2,3-b]pyridine-3-carboxylic acid amide derivative (Vd'). The said derivative is stirred, together with a Grignard reagent, in a suitable solvent which does not affect adversely on the reaction (e.g. tetrahydrofuran and ethyl ether), at a temperature ranging from about 0 to 80° C. to give a corresponding ketone derivative (Ve). The Production Method is shown in Scheme 15:

Scheme 14

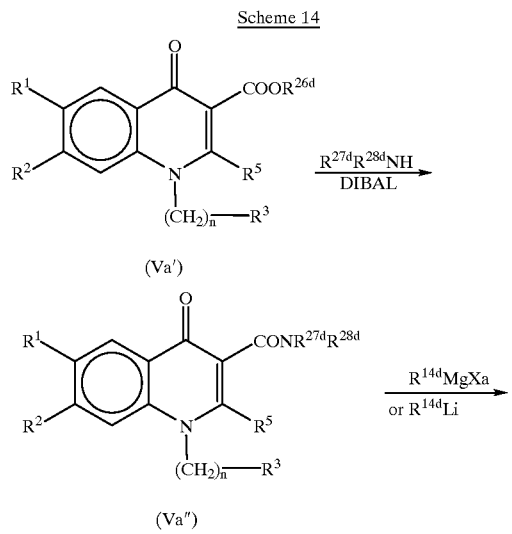

Scheme 15

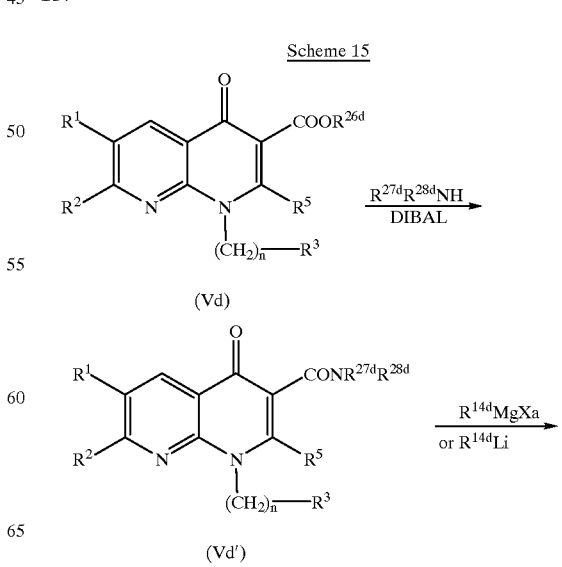

-continued

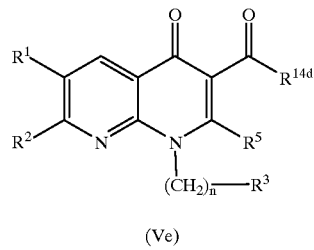

(Ve)

wherein $R^{26d}$ is $C_{1-6}$ alkyl or $C_{6-14}$ aryl, $R^{27d}$ and $R^{28d}$ are each hydrogen or hydrocarbon residue, and other symbols are of the same meaning as defined above f) and k).

The $C_{1-6}$ alkyl and $C_{6-14}$ aryl shown by the above $R^{26d}$ are of the same meaning as defined above.

The hydrocarbon residue shown by the above $R^{27d}$ and $R^{28d}$ is of the same meaning as the hydrocarbon residue in the carbonyl group optionally substituted with hydrocarbon residue shown by the above-mentioned R'.

Production Method 16

4,7-Dihydro-2-halogeno-4-oxothieno[2,3-b]pyridine derivative (XIp) is dissolved in a suitable solvent which does not affect adversely on the reaction (e.g. ethers including 1,2-dimethoxyethane, tetrahydrofuran and dioxane and alcohols including ethyl alcohol). To the solution is added, in the presence of equimolar to an excess amount (2 to 10 equivalents) of a suitable base (e.g. sodium carbonate), a suitable aryl boric acid derivative (e.g. phenyl boric acid, 3-methoxyphenyl boric acid and 4-ethoxycarbonyl phenyl boric acid). To the mixture is added, in the streams of an inert gas (e.g. argon gas), a suitable catalyst [e.g. palladium metal including tetrakis (triphenylphosphine) palladium]. The mixture is stirred for a period ranging from several minutes to several hours at a temperature ranging from about 10 to 100° C. Insoluble substances are removed to leave the desired derivative (XIq). The foregoing Production Method 16 is shown in Scheme 16:

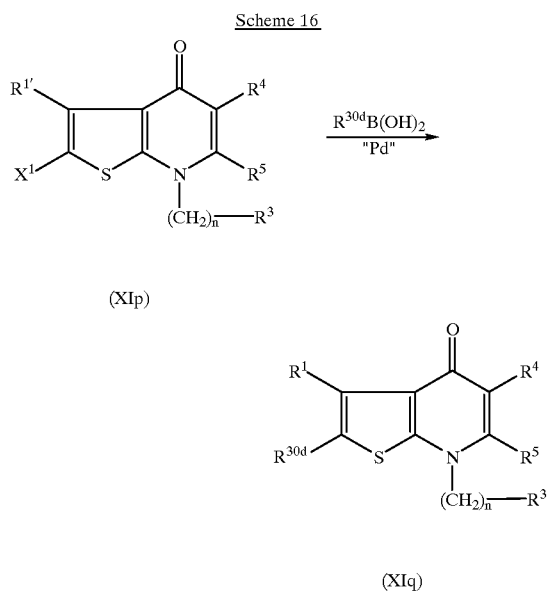

wherein wherein X' is halogen $R^{30d}$ is an optionally substituted aryl group, and other symbols are of the same meaning as defined above.

Production Method 17

Production of a derivative which has 2,5-dioxo-4-imidazolidinyl at 5-position is illustrated in Scheme 17, infra:

The formyl derivative (ih), which is obtained in the above Production Method 5 or its similar method, is reacted with a sodium bisulfite in an appropriate solvent, e.g. water, ethanol. The reaction is carried out at 0° C. to 80° C. under stirring to give a sulfuric acid additive (iih).

To the additive (iih) is added a cyano compound, e.g. potassium cyanide, sodium cyanide, in an appropriate solvent, e.g. aqueous ethanol, aqueous tetrahydrofuran, dioxane, in the presence of an equivalent to an excess amount of a base, e.g. ammonium carbonate. The reaction is carried out at 0° C. to 80° C. under stirring, and under refluxing when required, to give an imidazolidinyl derivative (XIIa).

The foregoing method is shown in Scheme 17. In Scheme 17, all the groups have the same meaning as defined above.

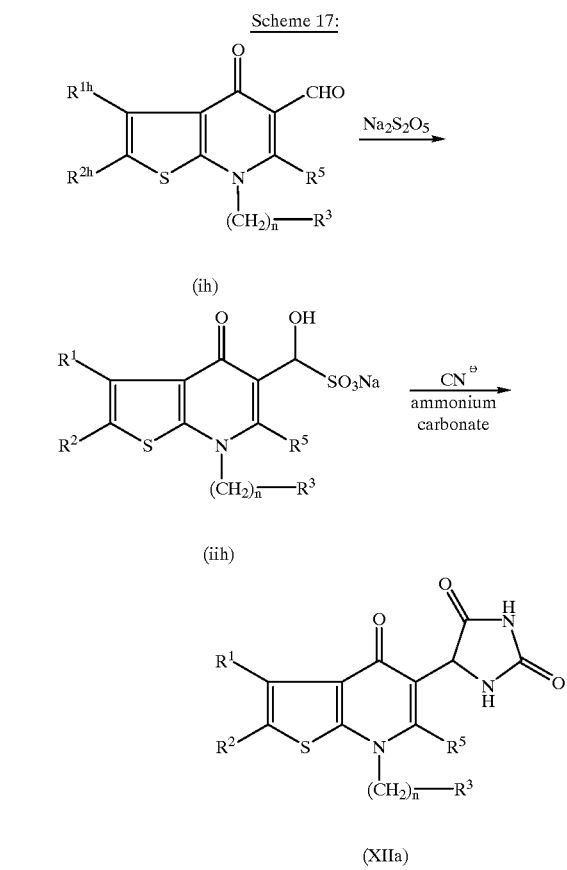

Production Method 18

Production of a compound which has an oxazolyl group at 5-position is illustrated in Scheme 18, infra:

The derivative (iiih), which has a formyl group at 5-position, is reacted with an equivalent to excess amount of tosylmethylisoniazide in an appropriate solvent, e.g. methanol, ethanol, in the presence of an equivalent to an excess amount of a base, e.g. potassium carbonate. The reaction is carried out at 0° C. to 80° C. under stirring, and under refluxing when required, to give a derivative (XIIb) which has an oxazolyl group at 5-position.

The foregoing production method is shown in Scheme 18. In scheme 18, other groups have the same meaning as defined above.

Scheme 18:

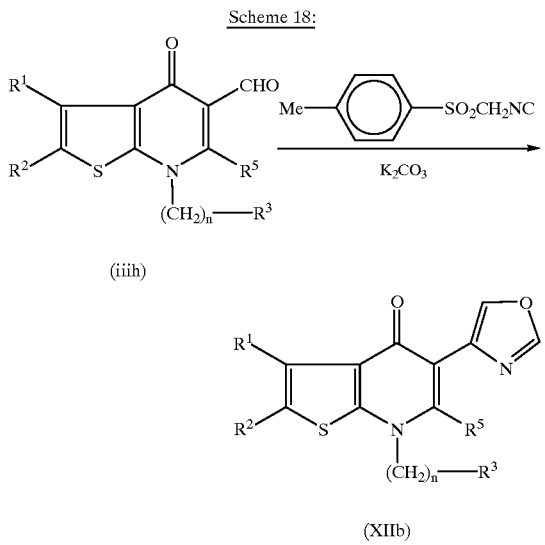

Production Method 19

Production of a compound having 4-imidazolyl group or 4-thiazolyl group at 5-position is illustrated in Scheme 19, infra:

4,7-Dihydro-5-acyl-4-oxothieno[2,3-b]pyridine derivative (ivh), obtained in Production Method 5 or 6, is dissolved in an appropriate solvent, e.g. acetic acid, methanol, tetrahydrofuran, ethylether, dioxane.

To the solution an equivalent to a small excess of halogenating agent, e.g. bromine or iodine, is added dropwise at room temperature or under ice-cooling. The mixture is stirred at a temperature of 0° C. to 80° C. to give an α-haloketon derivative (vh).

α-Haloketon derivative (vh) is dissolved in an appropriate solvent, e.g. methanol, tetrahydrofuran, ethylether, dioxane, dimethylformamide. To the solution is added an equivalent to a small excess amount of amidine derivative at room temperature or under ice-cooling. The mixture is stirred at a temperature of 0° C. to 80° C., and the system is heated if required, to give a 4-imidazolyl derivative (XIIc).

The α-haloketone derivative (vh) is reacted with a thiocarbamoyl derivative in an appropriate solvent, e.g. methanol, ethanol, dimethylformamide, dimethylacetamide, at a temperature of about 10° C. to 100° C. under stirring to give a 4-thiazolyl derivative (XIId).

Similar to the above, the α-haloketone derivative is reacted with a thioglycolic acid amide, and then subjected to a ring-closure reaction to give a 1,4-thiazinyl derivative.

The foregoing method of the production of imidazolyl derivative and thiazolyl derivative is shown in Scheme 19. In Scheme 19, $R^{43h}$ denotes hydrogen atom, $C_{1-6}$ alkyl or $C_{6-14}$ aryl. $R^{44h}$ denotes hydrogen atom, $C_{1-6}$ alkyl or $C_{6-14}$ aryl. $R^1$, $R^2$, $R^3$, $R^5$ and n have the same meaning as defined above. Xa denotes a halogen atom.

Scheme 19:

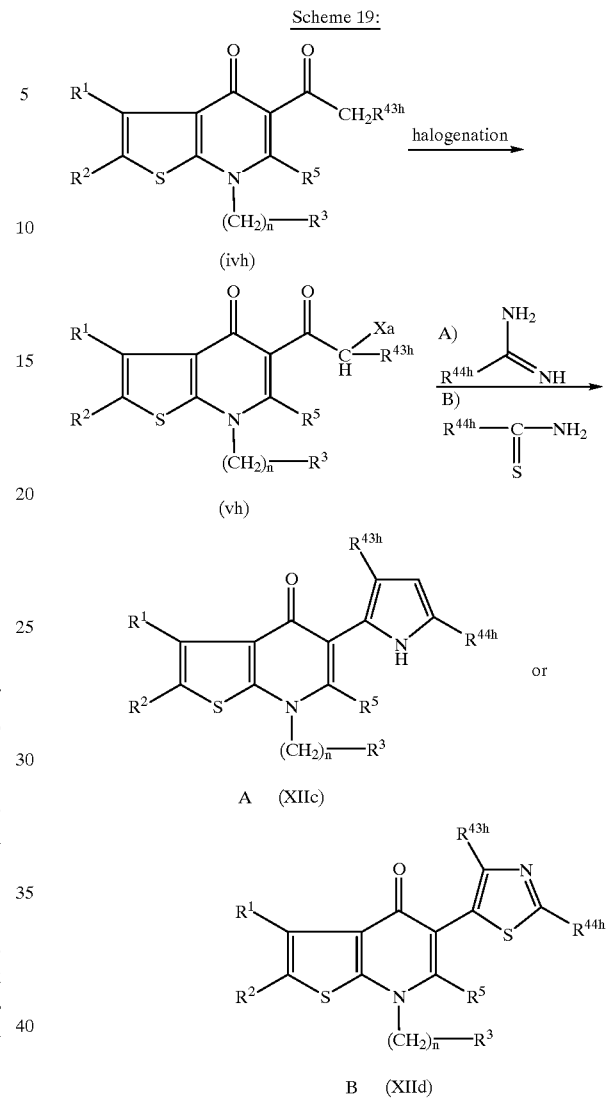

Production Method 20

Production of a compound having 2-oxazolyl group at 5-position is illustrated in Scheme 10, infra:

4,7-Dihydro-5-carbamoyl-4-oxothieno[2,3-6]pyridine derivative (vih), obtained by the first step in the above Production Method 6, is dissolved in an appropriate solvent, e.g. methanol, ethanol, tetrahydrofuran, dioxane, and to the solution is added an equivalent to a small excess of α-haloketone compound dropwise at room temperature or under ice-cooling. The mixture is stirred at 0° C. to 80° C., and refluxed under heating if required, to give a 2-oxazolyl derivative (XIIe).

The foregoing method is shown in Scheme 20. In Scheme 20, $R^{45h}$ denotes hydrogen atom, $C_{1-6}$ alkyl or $C_{6-14}$ aryl. Xa denotes a halogen atom and $R^1$, $R^2$, $R^3$, $R^5$ and n have the same meaning as defined above.

Scheme 20:

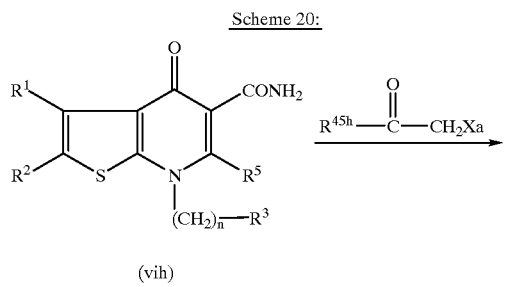

(vih)

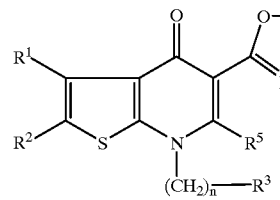

(XIIe)

Production Method 21

Production of a compound having 2-thiazolyl at 5-position is illustrated in Scheme 11, infra:

To a solution of 4,7-Dihydro-5-carbamoyl-4-oxothieno[2,3-b]pyridine derivative (vih) in an appropriate solvent, e.g. toluene, tetrahydrofuran, dioxane, an equivalent amount or a small excess amount of thioamide reagent, e.g. Lawessons reagent, is added under room temperature or ice-cooling. The mixture is stirred at a temperature of 0° C. to 80° C., and subjected to refluxing under heating if required, to give a 4,7-dihydro-5-thiocarbamoyl-4-oxothieno[2,3-b]pyridine derivative (viih).

Said thicarbamoyl derivative (viih) is dissolved in an appropriate solvent, e.g. methanol, ethanol, tetrahydrofuran, dioxane, and to the solution is added dropwise an equivalent amount to a small excess amount of α-haloketone compound at room temperature or under ice-cooling. The mixture is stirred at a temperature of about 0° C. to 80° C., and is subjected to refluxing under heating, to give 2-thiazoly derivative (XIIf).

The foregoing method is shown in Scheme 21. In Scheme 21, $R^{46h}$ denotes hydrogen, $C_{1-6}$ alkyl or $C_{6-14}$ aryl. Xa denotes a halogen atom. $R^1$, $R^2$, $R^3$, $R^5$ and n have the same meaning as defined above.

Scheme 21:

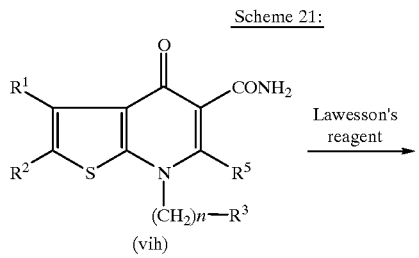

Production Method 22

Production of a compound having 3-pyrazolyl group at 5-position is illustrated in Scheme 12, infra:

To a solution of 4,7-dihydro-5-acetyl-4-oxothieno[2,3-b]pyrimidine (viiih), obtained by the method of Production Method 6, in an appropriate solvent, e.g. methanol, ethanol, tetrahydrofuran, dioxane is added dropwise an excess amount of formyl ethyl ester and a base, e.g. sodium ethoxide, at room temperature or under ice-cooling. The mixture is stirred at a temperature of 0° C. to 80° C. to give an α-formylketone derivative (ixh).

The α-formylketone derivative (ixh) is dissolved in an appropriate solvent, e.g. water, methanol, tetrahydrofuran, dioxano, dimethylformamide. To the solution is added an equivalent to a small excess of hydrazine derivative or its salt at room temperature or under ice-cooling. The mixture is stirred at a temperature of about 0° C. to 80° C., and subjected to refluxing under heating if required, to give a 3-pyrazolyl derivative (XIIg).

The foregoing method is shown in Scheme 22. In Scheme 22, $R^1$, $R^2$, $R^3$, $R^5$ and n have the same meaning as defined above.

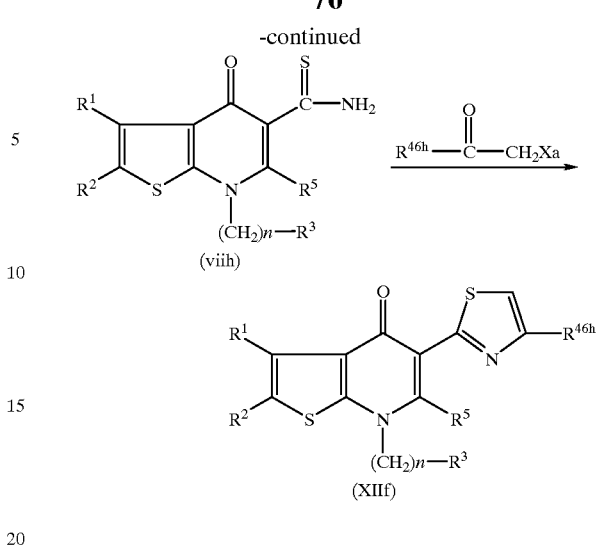

Scheme 22:

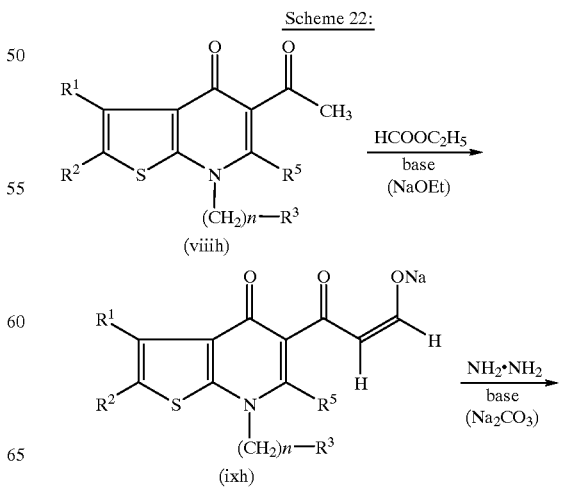

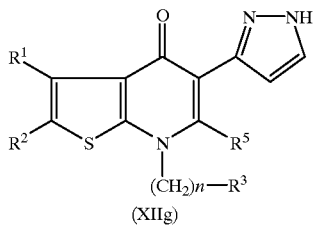

(XIIg)

Production Method 23

Production of a compound having 2-triazolyl at 5-position is illustrated in Scheme 23, infra:

4,7-Dihydro-5-thiocarbamoyl-4-oxothieno[2,3-b] pyrimidine derivative (xh), which is produced in the first process of Production Method 21, is dissolved in an appropriate solvent, e.g. ethyl ether, dimethylformamide, tetrahydrofurane, dioxane, dichloromethane. To the soluion is added an equivalent amount to a small excess amount of methyl iodide at a temperature of 0° C. to 80° C., and the mixture is subjected to refluxing under heating if required, to give a derivative of tetra salt.

To a solution of the derivative in an appropriate solvent, e.g. dimethylformamide, or to the derivative without such solvent, is added an excess amount of formic acid hydrazide at room temperature or under ice-cooling.

The mixture is stirred at room temperature to 200° C., to give a 2-triazol derivative (XIIh).

The foregoing method is shown in Scheme 23. In Scheme 23, the groups have the same meaning as defined above.

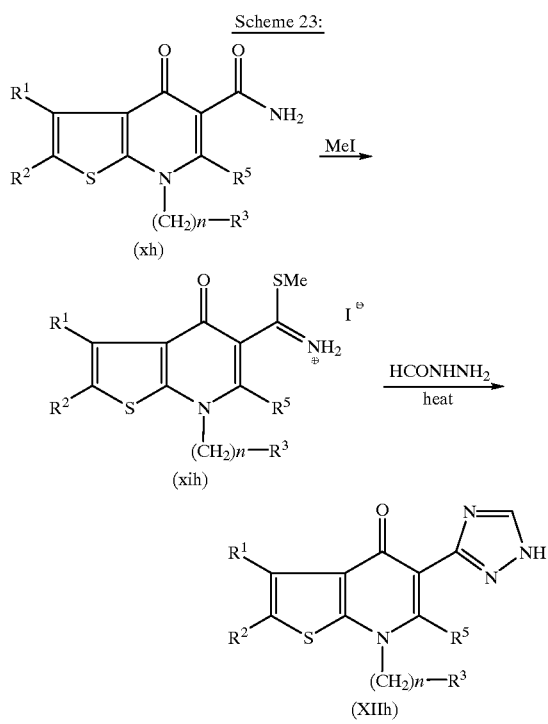

Production Method 24

Production of a compound having 2-oxazolinyl at 5-position illustrated in Scheme 14, infra:

2,7-Dihydro-4-oxothieno[2,3-b]pyridine-5-carboxylic acid ester (xiih) is added dropwise under ice-cooling to an excess amount of a solution of aluminum amide of ethanol amine in dichloromethane. The mixture is stirred for one to 4 hours at room temperature to produce an amide derivative.

To the solution of the amide derivative in an appropriate solvent, e.g. dichloromethane, ethyl ether, tetrahydrofuran, is added thionyl chloride under ice-cooling.

The mixture is stirred at a temperature of 0° C. to room temperature to give a 2-oxazolinyl derivetive (XIIi).

The foregoing method is shown in Scheme 24. In the Scheme 24, $R^1$, $R^2$, $R^3$, $R^5$ and n have the same meaning as defined above.

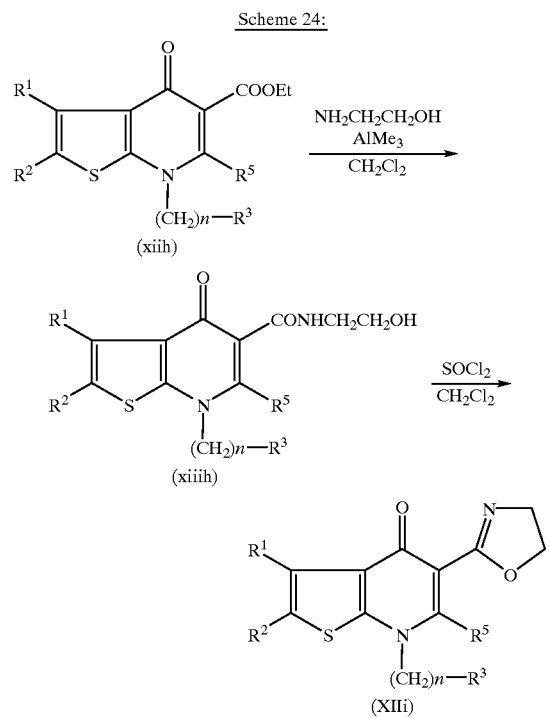

Production Method 25

Production of the compound wherein $R^{4h}$ is a group bonded through a nitrogen atom is illustrated in Scheme 25, infra:

The compound (xivh), which can be produced by a similar manner of Production Methods 5 or 6, is dissolved in an appropriate solvent, e.g. pyridine. To the solution is added an equivalent to a small excess amount of hydroxylamine derivative or its salt, and the mixture is reacted at room temperature or under an elevated temperature, to produce oxime derivative (xvh). The oxime derivative (xvh) is dissolved in an appropriate solvent, e.g. pyridine, and to the solution is added an equivalent to a small excess amount of an acylating agent, e.g. acid halide, acid anhydride, sulfonic acid halide.

The mixture is reacted, at room temperature or under heating for 1 to 12 hours to give a dislocation form (XIIj).

The dislocation form (XIIj) is dissolved in an appropriate solvent, e.g. ethylalcohol, and to the solution is added an alkali, e.g. an sodium hydroxide solution, and the mixture is stirred for about 2 hours to cause an alkali hydrolysis reaction, whereby a primary amino derivative (XIIk) is produced.

The foregoing method is shown in Scheme 25. In Scheme 25, $R^1$, $R^2$, $R^3$, $R^5$ and n have the same meaning as defined above. Ac means acetyl group.

Scheme 25:

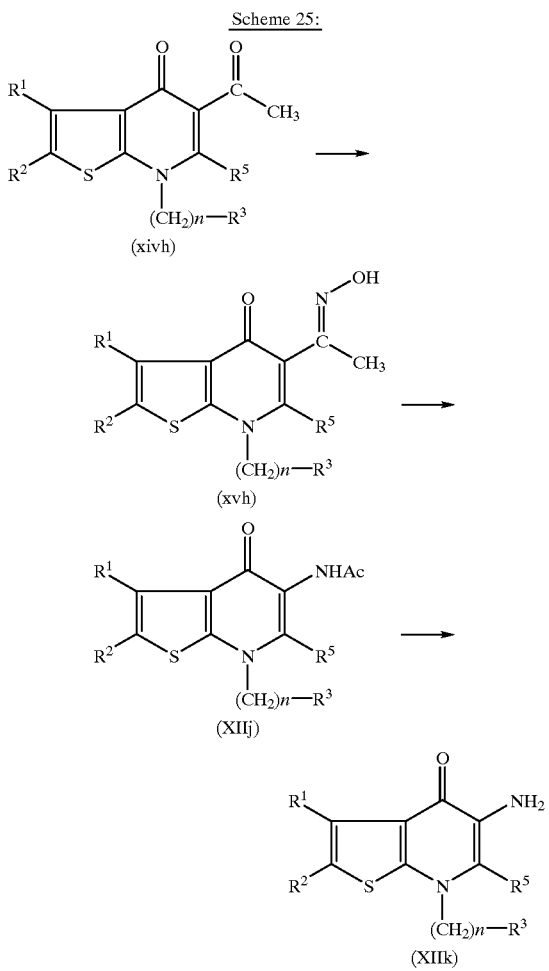

From thus obtained primary amino derivative (XIIk), various derivatives can be produced by alkylation, acylation, sulfonation, imidation and so forth.

Production Method 26

Production of the compound wherein $R^4$ is a group bonded through an oxygen atom is illustrated in Scheme 26, infra:

The compound (xvih), which can be obtained by the method described in Prodcution Methods 5 or 6, is dissolved in an appropriate solvent, e.g. dichloromethane. To the solution is added a small excess amount, e.g. 1.2 to 1.5 equivalent, of peracids, e.g. chlorobenzoic acid, and the mixture is stirred for 1 to 6 hours to give a dislocation form (XIIm).

The dislocation form (XIIm) is subjected to a reaction by stirring the mixture of the dislocation form (XIIm) with an alkali, e.g. 2N sodium hydroxide solution, in an appropriate solvent, e.g. tetrahydrofuran, at room temperature or under heating, e.g. 40 to 60° C., for 1 to 12 hours, to give an alcoholic derivative (XIIn).

The alcoholic derivative (XIIn) is dissolved in an appropriate solvent, e.g. dimethylformamide, and to the solution are added an alkali, e.g. potassium carbonate, and alkyl halide, e.g. isopropyl bromide, and the mixture is stirred for about one to 24 hours at room temperature to heating, e.g. 40 to 80° C., to give alkoxy derivative (XIIo).

Furthermore, when the alkoxy group is isopropoxy group, the alkoxy derivative is dissolved in an appropriate solvent, e.g. dichloromethane, an excess amount of Lewis acid, e.g. borone trichloride, is added to the solution and the mixture is stirred for one to 6 hours under ice-cooling or at room temperature, to give de-alkylated alcoholic derivative (XIIn).

The foregoing methods are shown in Scheme 26. In Scheme 26, $R^1$, $R^2$, $R^3$, $R^5$ and n have the same meaning as defined above. $R^{30h}$ and $R^{4'}$ denote a $C_{1-6}$ alkyl group. Xa denotes a halogen atom.

Scheme 26:

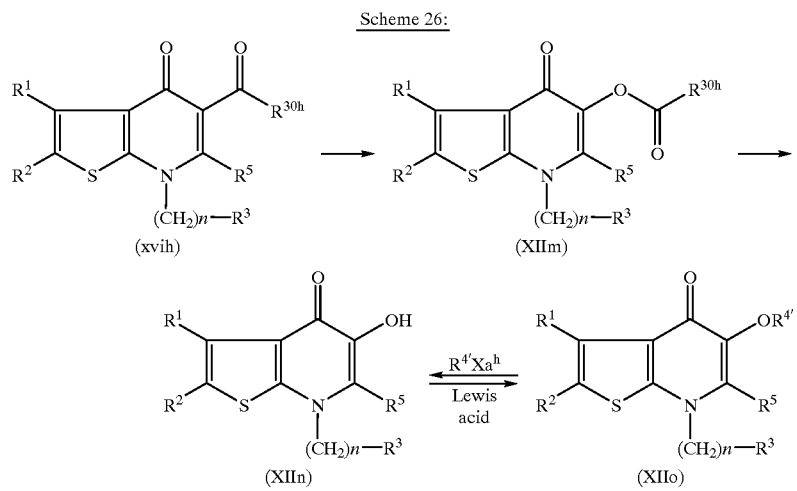

From thus obtained alcoholic derivative (XIIn), various derivatives can be produced by alkylation acylation, alkenylation, sulfonation and so forth.

Production Method 27

Production of the compound wherein $R^4$ is a group bonded through a sulfur atom is illustrated in Scheme 27, infra:

At first, thioglycolic acid ester is reacted with an alkali iodide, and then the product is reacted with a dimethylaminomethylene compound to give a compound (xviih).

The 2-aminothiophen derivative (xviiih), which is obtained in the above Production Method 1, Scheme 1, is dissolved in an appropriate solvent, e.g. ethyl alcohol, and to the solution is added a base, e.g. an aqueous sodium hydroxide solution, to cause to alkali hydrolysis to give a compound (xixh).

The compound (xixh) is reacted with the compound (xviih) shown above by stirring in an appropriate solvent, or without any solvent, under heating, e.g. at 80 to 150° C., for 1 to 6 hours to give an amino substituted derivative (xxh).

The derivative (xxh) is heated, e.g. at 150 to 250° C., in an appropriate solvent, e.g. diphenyl ether, for 30 minutes to 3 hours to give a cyclic form (xxih).

The cyclic form (xxih) is reacted with a compound of the formula: Xa—$(CH_2)_n$—$R^3$ by a similar manner as described above in the reaction with a compound of the formula: Xa—$(CH_2)_n$—$R^3$ in the Production Method 1, to give a compound (XIIp).

Furthermore, the compound (XIIp) is reacted by stirring with an equivalent to an excess amount of a peracid compound, e.g. m-chlorobenzoic acid, in an appropriate solvent, e.g. dichloromethane, under ice-cooling for 5 minutes to about 2 hours to give sulfoxide derivative (XIIq).

The foregoing methods are shown in Scheme 27. In Scheme 17. $R^1$, $R^2$, $R^3$, Xa and n have the same meaning as defined above. $R^{4'''}$ denotes a $C_{1-6}$ alkyl group.

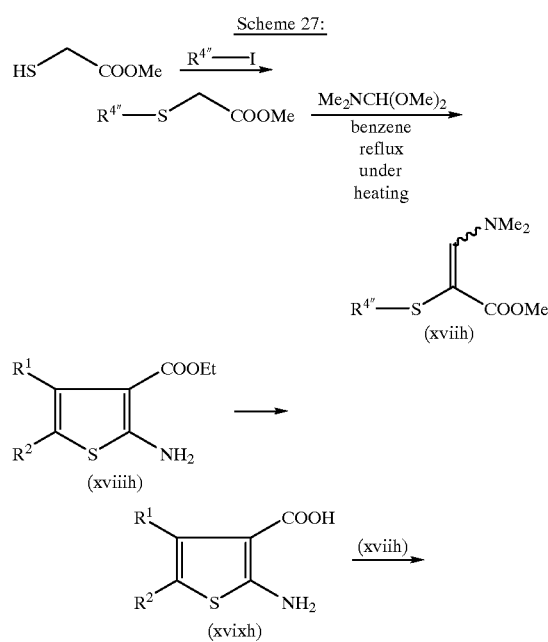

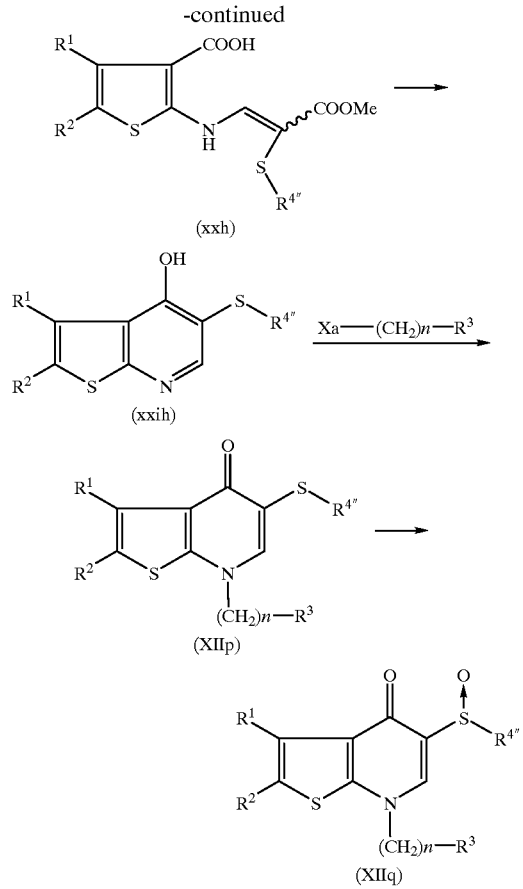

Production Method 28

Production of the Compound wherein it has a phenyl group substituted by an alkenyl group which may optionally be substituted at 2-position is illustrated in Scheme 28, infra:

4,7-Dihydro-2-(4-aminophenyl)-4-oxothieno[2,3-b] pyrimidine derivative (XIIr) is reacted with diazonizing agent, e.g. sodium nitrite, isoamyl nitrite, in an appropriate proper solvent, e.g. dimethylformamide, dichloromethane, tetrahydrofuran, dioxane, acetenitrile, water, etc, to give a diazonium salt.

To the diazonium salt is added one equivalent to excess amount of an alkenyl derivative, e.g. olephine compound, and palladium catalyst, e.g. bis(dibenzylideneacetone) palladium. The reaction is conducted at 0° C. to 80° C. under stirring, to give the desired product, i.e. the compound (XIIs).

The foregoing production method is shown in Scheme 28. In Scheme 28, $R^{32h}$ and $R^{33h}$ independently are a $C_{1-6}$ acyl group, $R^{34h}$ denotes a hydrogen atom or $C_{1-6}$ alkyl.

The $C_{1-6}$ acyl and $C_{1-6}$ alkyl are of the same as defined in above n) and f). Other groups have the same meaning as defined above.

83

Scheme 28:

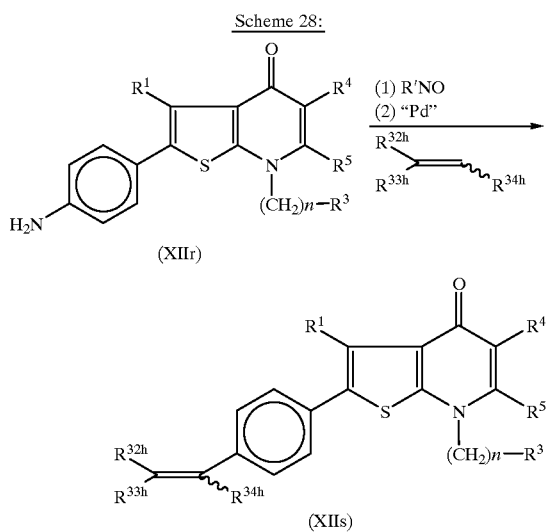

Production Method 29

Production of a compound which has an aminophenyl group substituted by (1) an optionally substituted alkyl group or (2) an optionally substituted homo-cyclic group is illustrated in Scheme 29, infra:

4,7-Dihydro-2-(4-aminophenyl)-4-oxothieno[2,3-b] pyrimidine derivative (XIIIt) is dissolved in an appropriate solvent, e.g. acetic acid, dimethylformamide, dichloromethane, tetrahydrofuran, dioxane. To the solution is added one equivalent to excess amount of Michael acceptor derivative, e.g. acrylic acid ester, or an oxyrane derivative, e.g. epoxy compound. The reaction is carried out at 0° C. to 80° C. under stirring to give the desired compound (XIIu).

The foregoing production method is shown in Scheme 29. In Scheme 29, $R^{35h}$ to $R^{39h}$ denote $C_{1-6}$ alkyl group —$R^{40h}$ denotes a group —$C(R^{36h})$—CO—$R^{35h}$ or a group —$C(OH)R^{36h}R^{39h}$. Other groups have the same meaning as defined above.

Scheme 29:

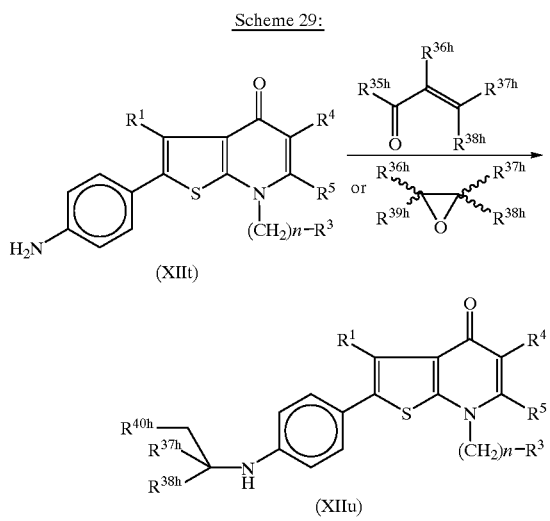

Production Method 30

Production of a compound which has an aminophenyl group substituted by (1) an optionally substituted alkyl or (2) an optionally substituted homo-cyclic group is illustrated in Scheme 20, infra:

84

4,7-Dihydro-2-(4-aminophenyl)-4-oxothieno[2,3-b] pyrimidine derivative (XIIv) is dissolved in an appropriate solvent, e.g. pyridine, dimethylformamide, dichloromethane, tetrahydrofuran, ethylether, dioxane. To the solution is added one equivalent to one excess amount of acid chloride or acid anhydride, e.g. trifluoroacetic acid anhydride. The reaction is carried out at 0° C. to 80° C. under stirring to give a derivative (XIIw).

The obtained derivative (XIIw) is dissolved in a solvent, e.g. pyridine, dimethylformamide, dichloromethane, tetrahydrofuran, ethylether, dioxane, acetone, and to the solution is added one equivalent to an excess amount of a base, e.g. potassium carbonate, triethylamine, sodium hydrogen, and one equivalent to one excess amount of a halogenated alkyl, e.g. methyl iodide, propyl iodide, benzyl iodide. The reaction is carried out at 0° C. to 80° C. under stirring.

The obtained derivative is subjected to alkali hydrolysis using small excess amount of 1N sodium hydroxide in an appropriate solvent, e.g. tetrahydrofuran, dioxane, ethanol, methanol, acetone, to give the desired derivative (XIIx).

The foregoing method is shown in Scheme 30. In Scheme 30, the group $R^{41h}$ represents $C_{1-6}$ alkyl or trifluoromethyl. The group $R^{42h}$ is an optionally substituted $C_{1-6}$ alkyl group or an optionally substituted homo-cyclic group. Other groups have the same meaning as defined above.

Scheme 30:

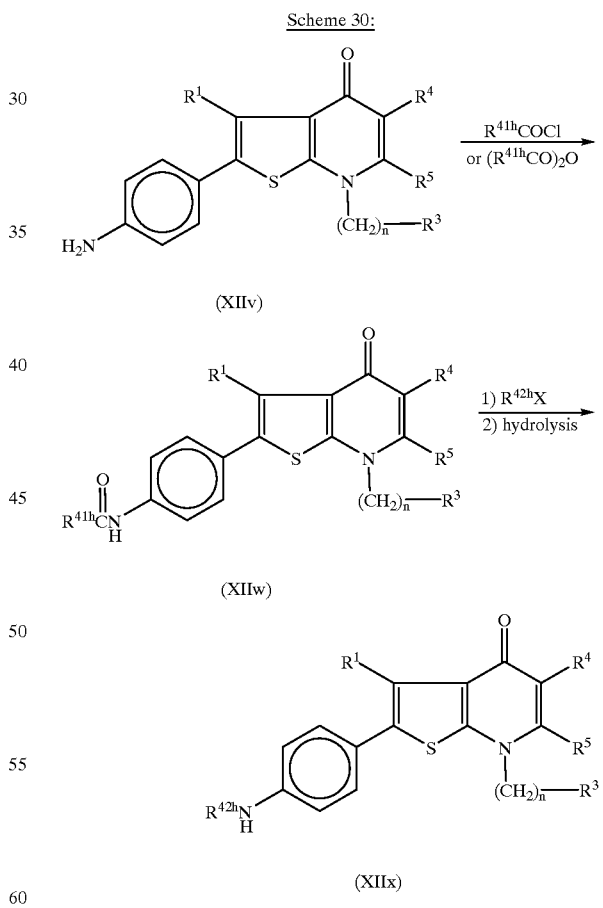

Production Method 31: Exchange the group at 3-position

The group at 3-position of the compound can be exchanged by the following method as illustrated in Scheme 31.

The compound (XIIy) is stirred together with N-bromosuccinimide (NBS) in an appropriate solvent, e.g.

halogenated hydrocarbons such as carbon tetrachloride and chloroform, in the presence of α, α'-azobisisobutyronitrile (AIBN), at a temperature ranging from about 30 to 100° C. to give a compound (II'), and if required the compound (II') is subjected to a reaction with aliphatic carboxylic acid, alkylsulfonic acid, or alkylarylsulfonic acid to cause a reaction of exchanging the group at 3-position.

The compound (II') is reacted with an equivalent mole to a small excess amount (about 3 mole) of primary or secondary amine, e.g. $R^{1'}$—H to give a compound (III'). The reaction can be carried out in an appropriate solvent which does not adversely effect the reaction. As the solvent, mention is made of amides such as dimethylformamide or dimethylacetamide, nitriles such as acetonitrile, alcohols such as ethanol, and furthermore diethoxyethane, tetrahydrofuran, dioxane, toluene, dichloromethane, chloroform, ethylether, acetone and ethyl acetate can be used. In this reaction, if necessary, a base may be used. As the base, mention is made of a tertiary organic amine, e.g. trimethylamine, triethylamine, diisopropylamine, pyridine, 1,8-diazabicyclic[5,4,0]-7-undecene (DBU), and an inorganic salt, e.g. anhydrous potassium carbonate. The reaction is carried out at a temperature of about 10 to 100° C. The reaction time is about 0.5 to 8 hours. When the reaction is carried out under stirring, the reaction proceeds smoothly.

This reaction gives the compound (III'). The described above is shown in Scheme 21 below:

In Scheme 31, the group $R^{1''}$ denotes a hydrogen atom or a $C_{1-6}$ alkyl group, the group $R^{1'''}$ denotes a group bonded through a nitrogen atom. The group bonded through a nitrogen atom has the same meaning as defined above. The groups $R^2$, $R^3$, $R^4$, $R^5$ and m have the same meaning as defined above. m denotes an integer of 0 to 6. X denotes a leaving group.

As the leaving group shown by X, mention is made of, for example, a group which is potentially substituted by a nucleophilic reagent such as a hydrocarbon residue having a hetero atom, e.g. an oxygen atom, a sulfur atom, a nitrogen atom, being negatively charged. The preferable examples of the leaving group include halogen, e.g. iodine, bromine chlorine, $C_{1-8}$ alkanoyloxy, e.g. acetoxy, $C_{1-6}$ alkylsulfonyloxy, e.g. methanesulfonyloxy, $C_{1-6}$ alkyl-$C_{6-14}$ arylsulfonyloxy, e.g. p-toluenesulfonyloxy.

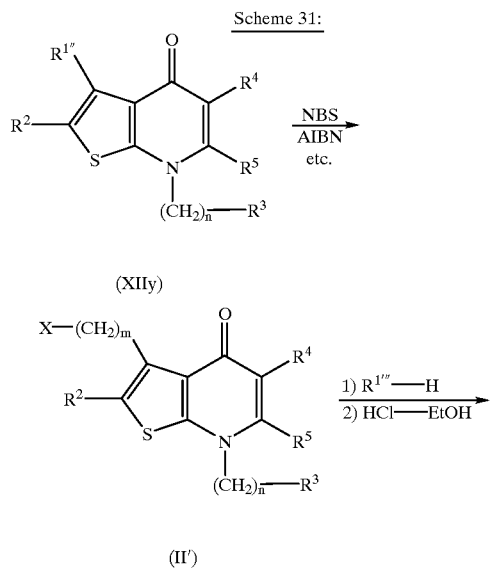

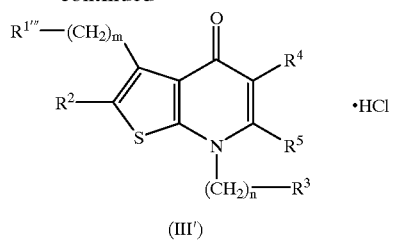

Production Method 32

A thienopyridine-5-carboxylic acid derivative having an optionally substituted branched alkoxycarbonyl group at the 5-position can be produced by allowing a compound having alkoxycarbonyl group at the 5-position, which is produced by substantially the same method described in PCT International Publication No. WO95/28405, or a salt thereof, to react with a compound represented by the general formula $R^{4j}$—OH, wherein $R^{4j}$ stands for an optionally substituted branched alkoxy group whose specific examples are the same as described in the foregoing or a salt thereof. This reaction is conducted by dissolving the starting compound in an adequate solvent (e.g. isopropyl alcohol and 3-pentyl alcohol), adding to the solution a compound represented by the general formula $Ti(OR^{4j})_4$, wherein $R^{4j}$ stands for a branched alkoxy group, (e.g. isopropyl titanate (titan tetraisopropoxide), titanic acid (3-pentyl)) or a salt thereof, and by stirring the mixture at a temperature ranging from about 0 to 120° C., more preferably from about 10 to 20° C., for about 1 to 24 hours, preferably about 1 to 12 hours. Or, the said thienopyridine-5-carboxylic acid derivative can be produced by stirring a compound having carboxyl group at the 5-position in an adequate solvent (e.g. dimethylformamide) in the presence of an adequate agent for converting into acid chloride (e.g. phosphorus oxychloride), a base (e.g. N,N-dimethylaminopyridine) and alcohol (e.g. 2,4-dimethyl-3-pentanol), at room temperature or under heating (about 100° C.), for about 1 to 12 hours.

Production Method 33

A thienopyridine-5-carboxylic acid of this invention having carboxyl group at the 5-position can be produced by subjecting a compound having alkoxycarbonyl group at the 5-position, which is produced by substantially the same method as that described in the official gazette of International Application WO95/28405 Laid-Open Under PCT, or a salt thereof to hydrolysis. The hydrolysis is conducted by dissolving the starting compound in an adequate solvent which does not exert undesirable influence on the reaction (ethers such as tetrahydrofuran or dioxane, or alcohols such as ethyl alcohol), adding to the solution an acid (e.g. inorganic acid such as hydrochloric acid) or an aqueous alkaline solution (e.g 1–4N aqueous solution of alkali metal hydroxide such as sodium hydroxide, potassium hydroxide or lithium hydroxide), and stirring at a temperature ranging from about 10 to 100° C. for about 1 to 4 hours.

Production Method 34

The compound (XV) can be produced by allowing a 5-carboxy-4,7-dihydro-4-oxothieno[2,3-b]pyridine derivative, which is produced by a method analogous to the method disclosed in PCT International Publication No. WO95/28405, or a salt thereof to react with a compound represented by the general formula $R^{2k'}$—$Y^k$, wherein $R^{2k'}$ stands for alkyl group having 1 to 3 alkenyl optionally substituted with (i) halogen, (ii) cycloalkyl or (iii) alkyl, and Y stands for halogen atom, or a salt thereof.

This reaction is conducted usually in a solvent, as exemplified by amides such as dimethylformamide, nitrites such as acetonitrile and ethers such as tetrahydrofuran. This reaction is conducted by dissolving the starting compound in any of these solvents and by adding to the solution a compound represented by the general formula $R^{2k'}$—$Y^k$ (e.g. allyl bromide, cycloprolylmethyl chloride, 1-bromo-2-butene, crotyl bromide (i.e. 1-bromo-2-methyl-2-propene), 1-bromo-3-butene, 2,2,2-trifluoroethyl iodide) or a salt and a basic compound thereof (e.g. potassium carbonate, sodium hydride and triethylamine). The reaction temperature ranges from about 0 to 100° C., preferably from about 0 to 40° C. The reaction time ranges from about 1 to 200 hours, preferably from about 1 to 48 hours. This reaction can be conducted efficiently by stirring.

Production Method 35

A thienopyridine derivative, which is the compound (XV) wherein $R^{2k}$ stands for an optionally substituted alkoxy group, can be produced through ester exchange by allowing a 5-ethoxycarbonyl-4,7-dihydro-4-oxothieno[2,3-b]pyridine derivative produced by the method analogous to that disclosed in PCT International Publication No. WO95/28405 or a salt thereof to react with a compound represented by the general formula $R^{2k}$—H, wherein $R^{2k}$ is of the same meaning as defined above, or a salt thereof. This reaction is conducted usually in a solvent, as exemplified by alcohols such as isopropyl alcohol. This reaction can be conducted by dissolving the starting compound in any of these solvents and by adding to the solution a compound represented by the general formula Ti($R^{2k}$)4 (e.g. isopropyl titanate, e.g. titan (N) tetraisopropoxide). The reaction temperature ranges from about 0 to 100° C., preferably from about 0 to 40° C. The reaction time ranges from about 1 to 24 hours, preferably from about 1 to 6 hours. This reaction can be conducted efficiently by stirring. Or, the reaction can be conducted by dissolving the compound (I), wherein $R^{2k}$ is carboxyl group, in a solvent (e.g. amides such as dimethylformamide), then by allowing the solution to react with alcohol (e.g. 2,4-dimethyl-3-pentanol). This reaction is conducted by adding, to the reaction system, an acid-chloridation agent such as phosphorus oxychloride and a base such as N,N-dimethylaminopyridine. The reaction is conducted at a temperature ranging from room temperature to about 100° C. under heating. The reaction time ranges from about 1 to 12 hours. This reaction is conducted efficiently by stirring.

Production Method 36

A thieno[2,3-b]pyridine-5-carboxylic acid derivative, which is the compound (XV) wherein —CO—$R^{2k}$ is carboxyl group, can be produced by subjecting the compound (XV) wherein $R^{2k}$ is alkoxy group or a salt thereof, which is produced by the method disclosed in PCT International Publication No. WO95/28405 or an analogous method thereto, to hydrolysis. The hydrolysis is conducted by adding, to a solution of the starting compound in a solvent, an acid (e.g. inorganic acid such as hydrochloric acid) or an aqueous solution of alkali (e.g. a 1–4N aqueous solution of alkali metal hydroxide such as sodium hydroxide, potassium hydroxide or lithium hydroxide). As the solvent, use is made of, for example, ethers such as tetrahydrofuran or dioxane, and alcohols such as ethyl alcohol. The reaction temperature ranges from about 1 to 100° C. The reaction time ranges from about 1 to 4 hours. The reaction is conducted efficiently by stirring.

The compound (XXI) can be produced by the method of the Production Method 10 or a method shown below, i.e. Production Method 37.

Production Method 37

In place of the method for producing compound (IIa) from the compound (ii) in the above scheme 13, any per se conventional methods can be employed, for example the following processes for producing the compound (IIa) from the compound (ii). Namely, the compound (ii) is dissolved in an appropriate solvent, e.g. methanol, ethanol, which does not adversely affect the reaction, 2N sodium hydroxide is added, and the mixture is reacted at room temperature to heating (till about 100° C.) for one to 12 hours. The obtained compound wherein —COOEt is converted to —COOH is dissolved in an appropriate solvent, e.g. dioxane, and to the solution is added an equivalent amount of triphosgene and the mixture is reacted at a temperature of 80 to 150° C. for one to 10 hours under stirring. The obtained 1-hydroxy oxazine compound is treated in a manner similar to that of the reaction of the compound (XVI) to the compound (IIa) as mentioned above. Thus obtained oxazine compound to which the group $R^{1y}$ is introduced at 1-position is dissolved in an appropriate solvent, e.g. dichloromethane, to the solution is added an equivalent amount to a small excess amount of an amine, e.g. ammonium, alkylamine, arylamine, and the mixture is reacted at room temperature to heating (till about 100° C.) for 1 to 12 hours under stirring. Then, to the reaction mixture is added triphosgene again and triethylamine as a base, the mixture is reacted at about 100° C. under reflux for 1 to 6 hours, to give a compound of the formula (IIa).

The compound (XXX) and its salt can be produced easily by per se known methods, as exemplified by the Production Method 3, the Production Method 14, or the following procedures.

As the leaving group shown by $X^a$, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen, e.g. iodine, bromine chlorine, $C_{1-8}$ alkanoyloxy, e.g. acetoxy, $C_{1-6}$ alkylsulfonyloxy, e.g. methanesulfonyloxy, $C_{1-6}$ alkyl-$C_{6-14}$ arylsulfonyloxy, e.g. p-toluenesulfonyloxy.

Production Method 38

To a solution of 3-halogenated aniline derivative (iz) is added an equivalent mole to a small excess amount of ethoxymethylene melonic acid diethylester, the mixture is stirred for one to 4 hours at a temperature of 100° C. to 150° C. to give an additive form (iiz). The additive form (iiz) is dissolved stepwise in an appropriate solvent, e.g. polyphosphoric acid, polyphosphoric acid ester (PPE), Dowtherm, the mixture is stirred at room temperature to heating to give a quinoline derivative (iiiz). The derivative (iiiz) is dissolved in an appropriate solvent, i.e. one which does not adversely affect the reaction, e.g. dimethylformamide, dichloromethane, tetrahydrofuran, ethylether, dioxane, aceton.

To the solution is added one equivalent to a small excess amount of a base, e.g. potassium carbonate, triethylamine, sodium hydrogen, one equivalent to excess amount of halogens alkyl derivative, e.g. methyl iodide, propyl iodide, benzyl iodide, and the mixture is stirred at a temperature of 0° C. to 80° C. to give a quinoline derivative (ivz).

Thus obtained derivative (ivz) or its salt and an equivalent mole to a small excess amount (about 3 mole) of an aryl boric acid derivative, i.e. $R^{III}$—B(OH)$_2$, e.g. $R^{2z}$—B(OH)$_2$, are reacted to give the compound (XXXa) shown in the following Scheme 37. The reaction is carried out in an appropriate solvent which does not adversely affect the reaction. As the solvent, mention is made of dimethoxyethane, tetrahydrofuran, dioxane, benzene, toluene, ethylether, dimethylformamide, dimethylacetamide and ethanol. This reaction is carried out in the presence of a base. As the base, mention is made of inorganic base such as sodium carbonate, sodium hydrogencarbonate, potassium carbonate, potassium hydrogencarbonate, sodium hydroxide, potassium hydroxide, thallium carbonate or an organic base such as triethylamine. In order to proceed the reaction smoothly, a catalytic amount of palladium derivative, e.g. tetrakistriphenylphosphine palladium, may be added to the reaction system. It is preferable to carry out the reaction in a stream of an inert gas, e.g. argon gas, nitrogen gas. The reaction is carried out at room temperature to about 150° C. and it is preferable to carry out the reaction under reflux. The reaction time is about 1 to 12 hours. This reaction gives the desired product (XXXa).

The foregoing methods are shown in Scheme 32. In Scheme 32, Et denotes ethyl, $Y^z$ denote halogen, whose examples are the same as above, and the other groups have the same meaning as defined above.

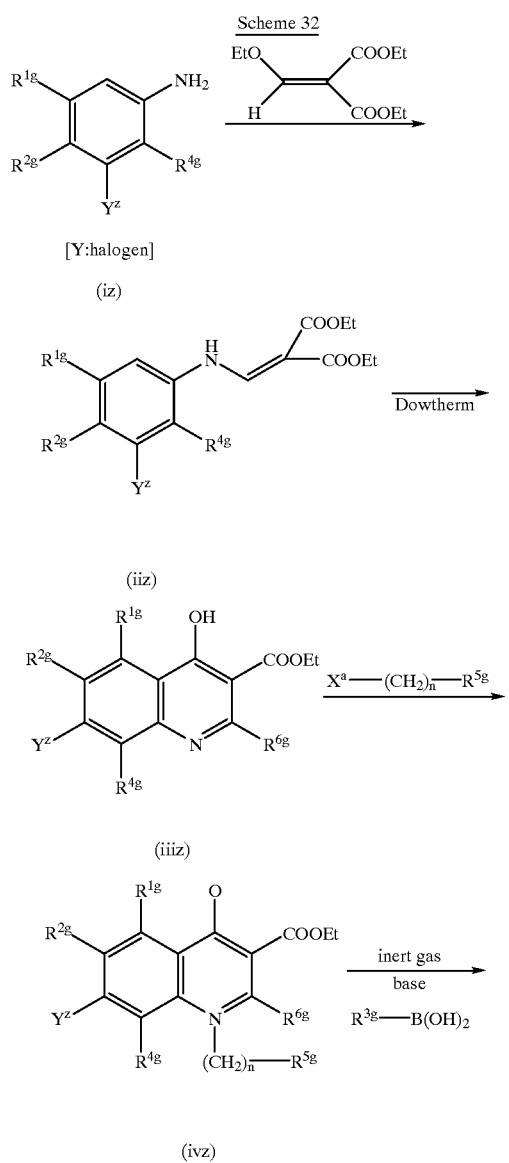

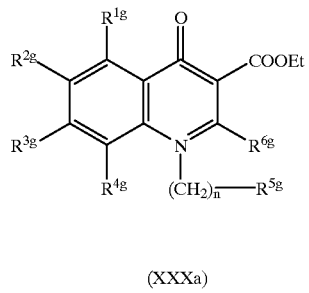

(XXXa)

Production Method 38

Exchange the group at 6-position:

The compound (vz) is stirred together with N-bromosuccinimide (NBS) in an appropriate solvent, e.g. halogenated hydrocarbons such as carbon tetrachloride and chloroform in the presence of α, α'-azobisisobutyronitrile (AIBN), at a temperature ranging from about 30 to 100° C. for 0.5 to 6 hours to give a compound (viz).

The compound (viz), or its salt is reacted with about equivalent mole of an amine of the formula: $R^{1z'}$—H, e.g. the compound shown by the formula: $HNR^{5z}R^{6z}$, to produce the compound (XXXb). The reaction is carried out in an appropriate solvent which does not adversely affect the reaction. As the solvent, mention is made of amides such as dimethylformamide and dimethylacetamide, nitrils such as acetonitrile, alcohols such as ethanol, furthermore in the reaction dimethoxyethane, tetrahydrofuran, dioxane, dichloromethane, acetonitrile, acetone, ethyl acetate can be used as a solvent. The reaction is carried out in the presence of a base such as tertiary organic amine, e.g. triethylamine, trimethylamine, diisopropylethylamine, N-methylmorpholine. The reaction temperature is normally about 10 to 100° C. The reaction time is about 1 to 10 hours. It is preferable to carry out the reaction under stirring.

This reaction gives the compound (XXXb). The production method 2 described above is shown in Scheme 2: In Scheme 2, $R^{1z'}$ denotes an optionally substituted amino group, $Z^z$ is a leaving group. Other groups have the same meaning as defined above.

Scheme 33

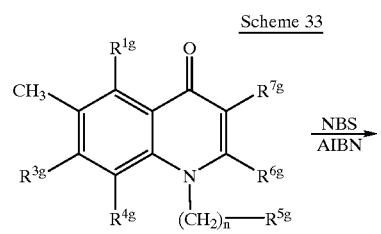

(vz)

91

-continued

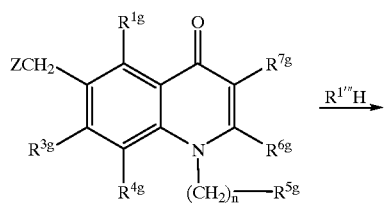

(viz)

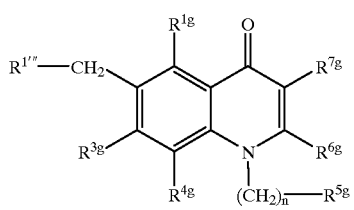

(XXXb)

Production Method 40

An anthranilic acid derivative (viiz) is stirred at a temperature ranging from about 30 to 110° C. together with an equivalent or an excess amount of triphosgene in an appropriate solvent, e.g. ethers such as tetrahydrofuran and 1,4-dioxane, to give an isatoic acid anhydride derivative (viiiz). Then, a halogenated derivative is stirred at a temperature ranging from about 40 to 130° C. in an appropriate solvent, e.g. ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide, in the presence of a base, e.g. alkali metal carbonate such as potassium carbonate, alkali metal hydride such as sodium hydride and potassium hydride, and alkali metal alkoxide such as potassium-butoxide, to give a substituted derivative (xiz). The derivative (xiz) is allowed to react with an equivalent or a little excess amount, e.g. about 1.1 to 1.5 equivalent, of a β-keto-acid ester derivative relative to the compound at a temperature ranging from 40 to 110° C. in an appropriate solvent, e.g. ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide, in the presence of a base, e.g. alkali metal carbonate such as potassium carbonate, alkali metal hydride such as sodium hydride and potassium hydride, and alkali metal alkoxide such as potassium-butoxide, to give the compound (XXXc). The foregoing Production Method 39 is shown in Scheme 34. In Scheme 34, Xa denotes a leaving group especially halogen, and $R^{g'}$ denotes an alkyl group. Other groups have the same meaning as defined above.

92

Scheme 34

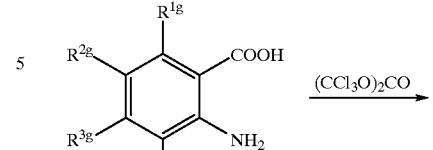

(viiz)

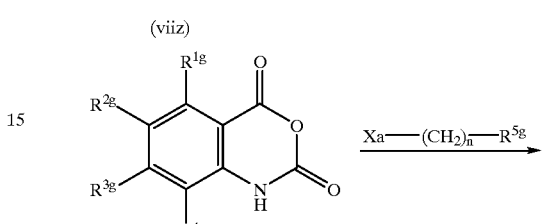

(viiiz)

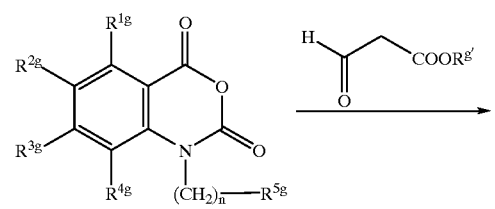

(ixz)

(XXXc)

Other Methods

The substituents on the compound can be converted to other substituents by per se known and conventional methods. Examples of the methods are shown below.

(i) The nitro group as the substituent can be converted to an amino group when the starting compound is dissolved in an appropriate solvent, e.g. ethanol, methanol, and (a) to the solution is added palladium-carbon, and the mixture is reacted at room temperature for one to 12 hours under hydrogen atmosphere, or (b) to the solution is added iron powder and hydrochloric acid, and the mixture is reacted at room temperature for one to 12 hours.

(ii) The amino group can be converted to an acylated amino group by dissolving the starting compound in an appropriate solvent, e.g. tetrahydrofuran, dimethylsulfoxide, to the solution is added potassium carbonate, pyridine and triethylamine as a base and acid anhydride or acid halide. The mixture is reacted at a room temperature for one to 10 hours under stirring.

(iii) From an amino compound, a compound having an amino group is converted to alkenyl-amino compound. For example, the starting compound is dissolved in an appropriate solvent, e.g. acetic acid, dimethylformamide, dichloromethane, tetrahydrofuran, dioxane, acetonitrile, to the solution is added diazonizing agent, e.g. sodium nitrite, isoamyl nitrite, to the mixture is added palladium catalyst, e.g. bis(dibenzylideneacetone)palladium and one to excess equivalent of alkenyl derivative, and the mixture is stirred at room temperature to heating (about 80° C.) for one to 12 hours.

(iv) A carbon atom can be introduced to the amino group, for example, to the starting compound in an appropriate solvent, e.g. acetic acid, dimethylformamide, dichloromethane, tetrahydrofuran, dioxane, is added an acrylic acid derivative or oxirane derivative, e.g. epoxide compound. The mixture is stirred at 0 to 80° C. for 6 to 24 hours.

(v) A sulfur atom can be introduced to the amino group in the compound, for example, to the starting compound in an appropriate solvent, e.g. pyridine, dimethylformamide, dichloromethane, tetrahydrofuran, ethylether, dioxane, is added halide of sulfur compound. The mixture is stirred at 0 to 80° C. for 6 to 24 hours.

(vi) The substituent, formyl group, can be converted to methyl group by dissolving a starting compound in an appropriate solvent, e.g. tetrahydrofuran, and to the mixture is added an organic borane, derivative, e.g. dimethylsulfide borane, and the mixture is reacted at room temperature to heating under reflux for a several hours, e.g. one to 3 hours.

(vii) From methoxy derivative, actonyloxy derivative can be prepared by dissolving the starting material in an appropriate solvent, e.g. dichloromethane, and to the solution is added one to excess equivalent of Lewis acid, e.g. aluminium chloride, and thiol compound or sulfide compound, e.g. dimethylsulfide, and the mixture is reacted at under ice-cooling or at room temperature for one to 10 hours, and then the obtained hydroxy derivative is dissolved in an appropriate solvent, e.g. dimethylformamide, to the solution is added a base, e.g. sodium hydroxide or potassium carbonate, and an alkyl halide. The mixture is reacted at a room temperature for one to 12 hours.

(viii) A methoxy group can be changed to isopropoxy by dissolving the starting material in an appropriate solvent, e.g. dichloromethane, to the solution is added one to excess equivalent of Lewis acid, e.g. aluminum chloride, and thiol compound or sulfide compound, e.g. dimethylsulfide, and the mixture is reacted at room temperature to ice-cooling for one to 10 hours.

(ix) An aminocarbonyl group can be introduced by dissolving a starting compound having halogen atom in an appropriate solvent, e.g. dimethoxyethane, to the solution is added arylborric acid derivative, a base, e.g. sodium carbonate, a palladium compound e.g. tetrakis (triphenylphosphine)palladium(0), as a catalyst and the mixture is refluxed 1 to 6 hours.

(x) An alkylthio compound can be converted to an alkylsulfinyl compound or an alkylsulfonyl compound by reacting a starting compound with an oxidizing agent, e.g. metachloroperbenzoic acid, in an appropriate solvent, e.g. dichloromethane, under ice-cooling to heating. With vigorous heating or by treating with an excess amount of oxidizing agent, an alkylsulfonyl compound is obtained.

(xi) The hydroxyl group in the starting compound can be substituted by various kinds of groups. The reaction is carried out in an appropriate solvent, e.g. dimethylformamide (DMF), acetonitrile, acetone. To the solution of the starting compound is added halide such as alkyl halide, e.g. propyl iodide, isobutyl iodide, ethybromo acetate, or aralkyl halide, e.g. benzylchlolide. The mixture is stirred at 0 to 40° C. for 2 to 18 hours.

For example, in the case of ethyl bromoacetate, the obtained acetic acid ester is hydrolyzed in an adequate solvent and base, e.g. iN NaOH solution in ethyl alcohol, at room temperature for 2 to 12 hours. The acetic acid compound is dissolved in an adequate solvent, e.g. tetrahydrofuran (THF). To the solution is added isobutyl chloroformate in the presence of an adequate base, e.g. $Et_3N$, and the reaction is carried out at 0° C. for 1 to 4 hours. To the solution is added adequate amine derivatives, e.g. methylamine, propylamine, piperidine. The reaction is carried out at 0° C. to room temperature for 1 to 12 hours.

Said starting compound which has a hydroxyl group is produced by acid-hydrolysis of a compound such as one having an alkoxy group. The acid hydrolysis is carried out in a conventional manner for example by adding 1N hydrochloric acid in an appropriate solvent such as tetrahydrofuran or alcohol, e.g. methanol, ethanol, at 0° C. to room temperature for one to 10 hours.

(xii) The present compound is an having alkanoyl-phenyl group can be produced by the introduction of a alkanoylphenyl group to the halogenated compound. The halogenated compound is obtained by the halogenation reaction with the starting compound. The halogenation is carried out in an adequate solvent, e.g. carbontetrachloride or chloroform. To the solution is added N-bromosuccinimide and catalytic amount of 2,2'-azobis-(isobutyronitrile). The reaction is carried out at 100 to 120° C. for 1 to 4 hours. The introduction reaction of alkanoyl phenyl group is carried out in an appropriate degased solvent, e.g. dimethoxyethane (DME). To the solution is added alkanoyl phenyl borate, palladium compound, e.g. $Pd(PPh_3)_4$(Ph=phenyl) and sodium carbonate (2M, $Na_2CO_3$). The alkanoyl phenyl borate is synthesized by the reaction of alkanoyl phenyl bromide with adequate borate, e.g. $(i-PrO)_3B$(Pro=propyl) in the presence of adequate base, e.g. BuLi (Bu=butyl). The introduction reaction is carried out at room temperature to 120° C. for 1 to 12 hours under inert gas atmosphere.

(xiii) The present compound having alkylphenyl group can be produced by the similar manner as shown in (xii) with alkyl phenyl borates instead of alkanoyl phenyl borates.

Any other group in the compound can be introduced by any known per se known methods.

(xiv) The present compound having alkoxycarbonyl group, can be produced by introducing a cyano group, and then subjecting the obtained compound to esterification.

In the reaction of the introduction of cyano group, the starting compound is dissolved in an appropriate solvent, e.g. dimethylsulfoxide (DMSO), and to the solution is added sodium cyanide. The reaction is carried out at 40 to 60° C. for 2 to 12 hours.

The esterification reaction is carried out in an appropriate solvent such as ethyl alcohol. The reaction is conducted by mixing the starting compound and alcohol solution, e.g. ethyl alcohol, saturated with hydrochloric acid. The reaction is carried out at 80 to 120° C. for 12 to 48 hours.

(xv) The present compound having an alkyl group which is substituted by a sulfonamide group can be synthesized by (i) halogenation of this alkyl group and (ii) nucleophilic substitution of this halogen with a sulfonamide compound in the presence of appropriate base, e.g. sodium hydride.

The halogenation is carried out in an appropriate solvent, e.g. carbon tetrachloride. To the solution is added N-bromosuccinimide or catalytic amount of 2,2'-azobis (isobutyronitrile). The reaction is carried out at 100 to 120° C. for 1 to 4 hours.

The nucleophilic substitution reaction is carried out in an appropriate solvent such as N,N-dimethylformamide (DMF). To the solution is added sodium hydride washed with n-hexane and sulfonamide derivatives, e.g. methanesulfonamide, ethanesulfonamide, benzenesulfonamide. The reaction is carried out at 0 to 40° C. for 1 to 24 hours.

(xvi) The protective group, e.g. methoxymethyl, substituted on the hydroxyl group in the present compound can be removed. The starting compound is dissolved in an appropriate solvent, e.g. ethanol, to the solution is added an acid, e.g. hydrochloric acid, hydrogen chloride in ethanol, under ice-cooling, and the mixture is stirred for 0.5 to 5 hours.

(xvii) An acyl group or an acetonyl group can be introduced to the hydroxyl group in the compound. The starting compound having a hydroxyl group is dissolved in an appropriate solvent, e.g. dichloromethane, dimethylformamide, to the solution is added an appropriate base, e.g. triethylamine, pyridine. To the mixture is further added an excess amount of acid halide, acid chloride or alkyl halide. The mixture is stirred at room temperature for 6 to 24 hours.

(xviii) A carbonyl group in the compound can be converted to a group of the formula: —C(OH)H—. The starting compound having a carbonyl group is dissolved in an appropriate solvent, e.g. methanol, ethanol, and to the solution is added a small excess amount of a reducing agent, e.g. sodium boron hydride. The mixture is stirred at room temperature for 1 to 3 hours.

The pharmaceutical in the present invention include (1) pharmaceutical composition comprising a compound having LH—RH activity and a compound having LH—RH antagonizing activity and (2) pharmaceutical in which a compound having LH—RH activity and a compound having LH—RH antagonizing activity are prepared separately.

The pharmaceutical of the present invention has activity to suppress a transient elevation (flare) of serum concentrations of steroid hormones, e.g. testosterone and estorogen. Furthermore, the pharmaceutical desensitizes the LH and FSH secretory cells of the hypophysis and this desensitization is lasting. Furthermore, the suppression of testosterone or estrogen activity is amplified. In addition, its toxicity is low. Therefore, the pharmaceutical of the present invention can be safely used in the prevention or treatment of diseases depending upon sex hormone, i.e. male hormone or female hormone or the prevention or treatment of diseases occurring due to an excess of such hormones in mammals (e.g. human, monkey, bovine, horse, dog, cat, rabbit, rat, mouse, etc.). Thus, the pharmaceutical of the present invention is useful for the prevention or treatment of sex hormone-dependent cancers (e.g. prostatic cancer, uterine cancer, breast cancer, tumor of the pituitary, etc.), prostatic hypertrophy, hystereoma, endometriosis, precocious puberty, amenorrhea, premenstrual syndrome, polycystic ovary syndrome, acne, and other diseases. Furthermore, the pharmaceutical is useful for modulation of genital activity in both male and female individuals (e.g. gestation modulator, menstrual cycle modulator, etc.), too. Moreover, the pharmaceutical of the present invention can be provided as a contraceptive for use by the male or the female partner or, by taking advantage of the rebound phenomenon following withdrawal which induces ovulation, can be used in the treatment of sterility. In addition, the pharmaceutical of the invention finds application in the field of animal production for the purpose of aligning the estrus or heat of animals, improving the quality of meat, or promoting growth of animals.

It is also an effective modality to use the pharmaceutical of the invention in combination with a steroidal or a non-steroidal antiandrogen or antiesterogen. Cancer chemotherapeutic agents can also be used concomitantly. Preferable example for such a combined use includes hormonal drug, alkylating agent, antimetabolite, antineoplastic antibiotic, plant alkaloid and immunomodulator (BRM). The hormonal drug that can be used includes but is not limited to fosfestrol, diethylstilbestrol, chlorotrianisene, medroxyprogesterone acetate, megesterol acetate, chlormadinone acetate, cyproterone acetate, danazol, allylestrenol, gestrinone, mepartricin, laroxifene, ormeloxifene, levormeloxifene, antiesterogens (e.g. tamoxifen citrate, toremifene citrate, etc.), mepitiostane, testrolactone, aminoglutethimide, droloxifene, epitiostanol, ethinylestradiol sulfonate, aromatase inhibitors (e.g. fadrozole hydrochloride, anastrozole, letrozole, Excemestane, danazol (Bonzol), formestane, etc.), antiandrogens (e.g. flutamide, bicalutamide, nilutamide, etc.), 5α-reductase inhibitors (e.g. finasteride, epristeride, etc.), adrenocorticoids (e.g. dexamethasone, prednisolone, betamethasone, triamcinolone, etc.), androgen synthesis inhibitors (e.g. abiraterone, ketoconazole, 17α-hydroxylase/$C_{17-20}$ lyase inhibitor, etc.), retinoids and retinoid metabolism retardants (e.g. liarozole etc.), etc.

The alkylating agent includes but is not limited to nitrogen mustard, nitrogen mustard N-oxide hydrochloride, chlorambucil, cyclophosphamide, ifosphamide, thiotepa, carboquone, improsulfan tosylate, busulfan, nimustine hydrochloride, mitobronitol, melphalan, dacarbazine, ranimustine, estramustine sodium phosphate, triethylenemelamine, carmustine, lomustine, streptozotocin, pipobroman, etoglucid, carboplatin, cisplatin, miboplatin, nedaplatin (neoplatin), oxaliplatin, altretamine, ambamustine, diprospidium hydrochloride, fotemustine, prednimustine, pumitepa, ribomustin, temozolomide, treosulfan, trophosphamide, zinostatin stimalamer, carboquone, adozelesine, cystemustine, bizelesin, etc.

The antimetabolite includes but is not limited to mercaptopurine, 6-mercaptopurine riboside, thioinosine, methotrexate, enocitabine, cytarabine, cytarabine ocfosfate, ancitabine hydrochloride, 5-FU drugs (e.g. fluorouracil, tegafur, UFT, doxifluridine, carmofur, galocitabine, emitefur, etc.), aminopterin, leucovorin calcium, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, and ambamustine.

The antineoplastic antibiotic includes but is not limited to actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarcinostatin, mithramycin, sarcomycin, carzinophilin, mitotane, zorbicin hydrochloride, mitoxantrone hydrochloride, idarubicin hydrochloride, etc.

The plant alkaloid includes but is not limited to etoposide, etoposide phosphate, vinblastine sulfate, vincristine sulfate, vindesine sulfate, teniposite, paclitaxel, and pinosylvin.

The immunomodulator (BRM) includes but is not limited to picibanil, krestin, sizofiran, lentinan, ubenimex, interferons, interleukins, macrophage colony stimulating factor, granulocyte colony stimulating factor, erythropoietin, phymphotoxin, BCG vaccine, Corynebacterium parvum, levamisole, polysaccharide K, and procodazole.

As other drugs that can be used, there can be mentioned L-asparaginase, aceglatone, procarbazine hydrochloride, protoporphyrin-cobalt complex, hematoporphyrinmercury disodium, topoisomerase I inhibitors (e.g. irinotecan, topotecan, etc.), topoisomerase II inhibitors (e.g. sobuzoxane etc.), differentiation inducers (e.g. retinoids, vitamin D, etc.), proliferation factor inhibitors (e.g. suramin etc.), vascularization inhibitors, and α-blockers (e.g. tamsulosin hydrochloride etc.), among others.

Other anticancer therapies that can be used are surgery, radiation therapy, and thermotherapy. Furthermore, as specific examples of concomitant drugs that can be used in combination with the pharmaceutical of the present invention in the prevention or treatment of prostatic hypertrophy, there can be mentioned therapeutic agents for dysuria or micturition difficulty [e.g. Harnal (tamsulosin) etc.] in addition to said antiandrogens, 5α-reductase inhibitors, androgen synthesis inhibitors, and aromatase inhibitors.

Taking prostatic cancer as an example, chemotherapeutic drugs such as ifosfamide, UTF, adriamycin, peplomycin, cisplatin, etc. can be used concomitantly with the pharmaceutical of the present invention. In carcinoma of the breat, cyclophosphamide, 5-FU, UFT, methotrexate, adriamycin, mitomycin C, mitoxantrone, etc. can be used as concomitant chemotherapeutic agents.

The compounds using for the pharmaceutical of this invention may form a salt.

As such a salt physiologically acceptable acid addition salts are preferable. Examples of such salts include those with an inorganic acid (e.g. hydrochloric acid, hydrobromic acid, nitric acid, sulfuric acid, phosphoric acid and boric acid) or those with an organic acid (e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid). Further, when the compound of this invention has an acid group such as —COOH, the compound may form a salt with an inorganic base (e.g. an alkali metal or alkaline earth metal such as sodium, potassium, calcium and magnesium; ammonia) or an organic base (e.g. trimethylamine, triethylamine, pyridine, picolin, ethanolamine, diethanolamine, triethanolamine, dicyclohexylamine and N,N'-dibenzylethylenediamine).

The compounds or salts thereof which are used for the pharmaceutical of the present invention can be isolated and purified by a conventional separating means such as recrystallization, distillation and chromatography. In the case where the compound is produced in the free form, it can be converted to a salt thereof by a per se conventional means or a method analogous thereto. On the contrary, when it is obtained in the form of a salt, it can be converted to its free form or to any other salt.

In the case where the compound or a salt thereof used for the present invention is an optically active compound, it can be separated into d-compound and l-compound by means of a conventional optical resolution.

As the preparation at the time of administration, the compound having LH—RH activity and the compound having LH—RH antagonizing activity can be administered orally or non-orally in accordance with per se known means. Particularly, the case where the compound having LH—RH activity is non-oral agent, and the compound having LH—RH antagonizing activity is oral gent is preferable. At the preparation they are mixed with a pharmaceutically acceptable carrier and usually administered orally as a solid preparation such as tablet, capsule, granule or powder, or non-orally as intravenous, subcutaneous or intramuscular injection, or as suppository, sublingually administrable tablet or transnasal agent. Further, they can be sublingually, subcutaneously or intramuscularly administered as a prolonged release formulation such as sublingually administrable tablets, or microcapsules. Especially, as the preparation of the compound having luteinizing hormone releasing hormone activity, for example, injection, subcutaneous (including implant), or transnasal agent etc. is preferable.

To the compound which is used for the pharmaceutical of this invention, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method.

For administration of the compound or a salt thereof to a human being, for instance, it can be administered either as it is alone or in the form of a pharmaceutical composition containing a suitable pharmacologically acceptable carrier, excipient, and/or diluent, whether orally or non-orally with assurance of safety.

Examples of the above-mentioned pharmaceutical are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

As the above-mentioned pharmaceutically acceptable carriers, conventional various organic or inorganic carriers are used, and they are incorporated as excipients, lubricants, binders and disintegrants in solid compositions; and as solvents, solubilisers, suspending agents, isotonizing agents, buffering agents and pain-easing agents in liquid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and more volatile silicon dioxide. Preferable examples of above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxymethyl cellulose and polyvinyl pyrrolidone. Preferable examples of the above-mentioned disintegrants include starch, carboxymethyl cellulose, carboxymethyl cellulose calcium, cross carmelose sodium, cross carmelose sodium and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, trisaminomethane, cholesterol, triethanolamine, sodium carbonate and sodium citrate. Preferable examples of the above-mentioned suspending agents include surfactants such as stearyl triethanolamine, sodium sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glycerin and D-mannitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid.

Such pharmaceutical compositions can be manufactured by a per se known method commonly used in preparing pharmaceutical compositions.

The compound of the present invention or a salt thereof can be made into injections either in a form of an aqueous injection together with dispersing agents [e.g. Tween 80 (Atlas Powder, U.S.A.), HCO 80 (Nikko Chemicals, Japan), polyethylene glycol, carboxymethylcellulose, sodium alginate, etc.], preservatives (e.g. methyl paraben, propyl paraben, benzyl alcohol, etc.), isotonizing agents (e.g. sodium chloride, mannitol, sorbitol, glucose, etc.) and the like or in a form of an oily injection by dissolving, suspending or emulsifying in plant oil (e.g. olive oil, sesame oil, cotton seed oil, corn oil, etc.), propylene glycol and the like.

In preparing a pharmaceutical composition for oral use, the compound of the present invention or a salt thereof is molded by compressing, for example, with fillers (e.g. lactose, sucrose, starch, etc.), disintegrating agents (e.g. starch, calcium carbonate, etc.), binders (e.g. starch, gum arabic, carboxymethylcellulose, polyvinylpyrrolidone, hydroxypropylcellulose, etc.) or lubricants (e.g. talc, magnesium stearate, polyethylene glycol 6000, etc.) and the like. If necessary, the composition is coated by a per se known method with an object of masking the taste, enteric coating or long-acting. Examples of the coating agent therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), pigment (e.g. rediron oxide, titanium dioxide, etc.) and the like. Subcoating layer may be provided between the enteric coating and the core according to per se known method.

In preparing an external composition, the compound of the present invention or a salt thereof as it is or a salt thereof is subjected to a per se known method to give a solid, semisolid or liquid agent for external use. For example, the solid preparation is manufactured as follows. Thus, the compound of the present invention as it is or after adding/mixing fillers (e.g. glycol, mannitol, starch, microcrystalline cullulose, etc.), thickeners (e.g. natural gums, cellulose derivatives, acrylic acid polymers, etc.) and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent (e.g. carbonic acid, phosphoric acid, citric acid, hydrochloric acid, sodium hydroxide, etc.), an antiseptic agent (e.g. p-hydroxybenzoates, chlorobutanol, benzalkonium chloride, etc.) and the like.

In the manufacture of an ointment for example, the compound of the present invention or a salt thereof can be made into an oily or an aqueous solid, semisolid or liquid ointment. Examples of the oily base material applicable in the above-mentioned composition are glycerides of higher fatty acids [e.g. cacao butter, Witepsols (manufactured by Dynamite-Nobel), etc.], medium fatty acids [e.g. Miglyols (manufactured by Dynamite-Nobel), etc.] and plant oil (e.g. sesame oil, soybean oil, cotton seed oil, etc.) and the like. Examples of the aqueous base material are polyethylene glycols and propylene glycol and those of the base material for aqueous gel are natural gums, cellulose derivatives, vinyl polymers, acrylic acid polymers, etc.

The above-mentioned controlled release dosage form includes sustained-release microcapsules.

While such microcapsules can be manufactured by per se known technique, the particularly preferred are the sustained-release microcapsules manufactured by the method which comprises preparing a W/O emulsion using a liquid containing a water-soluble active substance and a drug carrier [such as a natural or synthetic gel-forming substance (e.g. gelatin) or a macromolecular substance (e.g. polyvinyl alcohol)] as an internal phase and a solution of a high polymer [e.g. poly(lactic acid) or poly(lactide-co-glycolide] as an external oil phase, thickening the internal phase to a viscosity of at least about 5000 cps or even solidifying it, and subjecting the emulsion to a in-water drying process (JP-A 57087/1989) or the sustained-release microcapsules manufactured by the method which comprises preparing a W/O emulsion using an internal water phase containing about 20–70 weight % of a bioactive polypeptide and an oil phase containing a copolymer or homopolymer having a lactic acid/glycolic acid ratio of 80/20–100/0 and a weight average molecular weight of 7,000–30,000 as a release control agent and microencapsulating the W/O emulsion (JP-A 321622/1992).

The above sustained-release microcapsules may be used in the form of a controlled release pellet injection (an implant).

The above-mentioned transnasal drug delivery system (DDS) can also be manufactured by per se known technique. For example, such a DDS can be provided by the following procedure. Thus, the compound or salt of the present invention is formulated with, for example, an isotonizing agent (e.g. sodium chloride, sodium citrate, glycerin, sorbitol, mannitol, glucose, boric acid, sucrose, polyethylene glycol, Tween 80, sodium monohydrogen phosphate, sodium dihydrogen phosphate, etc.), a buffer (e.g. sodium chloride, sodium citrate, boric acid, borax, sodium monohydrogen phosphate, sodium dihydrogen phosphate, etc.), a preservative (e.g. parabens such as methyl p-hydroxybenzoate, invert soaps such as benzalkonium chloride, alcohol derivatives such as benzyl alcohol, organic acids (e.g. sorbic acid) and their salts, phenol and other preservatives), a stabilizer (e.g. cysteine, thiosorbitol, tartaric acid, citric acid, sodium carbonate, ascorbic acid, glycine, sodium sulfite, etc.), a thickener (e.g. glycerin, polyethylene glycol, sorbitol, mannitol, methylcellulose, carboxymethylcellulose sodium, hydroxypropylmethylcellulose, hydroxypropylcellulose, polyvinyl alcohol, polyvinylpyrrolidone, etc.), a suspending agent (e.g. methylcellulose, carboxymethylcellulose sodium, hydroxypropylmethylcellulose, hydroxypropylcellulose, polyethylene glycol, Tween 80, etc.), a bile acid-related surfactant (e.g. glycocholic acid, cholic acid, taurocholic acid, cholanic acid, ethocholic acid, deoxycholic acid, chenodeoxycholic acid, dehydrocholic acid, glycodeoxycholic acid, etc.) (JP-B 25068/1994) or a cyclodextrin [e.g. α-cyclodextrin, β-cyclodextrin, γ-cyclodextrin, and their derivatives (e.g. methyl, hydroxyethyl, glycosyl, carboxymethylethyl and other derivatives) (JP-B 19092/1990) is added to the compound or salt of the invention and the resulting composition is provided as an aqueous solution or suspension.

Furthermore, the compound or salt of the invention can be processed into an aerosol (JP-A 211237/1988).

The daily dosage of the pharmaceutical of the present invention is not particularly restricted but should be selected with reference to the severity of illness, the recipient's age, gender, body weight and sensitivity, the timing and interval of dosing, the nature, formulation and type of the dosage form, and the species of active compound. In terms of the compound having LH—RH activity, the dosage should only be sufficient to desensitize the pituitary LH and FSH secretory cells without inducing side effects. Usually, however, the dosage per kg body weight of a mammal may be about 0.00003–3 mg, preferably about 0.0003–0.3 mg, and more preferably about 0.002–0.01 mg in an subcutaneous dosage form, which dosage is usually administered in 1–4 divided doses. The dosage for use in animal or fish production can also be selected with reference to the above dosage. Thus, about 0.0003–3 mg or preferably about 0.001–0.03 mg of the compound per kg body weight of the recipient creature is administered, usually in 1–3 divided doses daily. The daily dosage of sustained-release dosage forms is also selected with reference to the above dosage.

The duration and amount of administration of the LH—RH antagonist compound can be freely selected only if the flare due to the LH—RH agonist compound can be controlled and the pituitary LH and FSH secretory cells can be successfully desensitized without eliciting onset of any remarkable side effect. The daily dosage as the LH—RH antagonist compound cannot be stated in general terms because it varies with the severity of illness, the recipient's age, gender, body weight, and sensitivity, the timing and interval of dosing, the nature, formulation, and type of the dosage form, and a species of active compound. Usually, however, the dosage per kg body weight of a mammal may be about 0.1–160 mg, preferably about 0.1–40 mg, more preferably about 0.1–30 mg or about 0.1–20 mg, and most preferably 0.1–10 mg in an oral dosage form, which dosage is usually administered in 1–4 divided doses daily. The dosage for use in animal production or fish production can also be selected with reference to the above dosage. Thus, about 0.01–10 mg or preferably about 0.02–5 mg per kg body weight of the recipient is administered, usually in 1–3 divided doses daily. In the case of a sustained-release dosage form, too, the same daily dosage as above is used as the basis.

In the pharmaceutical of the present invention, the ratio of the administration amount of the LH—RH antagonist compound to the LH—RH agonist compound may for example be about $10–10^6/1$ by weight, preferably about $10–10^5/1$ by weight, more preferably about $10–10^4/1$ by weight, and most preferably about $10^2–10^4/1$ by weight.

In administering the pharmaceutical of the present invention, the two dosage components can be administered concurrently but it is preferable to administer the LH—RH antagonist compound in the first place and the LH—RH agonist compound in the second place. Thus, in this sequential or staggered administration, the LH—RH antagonist compound is preferably administered first and, only after its blood concentration has reached a sufficient level, the LH—RH agonist compound is administered. While the preferred time lag varies with the dosage form and other factors, the mode of administering the LH—RH agonist compound at least one hour after administration of the LH—RH antagonist compound or the mode of administering the LH—RH agonist compound one hour to one day or one week after administration of the LH—RH antagonist compound can be employed.

The preferred regimen may for example be that of administering about 0.1–10 mg/kg of the LH—RH antagonist compound in an oral dosage form and, after 2–6 hours, administering about 0.001–0.03 mg/kg/day of the LH—RH agonist compound either in a sustained release subcutaneous dosage form (e.g. microcapsules) or in a transnasal DDS. (In the case of, for example, a 30-day sustained release dosage form, 30 times the daily dose is used). Thereafter, the oral dosage form is administered 1–4 times a day (daily dose 0.1–10 mg/kg) for 3–14 consecutive days.

An alternative regimen may be that of administering about 0.1–10 mg/kg/day of the LH—RH antagonist compound in a subcutaneous dosage form (injection) subcutaneously and, after 1–6 hours, administering about 0.001–0.03 mg/kg/day of the LH—RH agonist compound either in a sustained release dosage form (e.g. microcapsules) or in a transnasal DDS. (In the case of, for example, a 30-day sustained release preparation, 30 times the daily dose is used). Then, the subcutaneous dosage form is administered 1–4 times a day (daily dosage 0.1–10 mg/kg) for 3–14 consecutive days.

A further alternative regimen may be that of administering about 0.1–10 mg/kg/day of the LH—RH antagonist compound in a sustained release dosage form (e.g. microcapsules) (in the case of, for example, a 30-day controlled release dosage form, 30 times the daily dose) subcutaneously and, after about 1–6 hours, administering about 0.001–0.03 mg/kg/day of the LH—RH agonist compound in a sustained release dosage form (e.g. microcapsules) (in the case of, for example, a 30-day controlled release dosage form, 30 times the daily dose) subcutaneously.

As a further alternative, it is possible to administer the LH—RH antagonist compound beforehand for a given time period and, then, administer the LH—RH agonist compound. For example, 0.1–10 mg/kg/day of the LH—RH antagonist compound is administered subcutaneously or orally for 1 day to 3 weeks or the same dose of a sustained release dosage form is administered and, then, the LH—RH agonist compound is administered.

While the LH—RH agonist compound and LH—RH antagonist compound according to the present invention can be used in the above modes of combination, the respective compounds may be provided in distinct dosage forms in a kit. In a typical case, it is indicated on the direct container, carton, and/or package insert for each component dosage form that the tablet or injection, for instance, of the LH—RH antagonist compound should be first administered and, after 1–6 hours, the sustained release dosage form or transnasal DDS of the LH—RH agonist compound be administered or that the tablet or injection of the LH—RH antagonist compound should be first administered repeatedly for 1–3 weeks and, thereafter, the sustained release dosage form or transnasal DDS of the LH—RH agonist compound be administered.

Each of the LH—RH agonist compound and the LH—RH antagonist compound is usually incorporated into a pharmaceutical or pharmaceuticals in an amount of about 1 to 99 weight %.

EXAMPLES

By way of the following Experimental Example, Examples and Reference Examples, the present invention will be described more specifically, but they are not intended to limit the scope of this invention thereto.

Among compounds employed in the following, Compound E-1 is 4,7-dihydro-3-(N-methyl-N- benzylaminomethyl)-7-(2-methoxybenzyl)-2-(4-methoxyphenyl)-4-oxothieno[2,3-b]pyridine-5-carboxylic acid ethyl ester hydrochloride, Compound E-2 is 2-(4-acetylaminophenyl)-4,7-dihydro-3-(N-methyl-N-benzylaminomethyl)-7-(2-methoxybenzyl)-4-oxothieno[2,3-b]pyridine-5-carboxylic acid ethyl ester, Compound E-3 is 5-n-butyryl-4,7-dihydro-3-(N-methyl-N-benzylaminomethyl)-7-(2-fluorobenzyl)-2-(4-methoxyphenyl)-4-oxothieno[2,3-b]pyridine hydrochloride, Compound E-4 is 5-benzoyl-4,7-dihdyro-3-(N-methyl-N-benzylaminomethyl)-7-(2-fluorobenzyl)-2-(4-methoxyphenyl)-4-oxothieno[2,3-b]pyridine hydrochloride, Compound E-5 is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine, and Compound E-6 is 7-(2,6-difluorobenzyl)-4,7-dihydro-3-(N-methyl-N-benzylaminomethyl)-5 -isobutyryl-2-(4-propionylaminophenyl)-4-oxo-thieno[2,3-b]pyridine hydrochloride and E-7 is 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine hydrochloride. These compounds are described in PCT International Publication No. WO95/28405.

Reference Example (a)

Using Compound E-5 (100 mg) whose chemical formula is shown in the bottom in Table 19 mentioned hereinafter, lactose (165 mg), corn starch (25 mg), polyvinylalcohol (4 mg) and magnesium stearate (1 mg), tablets are prepared by a conventional method.

Reference Example (b)

Compound E-5 (0.5 g) is dissolved in distilled water for injection to make the whole volume 100 ml. The solution is subjected to sterilized filtration with 0.22 μm membrane filter (manufactured by Sumitomo Electric Industries, Ltd. or by Zartolius, Inc.), 2 ml each of which is distributed to sterilized vials, followed by lyophilization by a conventional means to give lyophilized injectable solution of 100 mg/vial.

Reference Example (c)

| (1)  | Compound E-5 | 5 g |
|------|-------------|-----|
| (2)  | Lactose · crystalline cellulose (granules) | 330 g |
| (3)  | D-mannitol | 29 g |
| (4)  | Hydroxypropyl cellulose of low substitution degree | 29 g |
| (5)  | Talc | 25 g |
| (6)  | Hydroxypropyl cellulose | 50 g |
| (7)  | Aspartame | 3 g |
| (8)  | Glycyrrhizic acid dipotassium salt | 3 g |
| (9)  | Hydroxypropylmethyl cellulose 2910 | 30 g |
| (10) | Titanium oxide | 3.5 g |
| (11) | Yellow iron sesquioxide | 0.5 g |
| (12) | Light anhydrous silicic acid | 1 g |

In pure water are suspended or dissolved (1), (3), (4), (5), (6), (7) and (8). The granule of (2) is coated with the suspension or solution to prepare raw fine granules, which are coated with (9) to (11) prepare coated fine granules, which are mixed with (12), to give 500 g of fine granules containing 1% of the Compound E-5. 500 mg each of thus-prepared fine granules is packed.

Reference Example (d)

Using Compound E-1, E-2, E-3, E-4 or E-5 (100 mg), lactose (165 mg), corn starch (25 mg), hydroxy propyl cellulose (9 mg) and magnesium stearate (1 mg), tablets are prepared by a conventional method.

Reference Example (e)

Using Compound E-6 or E-7 (100 mg), crystalline cellulose (50 mg), low substituted hydroxypropylcellulose-31 (30 mg), hydroxypropylcellulose L (6 mg) and magnesium stearate (1 mg), tablets are prepared by a conventional method.

Reference Example (f)

Using the compound which is produced in Reference Example 2:16 (100 mg) below mentioned, lactose (150 mg), cross carmelose sodium (30 mg), hydroxypropylcellulose (6 mg) and magnesium stearate (1 mg), tablets are prepared by a conventional method.

Reference Example (g)

Using the compound which is produced in Reference Example 3:30 (100 mg) below mentioned, lactose (165 mg), corn starch (25 mg), polyvinyl alcohol (4 mg) and magnesium stearate (1 mg), tablets are prepared by a conventional method.

Reference Example (h)

Using the compound which is produced in Reference Example 4:2 (100 mg), lactose (150 mg), low substituted hydroxypropylcallulose-31 (30 mg), polyvinylpyrrolidone (10 mg) and magnesium stearate (1 mg), tablets are prepared by a conventional method.

Reference Example (i)

Using the compound which is produced in Reference Example 5:5(1) (100 mg) below mentioned, lactose (150 mg), carboxymethylcellulose calcium (30 mg), hydroxypropylcellulose (6 mg) and magnesium stearate (1 mg), tablets are prepared by a conventional method.

Reference Example (j)

Using the compound which is produced in Reference Example 6:21 (100 mg) below mentioned, lactose (165 mg), corn starch (25 mg), polyvinyl alcohol (4 mg) and magnesium stearate (1 mg), tablets are prepared by a conventional method.

Reference Example (k)

Using the compound which is produced in Reference Example 7:6 (100 mg) below mentioned, lactose (165 mg), corn starch (25 mg), polyvinyl alcohol (4 mg) and magnesium stearate (1 mg), tablets are prepared by a conventional method.

Reference Example (l)

Compound E-1, E-2, E-3, E-4 or E-5 (0.5 g) and mannitol (1 g) are dissolved in distilled water for injection to make the whole volume 100 ml. The solution is subjected to sterilized filtration with 0.22 μm membrane filter (manufactured by Sumitomo Electric Industries, Ltd. or by Zartolius, Inc.), 10 ml each of which is distributed to sterilized vials, followed by lyophilization by a conventional means to give lyophilized injectable solution of 50 mg/vial.

Reference Example (m)

| | |
|---|---|
| (1) Compound E-1, E-2, E-3, E-4 or E-5 | 100 g |
| (2) Lactose | 234 g |
| (3) Corn starch | 150 g |
| (4) Hydroxypropyl cellulose | 45 g |
| (5) Light anhydrous silicic acid | 1 g |
| total amount | 500 g |

The above (1), (2) and (3) are mixed in a fluidized-bed granulating machine, and an aqueous solution of (4) is sprayed to the mixture in the granulating machine to give fine granules. After mixing with the (5), 500 mg each of thus prepared fine granules are packed.

In the following Reference Examples, $^1$H-NMR spectra are taken with the Varian GEMINI 200 (200 MHz) type spectrometer, JEOL LAMBDA300 (300 MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

Reference Example 1

The compounds shown in the following Tables 1 to 21 are produced in accordance with the methods described in PCT International Publication No. WO95/28405.

TABLE 1

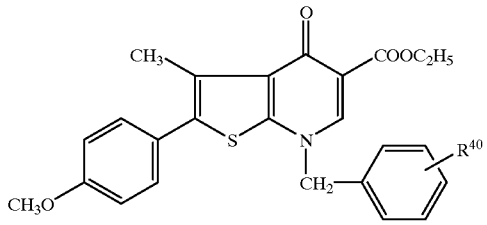

| $R^{40}$ | m.p. (° C.) |
|---|---|
| 2-methoxy | 165–167 |
| hydrogen | 170–172 |
| 3-methoxy | 153–155 |
| 4-methoxy | 132–134 |
| 2-methyl | 199–201 |
| 2-acetoxy | 154–156 |
| 2-methylthio | 152–154 |
| 4-nitro | 98–99 |

TABLE 1-continued

| $R^{40}$ | m.p. (° C.) |
|---|---|
| 4-(2-cyanophenyl) | 134–136 |
| 4-(2-t-butoxy-carbonyl)phenyl | 120–122 |

TABLE 2

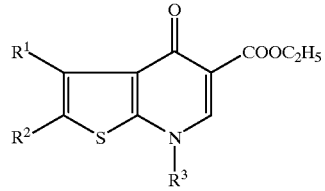

| $R^1$ | $R^2$ | $R^3$ | m.p. (° C.) |
|---|---|---|---|
| methyl | 4-nitrophenyl | 2-methoxybenzyl | 194–195 |
| methyl | phenyl | 2-methoxybenzyl | amorphous |
| phenyl | methyl | 2-methoxybenzyl | 184–186 |
| methyl | benzyl | 2-methoxybenzyl | 65–70 |
| methyl | phenylacetyl | 2-methoxybenzyl | 167–170 |
| methyl | 2-methoxyphenyl | 2-methoxybenzyl | 194–196 |
| methyl | bromine | 2-methoxybenzyl | 161–163 |
| methyl | 4-nitrophenyl | 2-fluorobenzyl | 184–186 |
| methyl | 4-methoxyphenyl | 2-fluorobenzyl | 117–120 |
| methyl | 4-methoxyphenyl | 2,6-difluorobenzyl | amorphous |
| methyl | 4-nitrophenyl | 2,6-difluorobenzyl | 215–217 |
| methyl | 4-nitrophenyl | 2-chloro-6-fluorobenzyl | 211–213 |
| methyl | phenyl | 2,6-difluorobenzyl | 184–186 |
| methyl | phenyl | 2-chloro-6-fluorobenzyl | 171–173 |
| methyl | 4-methoxyphenyl | 1-naphthyl | 193–195 |
| methyl | 4-methoxyphenyl | 2-methoxyphenethyl | 134–136 |
| methyl | 4-methoxyphenyl | phenethyl | 182–184 |
| methyl | 4-methoxyphenyl | 3-phenylpropyl | 147–149 |
| methyl | 4-methoxyphenyl | cinnamyl | 170–172 |
| methyl | 4-methoxyphenyl | 3-picolyl | 142–144 |
| methyl | bromine | 2-fluorobenzyl | 211–213 |
| methyl | bromine | 2,6-difluorobenzyl | 175–176 |

TABLE 3

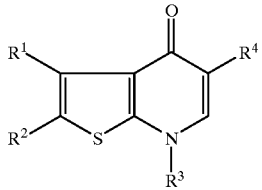

| R¹ | R² | R³ | R⁴ | m.p. (° C.) |
|---|---|---|---|---|
| methyl | 4-methoxyphenyl | 2-methoxybenzyl | hydroxymethyl | 153–156 |
| methyl | 4-methoxyphenyl | 2-methoxybenzyl | acetoxymethyl | 158–159 |
| bromomethyl | 4-mehoxyphenyl | 2-methoxybenzyl | ethoxycarbonyl | 200–201 |

TABLE 4

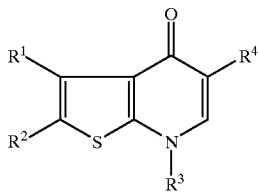

| R¹ | R² | R³ | R⁴ | m.p. (° C.) |
|---|---|---|---|---|
| bromomethyl | 4-nitrophenyl | 2-methoxybenzyl | ethoxycarbonyl | 173–175 |
| bromomethyl | 4-methoxyphenyl | 2-methoxybenzyl | acetoxymethyl | 131–133 |
| bromomethyl | phenyl | 2-methoxybenzyl | ethoxycarbonyl | 194–196 |
| phenyl | bromomethyl | 2-methoxybenzyl | ethoxycarbonyl | amorphous |
| bromomethyl | benzoyl | 2-methoxybenzyl | ethoxycarbonyl | amorphous |
| bromomethyl | 2-methoxyphenyl | 2-methoxybenzyl | ethoxycarbonyl | amorphous |
| bromomethyl | bromide | 2-methoxybenzyl | ethoxycarbonyl | 174–175 |
| bromomethyl | 3-methoxyphenyl | 2-methoxybenzyl | ethoxycarbonyl | 83–86 |
| bromomethyl | 4-nitrophenyl | 2-fluorobenzyl | ethoxycarbonyl | 202–204 |
| bromomethyl | 4-methoxyphenyl | 2-fluorobenzyl | ethoxycarbonyl | amorphous |
| bromomethyl | 4-nitrophenyl | 2,6-difluorobenzyl | ethoxycarbonyl | 200–202 |
| bromomethyl | 4-nitrophenyl | 2-chloro-6-fluorobenzyl | ethoxycarbonyl | 175–177 |
| bromomethyl | 4-methoxyphenyl | 2-fluorobenzyl | 1-acetoxyethyl | amorphous |
| bromomethyl | 4-nitrophenyl | 2,6-difluorobenzyl | benzoyl | amorphous |
| bromomethyl | 4-nitrophenyl | 2,6-difluorobenzyl | isobutyryl | 236–238 |
| bromomethyl | 4-methoxyphenyl | 2,6-difluorobenzyl | isobutyryl | 123–124 |
| bromomethyl | 4-methoxyphenyl | 2-fluorobenzyl | acetyl | 226–228 |
| bromomethyl | 4-methoxyphenyl | 2-fluorobenzyl | propionyl | 186–187 |
| bromomethyl | 4-methoxyphenyl | 2-fluorobenzyl | butyryl | 165–166 |

TABLE 4-continued

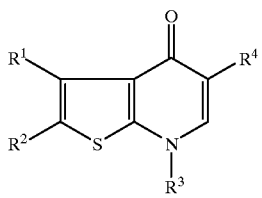

| R¹ | R² | R³ | R⁴ | m.p. (° C.) |
|---|---|---|---|---|
| bromomethyl | 4-methoxyphenyl | 2-fluorobenzyl | hexanoyl | 168–169 |
| bromomethyl | 4-methoxyphenyl | 2-fluorobenzyl | valeryl | 173–174 |
| bromomethyl | 4-methoxyphenyl | 2-fluorobenzyl | heptanoyl | 146–147 |
| bromomethyl | 4-methoxyphenyl | 2-fluorobenzyl | isovaleryl | 187–189 |
| bromomethyl | 4-methoxyphenyl | 2-fluorobenzyl | benzoyl | 145–147 |
| bromomethyl | 4-ethoxycarbonylphenyl | 2-methoxybenzyl | ethoxycarbonyl | 196–198 |
| bromomethyl | 4-methoxymethoxyphenyl | 2-fluorobenzyl | ethoxycarbonyl | 115–120 |
| bromomethyl | 4-diethylaminocarbonylphenyl | 2-fluorobenzyl | ethoxycarbonyl | amorphous |
| bromomethyl | 4-ethoxycarbonylphenyl | 2,6-difluorobenzyl | benzoyl | 190–192 |
| bromomethyl | 4-butoxyphenyl | 2-fluorobenzyl | ethoxycarbonyl | 138–140 |
| bromomethyl | 4-methoxyphenyl | 2-fluorobenzyl | cyano | 216–218 |

TABLE 5

Structure: R¹ substituted thieno[2,3-b]pyridine with 4-methoxyphenyl at position 6, 2-methoxybenzyl on N, and COOC₂H₅ group.

| R¹ | m.p. (° C.) |
|---|---|
| benzylaminomethyl | 118–119 (hydrochloride) |
| anilinomethyl | 173–174 |
| phenethylaminomethyl | 148–151 (oxalate) |
| phenylpropylaminomethyl | 116–118 (hydrochloride) |
| N'-methylpiperazinylmethyl | 138–139 |
| N'-phenylpiperazinylmethyl | 189–190 |
| 4-phenylpiperidinomethyl | 165–167 (oxalate) |
| N'-benzylpiperazinylmethyl | 109–110 (oxalate) |
| phthalimidomethyl | 221–223 |
| 1,2,3,4-tetrahydro isoquinolylmethyl | 156–158 (hydrochloride) |
| benzhydrylaminomethyl | 133–135 (hydrochloride) |
| N-phenyl-N-benzylaminomethyl | 93–95 (hydrochloride) |
| methylaminomethyl | 118–120 (hydrobromide) |
| ethylaminomethyl | 114–116 (hydrobromide) |
| N-benzyl-N-methylaminomethyl | 96–98 (oxalate) |
| N-benzyl-N-methylaminomethyl | 147–152 (hydrochloride) |
| 2-methoxybenzylaminomethyl | 108–110 (hydrochloride) |
| 3-methylbenzylaminomethyl | 110–112 (hydrochloride) |
| 3,4-dimethoxybenzyl-aminomethyl | 129–131 (hydrochloride) |
| 2-phenylimidazo-1-ylmethyl aminomethyl | 130–132 |
| | 104–106 (hydrobromide) |
| N-benzyl-N-dimethylammonium methyl | 135–137 (bromide) |
| N-methyl-N-(2,3,4-trimethoxybenzyl)aminomethyl | 113–115 (hydrochloride) |
| N-methyl-N-(N-methylindol-3-yl)ethylaminomethyl | 151–153 (hydrochloride) |
| N-methyl-N-phenylpropylaminomethyl | 103–105 (hydrochloride) |
| N-methyl-N-(2-thiomethylbenzyl)aminomethyl | 115–117 (hydrochloride) |
| N-methyl-N-(3,5-trifluoro-methylbenzyl)aminomethyl | 130–132 (hydrochloride) |
| N-methyl-N-(2,6-dichlorobenzyl)aminomethyl | 124–126 (hydrochloride) |
| N-methyl-N-(2-nitrobenzyl)aminomethyl | 139–141 (hydrochloride) |
| t-butylaminomethyl | 126–128 (hydrobromide) |
| dimethylaminomethyl | 117–119 (hydrobromide) |
| N-methyl-N-(2-chlorobenzyl)-aminomethyl | 143–145 (hydrochloride) |
| N-methyl-N-(3-chlorobenzyl)-aminomethyl | 203–205 (hydrochloride) |
| N-methyl-N-(4-chlorobenzyl)-aminomethyl | 197–199 (hydrochloride) |
| N-methyl-N-(2-fluorobenzyl)-aminomethyl | 120–122 (hydrochloride) |
| dibenzylaminomethyl | 155–157 (hydrochloride) |
| N-hydroxyethyl-N-benzyl-aminomethyl | 112–114 (hydrochloride) |
| N-ethoxycarbonylethyl-N benzylaminomethyl | 78–80 (hydrochloride) |
| N-benzyl-N-acetamidomethyl | 77–82 (hydrochloride) |
| N-propyl-N-benzylaminomethyl | 103–107 (hydrochloride) |
| N-benzyl-N-phenethylaminomethyl | 105–111 (hydrochloride) |
| 2-indanylaminomethyl | 128–132 (hydrochloride) |
| N-methyl-N-(2-indanyl)aminomethyl | 121–125 (hydrochloride) |
| N-methyl-N-(3-nitrobenzyl)aminomethyl | 209–211 (hydrochloride) |
| N-methyl-N-(4-nitrobenzyl)aminomethyl | 199–201 (hydrochloride) |

TABLE 5-continued

| R¹ | m.p. (° C.) |
|---|---|
| N-methyl-N-(2-phenyl-benzyl)aminomethyl | 112–114 (hydrochloride) |

TABLE 6

Structure: thieno[2,3-b]pyridinone with R¹, R², R⁴ substituents and N-benzyl bearing R⁴¹.

| R¹ | R² | R⁴¹ | R⁴ | m.p. (° C.) |
|---|---|---|---|---|
| N-benzyl-N-methylamino-methyl | 4-nitro-phenyl | 2-methoxy | ethoxy-carbonyl | 124–126 (hydro-chloride) |
| N-benzyl-N-methylamino-methyl | 4-methoxy-phenyl | 2-methoxy | acetoxy-methyl | 108–117 (hydro-chloride) |
| N-benzyl-aminomethyl | phenyl | 2-methoxy | ethoxy-carbonyl | 167–169 (hydro-chloride) |
| N-benzyl-N-methylamino-methyl | phenyl | 2-methoxy | ethoxy-carbonyl | 117–120 (hydro-chloride) |
| phenyl | N-benzyl-aminomethyl | 2-methoxy | ethoxy-carbonyl | 195–197 (hydro-chloride) |
| N-benzyl-N-methylamino-methyl | benzoyl | 2-methoxy | ethoxy-carbonyl | 90–95 (hydro-chloride) |
| N-benzyl-aminomethyl | 2-methoxy-phenyl | 2-methoxy | ethoxy-carbonyl | 114–118 (hydro-chloride) |
| N-benzyl-N-methylamino-methyl | 2-methoxy-phenyl | 2-methoxy | ethoxy-carbonyl | 119–122 (hydro-chloride) |
| N-benzylamino-methyl | bromine | 2-methoxy | ethoxy-carbonyl | 207–211 (oxalate) |
| N-benzyl-N-methylamino-methyl | bromine | 2-methoxy | ethoxy-carbonyl | 112–116 (oxalate) |
| N-benzyl-N-methylamino-methyl | 3-methoxy-phenyl | 2-methoxy | ethoxy-carbonyl | 115–120 (hydro-chloride) |
| N-benzyl-N-methylamino-methyl | 4-ethoxy-carbonyl-phenyl | 2-methoxy | ethoxy-carbonyl | 122–125 (hydro-chloride) |
| N-benzyl-N-methylamino-methyl | 4-methoxy-phenyl | 2-fluoro-benzyl | cyano | 203–206 (hydro-chloride) |

TABLE 7

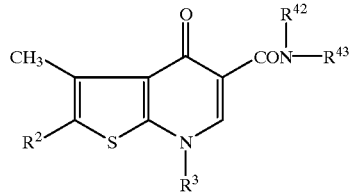

| R² | R³ | R⁴² | R⁴³ | m.p. (° C.) |
|---|---|---|---|---|
| 4-methoxy-phenyl | 2-methoxy-benzyl | N-benzyl-piperazinyl | hydrogen | 233–235 |
| 4-methoxy-phenyl | 2-methoxy-benzyl | 3-pyridyl | hydrogen | 214–216 |
| 4-methoxy-phenyl | 2-methoxy-benzyl | dimethyl-aminopropyl | hydrogen | 160–164 |
| 4-methoxy-phenyl | 2-methoxy-benzyl | 3-pyridyl-methyl | hydrogen | 168–170 |
| 4-nitro-phenyl | 2,6-difluoro-benzyl | methyl | methoxy | 223–224 |
| phenyl | 2,6-difluoro-benzyl | methyl | methoxy | amorphous |

TABLE 8

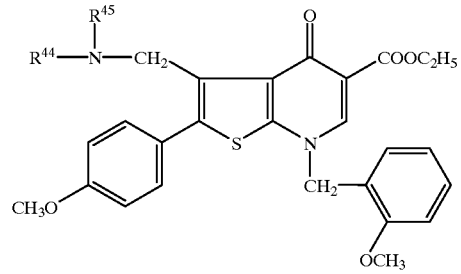

| R⁴⁴ | R⁴⁵ | m.p. (° C.) (hydrochloride) |
|---|---|---|
| 2-methoxybenzyl | methyl | 107–109 |
| 2-methylbenzyl | methyl | 120–122 |
| 3-methoxybenzyl | methyl | 74–76 |
| 4-methoxybenzyl | methyl | 126–128 |
| 2,3-dimethoxybenzyl | methyl | 99–101 |
| 2-bromobenzyl | methyl | 141–143 |
| phenethyl | ethyl | 133–135 |
| 2-methoxyphenethyl | methyl | 154–156 |
| 2'-cyanobiphenyl-4-methyl phenylcarbamoyl | methyl | 120–122 |
| 3-phenyl-2-propenyl | methyl | 89–91 |
| allyl | methyl | 152–154 |
| 3-pyridylmethyl | methyl | 138–140 |
| 1-naphthylmethyl | methyl | 160–162 |
| 2-naphthylmethyl | methyl | 161–163 |
| α-methylbenzyl | methyl | 148–150 |
| 2-hydroxybenzyl | methyl | 149–151 |
| 2-methoxycarbonyl-benzyl | methyl | 178–180 |
| 2-trifluoromethyl-benzyl | methyl | 129–131 |
| 2-thenyl | methyl | 121–123 |
|  |  | 133–135 |

TABLE 9

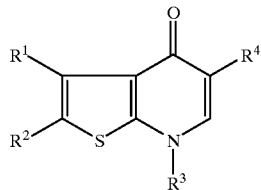

| R¹ | R² | R³ | R⁴ | m.p. (° C.) |
|---|---|---|---|---|
| N-methyl-N-benzylaminomethyl | 4-aminophenyl | 2-methoxybenzyl | ethoxycarbonyl | 120–122 |
| N-methyl-N-benzylaminomethyl | 4-methoxyphenyl | 2-methoxybenzyl | hydroxymethyl | 135–140 (hydrochloride) |
| N-methyl-N-benzylaminomethyl | 4-methoxyphenyl | 2-methoxybenzyl | carboxamide (—CO—NH₂) | 152–157 (hydrochloride) |
| N-methyl-N-benzylaminomethyl | 4-methoxyphenyl | 2-methoxybenzyl | N,N-dimethyl-carboxamide | 136–144 (hydrochloride) |
| N-methyl-N-benzylaminomethyl | 4-methoxyphenyl | 2-methoxybenzyl | N'-benzyl-piperazinocarbonyl | 168–174 (hydrochloride) |
| N-methyl-N-benzylaminomethyl | 4-methoxyphenyl | 2-methoxybenzyl | piperidinocarbonyl | 133–142 (hydrochloride) |
| methyl | 3-methoxyphenyl | 2-methoxybenzyl | ethoxycarbonyl | amorphous |
| N-methyl-N-benzylaminomethyl | 4-methoxyphenyl | 2-methylthiobenzyl | ethoxycarbonyl | 118–120 (hydrochloride) |
| N-methyl-N-benzylaminomethyl | 4-methoxyphenyl | 3-methoxybenzyl | ethoxycarbonyl | 109–113 (hydrochloride) |
| N-methyl-N-benzylaminomethyl | 4-methoxyphenyl | 4-methoxybenzyl | ethoxycarbonyl | 200–204 (hydrochloride) |

TABLE 9-continued

| $R^1$ | $R^2$ | $R^3$ | $R^4$ | m.p. (° C.) |
|---|---|---|---|---|
| N-methyl-N-benzylaminomethyl | 4-methoxyphenyl | 2-fluorobenzyl | ethoxycarbonyl | 203–207 (hydrochloride) |
| N-methyl-N-benzylaminomethyl | 4-methoxyphenyl | 1-naphthylmethyl | ethoxycarbonyl | 187–192 (hydrochloride) |
| N-methyl-N-benzylaminomethyl | 4-methoxyphenyl | 2-naphthylmethyl | ethoxycarbonyl | 122–125 (hydrochloride) |
| N-methyl-N-benzylaminomethyl | 4-methoxyphenyl | 2-methoxyphenethyl | ethoxycarbonyl | 76–81 (hydrochloride) |
| N-methyl-N-benzylaminomethyl | 4-methoxyphenyl | 2-trifluoromethyl- | ethoxycarbonyl | 189–194 (hydrochloride) |
| N-methyl-N-benzylaminomethyl | 4-methoxyphenyl | 2-methoxybenzyl | formyl | 181–185 |
| N-methyl-N-benzylaminomethyl | 4-acetylaminophenyl | 2-methoxybenzyl | ethoxycarbonyl | 161–163 |
| N-methyl-N-benzylaminomethyl | 4-formylaminophenyl | 2-methoxybenzyl | ethoxycarbonyl | 185–187 |
| methyl | 4-methoxyphenyl | 2-fluorobenzyl | hydroxymethyl | 184–185 |
| N-methyl-N-benzylaminomethyl- | 4-methoxyphenyl | 2-fluorobenzyl | hydroxymethyl | amorphous |

TABLE 10

| $R^1$ | $R^2$ | $R^3$ | $R^4$ | m.p. (° C.) |
|---|---|---|---|---|
| N-methyl-N-benzylaminomethyl | 4-nitrophenyl | 2-fluorobenzyl | ethoxycarbonyl | 140–144 |
| N-methyl-N-benzylaminomethyl | 4-nitrophenyl | 2,6-difluorobenzyl | ethoxycarbonyl | 145–147 |
| N-methyl-N-benzylaminomethyl | 4-nitrophenyl | 2-chloro-6-fluorobenzyl | ethoxycarbonyl | 175–177 |
| N-methyl-N-benzylaminomethyl | 4-aminophenyl | 2-fluorobenzyl | ethoxycarbonyl | 158–160 |
| N-methyl-N-benzylaminomethyl | 4-aminophenyl | 2,6-difluorobenzyl | ethoxycarbonyl | 195–196 |
| N-methyl-N-benzylaminomethyl | 4-aminophenyl | 2-chloro-6-fluorobenzyl | ethoxycarbonyl | 144–146 |
| methyl | 4-methoxyphenyl | 2-fluorobenzyl | formyl | colorless crystals |

TABLE 11

| $R^{40}$ | $R^{46}$ | |
|---|---|---|
| 2-fluoro | methyl | amorphous |
| 2-methoxy | methyl | amorphous |
| 2-fluoro | ethyl | amorphous |
| 2-fluoro | n-propyl | amorphous |
| 2-fluoro | phenyl | amorphous |
| 2-fluoro | isopropyl | amorphous |
| 2-fluoro | n-butyl | amorphous |
| 2-fluoro | sec-butyl | amorphous |
| 2-fluoro | t-butyl | amorphous |
| 2-fluoro | n-pentyl | amorphous |
| 2-fluoro | cyclopentyl | amorphous |
| 2-fluoro | n-hexyl | amorphous |
| 2-fluoro | cyclohexyl | amorphous |
| 2-fluoro | 4-fluorophenyl | amorphous |
| 2-fluoro | benzyl | amorphous |

TABLE 12

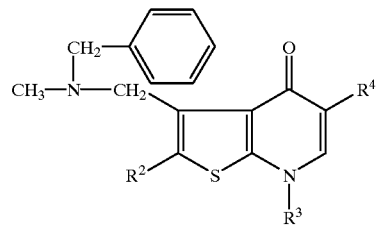
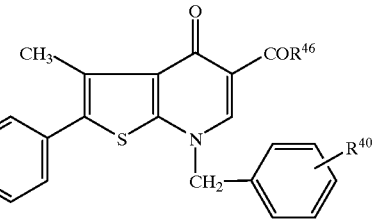

| $R^{40}$ | $R^{46}$ | m.p. (° C.) |
|---|---|---|
| 2-fluoro | methyl | 215–216 |
| 2-methoxy | methyl | 156–157 |
| 2-fluoro | ethyl | 180–181 |
| 2-fluoro | n-propyl | 170–171 |
| 2-fluoro | phenyl | 183–184 |
| 2-fluoro | isopropyl | 173–174 |
| 2-fluoro | n-butyl | 162–163 |
| 2-fluoro | sec-butyl | 132–133 |
| 2-fluoro | t-butyl | 141–144 |
| 2-fluoro | n-pentyl | 145–147 |
| 2-fluoro | cyclopentyl | 182–183 |
| 2-fluoro | n-hexyl | 125–126 |
| 2-fluoro | cyclohexyl | 191–192 |
| 2-fluoro | 4-fluorophenyl | 187–188 |

TABLE 13

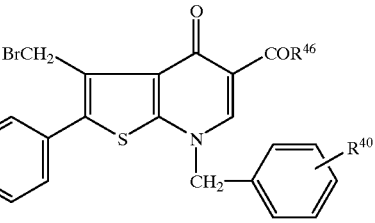

| $R^{40}$ | $R^{46}$ | m.p. (° C.) |
|---|---|---|
| 2-fluoro | methyl | 226–228 |
| 2-methoxy | methyl | 206–208 |
| 2-fluoro | ethyl | 186–187 |
| 2-fluoro | n-propyl | 165–166 |
| 2-fluoro | phenyl | 145–147 |
| 2-fluoro | isopropyl | 123–124 |
| 2-fluoro | n-butyl | 173–174 |
| 2-fluoro | sec-butyl | 146–148 |
| 2-fluoro | t-butyl | 98–99 |
| 2-fluoro | isobutyl | 187–189 |
| 2-fluoro | n-pentyl | 168–169 |
| 2-fluoro | cyclopentyl | 166–167 |
| 2-fluoro | n-hexyl | 146–147 |
| 2-fluoro | cyclohexyl | 169–170 |
| 2-fluoro | 4-fluorophenyl | 135–136 |

TABLE 14

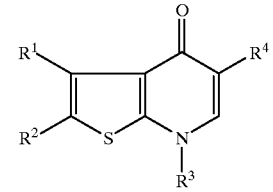

| $R^2$ | $R^3$ | $R^4$ | m.p. (° C.) |
|---|---|---|---|
| 4-methoxyphenyl | 2-fluorobenzyl | acetyl | 185–193 |
| 4-methoxyphenyl | 2-methoxybenzyl | acetyl | 124–130 (hydrochloride) |
| 4-methoxyphenyl | 2-fluorobenzyl | propionyl | 163–172 (hydrochloride) |
| 4-methoxyphenyl | 2-fluorobenzyl | n-butyryl | 145–150 (hydrochloride) |
| 4-methoxyphenyl | 2-fluorobenzyl | benzoyl | 154–161 (hydrochloride) |
| 4-N'-methyl-ureidophenyl | 2-fluorobenzyl | ethoxycarbonyl | 216–220 |
| 4-acetyl-aminophenyl | 2-fluorobenzyl | ethoxycarbonyl | 118–120 |
| 4-propionyl-aminophenyl | 2-fluorobenzyl | ethoxycarbonyl | 221–223 |
| 4-isobutyryl-aminophenyl | 2-fluorobenzyl | ethoxycarbonyl | 118–192 |
| 4-benzoyl-aminophenyl | 2-fluorobenzyl | ethoxycarbonyl | 141–143 |
| 4-methane-sulfonamido-phenyl | 2-fluorobenzyl | ethoxycarbonyl | >300 |

TABLE 15

| $R^1$ | $R^2$ | $R^3$ | $R^4$ | m.p. (° C.) |
|---|---|---|---|---|
| cyanomethyl | 4-methoxyphenyl | 2-fluorobenzyl | ethoxycarbonyl | oily product |
| ethoxycarbonyl-methyl | 4-methoxyphenyl | 2-fluorobenzyl | ethoxycarbonyl | 199–201 |
| hydroxyethyl | 4-methoxyphenyl | 2-fluorobenzyl | ethoxycarbonyl | amorphous |
| N-methyl-N-benzylamino-methyl | 4-methoxyphenyl | 2-fluorobenzyl | ethoxycarbonyl | amorphous |
| methyl | 4-methoxyphenyl | 2-fluorobenzyl | 1-acetoxy-ethyl | 145–146 |
| N-methyl-N-benzylamino-methyl | 4-methoxyphenyl | 2-fluorobenzyl | 1-acetoxy-ethyl | 183–187 |
| N-methyl-N-benzylamino-methyl | 4-nitrophenyl | 2,6-difluoro-benzyl | benzoyl | 197–199 |
| N-methyl-N-benzylamino-methyl | 4-nitrophenyl | 2,6-difluoro-benzyl | isobutyryl | 151–152 |

TABLE 15-continued

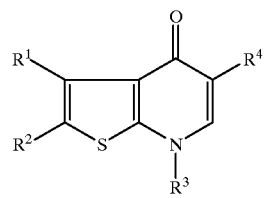

| R¹ | R² | R³ | R⁴ | m.p. (° C.) |
|---|---|---|---|---|
| N-methyl-N-benzylamino-methyl | 4-ethoxy-carbonyl-phenyl | 2,6-difluoro-benzyl | benzoyl | 175–180 (hydrochloride) 169–171 (free base) |
| N-methyl-N-benzylamino methyl | 4-butoxy-phenyl | 2-fluoro-benzyl | ethoxy-carbonyl | 200–202 |
| N-methyl-N-benzylamino-methyl | 4-methoxy-phenyl | 2-fluoro-benzyl | 1-hydroxy-ethyl | 183–187 |

TABLE 16

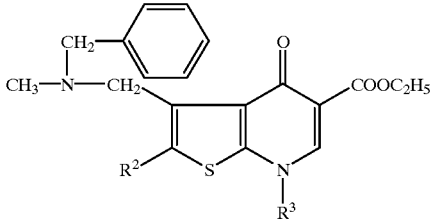

| R² | R³ | m.p. (° C.) |
|---|---|---|
| 4-N'-methyl-ureidophenyl | 2-chloro-6-fluorobenzyl | 199–200 |
| 4-N'-methyl-ureidophenyl | 2-chloro-6-fluorobenzyl | 182–184 |
| 4-propionyl-aminophenyl | 2-chloro-6-fluorobenzyl | 172–173 |
| 4-N'-methyl-ureidophenyl | 2,6-difluoro-benzyl | 214–215 |
| 4-propionyl-aminophenyl | 2,6-difluoro-benzyl | 100–102 |
| 4-N'-methylthio-ureidophenyl | 2,6-difluoro-benzyl | 215–217 |
| 4-(2-methoxy-propionyl-amino)phenyl | 2,6-difluoro-benzyl | 110–112 |
| 4-n-butyryl-aminophenyl | 2-fluoro-benzyl | 203–204 |
| 4-valeryl-aminophenyl | 2-fluoro-benzyl | 206–208 |
| 4-ethoxy-carbonylamino-phenyl | 2-fluoro-benzyl | amorphous |
| 4-N'-methyl-thioureido-phenyl | 2-fluoro-benzyl | 204–205 |
| 4-N'-phenyl-ureidophenyl | 2-fluoro-benzyl | 205–207 |

TABLE 17

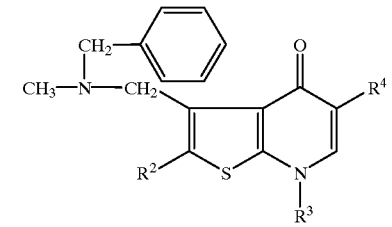

| R² | R³ | R⁴ | m.p. (° C.) |
|---|---|---|---|
| 4-nitro-phenyl | 2,6-difluoro-benzyl | (N-isopropyl)-carboxamide | 200–202 |
| 4-N'-methyl-ureidophenyl | 2,6-difluoro-benzyl | N-isopropyl-N-methylcarboxamide | 133–135 (184–186 as hydrochloride) |
| 4-N'-methyl-ureidophenyl | 2,6-difluoro-benzyl | N-methyl-O-methylhydroxamic acid | 138–140 |
| 4-propionyl-aminophenyl | 2,6-difluoro-benzyl | N,N-dimethyl-carboxamide | 110–112 |
| 4-propionyl-aminophenyl | 2,6-difluoro-benzyl | pyrrolidinylamide | 130–132 |
| 4-propionyl-aminophenyl | 2,6-difluoro-benzyl | N',N'-dimethyl-amino-1,3-propylcarboxamide | 90–92 |
| 4-propionyl-aminophenyl | 2,6-difluoro-benzyl | N-methyl-N-butyl-carboxamide | 120–122 |
| 4-N'-methyl-ureidophenyl | 2,6-difluoro-benzyl | N-methyl-N-benzo-carboxamide | 135–137 (179–181 as hydrochloride) |
| 4-N'-methyl-ureidophenyl | 2,6-difluoro-benzyl | N-isopropyl-carboxamide | 148–150 |
| 4-nitro-phenyl | 2,6-difluoro-benzyl | N-methyl-O-methylhydroxamic acid | 100–102 |
| 4-propionyl-aminophenyl | 2,6-difluoro-benzyl | N-isopropyl-carboxamide | 144–146 |
| 4-propionyl-aminophenyl | 2,6-difluoro-benzyl | N-butyl-carboxamide | 107–109 |
| 4-N'-methyl-ureidophenyl | 2-chloro-6-fluorobenzyl | N-isopropyl-carboxamide | 172–174 |
| 4-propionyl-aminophenyl | 2-chloro-6-fluorobenzyl | N-isopropyl-carboxamide | 120–122 |
| 4-propionyl-aminophenyl | 2-chloro-6-fluorobenzyl | N-butyl-carboxamide | 105–107 |
| 4-acetyl-aminophenyl | 2-fluoro-benzyl | N-isopropyl-carboxamide | 184–186 |
| 4-propionyl-aminophenyl | 2,6-difluoro-benzyl | N-methyl-O-methylhydroxamic acid | amorphous |
| 4-N'-methyl-ureidophenyl | 2,6-difluoro-benzyl | N-methyl-N-(2-pyridyl)-carboxamide | 156–158 (hydrochloride) |
| 4-propionyl aminophenyl | 2,6-difluoro-benzyl | N-methyl-N-(2-pyridyl)-carboxamide | 148–150 (hydrochloride) |
| 4-N'-methyl ureidophenyl | 2,6-difluoro-benzyl | N-methyl-N-benzyl carboxyamide | 125–127 (hydrochloride) |

TABLE 18

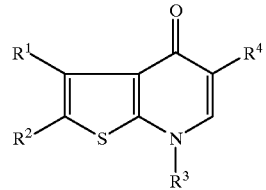

| R¹ | R² | R³ | R⁴ | m.p. (° C.) |
|---|---|---|---|---|
| methyl | bromine | 2,6-difluoro-benzyl | N-methyl-O-methyl-hydroxamic acid | 192–194 |
| methyl | 4-nitro-phenyl | 2,6-difluoro-benzyl | benzoyl | 114–116 |
| N-methyl-N-benzyl-aminomethyl | 4-nitro-phenyl | 2,6-difluoro-benzyl | iso-butyryl | 236–238 (hydrochloride) |
| N-methyl-N-benzyl-aminomethyl | phenyl | 2,6-difluoro-benzyl | iso-butyryl | 204–205 |
| methyl | bromine | 2,6-difluoro-benzyl | benzoyl | 229–230 |
| N-methyl-N-benzyl-aminomethyl | 4-amino-phenyl | 2,6-difluoro-benzyl | benzoyl | 126–128 |
| N-methyl-N-benzyl-aminomethyl | 4-amino-phenyl | 2,6-difluoro-benzyl | isobutyryl | amorphous |

TABLE 19

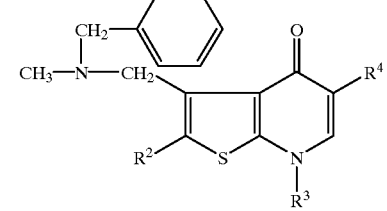

| R² | R³ | R⁴ | m.p. (° C.) (free form) | m.p. (° C.) (HCL salt) |
|---|---|---|---|---|
| 4-propionyl-aminophenyl | 2,6-difluoro-benzyl | benzoyl | 226–228 | 218–220 |
| 4-(N'-methyl ureidophenyl) | 2,6-difluoro-benzyl | benzoyl | 238–240 | 230–232 |
| 4-propionyl-aminophenyl | 2,6-difluoro-benzyl | iso-butyryl | 201–204 | 207–214 |
| 4-(N'-methyl-ureidophenyl) | 2,6-difluoro-benzyl | iso-butyryl | 207–210 | 222–226 |
| 4-ethane-sulfonamide-phenyl | 2,6-difluoro-benzyl | benzoyl | * | 185–187 |
| 4-isobutyryl-aminophenyl | 2,6-difluoro-benzyl | benzoyl | * | 216–218 |
| 4-(N',N'-dimethyl-ureidophenyl) | 2,6-difluoro-benzyl | benzoyl | * | 180–183 |
| 4-(N'-isopropyl-ureidophenyl) | 2,6-difluoro-benzyl | benzoyl | 245–247 | — |
| 4-pyrrolidine-carboxamide-phenyl | 2,6-difluoro-benzyl | benzoyl | * | 176–178 |
| phenyl | benzyl | benzoyl | | |
| 4-(2,2,2-trifluoro-ethoxy-carboxylamino-phenyl) | 2,6-difluoro-benzyl | benzoyl | * | 232–234 |
| 4-isobutyryl-aminophenyl | 2,6-difluoro-benzyl | iso-butyryl | 188–189 | 192–197 |

*Salts are prepared from the corresponding free form without measuring the melting point.

TABLE 20

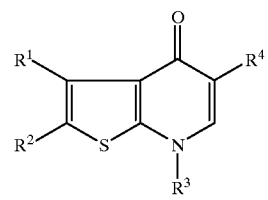

| R¹ | R² | R³ | R⁴ | m.p. (° C.) (HCl salt) |
|---|---|---|---|---|
| N-methyl-N-benzyl-amino-methyl | 4-nitrophenyl | 2,6-difluoro-benzyl | benzoyl | 197–199 |
| N-methyl-N-benzyl-amino-methyl | 4-propionyl-amino-phenyl | 2,6-difluoro-benzyl | iso-butyryl | 207–214 |
| N-methyl-N-benzyl-amino-methyl | 4-(N'-methyl-ureido-phenyl) | 2,6-difluoro-benzyl | iso-butyryl | 222–226 |
| N-methyl-N-benzyl-amino-methyl | 4-propionyl-amino-phenyl | 2,6-difluoro-benzyl | benzoyl | 218–220 |
| N-methyl-N-benzyl-amino-methyl | 4-(N'-methyl-ureido-phenyl) | 2,6-difluoro-benzyl | benzoyl | 230–232 |
| methyl | 4-hydroxy-phenyl | 2-fluoro-benzyl | ethoxy-carbonyl | 225–227 |
| N-methyl-N-benzylamino-methyl | 4-hydroxy-phenyl | 2-fluoro-benzyl | ethoxy-carbonyl | 231–235 |
| methyl | 4-n-butoxy-phenyl | 2-fluoro-benzyl | ethoxy-carbonyl | 119–121 |
| methyl | 4-(4-nitro-benzyloxy-carbonyl)phenyl | 2-fluoro-benzyl | ethoxy-carbonyl | 188–190 |
| methyl | 4-ethoxy-carbonylphenyl | 2,6-difluoro-benzyl | benzoyl | 221–223 |
| methyl | 4-methoxy-methoxyphenyl | 2-fluoro-benzyl | ethoxy-carbonyl | 112–113 |
| methyl | 4-ethoxy carbonyl-phenyl | 2-methoxy-benzyl | ethoxy-carbonyl | 171–172 |

TABLE 21

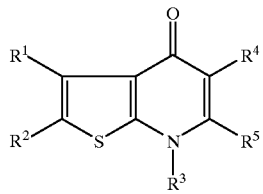

| R¹ | R² | R³ | R⁴ | R⁵ | m.p. (° C.) |
|---|---|---|---|---|---|
| N-methyl-N-benzylaminomethyl | 4-N-ethyl-aminocarbonyl-phenyl | 2,6-difluorobenzyl | benzoyl | hydrogen | 156–160 (hydrochloride) |
| N-methyl-N-benzylaminomethyl | 4-N,N-diethylaminocarboxy-phenyl | 2-fluorobenzyl | ethoxycarbonyl | hydrogen | 110–113 (hydrochloride) |
| N-methyl-N-benzylaminomethyl | 4-N-propylaminocarboxy-phenyl | 2,6-difluorobenzyl | benzoyl | hydrogen | 153–157 (hydrochloride) |
| N-methyl-N-benzylaminomethyl | 4-N-allyl-aminocarboxy-phenyl | 2,6-difluorobenzyl | benzoyl | hydrogen | 152–156 (hydrochloride) |
| N-methyl-N-benzylaminomethyl | 4-methoxyphenyl | 2-fluorobenzyl | ethoxymethyl | hydrogen | 200–204 (hydrochloride) |
| N-methyl-N-benzylaminomethyl | 4-methoxyphenyl | 2-fluorobenzyl | benzyloxymethyl | hydrogen | 77–83 (hydrochloride) |
| N-methyl-N-benzylaminomethyl | 4-methoxyphenyl | 2-fluorobenzyl | ethylthiomethyl | hydrogen | 213–217 (hydrochloride) |
| N-methyl-N-benzylaminomethyl | 4-propionylaminophenyl | 2,6-difluorobenzyl | ethoxycarbonyl | isobutyl | 135–137 (hydrochloride) |
| methyl | 4-methoxyphenyl | 2-fluorobenzyl | cyano | hydrogen | 215–216 |
| N-methyl-N-benzylaminomethyl | 4-methoxyphenyl | 2-fluorobenzyl | ethylsulfinyl-methyl | hydrogen | 216–219 (hydrochloride) |

Reference Example 2:1
(1) Production of 4,7-dihydro-5-hydroxymethyl-7-(2-fluorobenzyl)-2-(4-methoxyphenyl)-3-methyl-4-oxothieno[2,3-b]pyridine:

The titled compound is produced from 4-hydroxy-5-hydroxymethyl-2-(4-methoxyphenyl)-3-methylthieno[2,3-b]pyridine, which is obtained in PCT International Publication No. WO95/28405 Reference Example 11, 2-fluorobenzyl chloride and potassium iodide.

m.p. 159–160 ° C.

(2) Production of 4,7-dihydro-2-phenyl-3-methyl-7-(2,6-difluorobenzyl)-4-oxothieno[2,3-b]pyridine-5-carboxylic acid ethyl ester:

The titled compound is produced by a similar manner as those of the Reference Example 2:1(1).

m.p. 184–186° C.

Reference Example 2:2
Production of methyl 2-isopropylthioacetate:
The titled compound is produced from thioglycolic acid methyl ester and isopropyl iodide.

¹H-NMR (CDCl₃) δ: 1.26(6H,d,J=6.6 Hz), 3.01–3.09(1H, m), 3.25(2H,s), 3.72(3H,s).

Reference Example 2:3
Production of methyl 2-(N,N-dimethylaminomethylene)-2-isopropylthioacetate:

The titled compound is produced from the compound, which is obtained in Reference Example 2:2, and N,N-dimethylformamidedimethylacetal.

¹H-NMR (CDCl₃) δ: 1.19(6H,d,J=6.6 Hz), 2.89–2.98(1H, m), 3.26(6H,s), 3.72(3H,s), 7.88(1H,s).

Reference Example 2:4
Production of 2-amino-5-phenyl-4-methylthiophene-3-carboxylic acid:

The titled compound is produced from 2-amino-5-phenyl-4-methylthiophene-3-carboxylic acid ethyl ester (13 mg, 50 mmol), which is obtained in PCT International Publication No. WO95/28405 Reference Example 3, and 2N sodium hydroxide solution. Thus obtained compound is used for next reaction step without purification.

Reference Example 2:5
Production of methyl (3-carboxy-5-phenyl-4-methylthiophen-2-yl)-aminomethylene-(2-isopropylthio) acetate:

The titled compound is produced from the compound which is obtained in Reference Example 2:4 and the compound which is obtained in Reference Example 2:3.

m.p. 119–121° C.

Reference Example 2:6
Production of 4-hydroxy-2-phenyl-3-methyl-5-isopropylthiothieno[2,3-b]pyridine:

The titled compound is produced from the compound which is obtained in Reference Example 2:5 and diphenylether.

¹H-NMR (CDCl₃) δ: 1.30(6H,d,J=6.6 Hz), 2.64(3H,s), 3.07–3.16(1H,m), 7.37–7.54(5H,m), 8.45(1H,s).

Reference Example 2:7
Production of 4,7-dihydro-2-(4-methoxyphenyl)-3-methyl-5-(oxazol-5-yl)-7-(2-fluorobenzyl)-4-oxothieno[2,3-b]pyridine:

The titled compound is produced from 4,7-dihydro-2-(4-methoxyphenyl)-3-methyl-5-formyl-7-(2-fluorobenzyl)-4-oxothieno[2,3-b]pyridine which is obtained in PCT International Publication No. WO95/28405 Working Example 28, tosylmethylisocyanide and potassium carbonate.

m.p. 235–236° C.

Reference Example 2:8 Production of 4,7-dihydro-2-(4-methoxyphenyl)-3- bromomethyl-5-(oxazol-5-yl)-7-(2-fluorobenzyl)-4- oxothieno[2,3-b]pyridine:

The titled compound is produced from the compound which is produced in Reference Example 2:7, N-bromosuccinimide and α,α'-azobisisobutyronitrile.

m.p. 234–236° C.

Reference Example 2:9

Production of 3-(N-benzyl-N-methylaminomethyl)-4,7-dihydro-2-(4-methoxyphenyl)-5-(oxazol-5-yl)-7-(2-fluorobenzyl)-4-oxothieno[2,3-b]pyridine:

The titled compound is production from the compound which is obtained in Reference Example 2:8, ethyldiisopropylamine and N-benzylmethylamine.

m.p. 144–150° C.

Reference Example 2:10

Production of 4,7-dihydro-2-phenyl-3-methyl-5-acetylamino-7-(2,6-difluorobenzyl)-4-oxothieno[2,3-b]pyridine:

From the compound, which is produced in PCT International Publication No. WO95/28405 Working Example 3(13), O-methyl-N-methylhydroxylamine hydrochloride, and diisopropylethylamine, and trimethyl aluminum in hexane, a compound which is N-methyl-O-hydroxamic acid at 5-position is produced.

From thus obtained compound and methyl magnesium chloride, 4,7-dihydro-2-phenyl-3-methyl-5-acetyl-7-(2,6-difluorobenzyl)-4-oxothieno[2,3-b]pyridine is produced.

A reaction of 4,7-dihydro-2-phenyl-3-methyl-5-acetyl-7-(2,6-difluorobenzyl)-4-oxothieno[2,3-b]pyridine with hydroxylamine hydrochloride, and a reaction thus obtained compound with p-toluensulfonic acid chloride gives the titled compound.

$^1$H-NMR (CDCl$_3$) δ: 2.20(3H,s), 2.70(3H,s), 5.23(2H,s), 6.99(2H,t), 7.3–7.5(6H,m), 8.53(1H,s), 9.11(1H,s).

Reference Example 2:11

Production of 4,7-dihydro-2-phenyl-3-methyl-5-amino-7-(2,6-difluorobenzyl)-4-oxothieno[2,3-b]pyridine:

From the compound which is obtained in Reference Example 2:10 and 2N sodium hydroxide, the titled compound is produced.

$^1$H-NMR (CDCl$_3$) δ: 2.71(3H,s), 3.3–4.3(2H,brs), 5.14 (2H,s), 6.98(2H,t), 7.17(1H,s), 7.3–7.5(6H,m).

Reference Example 2:12

Production of 4,7-dihydro-2-(4-nitrophenyl)-3-methyl-5-acetoxy-7-(2,6-difluorobenzyl)-4-oxothieno[2,3-b]pyridine:

From 4,7-dihydro-2-phenyl-3-methyl-5-acetyl-7-(2,6-difluorobenzyl)-4-oxothieno[2,3-b]pyridine which is obtained in Reference Example 2:10 and m-chloroperbenzoic acid, the titled compound is produced.

m.p. 216–217° C.

Reference Example 2:13

Production of 4,7-dihydro-2-(4-nitrophenyl)-3-methyl-5-isopropoxy-7-(2,6-difluorobenzyl)-4-oxothieno[2,3-b]pyridine:

The compound which is obtained in Reference Example 2:12 is subjected to hydrolysis with 1N sodium hydroxide, and from thus obtained compound and isopropyl iodide, the titled compound is produced.

m.p. 188–189° C.

Reference Example 2:14

(1) Using the compound which is obtained in Reference Example 2:13 and by a similar manner as in Reference Example 2:8, the following compound is produced.

4,7-dihydro-2-(4-nitrophenyl)-3-bromomethyl-5-isopropoxy-7-(2,6-difluorobenzyl)-4-oxothieno[2,3-b]pyridine. Yellow amorphous.

H-NMR (CDCl$_3$) δ: 1.31(6H,d), 4.68(1H,m), 5.04(2H,s), 5.27(2H,s), 7.03(2H,t), 7.4–7.5(2H,m), 7.85(2H,d), 8.33(2H,d).

(2) The compound which is obtained in Reference Example 2:14(1) is used and by a similar manner as in Reference Example 2:9, the following compound is produced.

4,7-dihydro-2-(4-nitrophenyl)-3-(N-benzyl-N-methylaminomethyl)-5-isopropoxy-7-(2,6-difluorobenzyl)-4-oxothieno[2,3-b]pyridine. Yellow amorphous.

$^1$H-NMR (CDCl$_3$) δ: 1.33(6H,d), 2.23(3H,s), 3.70(2H,s), 4.23(2H,s), 4.64(1H,m), 5.22(2H,s), 7.01(2H,t), 7.1–7.5(7H,m), 8.11(2H,d), 8.23(2H,d).

(3) The compound which is obtained in Reference Example 2:14(2) is used and by a similar manner as in Reference Example 2:26 below mentioned, the following compound is produced.

4,7-dihydro-2-(4-aminophenyl)-3-(N-benzyl-N-methylaminomethyl)-5-isopropoxy-7-(2,6-difluorobenzyl)-4-oxothieno[2,3-b]pyridine. Colorless amorphous.

$^1$H-NMR (CDCl$_3$) δ: 1.30(6H,d), 2.18(3H,s), 3.70(2H,s), 3.92(2H,brs), 4.18(2H,s), 5.16(2H,s), 6.70(2H,d), 6.95 (2H,t), 7.1–7.5(7H,m), 7.60(2H,d). (4) The compound which is obtained in Reference Example 2:14(3) is used and by a similar manner as in Reference Example 2:27 below mentioned, the following compound is produced. 4,7-dihydro-2-(4-isobutyrylaminophenyl)-3-(N-benzyl-N- methylaminomethyl)-5-isopropoxy-7-(2, 6-difluorobenzyl)-4-oxothieno[2,3-b]pyridine. Yellow amorphous.

$^1$H-NMR (CDCl$_3$) δ: 1.21(6H,d), 1.35(6H,d), 2.42(3H,s), 2.95(1H,m), 3.73(2H,s), 4.25(2H,s), 4.63(1H,m), 5.35 (2H,s), 6.99(2H,t), 7.2–7.5(8H,m), 7.69(1H,s), 7.95 (2H,d), 9.82(1H, brs).

Reference Example 2:15

Production of 4,7-dihydro-2-(4-isobutyrylaminophenyl)-3-(N-benzyl-N-methylaminomethyl)-5-hydroxy-7-(2,6-difluorobenzyl)-4-oxothieno[2,3-b]pyridine:

From the compound which is obtained in Reference Example 2:14(4) and boron trichloride, the titled compound is produced.

$^1$H-NMR (CDCl$_3$) δ: 1.25(6H,d), 2.12(3H,s), 2.60(1H,m), 3.63(2H,s), 4.14(2H,s), 5.17(2H,s), 6.98(2H,t), 7.1–7.3 (5H,m), 7.3–7.5(2H,m), 7.5–7.9(5H,m).

Reference Example 2:16

Production of 4,7-dihydro-2-(4-isobutyrylaminophenyl)-3-(N-benzyl-N-methylaminomethyl)-5-isopropylsulfonyloxy-7-(2,6-difluorobenzyl)-4-oxothieno[2,3-b]pyridine hydrochloride:

From the compound which is obtained in Reference Example 2:15 and isopropylsulfonyl chloride, and then from thus obtained compound with hydrogen chloride in ether, the titled compound is produced.

m.p. 172–177° C.

Reference Example 2:17

Production of 4,7-dihydro-2-(4-isobutyrylaminophenyl)-3-(N-benzyl-N-methylaminomethyl)-5-isobutyryloxy-7-(2,6-difluorobenzyl)-4-oxothieno[2,3-b]pyridine hydrochloride:

From the compound which is obtained in Reference Example 2:15 and isobutyryl chloride, the titled compound is obtained.

m.p. 169–172° C.

Reference Example 2:18

Production of 4,7-dihydro-2-(4-isobutyrylaminophenyl)-3-(N-benzyl-N-methylaminomethyl)-5-ethoxycarbonylmethoxy-7-(2,6-difluorobenzyl)-4-oxothieno[2,3-b]pyridine and its hydrochloride:

From the compound which is obtained in Reference Example 2:15 and ethyl acetate bromide, the titled compound and its hydrochloride are obtained. Free form:

$^1$H-NMR (CDCl$_3$) δ: 1.2–1.3(9H,m), 2.20(3H,s), 2.83 (1H,brs), 3.74(2H,s), 4.1–4.2(4H,m), 4.82(2H,s), 5.22

(2H,s), 6.97(2H,t), 7.0–7.3(7H,m), 7.39(1H,m), 7.58 (1H,brs), 7.83(2H,brs). Hydrochloride:

m.p. 190–194° C.

Reference Example 2:19

Production of 4,7-dihydro-2-(4-isobutyrylaminophenyl)-3-(N-benzyl-N-methylaminomethyl)-5-carbamoylmethoxy-7-(2,6-difluorobenzyl)-4-oxothieno[2,3-b]pyridine:

From the free form which is obtained in Reference Example 2:18 and ammonium-ethanol, the titled compound is produced.

m.p. 237–238° C.

Reference Example 2:20

Production of 4,7-dihydro-2-phenyl-3-methyl-5-isopropylthio-7-(2,6-difluorobenzyl)-4-oxothieno[2,3-b]pyridine:

From the compound which is obtained in Reference Example 2:6 and 2,6-difluorobenzyl chloride, the titled compound is produced.

m.p. 129–131° C.

Reference Example 2:21

Production of 4,7-dihydro-2-phenyl-3-methyl-5-isopropylsulfinyl-7-(2,6-difluorobenzyl)-4-oxothieno[2,3-b]pyridine:

From the compound which is obtained in Reference Example 2:20 and m-chloroperbenzoic acid, the titled compound is produced.

m.p. 217–219° C.

Reference Example 2:22

Production of 4,7-dihydro-2-phenyl-3-methyl-5-isopropylsulfonyl-7-(2,6-difluorobenzyl)-4-oxothieno[2,3-b]pyridine:

The titled compound is obtained as a by-product by the manner of Reference Example 2:21.

m.p. 231–233° C.

Reference Example 2:23

Production of 4,7-dihydro-2-(4-nitrophenyl)-3-methyl-5-isopropylsulfinyl-7-(2,6-difluorobenzyl)-4-oxothieno[2,3-b]pyridine:

From the compound which is obtained in Reference Example 2:21 and a sodium nitrate solution in conc. sulfuric acid, the titled compound is produced.

m.p. 212–214° C.

Reference Example 2:24

Production of 4,7-dihydro-2-(4-nitrophenyl)-3-bromomethyl-5-isopropylsulfinyl-7-(2,6-difluorobenzyl)-4-oxothieno[2,3-b]pyridine:

From the compound which is obtained in Reference Example 2:23, N-bromosuccinimide (NBS) and α,α-azobisisobutyronitrile (AIBN), the titled compound is produced.

m.p. 176–181° C.

Reference Example 2:25

Production of 4,7-dihydro-2-(4-nitrophenyl)-3-(N-benzyl-N-methylaminomethyl)-5-isopropylsulfinyl-7-(2,6-difluorobenzyl)-4-oxothieno[2,3-b]pyridine:

From the compound which is obtained in Reference Example 2:24, ethyldiisopropylamine and N-methylbenzylamine, the titled compound is produced.
m.p. 98–103° C.

Reference Example 2:26

Production of 4,7-dihydro-2-(4-aminophenyl)-3-(N-benzyl-N-methylaminomethyl)-5-isopropylsulfinyl-7-(2,6-difluorobenzyl)-4-oxothieno[2,3-b]pyridine:

From the compound which is obtained in Reference Example 2:25, iron powder and conc. hydrogen chloride, the titled compound is produced.

m.p. 105–115° C.

Reference Example 2:27

Production of 4,7-dihydro-2-(4-isobutyrylaminophenyl)-3-(N-benzyl-N-methylaminomethyl)-5-isopropylsufinyl-7-(2,6-difluorobenzyl)-4-oxothieno[2,3-b]pyridine:

From the compound which is obtained in Reference Example 2:26 and isobutyryl chloride, the titled compound is obtained.

H-NMR (CDCl$_3$) δ: 1.04(6H,d,J=6.8 Hz), 1.27(3H,d,J=6.8 Hz), 1.51(3H,d,J=7.1 Hz), 2.16(3H,s), 2.07–2.67 (1H,m), 3.48–3.60(1H,m), 3.68(2H,s), 4.02–4.22(2H, Abq,J=12 Hz), 5.31–5.42(2H,Abq,J=15.0 Hz), 6.99 (2H,t,J=8.1 Hz), 7.14–7.45(6H,m), 7.68–7.75(4H,m), 7.86(1H,s), 7.93(1H,s).

Reference Example 2:28

Production of 4,7-dihydro-2-(4-isobutyrylaminophenyl)-3-(N-benzyl-N-methylaminomethyl)-5-isopropylsulfinyl-7-(2,6-difluorobenzyl)-4-oxothieno[2,3-b]pyridine hydrochloride:

From the compound which is obtained in Reference Example 2:27 and 1M hydrogen chloride in ether, the titled compound is produced.

m.p. 185–187° C.

Reference Example 2:29

The following compound is produced by a similar manner as above.

4,7-dihydro-2-(4-isobutyrylaminophenyl)-3-(N-benzyl-N-methylaminomethyl)-5-isopropylsulfonyl-7-(2,6-difluorobenzyl)-4-oxothieno[2,3-b]pyridine.

The compounds shown in the above Reference Examples 2:7 to 2:29 are listed in the following Tables 22 to 24.

TABLE 22

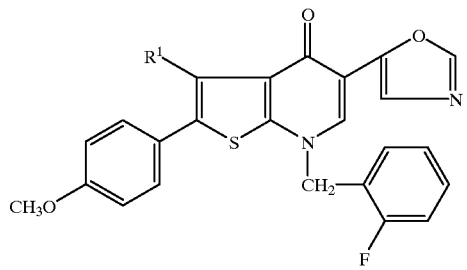

| Reference Example No. | R$^1$ |
|---|---|
| 2:7 | methyl |
| 2:8 | bromomethyl |
| 2:9 | N-benzyl-N-methylaminomethyl |

TABLE 23

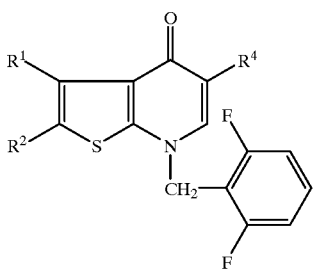

| Reference Example No. | R¹ | R² | R⁴ |
|---|---|---|---|
| 2:10 | methyl | phenyl | acetylamino |
| 2:11 | methyl | phenyl | amino |
| 2:12 | methyl | 4-nitrophenyl | acetoxy |
| 2:13 | methyl | 4-nitrophenyl | isopropoxy |
| 2:14(1) | bromomethyl | 4-nitrophenyl | isopropoxy |
| 2:14(2) | N-benzyl-N-methylaminomethyl | 4-nitrophenyl | isopropoxy |
| 2:14(3) | N-benzyl-N-methylaminomethyl | 4-aminophenyl | isopropoxy |
| 2:14(4) | N-benzyl-N-methylaminomethyl | 4-isobutyryl-aminophenyl | isopropoxy |
| 2:15 | N-benzyl-N-methylaminomethyl | 4-isobutyryl-aminophenyl | hydroxy |
| 2:16 | N-benzyl-N-methylaminomethyl | 4-isobutyryl-aminophenyl | isopropyl sulfonyloxy |
| 2:17 | N-benzyl-N-methylaminomethyl | 4-isobutyryl-aminophenyl | isobutyryloxy |
| 2:18 | N-benzyl-N-methylaminomethyl | 4-isobutyryl-aminophenyl | ethoxycarbonyl-methoxy |
| 2:19 | N-benzyl-N-methylaminomethyl | 4-isobutyryl-aminophenyl | carbamoyl-methoxy |
| 2:20 | methyl | phenyl | isopropylthio |
| 2:21 | methyl | phenyl | isopropyl-sulfinyl |

TABLE 24

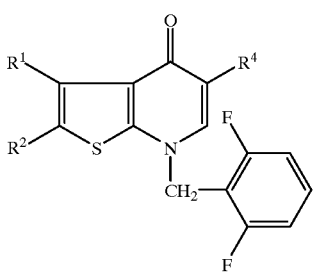

| Reference Example No. | R¹ | R² | R⁴ |
|---|---|---|---|
| 2:22 | methyl | phenyl | isopropylsulfonyl |
| 2:23 | methyl | 4-nitrophenyl | isopropylsulfinyl |
| 2:24 | bromomethyl | 4-nitrophenyl | isopropylsulfinyl |
| 2:25 | N-benzyl-N-methylaminomethyl | 4-nitrophenyl | isopropylsulfinyl |
| 2:26 | N-benzyl-N-methylaminomethyl | 4-aminophenyl | isopropylsulfinyl |
| 2:27 | N-benzyl-N-methylaminomethyl | 4-isobutyryl-aminophenyl | isopropylsulfinyl |
| 2:28 | N-benzyl-N-methylaminomethyl | 4-isobutyryl-aminophenyl | isopropylsulfinyl |
| 2:29 | N-benzyl-N-methylaminomethyl | 4-isobutyryl-aminophenyl | isopropylsulfonyl |

Reference Example 3:1

Production of 4,7-dihydro-7-(2,6-difluorobenzyl)-2-phenyl-3-methyl-4-oxothieno [2,3-b]pyridine-5-carboxylic acid ethyl ester:

From 4-hydroxy-2-phenyl-3-methylthieno[2,3-b]pyridine-5-canboxylic acid ethyl ester which is produced in PCT International Publication No. WO95/28405 Reference Example 9(l) and 2,6-difluorobenzyl chloride, the titled compound is produced.

m.p.171–173° C.

Reference Example 3:2

Production of 4,7-dihydro-7-(2,6-difluorobenzyl)-2-(4-nitrophenyl)-3-methyl-4-oxothieno[2,3-b]pyridine-5-carboxylic acid ethyl ester:

From the compound which is produced in Reference Example 3:1, sodium nitrate and conc. sulfuric acid, the titled compound is produced.

m.p. 260–261° C.

Reference Example 3:3

Production of 3-bromomethyl-4,7-dihydro-7-(2,6-difluorobenzyl)-2-(4-nitrophenyl)-4-oxothieno[2,3-b]pyridine-5-carboxylic acid ethyl ester:

From the compound which is produced in Reference Example 3:2, N-bromosuccinic acid imide and α,α'-azobisisobutyronitrile, the titled compound is produced.

m.p. 200–201° C.

Reference Example 3:4

Production of 3-(N-benzyl-N-methylaminomethyl)-4,7-dihydro-7-(2,6-difluorobenzyl)-2-(4-nitrophenyl)-4-oxothieno[2,3-b]pyridine-5-carboxylic acid ethyl ester hydrochloride:

From the compound which is produced in Reference Example 3:3, ethyl diisopropylamine and N-benzyl methylamine, the titled compound is produced.

m.p. 118–119° C. (hydrochloride).

Reference Example 3:5

Production of 3-(N-benzyl-N-methylaminomethyl)-4,7-dihydro-7-(2,6-difluorobenzyl)-2-(4-aminophenyl)-4-oxothieno[2,3-b]pyridine-5-carboxylic acid ethyl ester hydrochloride:

From the compound which is produced in Reference Example 3:4, iron powder and conc. hydrogen chloride, the titled compound is produced.

m.p. 195–196° C.

Reference Example 3:6

Production of 3-(N-benzyl-N-methylaminomethyl)-4,7-dihydro-7-(2,6-difluorobenzyl)-2-(4-trifluoroacetylaminophenyl)-4-oxothieno[2,3-b]pyridine-5-carboxylic acid ethyl ester:

From the compound which is produced in Reference Example 3:5 and trifluoroacetic anhydride, the titled compound is produced.

m.p. 147–149° C.

Reference Example 3:7

Production of 3-(N-benzyl-N-methylaminomethyl)-4,7-dihydro-7-(2,6-difluorobenzyl)-2-(4-trifluoroacetylaminophenyl)-4-oxothieno[2,3-b]pyridine-5-(N-methyl-O-methyl)hydroxamic acid:

From N,O-dimethoxyhydroxylamine hydrochloride, diisopropylamine, trimethyl aluminium in hexane and the compound which is produced in Reference Example 3:6, the titled compound is produced.

$^1$H-NMR (300 MHz, CDCl$_3$) δ: 2.15(3H,s), 3.35(3H,s), 3.63(2H,s), 3.73(2H,s), 4.15(2H,s), 5.20(2H,s), 7.00 (1H,t), 7.12–7.30(5H,m), 7.42(1H,m), 7.64(2H,d,J=8.7 Hz), 7.72(1H,s), 7.90(2H,d,J=8.4 Hz). Mass m/z 685 (MH)$^+$.

Reference Example 3:8

Employing the compound produced in PCT International Publication No. WO95/28405 Working Example 27(2) or the compound produced in the following Reference Example 3:14 as the starting material, substantially the same procedures as in Reference Example 3:6 and 3:7 are conducted to give the compounds set forth in Table 25.

TABLE 25

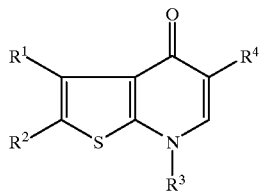

| Ref. Ex. 3:8 Cpd. No. | $R^1$ | $R^2$ | $R^3$ | $R^4$ | m.p. (° C.) |
|---|---|---|---|---|---|
| (1) | N-methyl-N-benzylaminomethyl | 4-isobutyryl-aminophenyl | 2,6-difluorobenzyl | N-methyl-O-methylhydroxamic acid | 152–154 |
| (2) | N-methyl-N-benzylaminomethyl | 4-propionyl-aminophenyl | 2,6-difluorobenzyl | N-methyl-O-methylhydroxamic acid | 139–140 |
| (3) | N-methyl-N-benzylaminomethyl | 4-methoxy-phenyl | 2,6-difluorobenzyl | N-methyl-O-methylhydroxamic acid | |

"N-methyl-O-methylhydroxamic acid" in the Table 25 means a group represented by the formula, —CO—N(OCH$_3$0CH$_3$.

Reference Example 3:9

Production of 3-(N-benzyl-N-methylaminomethyl)-4,7-dihydro-7-(2,6-difluorobenzyl)-5-isobutyryl-2-(4-isobutyrylaminophenyl)-4-oxothieno[2,3-b]pyridine hydrochloride:

Employing, as the starting material, the compound (Compound No. 3:8(1)) which is produced in Reference Example 3:8, isopropyl magnesium chloride, while adding to the reaction system tetrabutylammonium bromide to suppress side reactions, to give the titled compound.

m.p. 192–197° C. (hydrochloride).

Reference Example 3:10

Production of 3-(N-benzyl-N-methylaminomethyl)-4,7-dihydro-7-(2,6-difluorobenzyl)-5-benzoyl-2-(4-methoxyphenyl)-4-oxothieno[2,3-b]pyridine hydrochloride:

From the compound which is obtained in Reference Example 3:8 (Compound 3:8(3)), substantially the same procedure as in Reference Example 3:9 is conducted to produce the titled compound.

Reference Example 3:11

Production of 3-(N-benzyl-N-methylaminomethyl)-4,7-dihydro-7-(2,6-difluorobenzyl)-5-isobutyryl-2-(4-methoxyphenyl)-4-oxothieno[2,3-b]pyridine hydrochloride:

From the compound which is produced in Reference Example 3:8 (Compound No. 3:8(3)), substantially the same procedure as in PCT International Publication No. WO95/28405 Working Example 54 is conducted to produce the titled compound.

Reference Example 3:12

Production of 4-hydroxy-2-(4-methoxyphenyl)-3-bromomethylthieno[2,3-b]pyridine-5-acetic acid ethyl ester:

From the compound which is produced in PCT International Publication No. WO95/28405 Reference Example 8, substantially the same procedure as in Reference Example 3:3 is conducted to produce the titled compound.

Reference Example 3:13

Production of 4-hydroxy-2-(4-methoxyphenyl)-3-(N-benzyl-N-methylaminomethyl)thieno[2,3-b]pyridine-5-acetic acid ethyl ester:

From the compound which is produced in Reference Example 3:12, substantially the same procedure as in Reference Example 3:4 is conducted to produce the titled compound.

Reference Example 3:14

Production of 4,7-dihydro-7-(2,6-difluorobenzyl)-2-(4-methoxyphenyl)-3-(N-benzyl-N-methylaminomethyl)thieno[2,3-b]pyridine-5-acetic acid ethyl ester:

From the compound which is produced in Reference Example 3:13, substantially the same procedure as in Reference Example 3:1 is conducted to produce the titled compound.

Reference Example 3:15

Production of 4,7-dihydro-7-(2,6-difluorobenzyl)-2-(4-hydroxyphenyl)-5-benzoyl-3-(N-benzyl-N-methylaminomethyl)-4-oxothieno[2,3-b]pyridine hydrochloride:

From the compound which is produced in Reference Example 3:10, aluminium chloride and methyl disulfide, the titled compound is produced.

Reference Example 3:16

Production of 4,7-dihydro-7-(2,6-difluorobenzyl)-2-(4-hydroxyphenyl)-5-isobutyryl-3-(N-benzyl-N-methylaminomethyl)-4-oxothieno [2,3-b]pyridine hydrochloride:

Employing, as the starting material, the compound which is produced in Reference Example 3:11, substantially the same procedure as in Reference Example 3:15 is conducted to produce the titled compound.

Reference Example 3:17

Production of 3-[N-methyl-N-(N-methylindol-3-ylmethyl)aminomethyl-4,7-dihydro-7-(2,6-difluorobenzyl)-5-isobutyryl-2-(4-isobutyrylaminophenyl)-4-oxothieno[2,3-b]pyridine hydrochloride:

Employing the compound which is produced in Reference Example 3:2, 5-(N-methyl-O-methyl)hydroxamic acid is produced. Thus obtained compound is made into 5-isobutyryl compound and thus obtained compound is converted to 4-aminophenyl. The resultant compound is subjected to acylation-(introduction of isobutyryl group) then to bromination of the methyl at 3-position to give 3-bromomethyl-4,7-dihydro-7-(2,6-difluorobenzyl)-5-isobutyryl-2-(4-isobutyrylaminophenyl)-4-oxothieno[2,3-b]pyridine.

From this compound and 3-N-methylaminomethyl-N'-methyl indole, the titled compound is produced.

m.p. 170–172° C. (hydrochloride).

Reference Example 3:18

Substantially the same procedure as described in Reference Example 3:17 gives compounds set forth in Table 26 and Table 27.

From the compound which is produced in Reference Example 3:7 and phenyl magnesium chloride in tetrahydrofuran, the titled compound is produced.

m.p. 133–135° C.

TABLE 26

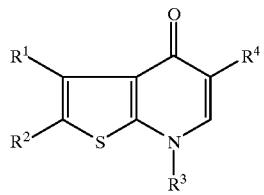

| Ref. Ex. 3:18 Cpd. No. | $R^1$ | $R^2$ | $R^3$ | $R^4$ | m.p. (° C.) |
|---|---|---|---|---|---|
| (1) | N-methyl-N-(2-fluorobenzyl)-aminomethyl | 4-isobutyryl-aminophenyl | 2,6-difluorobenzyl | isobutyryl | 135–137 (hydrochloride) |
| (2) | N-methyl-N-(2-bromobenzyl)-aminomethyl | 4-isobutyryl-aminophenyl | 2,6-difluorobenzyl | isobutyryl | 139–141 (hydrochloride) |
| (3) | N-methyl-N-(2-methylthiobenzyl)-aminomethyl | 4-isobutyryl-aminophenyl | 2,6-difluorobenzyl | isobutyryl | amorphous |
| (4) | N-methyl-N-(2-sulfamoylbenzyl)-aminomethyl | 4-isobutyryl-aminophenyl | 2,6-difluorobenzyl | isobutyryl | 240–242 (hydrochloride) |
| (5) | N-methyl-N-(2-pyridylmethyl)aminomethyl | 4-isobutyryl-aminophenyl | 2,6-difluorobenzyl | isobutyryl | 243–245 (hydrochloride) |

TABLE 27

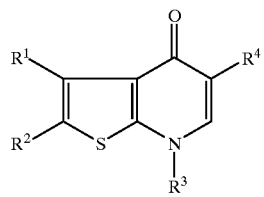

| Ref. Ex. 3:18 Cpd. No. | $R^1$ | $R^2$ | $R^3$ | $R^4$ | m.p. (° C.) |
|---|---|---|---|---|---|
| (6) | N-methyl-N-(3-pyridylmethyl)-aminomethyl | 4-isobutyryl-aminophenyl | 2,6-difluorobenzyl | isobutyryl | 181–183 (hydrochloride) |
| (7) | N-methyl-N-butylaminomethyl | 4-isobutyryl-aminophenyl | 2,6-difluorobenzyl | isobutyryl | 239–241 (hydrochloride) |
| (8) | N-methyl-N'-butylcarbamoylmethyl-aminomethyl | 4-isobutyryl-aminophenyl | 2,6-difluorobenzyl | isobutyryl | 156–158 (hydrochloride) |
| (9) | N-methyl-N-(2,6-dinitrobenzyl)-aminomethyl | 4-isobutyryl-aminophenyl | 2,6-difluorobenzyl | isobutyryl | 164–166 (hydrochloride) |
| (10) | hexamethylene tetraammoniummethyl-bromide | 4-isobutyryl-aminophenyl | 2,6-difluorobenzyl | isobutyryl | 184–186 |

Reference Example 3:19

Production of 3-(N-benzyl-N-methylaminomethyl)-4,7-dihydro-7-(2,6-difluorobenzyl)-5-benzoyl-2-(4-trifluoroacetylaminophenyl)-4-oxothieno[2,3-b]pyridine:

Reference Example 3:20

Employing the compound which is produced in PCT International Publication No. WO95/28405 Working Example 54, substantially the same procedure as described in Reference Example 3:19 is conducted to produce compounds set forth in Table 28 and Table 29.

TABLE 28

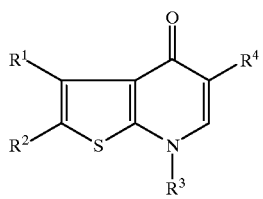

| Ref. Ex. 3:20 Cpd. No. | R¹ | R² | R³ | R⁴ | m.p. (° C.) |
|---|---|---|---|---|---|
| (1) | N-methyl-N benzylaminomethyl | 4-isobutyryl-aminophenyl | 2,6-difluorobenzyl | 4-methoxy-methoxybenzoyl | 151–153 (hydrochloride) |
| (2) | N-methyl-N-benzylaminomethyl | 4-isobutyryl-aminophenyl | 2,6-difluorobenzyl | 4-dimethylamino-benzoyl | 177–179 (hydrochloride) |
| (3) | N-methyl-N-benzylaminomethyl | 4-isobutyryl-aminophenyl | 2,6-difluorobenzyl | 4-methylthiobenzoyl | 170–172 (hydrochloride) |
| (4) | N-methyl-N-benzylaminomethyl | 4-isobutyryl-aminophenyl | 2,6-difluorobenzyl | 4-methylbenzoyl | 179–181 (hydrochloride) |
| (5) | N-methyl-N-benzylaminomethyl | 4-isobutyryl-aminophenyl | 2,6-difluorobenzyl | 4-methoxybenzoyl | 175–177 (hydrochloride) |
| (6) | N-methyl-N-benzylaminomethyl | 4-isobutyryl-aminophenyl | 2,6-difluorobenzyl | 3-methoxybenzoyl | 169–171 (hydrochloride) |
| (7) | N-methyl-N-benzylaminomethyl | 4-isobutyryl-aminophenyl | 2,6-difluorobenzyl | 2-methoxybenzoyl | 173–175 (hydrochloride) |
| (8) | N-methyl-N-benzylaminomethyl | 4-isobutyryl-aminophenyl | 2,6-difluorobenzyl | 2,4-dimethoxybenzoyl | 170–172 (hydrochloride) |
| (9) | N-methyl-N-benzylaminomethyl | 4-isobutyryl-aminophenyl | 2,6-difluorobenzyl | 2,5-dimethoxybenzoyl | 168–170 (hydrochloride) |
| (10) | N-methyl-N-benzylaminomethyl | 4-isobutyryl-aminophenyl | 2,6-difluorobenzyl | 3,4-dimethoxybenzoyl | 170–172 (hydrochloride) |

TABLE 29

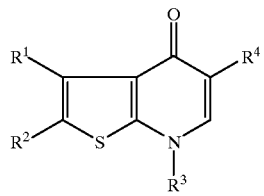

| Ref. Ex. 3:20 Cpd. No. | R¹ | R² | R³ | R⁴ | m.p. (° C.) |
|---|---|---|---|---|---|
| (11) | N-methyl-N-benzylaminomethyl | 4-isobutyryl-aminophenyl | 2,6-difluorobenzyl | 3,4-methylene-dioxybenzoyl | 173–175 (hydrochloride) |
| (12) | N-methyl-N-benzylaminomethyl | 4-isobutyryl-aminophenyl | 2,6-difluorobenzyl | 4-phenoxy-benzoyl | 173–174 (hydrochloride) |
| (13) | N-methyl-N-benzylaminomethyl | 4-propionyl-aminophenyl | 2,6-difluorobenzyl | isovaleryl | 220–224 (hydrochloride) |
| (14) | N-methyl-N-benzylaminomethyl | 4-propionyl-aminophenyl | 2,6-difluorobenzyl | valeryl | 220–224 (hydroch)oride) |
| (15) | N-methyl-N-benzylaminomethyl | 4-propionyl-aminophenyl | 2,6-difluorobenzyl | acetyl | 212–217 (hydrochloride) |
| (16) | N-methyl-N-benzylaminomethyl | 4-ethanesulfon-amidephenyl | 2,6-difluorobenzyl | isobutyryl | 177–182 (hydrochloride) |
| (17) | N-methyl-N-benzylaminomethyl | 4-propionyl-aminophenyl | 2,6-difluorobenzyl | propionyl | 233–237 (hydrochloride) |
| (18) | N-methyl-N-benzylaminomethyl | 4-propionyl-aminophenyl | 2,6-difluorobenzyl | butyryl | 228–233 (hydrochloride) |
| (19) | N-methyl-N-benzylaminomethyl | 4-propionyl-aminophenyl | 2,6-difluorobenzyl | 4,4-ethylene-dioxybutyryl | 210–215 (hdyrochloride) |
| (20) | N-methyl-N-benzylaminomethyl | 4-propionyl-aminophenyl | 2,6-difluorobenzyl | 2-thenoyl | 229–231 (hydrochloride) |

Reference Example 3:21

Production of 3-(N-benzyl-N-methylaminomethyl)-4,7-dihydro-7-(2,6-difluorobenzyl)-5-benzoyl-2-[4-(3-oxobutyl)aminophenyl]-4-oxothieno[2,3-b]pyridine hydrochloride:

From the compound which is produced in PCT International Publication No. WO95/28405 Working Example 54 and methyl vinyl ketone, the titled compound is produced.

m.p. 165–168° C. (hydrochloride).

Reference Example 3:22

From the compound which is produced in PCT International Publication No. WO95/28405 Working Example 54 and various vinyl compounds or oxirane compounds, compounds set forth in Table 30 are produced.

TABLE 30

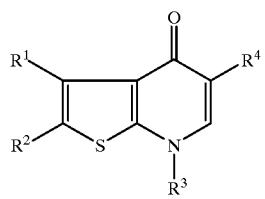

| Ref. Ex. 3:22 Cpd. No. | R¹ | R² | R³ | R⁴ | m.p. (° C.) |
|---|---|---|---|---|---|
| (1) | N-methyl-N-benzylaminomethyl | 4-(3-oxopentyl)-aminophenyl | 2,6-difluorobenzyl | benzoyl | 157–159 (hydrochloride) |
| (2) | N-methyl-N-benzylaminomethyl | 4-(2-hydroxy-cyclohexyl)-aminophenyl | 2,6-difluorobenzyl | benzoyl | 168–170 (hydrochloride) |
| (3) | N-methyl-N-benzylaminomethyl | 4-(2-hydroxypropyl)-aminophenyl | 2,6-difluorobenzyl | benzoyl | 152–154 (hydrochloride) |
| (4) | N-methyl-N-benzylaminomethyl | 4-(2-hydroxybutyl)-aminophenyl | 2,6-difluorobenzyl | benzoyl | 152–154 (hydrochloride) |
| (5) | N-methyl-N-benzylaminomethyl | 4-(2-hydroxy-isobutyl)-aminophenyl | 2,6-difluorobenzyl | benzoyl | 168–170 (hydrochloride) |

Reference Example 3:23

Production of 3-(N-benzyl-N-methylaminomethyl)-4,7-dihydro-7-(2,6-difluorobenzyl)-5-benzoyl-2-[4-(2-acetylvinylenephenyl)]-4-oxothieno[2,3-b]pyridine hydrochloride:

The compound which is produced in Reference Example 3:10 is treated with isoamyl nitrite, bisdibenzylidene acetone palladium and methyl vinyl ketone, and then subjected to a conventional method the titled compound is produced. m.p. 149–151° C. (hydrochlide).

Reference Example 3:24

From the compound which is produced in Reference Example 3:10 and various vinyl compounds, compounds set forth in Table 31 are produced.

TABLE 31

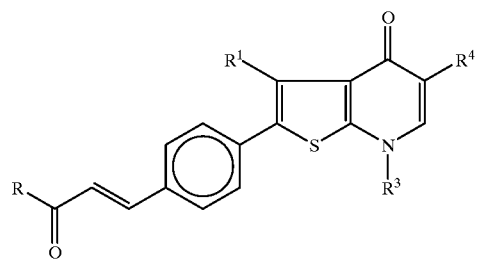

| Ref. Ex. 3:24 Cpd. No. | R¹ | R | R³ | R⁴ | m.p. (° C.) |
|---|---|---|---|---|---|
| (1) | N-methyl-N-benzylaminomethyl | phenyl | 2,6-difluorobenzyl | benzoyl | 137–139 |
| (2) | N-methyl-N-benzylaminomethyl | ethoxy | 2,6-difluorobenzyl | benzoyl | 154–155 (hydrochloride) |
| (3) | N-methyl-N-benzylaminomethyl | methoxy | 2,6-difluorobenzyl | benzoyl | 148–150 (hydrochloride) |
| (4) | N-methyl-N-benzylaminomethyl | hydroxy | 2,6-difluorobenzyl | benzoyl | 159–161 (hydrochloride) |
| (5) | N-methyl-N-benzylaminomethyl | ethyl | 2,6-difluorobenzyl | benzoyl | 168–170 (hydrochloride) |

Reference Example 3:25

Production of 3-(N-benzyl-N-methylaminomethyl)-4,7-dihydro-7-(2,6-difluorobenzyl)-5-benzoyl-2-[4-(N-ethyl-N-trifluoroacetylaminophenyl)]-4-oxothieno[2,3-b]pyridine:

From the compound which is produced in Reference Example 3:19, ethyl iodide and potassium carbonate, the titled compound is produced.

$^1$H-NMR (200 MHz, CDCl$_3$) δ: 1.23(3H,t,J=7.2 Hz), 2.12(3H,s), 3.62(2H,s), 3.83(2H,q,J=7.2 Hz), 4.16(2H,s), 5.31(2H,s), 7.03(2H,t,J=7.8 Hz), 7.12–7.32(7H,m), 7.37–7.47(3H,m), 7.55(1H,m), 7.89(2H,d,J=7.8 Hz), 7.96(3H,m).

Mass m/z 730(MH)$^+$.

Reference Example 3:26

Production of 3-(N-benzyl-N-methylaminomethyl)-4,7-dihydro-7-(2,6-difluorobenzyl)-5-benzoyl-2-(4-ethylaminophenyl)-4-oxothieno[2,3-b]pyridine hydrochloride:

From the compound which is produced in Reference Example 3:25 and 5N potassium hydroxide, the titled compound is produced.

m.p. 166–168° C. (hydrochloride).

Reference Example 3:27

From the compounds which are produced in Reference Example 3:19 or Reference Example 3:21 and various halogen compounds, compounds set forth in Table 32 are produced by a similar manner of Reference Example 3:25 or 3:26.

Reference Example 3:28

Production of 3-(N-benzyl-N-methylaminomethyl)-4,7-dihydro-7-(2,6-difluorobenzyl)-5-(4-hydroxybenzoyl)-2-(4-isobutyrylaminophenyl)-4-oxothieno[2,3-b]pyridine hydrochloride:

From the compound which is produced in Reference Example 3:20 (Compound No.1) and 10M hydrogen chloride in ethanol, the titled compound is produced.

m.p. 192–194° C. (hydrochloride).

Reference Example 3:29

Production of 3-(N-benzyl-N-methylaminomethyl)-4,7-dihydro-7-(2,6-difluorobenzyl)-5-(4-acetoxybenzoyl)-2-(4-isobutyrylaminophenyl)-4-oxothieno[2,3-b]pyridine hydrochloride:

From the compound which is produced in Reference Example 3:28, triethylamine and acetic anhydride, the titled compound is produced.

m.p. 167–169° C. (hydrochloride).

Reference Example 3:30

Production of 3-(N-benzyl-N-methylaminomethyl)-4,7-dihydro-7-(2,6-difluorobenzyl)-5-(1-hydroxyisobutyl)-2-(4-isobutyrylaminophenyl)-4-oxothieno[2,3-b]pyridine hydrochloride:

From the compound which is produced in Reference Example 3:9 and sodium boronhydride, the titled compound is produced.

m.p. 232–234° C. (hydrochloride).

Reference Example 3:31

Production of 3-(N-benzyl-N-methylaminomethyl)-4,7-dihydro-7-(2,6-difluorobenzyl)-5-(1-acetoxyisobutyl)-2-(4-isobutyrylaminophenyl)-4-oxothieno[2,3-b]pyridine hydrochloride:

From the compound which is produced in Reference Example 3:30, pyridine and acetic anhydride, the titled compound is produced.

m.p. 166–168° C. (hydrochloride).

Reference Example 3:32

Production of 4,7-dihydro-7-(2,6-difluorobenzyl)-2-(4-acetonyloxyphenyl)-5-benzoyl-3-(N-benzyl-N-methylaminomethyl)-4-oxothieno[2,3-b]pyridine hydrochloride:

Employing the compound which is produced in Reference Example 3:15 and chloroacetone, the titled compound is produced.

Reference Example 3:33

Production of 4,7-dihydro-7-(2,6-difluorobenzyl)-2-(4-acetonyloxyphenyl)-5-isobutyryl-3-(N-benzyl-N-methylaminomethyl)-4-oxothieno[2,3-b]pyridine hydrochloride:

TABLE 32

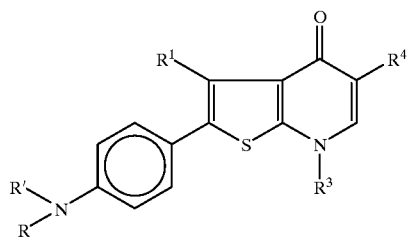

| Ref. Ex. 3:27 Cpd. No. | R$^1$ | R | R' | R$^3$ | R$^4$ | m.p. (° C.) |
|---|---|---|---|---|---|---|
| (1) | N-methyl-N-benzylaminomethyl | ethyl | ethyl | 2,6-difluorobenzyl | benzoyl | 144–146 (hydrochloride) |
| (2) | N-methyl-N-benzylaminomethyl | —(CH$_2$)$_4$— | | 2,6-difluorobenzyl | benzoyl | 154–156 (hydrochloride) |
| (3) | N-methyl-N-benzylaminomethyl | methyl | H | 2,6-difluorobenzyl | benzoyl | 152–154 (hydrochloride) |
| (4) | N-methyl-N-benzylaminomethyl | propyl | H | 2,6-difluorobenzyl | benzoyl | 154–156 (hydrochloride) |
| (5) | N-methyl-N-benzylaminomethyl | butyl | H | 2,6-difluorobenzyl | benzoyl | 145–147 (hydrochloride) |
| (6) | N-methyl-N-benzylaminomethyl | isobutyl | H | 2,6-difluorobenzyl | benzoyl | 157–159 (hydrochloride) |

From the compound which is produced in Reference Example 3:16 and chloroacetone, the titled compound is produced.

The structures of the compounds which are produced in the Reference Examples 3:17, 3:19, 3:21, 3:23, 3:25, 3:26, 3:28 to 3:32 are listed in Table 33.

TABLE 33

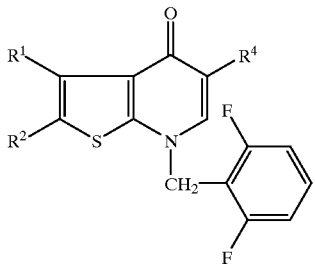

| Ref. Ex. No. | R¹ | R² | R⁴ |
|---|---|---|---|
| 3:17 | N-methyl-N-(N-methylindol-3-ylmethyl)-aminomethyl | 4-isobutyryl-aminophenyl | isobutyryl |
| 3:19 | N-benzyl-N-methylamino-methyl | 4-trifluoro-acetylamino-phenyl | benzoyl |
| 3:21 | N-benzyl-N-methylamino-methyl | 4-(3-oxobutyl)-aminophenyl | benzoyl |
| 3:23 | N-benzyl-N-methylamino-methyl | 4-(2-acetyl-vinylenephenyl | benzoyl |
| 3:25 | N-benzyl-N-methylamino-methyl | 4-(N-ethyl-N-trifluoroacetyl-aminophenyl) | benzoyl |
| 3:26 | N-benzyl-N-methylamino-methyl | 4-ethylamino-phenyl | benzoyl |
| 3:28 | N-benzyl-N-methylamino-methyl | 4-isobutyryl-aminophenyl | 4-hydroxy-benzoyl |
| 3:29 | N-benzyl-N-methylamino-methyl | 4-isobutyryl-aminophenyl | 4-acetoxy-benzoyl |
| 3:30 | N-benzyl-N-methylamino-methyl | 4-isobutyryl-aminophenyl | 1-hydroxy-isobutyl |
| 3:31 | N-benzyl-N-methylamino-methyl | 4-isobutyryl-aminophenyl | 1-acetoxy-isobutyl |
| 3:32 | N-benzyl-N-methylamino-methyl | 4-acetonyl-oxyphenyl | benzoyl |
| 3:33 | N-benzyl-N-methylamino-methyl | 4-acetonyl-oxyphenyl | isobutyryl |

Reference Example 4:1

Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid ethyl ester (hereinafter referred to as Compound 4:B):

From the compound which is produced in Working Example 27 described in PCT International Publication No. WO95/28405 (hereinafter referred to as Compound 4:A) and isobutyl chloride, the titled compound is produced.

m.p. 233–235° C.

Compound 4:A and Compound 4:B are shown in the following Table 34.

TABLE 34

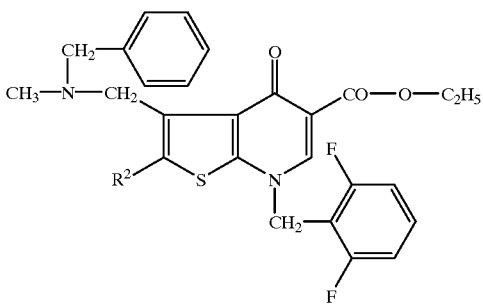

| Cpd. No. | R² |
|---|---|
| 4:A | 4-aminophenyl |
| 4:B | 4-isobutyrylaminophenyl |

Reference Example 4:2

Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid isopropyl ester hydrochloride (Compound 4:2):

From Compound 4:B, isopropyl alcohol and isopropyl titanate, the titled compound is produced.

m.p. 168–170° C.

Reference Example 4:3

The compounds set forth in Table 35 are produced in substantially the same manner as described in Reference Example 4:2. (In Table 35, the compounds No. 4:2 are shown inclusively.)

TABLE 35

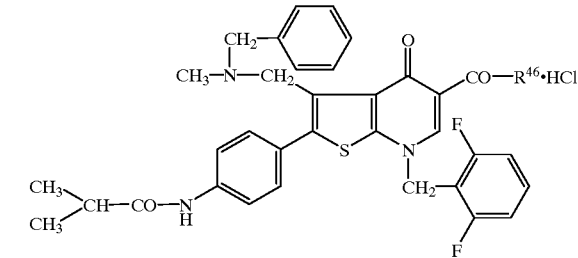

| Cpd. No. | R⁴⁶ | m.p. (hydrochloride) (° C.) |
|---|---|---|
| 4:2 | isopropoxy | 168–170 |
| 4:3(1) | sec-butoxy | 171–173 |
| 4:3(2) | cyclohexyloxy | 177–179 |
| 4:3(3) | 3-pentyloxy | 194–195 |
| 4:3(4) | 4-tetrahydropyranyloxy | 165–167 |
| 4:4 | H | 212–214 |
| 4:5 | 2,4-dimethyl-3-pentyl | 174–175 |
| 4:6 | 4-tetrahydropyranylthio | 174–176 |
| 4:7 | ethylthio | 251–253 |
| 4:8 | isopropylthio | 139–141 |

Reference Example 5:1
(1) Production of 4,7-dihydro-4-oxo-7-(2,6-difluorobenzyl)-2-(4-hydroxyphenyl)-3-methylthieno[2,3-b]pyridine-5-carboxylic acid ethyl ester:

From the compound which is produced in Working Example 3 (10) of PCT International Publication No. WO95/28405, i.e. 4-oxo-7-(2,6-difluorobenzyl)-2-(4-methoxyphenyl)-3-methyl-thieno[2,3-b]pyridine-5- carboxylic acid ethyl ester, aluminium chloride and dimethyl disulfide, the titled compound is produced.

m.p. 244–246° C.

(2) Production of 4,7-dihydro-4-oxo-7-(2,6-difluorobenzyl)-2-(4-methoxymethoxyphenyl)-3-methylthieno[2,3-b]pyridine-5-carboxylic acid ethyl ester:

From the compound which is produced in Reference Example 5:1(1), sodium hydride and chloromethyl methyl ether, the titled compound is produced.

$^1$H-NMR (300 MHz, CDCl$_3$) δ: 1.41(3H,t,J=7.2 Hz), 2.65(3H,s), 3.50(3H,s), 4.40(2H,q,J=7.2 Hz), 5.22(2H,s), 5.25(2H,s), 7.00(2H,t,J=8.3 Hz), 7.10(2H,d,J=6.8 Hz), 7.33–7.41(3H,m), 8.37(1H,s).

(3) Production of 4,7-dihydro-4-oxo-7-(2,6-difluorobenzyl)-2-(4-methoxymethoxyphenyl)-3-(N-benzyl-N-methylaminomethyl)-thieno[2,3-b]pyridine-5-carboxylic acid ethyl ester:

The compound, which is produced in Reference Example 5:1(2), is reacted with N-bromosuccinic acid imide and α,α'-azobisisobutyronitrile, thus obtained compound is reacted with ethyl diisopropylamine and N-methyl benzylamine to give the titled compound.

$^1$H-NMR (300 MHz, CDCl$_3$) δ: 1.39(3H,t,J=7.2 Hz), 2.20(3H,s), 3.51(3H,s), 3.93(2H,s), 4.20(2H,s), 4.40 (2H,q,J=7.2 Hz), 5.23(2H,s), 5.27(2H,s), 7.00(2H,t,J=8.3 Hz), 7.10(2H,d,J=6.8 Hz), 7.18–7.26(5H,m), 7.36–7.44(1H,m), 7.72–7.75(2H,m), 8.37(1H,s).

(4) Production of 4,7-dihydro-4-oxo-7-(2,6-difluorobenzyl)-2-(4-methoxymethoxyphenyl)-3-(N-benzyl-N-methylaminomethyl)-thieno[2,3-b]pyridine-5-N-methyl-O-methyl hydroxamic acid:

From the compound which is produced in Reference Example 5:1(3), N-methyl-O-methyl hydroxylamine hydrochloride, N-ethyl diisopropylamine and trimethyl ammonium, the titled compound is produced.

$^1$H-NMR (300 MHz, CDCl$_3$) δ: 2.21(3H,s), 3.34(3H,s), 3.54(3H,s), 3.72(2H,s), 3.76(3H,s), 4.19(2H,s), 5.23 (2H,s), 5.30(2H,s), 6.95(2H,t,J=8.3 Hz), 7.12(2H,d,J=6.8 Hz), 7.15–7.22(5H,m), 7.33–7.41(1H,m), 7.70–7.74(2H,m), 8.33(1H,s).

(5) Production of 4,7-dihydro-4-oxo-7-(2,6-difluorobenzyl)-2-(4-hydroxyphenyl)-3-(N-benzyl-N-methylaminomethyl)-5-benzoyl thieno[2,3-b]pyridine:

From the compound which is produced in Reference Example 5:1(4), phenyl magnesium bromide and 6N hydrochloric acid, the titled compound is produced.

$^1$-NMR (300 MHz, CDCl$_3$) δ: 2.37(3H,s), 3.91(2H,s), 4.30(2H,s), 5.38(2H,s), 6.98–7.05(4H,m), 7.21–7.38 (5H,m), 7.43–7.48(5H,m), 7.55–7.59(1H,m), 7.90(2H,d,J=7.1 Hz), 8.06(1H,s).

(6) Production of 4,7-dihydro-4-oxo-7-(2,6-difluorobenzyl)-2-(4-hydroxyphenyl)-3-(N-benzyl-N-methylaminomethyl)-5-isobutyrylthieno [2,3-b]pyridine:

From the compound which is produced in Reference Example 5:1(4), isopropyl magnesium chloride and 6N hydrochloric acid, the titled compound is produced.

$^1$H-NMR (300 MHz, CDCl$_3$) δ: 1.18(6H,d), 2.10(3H,s), 3.61(2H,s), 4.1–4.2(3H,m), 5.26(2H,s), 6.90(2H,d), 6.99(2H,t), 7.1–7.2(6H,m), 7.40(1H,m), 7.65(2H,d), 8.28(1H,s).

Reference Example 5:2

The compound which is produced in Reference Example 5:1(3) is subjected to hydrolysis using 1N sodium hydroxide to thereby convert the compound into one whose substituent at 5-position is carboxyl group. From the carboxylic acid derivative, N,N-dimethylaminopyridine, alcohol (e.g. isopropanol, cyclohexanol, sec-butanol, 3-pentanol or 2,4-dimethyl-3-pentanol) and phosphorus oxychloride to produce a compound whose substituent at 5-position is ester. The ester derivative is subjected to demethylation reaction in substantially the same manner as in Reference Example 5:1(1) to give the compound shown in Table 36.

TABLE 36

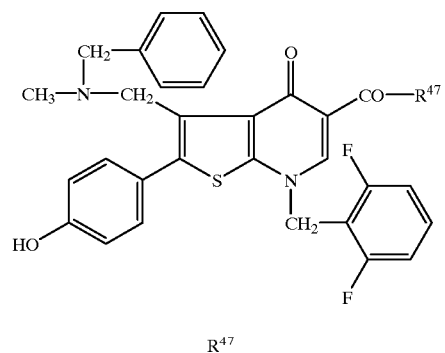

| $R^{47}$ |
|---|
| isopropoxy |
| cyclohexyloxy |
| sec-butoxy |
| 3-pentoxy |
| 2,4-dimethyl-3-pentoxy |
| ethoxy |

Reference Example 5:3

Production of 3-(N-methyl-N-benzylaminomethyl)-4,7-dihydro-7-(2,6-difluorobenzyl)-2-(4-allyloxyphenyl)-5-benzoyl-4-oxothieno[2,3-b]pyridine hydrochloride:

From the compound which is produced in Reference Example 5:1(5), potassium carbonate and allyl iodide, the titled compound is produced.

m.p. 120–122° C.

Reference Example 5:4

Employing the compound which is produced in Reference Example 5:1(5), substantially the same procedure as described in Reference Example 5:3 is conducted to give compounds shown in Table 37, including the compound of Reference Example 5:3.

TABLE 37

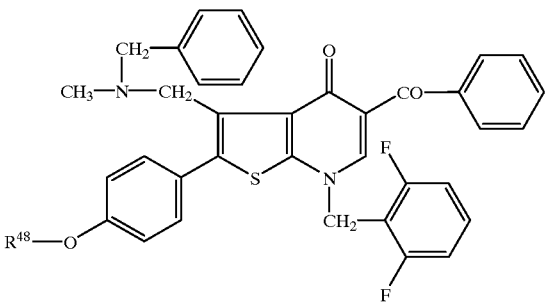

| Cpd. No. | $R^{48}$ |
|---|---|
| 5:3 | allyl |
| 5:4(1) | cyclopropylmethyl |
| 5:4(2) | 2-buten-1-yl |
| 5:4(3) | 2-methyl-2-propen-1-yl |
| 5:4(4) | 3-buten-1-yl |

Reference Example 5:5

Employing the compound which is produced in Reference Example 5:1(6), substantially the same procedure as described in Reference Example 5:3 is conducted to give compounds shown in Table 38.

TABLE 38

[Structure: thieno-pyridinone with R49-O-phenyl, CH3-N(CH2-phenyl)-, and CO-CH(CH3)2 group, and N-CH2-(2,6-difluorophenyl)]

| Cpd. No. | R49 | m.p. (hydrochloride) (° C.) |
|---|---|---|
| 5:5(1) | allyl | 182–184 |
| 5:5(2) | cyclopropylmethyl | 152–155 |
| 5:5(3) | 2-buten-1-yl | 126–130 |
| 5:5(4) | 2-methyl-2-propen-1-yl | 175–177 |
| 5:5(5) | 3-buten-1-yl | 141–144 |
| 5:5(6) | 2,2,2-trifluoroethyl | 128–130 |

Reference Example 5:6

Employing, the compound which is produced in Reference Example 5:2, substantially the same procedure as described in Reference Example 5:3 is conducted to give compounds shown in Table 39.

TABLE 39

[Structure: thieno-pyridinone with $R^{50}$-O-phenyl, CH3-N(CH2-phenyl)-, and CO-$R^{51}$ group, and N-CH2-(2,6-difluorophenyl)]

| Cpd. No. | R50 | R51 |
|---|---|---|
| 5:6(1) | allyl | isopropoxy |
| 5:6(2) | cyclopropylmethyl | isopropoxy |
| 5:6(3) | 2-buten-1-yl | isopropoxy |
| 5:6(4) | 2-methyl-2-propen-1-yl | isopropoxy |
| 5:6(5) | 3-buten-1-yl | isopropoxy |
| 5:6(6) | allyl | cyclohexyloxy |
| 5:6(7) | cyclopropylmethyl | cyclohexyloxy |
| 5:6(8) | 2-buten-1-yl | cyclohexyloxy |
| 5:6(9) | 2-methyl-2-proprn-1-yl | cyclohexyloxy |
| 5:6(10) | allyl | sec-butoxy |
| 5:6(11) | cyclopropylmethyl | sec-butoxy |
| 5:6(12) | 2-buten-1-yl | sec-butoxy |
| 5:6(13) | 2-methyl-2-propen-1-yl | sec-butoxy |
| 5:6(14) | allyl | 3-pentoxy |
| 5:6(15) | cyclopropylmethyl | 3-pentoxy |
| 5:6(16) | 2-buten-1-yl | 3-pentoxy |
| 5:6(17) | 2-methyl-2-propen-1-yl | 3-pentoxy |
| 5:6(18) | allyl | 2,4-dimethyl-3-pentoxy |
| 5:6(19) | cyclopropylmethyl | 2,4-dimethyl-3-pentoxy |
| 5:6(20) | 2-buten-1-yl | 2,4-dimethyl-3-pentoxy |

TABLE 39-continued

| Cpd. No. | R50 | R51 |
|---|---|---|
| 5:6(21) | 2-methyl-2-propen-1-yl | 2,4-dimethyl-3-pentoxy |
| 5:6(22) | allyl | ethoxy |

Reference Example 6:1

Employing an acetone derivative, the compound shown in Table 40 is produced in accordance with substantially the same manner as described in PCT International Publication No. WO95/28405 Reference Example 2.

TABLE 40

[Structure: thiophene with $R^{3y}$, $R^{4y}$, COOC2H5 and NH2 substituents]

| Ref. Ex. Cpd. No. | $R^{3'}$ | $R^{4y}$ |
|---|---|---|
| 6:1 | methyl | bromo |

Reference Example 6:2

Employing, the compounds which are produced in PCT International Publicaiton No. WO95/28405 Reference Examples 2, 3 or 19, compounds which are produced in accordance with the method described in PCT International Publicaiton No. WO95/28405 Reference Example 20 are set forth in Table 41.

TABLE 41

[Structure: thieno-pyrimidinedione with CH3, $R^{4y}$, $R^{2y}$ substituents]

| Ref. Ex. Cpd. No. | $R^{2y}$ | $R^{4y}$ | m.p. (° C.) |
|---|---|---|---|
| 6:2(1) | 3-methoxyphenyl | bromo | 245–247 |
| 6:2(2) | 3-isopropoxyphenyl | bromo | |
| 6:2(3) | 3-isopropoxyphenyl | 4-methoxyphenyl | |
| 6:2(4) | 3-methoxy-methoxyphenyl | 4-nitrophenyl | 263–267 |

Reference Example 6:3

Starting from the compounds which are produced in Reference Example 6:2, compounds which are produced in accordance with the method described in PCT International Publicaiton No. WO95/28405 Reference Example 23 are set forth in Table 42.

TABLE 42

| Ref. Ex. Cpd. No. | $R^{2y}$ | $R^{14y}$, $R^{15y}$ | $R^{4y}$ | m.p. (° C.) |
|---|---|---|---|---|
| 6:3(1) | 3-methoxyphenyl | 2,6-difluoro | bromo | 261–262 |
| 6:3(2) | 3-isopropoxyphenyl | 2,6-difluoro | bromo | |
| 6:3(3) | 3-isopropoxyphenyl | 2,6-difluoro | 4-methoxyphenyl | |

Reference Example 6:4

The compounds shown in Table 43 are produced from the compounds of Reference Example 6:3 by the method of Reference Example 6:35 mentioned below.

TABLE 43

| Ref. Ex. Cpd. No. | $R^{2y}$ | $R^{14y}$, $R^{15y}$ | $R^{4y'}$ |
|---|---|---|---|
| 6:4(1) | 3-methoxyphenyl | 2,6-difluoro | propylaminocarbonyl |
| 6:4(2) | 3-methoxyphenyl | 2,6-difluoro | isopropylaminocarbonyl |
| 6:4(3) | 3-isopropoxyphenyl | 2,6-difluoro | propylaminocarbonyl |
| 6:4(4) | 3-isopropoxyphenyl | 2,6-difluoro | isopropylaminocarbonyl |
| 6:4(5) | 3-isopropoxyphenyl | 2,6-difluoro | methoxy |

Reference Example 6:5

Production of 3-isobutyl-2,4(1H,3H)-dioxo-5-methyl-6-(4-methoxyphenyl)thieno[2,3-d]pyrimidine:

From the compound which is produced in PCT International Publicaiton No. WO95/28405 Reference Example 2, isovaleric acid, diphenylphosphoryl azide and triethylamine, the titled compound is produced.

m.p. 215–216° C.

Reference Example 6:6

Employing the compounds which are produced in PCT International Publicaiton No. WO95/28405 Reference Example 2 or 19, compounds which are produced in accordance with the method described in Reference Example 6:5 are set forth in Table 44.

TABLE 44

| Ref. Ex. Cpd. No. | $R^{2y}$ | $R^{4y'}$ | m.p. (° C.) |
|---|---|---|---|
| 1 | methoxyethyl | methoxy | 131–233 |
| 2 | 3,5-dimethoxyphenyl | methoxy | >300 |
| 3 | 3,5-dimethoxyphenyl | nitro | >300 |

Reference Example 6:7

Production of 2-amino-4-methyl-5-(4-methoxyphenyl)thiophene-3-carboxylic acid:

From the compound which is produced in PCT International Publicaiton No. WO95/28405 Reference Example 2 and 2N sodium hydroxide, the titled compound is produced.

m.p. 142–145° C.

Reference Example 6:8

Production of 2,4(1H)-dioxo-6-(4-methoxyphenyl)-5-)methylthieno[2,3-d]zoxazine:

From the compound which is produced in Reference Example 6:7 and triphosgene, the titled compound is produced.

m.p. 209–210° C.

Reference Example 6:9

Production of 2,4(1H)-dioxo-1-(2-fluorobenzyl)-6-(4-methoxyphenyl)-5-methylthieno[2,3-d]oxazine:

From the compound which is produced in Reference Example 6:8, potassium carbonate, potassium iodide and 2-fluorobenzylchloride, the titled compound is produced.

m.p. 162–163° C.

Reference Example 6:10

Production of 2,4(1H)-dioxo-1-(2,6-difluorobenzyl)-6-(4-methoxyphenyl)-5-methylthieno[2,3-d]oxazine:

From the compound which is obtained in Reference Example 6:9, 2,6-difluorobenzylchloride, potassium carbonate and potassium iodide, the titled compound is produced.

m.p. 189–190° C.

Reference Example 6:11

Production of 2,4-(1H,3H)-dioxo-1-(2-fluorobenzyl)-6-(4-methoxyphenyl)-3-(3-methoxypropyl)-5-methylthieno[2,3-d]pyrimidine:

From the compound which is obtained in Reference Example 6:9 and 3-methoxypropylamine, the titled compound is produced.

m.p. 113–115° C.

Reference Example 6:12

Employing the compounds which are produced in Reference Example 6:10, compounds which are produced in accordance with the method described in Reference Example 6:7 are set forth in Table 45.

TABLE 45

![Structure: thieno[2,3-d]pyrimidine with CH3O-phenyl, CH3, R2y, and CH2-phenyl(R14y, R15y) substituents]

| Ref. Ex. Cpd. No. | R14y, R15y | R2 | m.p. (° C.) |
|---|---|---|---|
| 6:12(1) | 2,6-difluoro | methoxypropyl | 173–174 |
| 6:12(2) | 2,6-difluoro | 3-methyl-thiophenyl | 243–245 |

Reference Example 6:13

Production of 2,4(1H,3H)-dioxo-3-phenyl-5-methyl-6-(4-methoxyphenyl)thieno[2,3-d]pyrimidine:

From the compound which is obtained in PCT International Publicaiton No. WO95/28405 Reference Example 19 and phenylisocyanate, the titled compound is produced.

m.p. >300° C.

Reference Example 6:14

Production of 2,4(1H,3H)-dioxo-5-methyl-3-(3-methoxyphenyl)-6-(4-methoxyphenyl)thieno[2,3-d]pyrimidine:

In substantially the same procedure as described in Reference Example 6:13, using 3-methoxyphenylisocyanate and the compound which is obtained in PCT International Publicaiton No. WO95/28405 Reference Example 19 and 28% sodium methoxide, the titled compound is produced.

m.p. >300° C.

Reference Example 6:15

Production of 2,4(1H,3H)-dioxo-1-(2,6-difluorobenzyl)-5-methyl-3-(3-methylsulfinylphenyl)-6-(4-methoxyphenyl)thieno[2,3-d]pyrimidine:

From the compound 6:12(2) which is obtained in Reference Example 6:12 and m-chloroperbenzoic acid, the titled compound is produced.

m.p. 267–268° C.

Reference Example 6:16

Production of 2,4(1H,3H)-dioxo-1-(2,6-difluorobenzyl)-5-methyl-3-(3-methylsulfonylphenyl)-6-(4-methoxyphenyl)thieno[2,3-d]pyrimidine:

In substantially the same procedures as described in Reference Example 6:15, using m-chloroperbenzoic acid again, from the compound which is obtained in Reference Example 6:15, the titled compound is produced.

m.p. 256–257° C.

Reference Example 6:17

Employing the compounds which are produced in accordance with the methods of Reference Example 6:5, 6:6, 6:13 or 6:14, compounds which are produced in accordance with the method described in Reference Example 6:9 are set forth in Table 46.

TABLE 46

![Structure: thieno[2,3-d]pyrimidine with R4y'-phenyl, CH3, R2y, and CH2-phenyl(R14y, R15y) substituents]

| Ref. Ex. 6:17 Cpd. No. | R2y | R14y, R15y | R4y' | m.p. (° C.) |
|---|---|---|---|---|
| (1) | isobutyl | 2-fluoro | methoxy | 136–138 |
| (2) | isobutyl | 2,6-difluoro | methoxy | 121–122 |
| (3) | methoxyethyl | 2-fluoro | methoxy | 102–104 |
| (4) | methoxyethyl | 2,6-difluoro | methoxy | 152–153 |
| (5) | 3,5-dimethoxyphenyl | 2-fluoro | methoxy | 250–252 |
| (6) | 3,5-dimethoxyphenyl | 2,6-difluoro | methoxy | 270–272 |
| (7) | 3,5-dimethoxyphenyl | 2,6-difluoro | nitro | 257–258 |
| (8) | phenyl | 2,6-difluoro | nitro | 280–282 |
| (9) | 3-methoxyphenyl | 2,6-difluoro | nitro | 231–234 |
| (10) | 3-isopropoxy-phenyl | 2,6-difluoro | nitro | |
| (11) | 3-methoxy-methoxyphenyl | 2,6-difluoro | nitro | 209–210 |

Reference Example 6:18

Production of 2,4(1H,3H)-dioxo-1-(2-fluorobenzyl)-5-bromomethyl-6-(4-methoxyphenyl)-3-(3-methoxypropyl)thieno[2,3-d]pyrimidine:

From the compound which is obtained in Reference Example 6:11, N-bromosuccinimide, α,α'-azobisisobutylonitrile and carbon tetrachloride, the titled compound is produced.

m.p. 105–107° C.

Reference Example 6:19

Employing the compounds which are produced in Reference Examples 6:11, 6:12, 6:15, 6:16 or 6:17, compounds which are produced in accordance with the method described in Reference Example 6:18 are set forth in Table 47.

TABLE 47

![Structure: thieno[2,3-d]pyrimidine with BrCH2, R4y'-phenyl, R2y, and CH2-phenyl(R14y, R15y) substituents]

| Ref. Ex. 6:19 Cpd. No. | R2 | R14, R15 | R4y' | m.p. (° C.) |
|---|---|---|---|---|
| (1) | methoxypropyl | 2,6-difluoro | methoxy | 166–167 |
| (2) | 3-methyl-mercaptophenyl | 2,6-difluoro | methoxy | 228–230 |
| (3) | 3-methyl-sulfinylphenyl | 2,6-difluoro | methoxy | 272–273 |
| (4) | 3-methyl-sulfonylphenyl | 2,6-difluoro | methoxy | 261–263 |

TABLE 47-continued

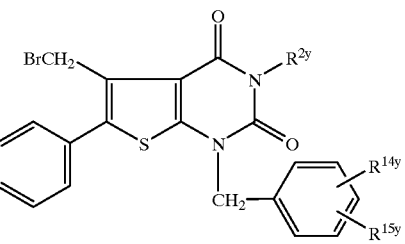

| Ref. Ex. 6:19 Cpd. No. | R² | R¹⁴, R¹⁵ | R⁴ʸ' | m.p. (° C.) |
|---|---|---|---|---|
| (5) | isobutyl | 2-fluoro | methoxy | 125–127 |
| (6) | isobutyl | 2,6-difluoro | methoxy | 155–157 |
| (7) | methoxylethyl | 2-fluoro | methoxy | 152–153 |
| (8) | methoxylethyl | 2,6-difluoro | methoxy | 150–151 |
| (9) | 3,5-dimethoxyphenyl | 2-fluoro | methoxy | 234–238 |
| (10) | 3,5-dimethoxyphenyl | 2,6-difluoro | methoxy | 251–253 |
| (11) | 3,5-dimethoxyphenyl | 2,6-difluoro | nitro | 245–247 |
| (12) | phenyl | 2,6-difluoro | nitro | 228–229 |
| (13) | 3-methoxyphenyl | 2,6-difluoro | nitro | 253–254 |
| (14) | 3-isopropoxyphenyl | 2,6-difluoro | nitro | |
| (15) | 3-methoxymethoxyphenyl | 2,6-difluoro | nitro | 207–209 |

Reference Example 6:20

Production of 2,4(1H,3H)-dioxo-6-(4-methoxyphenyl)-3-phenyl- 1-(2-fluorobenzyl)-5-(N-benzyl-N-methylaminomethyl)thieno[2,3-d]pyrimidine hydrochloride: (Compound 6:A)

From the compound which is produced in PCT International Publicaiton No. WO95/28405 Reference Example 26 (Compound No.5), ethyldiisopropylamine and methylbenzylamine, the titled compound is produced.

m.p. 140–143° C.

Starting from the compounds which are produced in PCT International Publicaiton No. WO95/28405 Reference Example 26, Reference Example 6:4, compounds which are produced in accordance with the method described in the above are set forth in Table 48.

TABLE 48

| | R²ʸ | R¹⁴ʸ, R¹⁵ʸ | R⁴ʸ'Rʸ | (° C.) |
|---|---|---|---|---|
| Compound | | | | |
| 6:A | phenyl | 2-fluoro | methoxy | phenyl | 140–143 (hydrochloride) |
| Ref. No. 6:20 Cpd. No. | | | | |
| (1) | methyl | 2-methoxy | methoxy | phenyl | 119–122 |
| (2) | methtl | 2-fluoro | methoxy | phenyl | 128–131 |
| (3) | phenyl | 2-methoxy | methoxy | phenyl | 97–105 |
| (4) | phenyl | 2-fluoro | nitro | phenyl | 140–143 |
| (5) | phenyl | 3-fluoro | methoxy | phenyl | 152–156 |
| (6) | phenyl | 4-fluoro | methoxy | phenyl | 165–170 |
| (7) | phenyl | 2,4-difluoro | methoxy | phenyl | 155–160 |
| (8) | phenyl | 2,6-difluoro | methoxy | phenyl | 160–162 |
| (9) | phenyl | 2-chloro, 6-fluoro | methoxy | phenyl | 150–155 |
| (10) | phenyl | 2-methylthio | methoxy | phenyl | 152–158 |
| (11) | benzyl | 2-fluoro | methoxy | phenyl | 128–134 |
| (12) | benzyl | 2,6-difluoro | methoxy | phenyl | 123–127 |
| (13) | 4-methoxyphenyl | 2-fluoro | methoxy | phenyl | 150–155 |
| (14) | 4-methoxyphenyl | 2,6-difluoro | methoxy | phenyl | 153–157 |
| (15) | cyclohexyl | 2-fluoro | methoxy | phenyl | 144–150 |

TABLE 48-continued

| | $R^{2y}$ | $R^{14y}, R^{15y}$ | $R^{4y'Ry}$(° C.) | | |
|---|---|---|---|---|---|
| (16) | cyclohexyl | 2,6-difluoro | methoxy | phenyl | 145–150 |
| (17) | phenyl | 2,6-difluoro | nitro | phenyl | 155–160 |
| (18) | 2-methoxyphenyl | 2-fluoro | methoxy | phenyl | 152–153 |
| (19) | 2-methoxyphenyl | 2,6-difluoro | methoxy | phenyl | 148–150 |
| (20) | 3-methoxyphenyl | 2-fluoro | methoxy | phenyl | 155–158 |
| (21) | 3-methoxyphenyl | 2,6-difluoro | methoxy | phenyl | 160–163 |
| (22) | 2-chlorophenyl | 2-fluoro | methoxy | phenyl | 147–152 |
| (23) | 2-chlorophenyl | 2,6-difluoro | methoxy | phenyl | 150–155 |
| (24) | 3-chlorophenyl | 2-fluoro | methoxy | phenyl | 148–153 |
| (25) | 3-chlorophenyl | 2,6-difluoro | methoxy | phenyl | 152–257 |
| (26) | 4-chlorophenyl | 2-fluoro | methoxy | phenyl | 161–164 |
| (27) | 4-chlorophenyl | 2,6-difluoro | methoxy | phenyl | 145–146 |
| (28) | 3-methoxyphenyl | 2,6-difluoro | propylaminocarbonyl | phenyl | |
| (29) | 3-methoxyphenyl | 2,6-difluoro | isopropylaminocarbonyl | phenyl | |
| (30) | 3-isopropoxyphenyl | 2,6-difluoro | propylaminocarbonyl | phenyl | |
| (31) | 3-isopropoxyphenyl | 2,6-difluoro | isopropylaminocarbonyl | phenyl | |
| (32) | 3-methoxyphenyl | 2,6-difluoro | methoxy | phenyl | 160–163 |
| (33) | 3-isopropoxyphenyl | 2,6-difluoro | methoxy | phenyl | |
| (34) | 3-methoxyphenyl | 2,6-difluoro | methoxy | 2-methylthiophenyl | |
| (35) | 3-methoxyphenyl | 2,6-difluoro | methoxy | 2-pyridyl | |
| (36) | phenyl | 2,6-difluoro | methoxy | 2-methylthiophenyl | |
| (37) | phenyl | 2,6-difluoro | methoxy | 2-pyridyl | |
| (38) | phenyl | 2,6-difluoro | methoxy | dimethylaminomethyl | |
| (39) | phenyl | 2,6-difluoro | methoxy | diethylaminomethyl | |
| (40) | phenyl | 2,6-difluoro | methoxy | 1-pyrrolidinylmethyl | |

Reference Example 6:21

Production of 6-(4-aminophenyl)-2,4-(1H,3H)-dioxo-1-(2,6-difluorobenzyl)-5-(N-methyl-N-benzylaminomethyl)-3-phenylthieno[2,3-d]pyrimidine:

Starting from the compound No. 17 produced in Reference Example 6:20, the titled compound is produced in accordance with the method described in PCT International Publicaiton No. WO95/28405 Working Example 60. Structure is shown in Table 49.

$^1$H-NMR (300 MHz, CDCl$_3$) δ: 2.05(3H,s), 3.56(2H,s), 3.81(2H,br s), 3.88(2H,s), 5.36(2H,s), 6.71(2H,d,J=8.7 Hz), 6.91(2H,t,J=8.7 Hz), 7.21–7.53(13H,m).

Reference Example 6:22

Production of 6-(4-acetylaminophenyl)-2,4(1H,3H)-dioxo-1-(2-fluorobenzyl)-5-(N-methyl-N-benzylaminomethyl)-3-phenylthieno[2,3-d]pyrimidine:

From the compound which is produced in PCT International Publicaiton No. WO95/28405 Working Example 60 and acetic anhydride, the titled compound is produced. The structure is shown in Table 49.

$^1$H-NMR (300 MHz, CDCl$_3$) δ: 2.06(3H,s), 2.19(3H,s), 3.57(2H,s), 3.90(2H,s), 5.30(2H,s), 7.04–7.57(16H,s), 7.70(2H,d,J=8.4 Hz).

Reference Example 6:23

Employing the compound which is produced in PCT International Publicaiton No. WO95/28405 Working Example 60, in accordance with substantially the same procedure as described in Reference Example 6:22, the following compounds are produced. The structures are shown in Table 49.

Ref.Ex.6:23 No. 1: 2,4(2H,3H)-Dioxo-1-(2-fluorobenzyl)-5-(N-methyl-N-benzylaminomethyl)-3-phenyl-6-(4-propionylaminophenyl)thieno[2,3-d]pyrimidine hydrochloride (m.p. 172–175° C.)

Ref.Ex.6:23 No. 2: 2,4(2H,3H)-Dioxo-1-(2-fluorobenzyl)-6-(4-isobutyrylaminophenyl)-5-(N-methyl-N-benzylaminomethyl)-3-phenylthieno[2,3-d]pyrimidine hydrochloride (m.p. 185–188° C.)

Ref.Ex.6-23 No. 3: 2,4(2H,3H)-Dioxo-1-(2-fluorobenzyl)-6-(4-methoxyacetylaminophenyl)-5-(N-methyl-N-benzylaminomethyl)-3-phenylthieno[2,3-d]pyrimidine hydrochloride (m.p. 157–162° C.)

TABLE 49

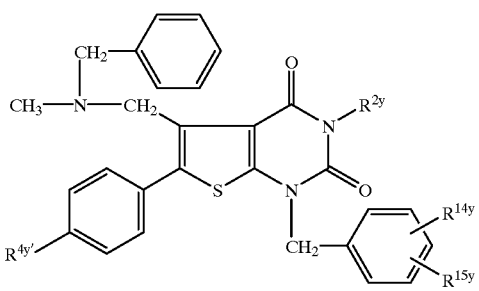

| Ref. Ex. Cpd. No. | $R^{2y}$ | $R^{14y}, R^{15y}$ | $R^{4y'}$ |
|---|---|---|---|
| 6:21 | phenyl | 2,6-difluoro | amino |
| 6:22 | phenyl | 2-fluoro | acetylamino |
| 6:23(1) | phenyl | 2-fluoro | propionylamino |
| 6:23(2) | phenyl | 2-fluoro | isobutyrylamino |
| 6:23(3) | phenyl | 2-fluoro | methoxyacetylamino |

Reference Example 6:24

Production of 2,4(1H,3H)-dioxo-1-(2-fluorobenzyl)-5-(N-benzyl-N-methylaminomethyl)-6-(4-methoxyphenyl)-3-(3-methoxypropyl)thieno[2,3-d]pyrimidine:

From the compound which is obtained in Reference Example 6:18, ethyldiisopropylamine and methylbenzylamine, the titled compound is produced. The structure is listed in Table 50.

m.p. 95–100° C.

Reference Example 6:25

Starting from the compounds which are produced in Reference Example 6:19, compounds which are produced in accordance with the method described in Reference Example 6:24 are set forth in Table 50. The compound 19 and 20 are produced by hydrolyzing the compound 21 to produce the compound 22, and by reacting the compound 22 with alkyl halide in the presence of a base.

TABLE 50

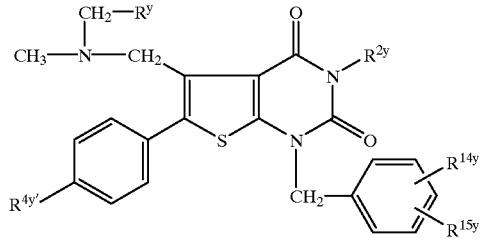

| Ref. Ex. Cpd. No. | $R^{2y}$ | $R^{14y}, R^{15y}$ | $R^{4y'}$ | $R^y$ | m.p. (° C.) |
|---|---|---|---|---|---|
| 6:24 | 3-methoxypropyl | 2-fluoro | methoxy | phenyl | 95–100 |
| 6:25(1) | methoxypropyl | 2,6-difluoro | methoxy | phenyl | 95–100 |
| 6:25(2) | 3-methylthiophenyl | 2,6-difluoro | methoxy | phenyl | 139–144 |
| 6:25(3) | 3-methylsulfinylphenyl | 2,6-difluoro | methoxy | phenyl | 153–156 |
| 6:25(4) | 3-methylsulfonylphenyl | 2,6-difluoro | methoxy | phenyl | 155–159 |
| 6:25(5) | isobutyl | 2-fluoro | methoxy | phenyl | 150–153 |
| 6:25(6) | isobutyl | 2,6-difluoro | methoxy | phenyl | 165–167 |
| 6:25(7) | methoxyethyl | 2-fluoro | methoxy | phenyl | 154–156 |
| 6:25(8) | methoxyethyl | 2,6-difluoro | methoxy | phenyl | 126–130 |
| 6:25(9) | 3,5-dimethoxyphenyl | 2-fluoro | methoxy | phenyl | 140–145 |
| 6:25(10) | 3,5-dimethoxyphenyl | 2,6-difluoro | mthoxy | phenyl | 146–148 |
| 6:25(11) | 3,5-dimethoxyphenyl | 2,6-difluoro | nitro | phenyl | 142–146 |
| 6:25(12) | phenyl | 2,6-difluoro | nitro | phenyl | 152–153 |
| 6:25(13) | 3-methoxyphenyl | 2,6-difluoro | nitro | phenyl | 142–144 |
| 6:25(14) | 3-isopropoxyphenyl | 2,6-difluoro | nitro | phenyl | amorphous (80–90) |
| 6:25(15) | 3-isopropoxyphenyl | 2,6-difluoro | nitro | 2-thiomethylphenyl | |
| 6:25(16) | 3-isopropoxyphenyl | 2,6-difluoro | nitro | 2-pyridyl | |

TABLE 50-continued

[Structure: thieno[2,3-d]pyrimidine with CH₂-Rʸ, CH₃-N-CH₂, R²ʸ, R⁴ʸ', R¹⁴ʸ, R¹⁵ʸ substituents]

| Ref. Ex. Cpd. No. | R²ʸ | R¹⁴ʸ, R¹⁵ʸ | R⁴ʸ' | Rʸ | m.p. (° C.) |
|---|---|---|---|---|---|
| 6:25(17) | 3-methoxyphenyl | 2,6-difluoro | nitro | 2-thiomethylphenyl | |
| 6:25(18) | 3-methoxyphenyl | 2,6-difluoro | nitro | 2-pyridyl | |
| 6:25(19) | 3-ethoxyphenyl | 2,6-difluoro | nitro | phenyl | 171–176 |
| 6:25(20) | 3-propoxyphenyl | 2,6-difluoro | nitro | phenyl | 149–151 |
| 6:25(21) | 3-methoxymethoxyphenyl | 2,6-difluoro | nitro | phenyl | 110–120 |
| 6:25(22) | 3-hydroxyphenyl | 2,6-difluoro | nitro | phenyl | 207–209 |
| 6:25(23) | 3-methoxyphenyl | 2,6-difluoro | nitro | diethylaminomethyl | |
| 6:25(24) | 3-methoxyphenyl | 2,6-difluoro | nitro | dimethylaminomethyl | |
| 6:25(25) | 3-methoxyphenyl | 2,6-difluoro | nitro | 1-pyrrolidinylmethyl | |

Reference Example 6:26

Production of 6-(4-aminophenyl)-2,4(1H,3H)-dioxo-1-(2,6-difluorobenzyl)-5-(N-benzyl-N-methylaminomethyl)-3-(3-methoxyphenyl)thieno[2,3-d]pyrimidine hydrochloride:

The compound 13 which is produced in Reference Example 6:25 is treated with 50% paradium-carbon powder in a hydrogen atmosphere to give the titled compound. The structure is listed in Table 51.

m.p. 162–165° C.

Reference Example 6:27

Starting from the compounds which are produced in Reference Example 6:25, compounds which are produced in accordance with the method described in Reference Example 6:26 are set forth in Table 51.

TABLE 51

[Structure: thieno[2,3-d]pyrimidine with CH₂-Rʸ, CH₃-N-CH₂, R²ʸ, NH₂-phenyl, R¹⁴ʸ, R¹⁵ʸ substituents]

| R²ʸ | R¹⁴ʸ, R¹⁵ʸ | Rʸ | m.p. (° C.) |
|---|---|---|---|
| Ref. Ex. 6:26 Cpd. No. | | | |
| 6:26 phenyl Ref. Ex. | 2,6-difluoro | methoxyphenyl | 162–165 |

TABLE 51-continued

| R²ʸ | R¹⁴ʸ, R¹⁵ʸ | Rʸ | m.p. (° C.) |
|---|---|---|---|
| 6:27 Cpd. No. | | | |
| (1) 3,5-dimethoxyphenyl | 2,6-difluoro | phenyl | 95–100 |
| (2) phenyl | 2,6-difluoro | phenyl | 139–144 |
| (3) 3-isopropoxyphenyl | 2,6-difluoro | phenyl | 138–140 |
| (4) 3-isopropoxyphenyl | 2,6-difluoro | 2-methylthiophenyl | |
| (5) 3-isopropoxyphenyl | 2,6-difluoro | 2-pyridyl | |
| (6) 3-methoxyphenyl | 2,6-difluoro | 2-methylthiophenyl | |
| (7) 3-methoxyphenyl | 2,6-difluoro | 2-pyridyl | |
| (8) 3-ethoxyphenyl | 2,6-difluoro | phenyl | 169–172 |
| (9) 3-propoxyphenyl | 2,6-difluoro | phenyl | 115–120 |
| (10) 3-methoxyphenyl | 2,6-difluoro | diethylaminomethyl | |
| (11) 3-methoxyphenyl | 2,6-difluoro | dimethylaminomethyl | |
| (12) 3-methoxyphenyl | 2,6-difluoro | 1-pyrrolidinylmethyl | |

Reference Example 6:28

Production of 2,4(1H,3H)-dioxo-1-(2,6-difluorobenzyl)-5-(N-benzyl-N-methylaminomethyl)-6-(4-formamidophenyl)-3-phenylthieno[2,3-d]pyrimidine:

From compound which is obtained in Reference Example 6:27(2), formic acid and acetic anhydride, the titled compound is produced. The structure is shown in Table 52.

m.p. 194–196° C.

Reference Example 6:29

Starting from the compounds which are produced in Reference Example 6:26 or 6:27, compounds which are produced in accordance with the method described in Reference Example 6:28 are set forth in Table 52.

TABLE 52

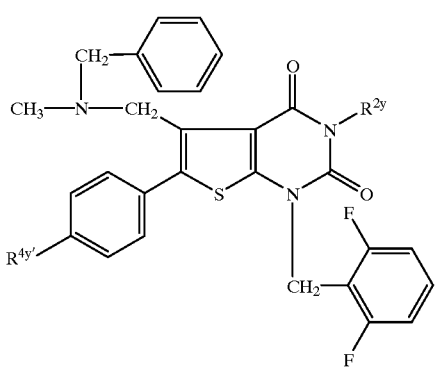

| Ref. Ex. Cpd. No. | $R^{2y}$ | $R^y$ | m.p. (° C.) |
|---|---|---|---|
| 6:28 | phenyl | phenyl | 194–196 |
| 6:29(1) | 3,5-dimethoxy-phenyl | phenyl | 239–243 |
| 6:29(2) | 3-methoxyphenyl | phenyl | 213–215 |
| 6:29(3) | 3-isopropoxy-phenyl | phenyl | |
| 6:29(4) | 3-isopropoxy-phenyl | 2-methylthio-phenyl | |
| 6:29(5) | 3-isopropoxy-phenyl | 2-pyridyl | |
| 6:29(6) | 3-methoxyphenyl | 2-methylthio-phenyl | |
| 6:29(7) | 3-methoxyphenyl | 2-pyridyl | |

Reference Example 6:30

Production of 2,4(1H,3H)-dioxo-1-(2,6-difluorobenzyl)-5-(N-benzyl-N-methylaminomethyl)-6-(4-methylaminophenyl)-3-(3-methoxyphenyl)thieno[2,3-d]pyrimidine hydrochloride:

The compound 2 which is obtained in Reference Example 6:29, is treated with dimethylsulfid borane and then hydrochloric acid (pH<2), and thus obtained compound is treated with 1N hydrogen chloride to give the titled compound. The structure is shown in Table 53.

m.p. 155–160° C.

Reference Example 6:31

Production of 2,4(1H,3H)-dioxo-1-(2,6-difluorobenzyl)-6-(4-propionylaminophenyl)-5-(N-benzyl-N-methylaminomethyl)-3-(3-methoxyphenyl)thieno[2,3-d]pyrimidine hydrochloride:

The compound which is obtained in Reference Example 6:26 is treated with triethylamine and propionyl chloride, and then with 1N hydrogen chloride in ether to give the titled compound. The structure is shown in Table 53.

m.p. 218–224° C.

TABLE 53

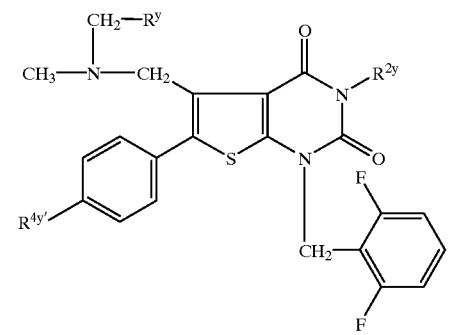

| Ref. Ex. Cpd. No. | $R^{2y}$ | $R^{4y'}$ |
|---|---|---|
| 6:30 | methoxyphenyl | methylamino |
| 6:31 | methoxyphenyl | propionylamino |

Reference Example 6:32

Starting from the compounds which are produced in Reference Example 6:26 or 6:27, compounds which are produced in accordancd with the method described in Reference Example 6:31 are set forth in Table 54.

TABLE 54

| Ref. Ex. 6:32 Cpd. No. | $R^{2y}$ | $R^{4y'}$ | $R^y$ | m.p. (° C.) |
|---|---|---|---|---|
| (1) | 3-methoxyphenyl | isobutyryl-amino | phenyl | 170–173 |
| (2) | phenyl | isobutyryl-amino | phenyl | 185–190 |
| (3) | 3,5-dimethoxy-phenyl | propionyl-amino | phenyl | 218–224 |
| (4) | 3,5-dimethoxy-phenyl | isobutynyl-amino | phenyl | 240–245 |
| (5) | 3-methoxyphenyl | N-methyl-N-propionyl-amino | phenyl | 138–143 |
| (6) | 3-methoxyphenyl | N-methyl-N-isobutyryl-amino | phenyl | 146–152 |
| (7) | phenyl | propionyl-amino | phenyl | 197–202 |
| (8) | phenyl | butyryl-amino | phenyl | 169–170 |
| (9) | phenyl | benzoyl-amino | phenyl | 167–169 |
| (10) | 3-methoxyphenyl | propionyl-amino | phenyl | 170–175 |

TABLE 54-continued

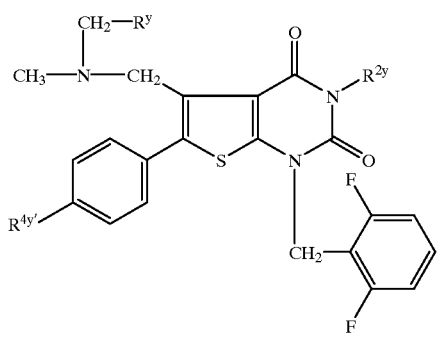

Ref. Ex. 6:32

| Cpd. No. | R²ʸ | R⁴ʸ' | Rʸ | m.p. (° C.) |
|---|---|---|---|---|
| (11) | 3-isopropoxy-phenyl | isobutyryl-amino | phenyl | |
| (12) | 3-isopropoxy-phenyl | isobutyryl-amino | 2-methylthio-phenyl | |
| (13) | 3-isopropoxy-phenyl | isobutyryl-amino | 2-pyridyl | |
| (14) | 3-methoxyphenyl | isobutyryl-amino | 3-methylthio-phenyl | |
| (15) | 3-methoxyphenyl | isobutyryl-amino | 2-pyridyl | |
| (16) | 3-isopropoxy-phenyl | propionyl-amino | phenyl | 179–181 |
| (17) | 3-ethoxyphenyl | propionyl-amino | phenyl | 164–168 |
| (18) | 3-propoxyphenyl | propionyl-amino | phenyl | 165–170 |
| (19) | 3-methoxyphenyl | ethylsul-fonylamino | phenyl | |
| (20) | 3-methoxyphenyl | trifluoro-acetylamino | phenyl | |
| (21) | 3-methoxyphenyl | isobutyryl-amino | diethylamino-methyl | |
| (22) | 3-methoxyphenyl | isobutyryl-amino | dimethylamino-methyl | |
| (23) | 3-methoxyphenyl | isobutyryl-amino | 1-pyrrolidinyl-methyl | |

Reference Example 6:33

In substantially the same procedure as described in Reference Example 6:31, using the compound which are obtained in Reference Example 6:26 or 6:27 and anhydrous trifluoro acetic acid, trifluoroacetylamino derivative are obtained. To the derivative is added halogeno derivative (e.g. propyl bromide, isopropyl bromide) in the presence of an appropriate base (e.g. potassium carbonate), and then subjecting to hydrolysis using 2N aqueous sodium hydroxide solution to give compounds set forth in Table 55.

TABLE 55

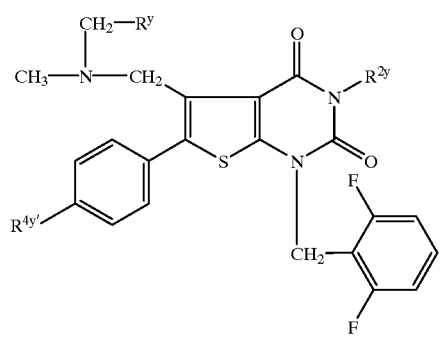

Ref. Ex. 6:33

| Cpd. No. | R²ʸ | R⁴ʸ' | Rʸ |
|---|---|---|---|
| (1) | 3-methoxyphenyl | propylamino | phenyl |
| (2) | 3-methoxyphenyl | isopropylamino | phenyl |
| (3) | 3-isopropoxy-phenyl | propylamino | phenyl |
| (4) | 3-isopropoxy-phenyl | isopropylamino | phenyl |
| (5) | 3-isopropoxy-phenyl | propylamino | 2-methylthio-phenyl |
| (6) | 3-isopropoxy-phenyl | propylamino | 2-pyridyl |
| (7) | 3-isopropoxy-phenyl | isopropylamino | 2-methylthio-phenyl |
| (8) | 3-isopropoxy-phenyl | isopropylamino | 2-pyridyl |
| (9) | 3-methoxyphenyl | ethylamino | phenyl |
| (10) | 3-isopropoxy-phenyl | ethylamino | phenyl |
| (11) | 3-methoxyphenyl | isopropylamino | 2-methylthio-phenyl |
| (12) | 3-methoxyphenyl | isopropylamino | 2-pyridyl |
| (13) | 3-methoxyphenyl | propylamino | 2-methylthio-phenyl |
| (14) | 3-methoxyphenyl | propylamino | 2-pyridyl |
| (15) | 3-methoxyphenyl | propylamino | diethylamino-methyl |

Reference Example 6:34

Employing the compounds which are obtained in Reference Example 6:26 or 6:27, the compounds set forth in Table 56 are produced by reacting the starting compounds with isoamyl nitrite, vinyl compound and palladium compound (e g. tetrakistri phenylphosphine palladium, dibenzylideneacetone palladium).

TABLE 56

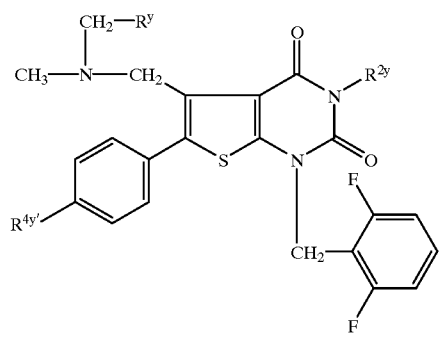

Ref. Ex. 6:34

| Cpd. No. | R²ʸ | R⁴ʸ' | Rʸ |
|---|---|---|---|
| (1) | 3-methoxyphenyl | ethoxycarbonyl- | phenyl |

TABLE 56-continued

[Structure: thiophene-pyrimidinedione with CH₂-Rʸ, CH₃-N-CH₂, R⁴ʸ'-phenyl, 2,6-difluorobenzyl, R²ʸ substituents]

Ref. Ex. 6:34

| Cpd. No. | R²ʸ | R⁴ʸ' | Rʸ |
|---|---|---|---|
| | | vinyl | |
| (2) | 3-methoxyphenyl | ethoxycarbonyl-vinyl | 2-methylthio-phenyl |
| (3) | 3-methoxyphenyl | ethoxycarbonyl-vinyl | 2-pyridyl |
| (4) | 3-methoxyphenyl | propionylvinyl | phenyl |
| (5) | 3-methoxyphenyl | propionylvinyl | 2-methylthio-phenyl |
| (6) | 3-methoxyphenyl | propionylvinyl | 2-pyridyl |
| (7) | 3-isopropoxy-phenyl | ethoxycarbonyl-vinyl | phenyl |
| (8) | 3-isopropoxy-phenyl | propionylvinyl | phenyl |
| (9) | 3-isopropoxy-phenyl | ethoxycarbonyl-vinyl | 2-methylthio-phenyl |
| (10) | 3-isopropoxy-phenyl | ethoxycarbonyl-vinyl | 2-pyridyl |
| (11) | 3-isopropoxy-phenyl | propionylvinyl | 2-methylthio-phenyl |
| (12) | 3-isopropoxy-phenyl | propionylvinyl | 2-pyridyl |
| (13) | 3-methoxyphenyl | propionylvinyl | dimethyl-aminomethyl |
| (14) | 3-methoxyphenyl | propionylvinyl | 1-pyrrolidinyl-methyl |
| (15) | 3-methoxyphenyl | propionylvinyl | diethylamino-methyl |

Reference Example 6:35

The compound 6:3(1) or 6:3(2) which are obtained in Reference Example 6:3, are treated with arylborric acid derivative, 2M aqueous sodium carbonate solution 1,2-dimethoxyethane and tetrakis(triphenylphosphine)palladium(0). To the resulting compound, N-methylbenzylamino group is introduced in accordance with the method described in Reference Example 6:18 and Reference Example 6:20 to give compounds set forth in Table 57.

TABLE 57

[Structure: thiophene-pyrimidinedione with CH₂-phenyl, CH₃-N-CH₂, R⁴ʸ'-phenyl, 2,6-difluorobenzyl, R²ʸ substituents]

Ref. Ex. 6:35

| Cpd. No. | R²ʸ | R⁴ʸ' |
|---|---|---|
| (1) | 3-methoxyphenyl | propylaminocarbonyl |
| (2) | 3-isopropoxyphenyl | propylaminocarbonyl |
| (3) | 3-methoxyphenyl | isopropylaminocarbonyl |
| (4) | 3-isopropoxyphenyl | isopropylaminocarbonyl |
| (5) | 3-methoxyphenyl | ethylaminocarbonyl |
| (6) | 3-methoxyphenyl | N-methyl-N-propyl-aminocarbonyl |

Reference Example 6:36

From the compounds which are obtained in Reference Example 6:20, dimethylsulfide and aluminium chloride, R⁴ʸ phenol derivative is produced.

From thus obtained compound, alkyl halide (e.g. chloro acetone) and a base (e.g. potassium carbonate), compounds set forth in Table 58 are produced.

TABLE 58

[Structure: thiophene-pyrimidinedione with CH₂-Rʸ, CH₃-N-CH₂, R⁴ʸ'-phenyl, 2,6-difluorobenzyl, R²ʸ substituents]

Ref. Ex. 6:36

| Cpd. No. | R²ʸ | R⁴ʸ' | Rʸ |
|---|---|---|---|
| (1) | phenyl | acetonyloxy | phenyl |
| (2) | phenyl | acetonyloxy | 2-methylthio-phenyl |
| (3) | phenyl | acetonyloxy | 2-pyridyl |
| (4) | phenyl | acetonyloxy | diethylamino-methyl |
| (5) | phenyl | acetonyloxy | dimethylamino-methyl |
| (6) | phenyl | acetonyloxy | 1-pyrrolidinyl-methyl |
| (7) | phenyl | allyloxy | phenyl |
| (8) | phenyl | propoxy | phenyl |
| (9) | phenyl | isobutoxy | phenyl |
| (10) | phenyl | cyclopropyl methoxy | phenyl |
| (11) | phenyl | allyloxy | diethylamino-methyl |

TABLE 58-continued

[Chemical structure diagram showing a thieno-pyrimidine derivative with substituents CH₂—R^y, CH₃—N—CH₂, R^{2y}, R^{4y'}, and a difluorobenzyl group]

| Ref. Ex. 6:36 Cpd. No. | $R^{2y}$ | $R^{4y'}$ | $R^y$ |
|---|---|---|---|
| (12) | phenyl | propoxy | diethylaminomethyl |

Reference Example 7:1

Production of (3-bromo-4-methylphenyl) aminomethylenemalonic acid diethylester:

From 3-bromo-4-methylaniline and ethoxymethylenemalonic acid diethylester, the titled compound is produced.

m.p. 66–67° C.

Reference Example 7:2

Production of 4-hydroxy-6-methyl-7-bromoquinoline-3-carboxylic acid ethylester:

The compound which is obtained in Reference Example 7:1 is treated with Dowtherm under heating to give the titled compound.

m.p. more than 250° C.

Reference Example 7:3

Production of 1,4-dihydro-1-(2,6-difluorobenzyl)-6-methyl-7-bromo-4-oxoquinoline-3-carboxylic acid ethylester:

From the compound which is obtained in Reference Example 7:2, potassium carbonate and 2,6-difluorobenzyl chloride, the titled compound is obtained.

m.p. 199–200° C.

Reference Example 7:4

Production of 1,4-dihydro-1-(2,6-difluorobenzyl)-6-methyl-7-(4-propionylaminophenyl)-4-oxoquinoline-3-carboxylic acid ethyl ester:

From the compound which is obtained in Reference Example 7:3, 2M sodium carbonate, 4-propionylaminophenyl boric acid tetrakistriphenylphosphinepalladium(O), the titled compound is produced.

m.p. 263–264° C.

Reference Example 7:5

Production of 6-bromomethyl-1,4-dihydro-1-(2,6-difluorobenzyl)-7-(4-propionylaminophenyl)-4-oxoquinoline-3-carboxylic acid ethyl ester:

From the compound which is obtained in Reference Example 7:4, N-bromosuccinimide and α,α'-azobisisobutyronitrile, the titled compound is produced.

m.p. 251–253° C.

Reference Example 7:6

Production of 6-(N-benzyl-N-methylaminomethyl)-1,4-dihydro-1-(2,6-difluorobenzyl)-7-(4-propionylaminophenyl)-4-oxoquinoline-3-carboxylic acid ethyl ester hydrochloride:

The compound which is obtained in Reference Example 7:5 is reacted with ethyldiisopropylamine and N-benzyl-N-methylamine, and then with 1N hydrogen chloride in ether, whereby the titled compound is obtained.

m.p. 165–168° C. (hydrochloride).

The compounds shown in the above Reference Examples 7:4 to 7:6 are listed in the following Table 59.

TABLE 59

[Chemical structure showing a quinoline derivative with $R^{1z}$, COO—C₂H₅, C₂H₅—CO—NH—, and a difluorobenzyl group]

| Ref. Ex. No. | $R^{1z}$ |
|---|---|
| 7:4 | methyl |
| 7:5 | bromomethyl |
| 7:6 | N-benzyl-N-methylaminomethyl |

Reference Example 8:1

Production of 4,7-dihydro-7-(2,6-difluorobenzyl)-3-(N-methyl-N-benzylaminomethyl)-2-(4-isobutyrylaminophenyl)-6-methyl-4-oxo-thieno[2,3-b]pyridine-5-carboxylic acid isopropyl ester hydrochloride:

To an anhydrous tetrahydrofuran solution (50 ml) of the compound obtained in Reference Example 4:2 (1.98 g, 2.78 mmole) was added dropwise a mixture of diethylether solution of methyl magnesium bromide (3.0 M, 4.63 ml, 13.9 mmole) and copper iodide (5.29 mg, 2.78 mmole), under ice-cooling. The mixture was stirred for 0.5 hour at the same temperature, to the resultant was added 1N hydrogen chloride under ice-cooling to adjust to not more than pH 2, and then the mixture was stirred for 0.5 hour at room temperature.

The reaction mixture was poured into a 500 ml aqueous solution of 0.1 N potassium hydroxide, the resultant was subjected to exttraction with chloroform, dried with a saturated aqueous solution of sodium chloride and dried $(Na_2SO_4)_1$ followed by distilling off the solvent under reduced pressure. The residue thus obtained was subjected to a purification procedure of silica gel column chromatography to give a yellow amorphous product (1.80 g, 96%).

To a tetrahydrofuran (15 ml) suspension of sodium hydride was added dropwise the tetrahydrofuran (15 ml) solution of the amorphous product (1.80 g, 2.67 mmole) obtained in the above at room temperature. After stirring the reaction mixture at 50° C. for 0.5 hour, a tetrahydrofuran (5 ml) solution of phenylselenyl chloride (1.02 g, 5.34 mmole) was added dropwise at 50° C. for one overnight. The reaction mixture was poured into 500 ml of distilled water, extracted with chloroform, dried with a saturated sodium chloride and dried ($Na_2SO_4$), followed by distilling off the solvent under reduced pressure. The residue was subjected to a purification procedure of silica gel column chromatography to give a colorless amorphous product (1.00 g, 86%). Thus obtained amorphous product was dissolved in chloroform, and to the solution was added 10N hydrogen chloride in ether to give a salt, and was recrystallized from chloroform-ether to give the titled compound as white powdery crystals. The structure of the compound is shown in the below-mentioned Table 60.

m.p. 163–165° C. Elemental Analysis for $C_{38}H_{39}N_3O_4SF_2 \cdot HCl \cdot 1.5H_2O$

|  | C | H | N |
|---|---|---|---|
| Calcd.: | 62.07; | 5.89; | 5.71 (%) |
| Found: | 62.31; | 5.81; | 6.04 (%) |

$^1$H-NMR (300 MHz, CDCl$_3$) δ: 1.23 (6H, d, J=6.8 Hz), 1.38 (6H, d, J=6.8 Hz), 2.10 (3H, s), 2.45 (3H, s), 2.54 (1H, m), 3.63 (2H, s), 4.13 (2H, s), 5.30 (1H, m), 5.34 (3H, s), 6.93 (2H, dd, J=8.1 Hz), 7.14–7.39 (6H, m), 7.59 (2H, d, J=8.6 Hz), 7.80 (2H, d, J=8.6 Hz).

Reference Example 8:2

Employing the compound produced in Reference Example 4:1 or 4:3 as the starting material, Reference Example 4:3(2), 4:3(3) or 4:3(4), a substantially the same procedure as described in Eample 11 was conducted to give compounds 8:2(1), 8:2(2), 8:2(3) and 8:2(4), whose structures are shown in the below-mentioned Table 60.

Reference Example 8:3

Employing the compound produced in Reference Example 4:1 as-the starting material, a substantially the same procedure as described in Reference Example 8:1 was conducted using ethylmagnesium bromide instead of methylmagnesium bromide to give the compound 8:3, whose structure is shown in the below-mentioned Table 60.

Reference Example 8:4

Employing the compound 5:6(1) or 5:6(22) produced in Reference Example 5:6 as a starting material, a substantially the same procedure as described in Reference Example 8:1 was conducted to give compounds 8:4(1) and 8:4(2), whose structures are shown in the following Table 60.

Employing the compound 5:6(2), 5:6(3), 5:6(6), 5:6(7) or 5:6(8) produced in Reference Example 5:6 as a starting material, a substantially the same procedure as described in Reference Example 8:1 was conducted to give compounds 8:4(3) to 8:4(7), whose structures are shown in the following Table 60.

TABLE 60

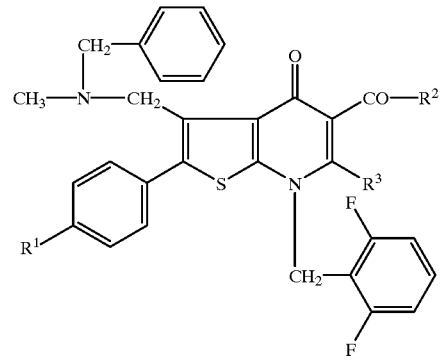

| Ref. Ex. Cpd. No. | R$^1$ | R$^2$ | R$^3$ | m.p. (° C.) |
|---|---|---|---|---|
| 8:1 | isobutyrylamino | isopropoxy | methyl | 163–165 (hydrochloride) |
| 8:2(1) | isobutyrylamino | ethoxy | methyl | 179–181 (hydrochloride) |
| 8:2(2) | isobutyrylamino | cyclohexyloxy | methyl | 158–160 (hydrochloride) |
| 8:2(3) | isobutyrylamino | 3-pentyloxy | methyl | 157–159 (hydrochloride) |
| 8:2(4) | isobutyrylamino | 4-tetrahydropyranyloxy | methyl | 170–172 (hydrochloride) |
| 8:3 | isobutyrylamino | ethoxy | ethyl | 135–137 (hydrochloride) |

TABLE 60-continued

| Ref. Ex. Cpd. No. | R$^1$ | R$^2$ | R$^3$ | m.p. (° C.) |
|---|---|---|---|---|
| 8:4(1) | allyloxy | isopropoxy | methyl | 143–145 (hydrochloride) |
| 8:4(2) | allyloxy | ethoxy | methyl | amorphous |
| 8:4(3) | 2-butene-1-yloxy | isopropoxy | methyl |  |
| 8:4(4) | allyloxy | cyclohexyloxy | methyl |  |
| 8:4(5) | cyclopropylmethoxy | cyclohexyloxy | methyl |  |
| 8:4(6) | 2-butene-1-yloxy | cyclohexyloxy | methyl |  |
| 8:4(7) | cyclopropylmethoxy | isopropoxy | methyl |  |

Reference Example (A)

In 1 ml of distilled water is dissolved 550 mg of leuprorelin acetate, and the resulting solution is added to a solution of 4 g poly(dl-lactic acid) (Lot. 890717, mol. wt. 14100, degree of dispersion 2.00) in 7.5 ml dichloromethane. Using a benchtop homogenizer (Polytron, Kinematica, Switzerland), the mixture is agitated for about 60 seconds to prepare a W/O emulsion. This emulsion is poured in 1000 ml of 0.25% aqueous solution of polyvinyl alcohol (PVA) preadjusted to 15° C., and using the benchtop homogenizer, processed into a W/O/W emulsion. This W/O/W emulsion is further agitated to evaporate dichloromethane and thereby solidify the internal W/O emulsion. The product is collected by centrifugation and redispersed in distilled water. This dispersion is further centrifuged to wash out the free drug and dispersant. The collected microcapsules are lyophilized for a further removal of the solvent and water and pulverized to provide microcapsules.

Reference Example (B)

In 1 ml of 20% aqueous solution of gelatin is dissolved 550 mg of leuprorelin acetate, and the resulting solution is added to a solution of 4 g poly(lactide-co-glycolide) (lactic acid-glycolic acid ratio=75:25, average molecular weight= 14,000) in 7.5 ml dichloromethane. Using a benchtop homogenizer (Polytron, Kinematica, Switzerland), the mixture is agitated for about 60 seconds to prepare a W/O emulsion. This emulsion is poured in 1000 ml of 0.25% aqueous solution of polyvinyl alcohol (PVA) preadjusted to 15° C. and processed in the benchtop homogenizer to prepare a W/O/W emulsion. This W/O/W emulsion is further agitated to evaporate dichloromethane and thereby solidify the internal W/O emulsion. The product is collected by centrifugation and redispersed in distilled water. This dispersion is further centrifuged to wash out the free drug and dispersant. The collected microcapsules are lyophilized for a further removal of the solvent and water and pulverized to provide microcapsules.

Reference Example (C)

One gram of α-cyclodextrin and 2 g of leuprorelin acetate are dissolved in 16 ml of an isotonic buffer solution (pH 7.4)

containing 0.12% of methyl p-hydroxybenzoate and 0.01% of propyl p-hydroxybenzoate, followed by addition of 200 mg of methylcellulose (Metolose 90SH4000, Sin-Etsu Chemical), and the mixture is stirred well to give a homogeneous slurry. This slurry is diluted with the buffer solution to make a total of 20 g. This products 100 mg, is filled in a nasal applicator for application into the nostrils.

Example 1

The injection according to Reference Example (b) and the microcapsules according to Reference Example (A) or (B) are provided as a pharmaceutical kit consisting of independent components.

Example 2

The injection according to Reference Example (b) and the transdermal DDS according to Reference Example (C) are provided as a pharmaceutical kit consisting of independent components.

Example 3

The tablet(s) according to Reference Example (a) and the microcapsules according to Reference Example (A) or (B) are provided as a pharmaceutical kit consisting of independent components.

Example 4

The tablet(s) according to Reference Example (a) and the transnasal DDS according to Reference Example (C) are provided as a pharmaceutical kit consisting of independent components.

Test Example 1

Compound E-5 (hereinafter referred to sometimes as antagonist compound 1) was suspended in solution I (0.5% methylcellulose-saline) at a final concentration of 7.5 mg/ml and the suspension was administered subcutaneously in a single dose to male SD rats (10 weeks old, n=6). The dosage was 30 mg/kg body weight. A control group of animals received the vehicle only. Twenty-four(24) hours after administration, the animals were anesthetized with ether and the blood was drawn from the carotid artery. Immediately then, EDTA (ethylenediaminetetracetic acid) and aprotinin were added to the blood at the final concentrations of 3 mg/ml and 300 U/ml, respectively. The blood was then centrifuged at 3000×g for 15 minutes and the concentration of testosterone in the separated plasma was determined by radioimmunoassay.

The expression 100−(blood testosterone concentration in compound administration group)/(blood testosterone concentration in control group)×100 was calculated to determine the testosterone antagonizing rate (%) of the test compound.

Antagonist compound 1 showed an antagonizing rate of 90%±5.

Test Example 2

Antagonist compound 1 was suspended in solution I (0.5% methylcellulose-saline) at a final concentration of 7.5 mg/ml and the suspension was administered subcutaneously in a single dose to crab-eating monkeys (4–6 years of age, n=3). The dosage was 30 mg/kg body weight. A control group of animals receiving the vehicle only was also provided. Twenty-four hours after administration, blood was drawn under no anesthesia and immediately EDTA (ethylenediaminetetracetic acid) and aprotinin were added at the final concentrations of 3 mg/ml and 300 U/ml, respectively. The mixture was centrifuged at 3000×g for 15 minutes and the concentration of testosterone in the separated plasma was determined by the radioimmunoassay method.

The expression 100−(blood testosterone concentration in compound administration group)/(blood testosterone concentration in control group)×100 was calculated to determine the testosterone antagonizing rate (%) of the compound.

The test antagonist compound gave an antagonizing rate of 80%±5.

Test Example 3

Antagonist compound 1 is suspended in solution I (0.5% methylcellulose-saline) at a final concentration of 7.5 mg/ml and the suspension is administered subcutaneously in a single dose to crab-eating monkeys (4–6 years of age, n=3). The dosage is 30 mg/kg body weight. A control group of animals receiving the vehicle only is also provided. Three hours after administration, a solution of LH-RH agonist (leuprorelin acetate) in saline (5 µg/kg) is administered sabcutaneously under no anesthesia. The blood is drawn 1, 2, 4, 6, 8, and 24 hours after administration and immediately EDTA (ethylene-diaminetetracetic acid) and aprotinin are added at the final concentrations of 3 mg/ml and 300 U/ml, respectively. The mixture is centrifuged at 3000×g for 15 minutes and the LH and testosterone concentrations in the plasma are determined by bioassay and radioimmunoassay, respectively.

The expression 100−(blood concentration of LH or testosterone in compound administration group)/(blood concentration of LH or testosterone in control group)×100 is calculated to determine the LH or testosterone antagonizing rate (%) of the test compound.

It is clear that the transient exacerbation (flare) with elevation of serum LH or testosterone owing to the pituitary-gonadotropic action (acute action) occurring immediately following an initial dose of leuprorelin acetate is successfully obviated.

Test Example 4

Antagonist compound 1 is suspended in solution I (0.5% methylcellulose-saline) at a final concentration of 7.5 mg/ml and the suspension is administered orally to male crab-eating monkeys (4–6 years of age, n=3) twice daily at 12-hour intervals for 7 days (a total of 15 doses). The-dosage is 60 mg/kg body weight. A control group of animals receiving the vehicle only is also provided. One hour after the first dose on day 2 (the 3rd dose), the sustained release LH-RH agonist (leuprorelin depot, microcapsules manufactured by the procedure described in Reference Example (A) is administered subcutaneously (0.15 mg/kg as leuprorelin) to conscious animals. The blood is drawn 1, 4, 8, 18, 30, 48, and 72 hours after administration and, thereafter, once daily for 2 weeks. To each blood sample, EDTA, (ethylenediaminetetracetic acid) and aprotinin are immediately added at the final concentrations of 3 mg/ml and 300 U/ml, respectively. This mixture is centrifused at 3000×g for 15 minutes and LH and testosterone concentrations in the plasma are determined by bioassay and radioimmunoassay, respectively.

The expression 100−(blood concentration of LH or testosterone in compound administration group)/(blood concentration of LH or testosterone in control group)×100 is calculated to determine the LH or testosterone antagonizing rate (%) of the test compound.

It is clear that the transient exacerbation (flare) with elevation of serum LH or testosterone associated with the pituitary-gonadotropic action (acute action) manifested immediately following an initial dose of leuprorelin depot is successfully obviated.

Test Example 5

Antagonist compound 1 is suspended in solution I (0.5% methylcellulose-saline) at a final concentration of 7.5 mg/ml and the suspension is administered orally to male crab-eating monkeys (4–6 years of age, n=3) twice daily at 12-hour intervals for 7 days (a total of 15 doses). The dosage is 60 mg/kg body weight. A control group of animals receiving the vehicle only is also provided. -One hour after the first dose on day 2 (the 3rd dose), the sustained release LH-RH agonist (leuprorelin depot, microcapsules manufactured by the procedure described in Reference Example (A)) is administered subcutaneously (0.45 mg/kg as leuprorelin) to conscious animals. The blood is drawn 1, 4, 8, 12, 24, 48, and 72 hours after administration and, thereafter, once daily for 2 weeks. To each blood sample, EDTA (ethylenediaminetetracetic acid) and aprotinin are immediately added at final concentrations of 3 mg/ml and 300 U/ml, respectively. This mixture is centrifused at 3000×g for 15 minutes and the plasma LH and testosterone concentrations are determined by the bioassay and radioimmunoassay methods.

The expression 100−(blood concentration of LH or testosterone in compound administration group)/(blood concentration of LH or testosterone in control group)×100 is calculated to determine the LH or testosterone antagonizing rate (%) of the compound.

It is clear that the transient exacerbation (flare) with elevation of serum LH or testosterone owing to the pituitary-gonadotropic action (acute action) manifested immediately following an initial dose of leuprorelin depot is successfully obviated.

Test Example 6

Antagonist compound 1 is suspended in solution I (0.5% methylcellulose-saiine) at a final concentration of 7.5 mg/ml and the suspension is administered orally to male crab-eating monkeys (4-6 years of age, n=3) twice daily at 12-hour intervals for 7 days (a total of 15 doses). The dosage is 60 mg/kg body weight. A control group of animals receiving the vehicle only is also provided. One hour after the first dose on day 2 (the 3rd dose), the sustained release LH-RH agonist (leuprorelin depot, microcapsules manufactured by the procedure described in Reference Example (B)) is administered subcutaneously (0.15 mg/kg as leuprorelin) to conscious animals. The blood is drawn 1, 4, 8, 12, 24, 48, and 72 hours after administration and, thereafter, once daily for 2 weeks. To each blood sample, EDTA (ethylenediaminetetracetic acid) and aprotinin are immediately added at final concentrations of 3 mg/ml and 300 U/ml, respectively. This mixture is centrifused at 3000×g for 15 minutes and the plasma LH and testosterone concentrations are determined by bioassay and radioimmunoassay, respectively.

The expression 100−(blood concentration of LH or testosterone in compound administration group)/(blood concentration of LH or testosterone in control group)×100 is calculated to determine the LH or testosterone antagonizing rate (%) of the compound.

It is clear that the transient exacerbation (flare) with elevation of serum LH or testosterone owing to the pituitary-gonadotropic action (acute action) manifested immediately following an initial dose of leuprorelin depot is successfully obviated.

Test Example 7

Antagonist compound 1 is suspended in solution I (0.5% methylcellulose-saline) at a final concentration of 7.5 mg/ml and the suspension is administered orally to male crab-eating monkeys (4–6 years of age, n=3) twice daily at 12-hour intervals for 28 days (a total of 57 doses). The dosage is 60 mg/kg body weight. A control group of animals receiving the vehicle only is also provided. One hour after the first oral dose on day 15 (the 29th dose), the sustained release LH-RH agonist (leuprorelin depot, microcapsules manufactured by the procedure described in Reference Example (B)) is administered subcutaneously (0.15 mg/kg as leuprorelin) to conscious animals. The blood is drawn 1, 4, 8, 12, 24, 48, and 72 hours after administration and, thereafter, once every 3 days for 4 weeks. To each blood sample, EDTA (ethylenediaminetetracetic acid) and aprotinin are immediately added at the final concentrations of 3 mg/ml and 300 U/ml, respectively. This mixture is centrifused at 3000×g for 15 minutes and the plasma LH and testosterone concentrations are determined by bioassay and radioimmunoassay, respectively.

The expression 100−(blood concentration of LH or testosterone in compound administration group)/(blood concentration of LH or testosterone in control group)×100 is calculated to determine the LH or testosterone antagonizing rate (%) of the compound.

It is clear that the transient exacerbation (flare) with elevation of serum LH or testosterone owing to the pituitary-gonadotropic action (acute action) occurring immediately following an initial dose of leuprorelin depot is successfully obviated.

[Industrial Applicability]

The pharmaceutical of the present invention is useful for avoiding the transient exacerbation (flare) with elevation of serum testosterone which is associated with the pituitary-gonadotropic action (acute action) manifested immediately following administration of an agonist. Moreover, the action of the agonist is amplified.

Therefore, the pharmaceutical of the present invention can be used with advantage in the therapy or prophylaxis of sex hormone-dependent diseases.

What is claimed is:

1. A method for treating a sex hormone-dependent disease in a mammal, which comprises administering to said mammal in need of the treatment a compound having luteinizing hormone activity, of the formula:

$$(\text{Pyr})\text{Glu-}R_1\text{-Trp-Ser-}R_2\text{-}R_3\text{-}R_4\text{-Arg-Pro-}R_5 \qquad (I)$$

wherein $R_1$ is His, Tyr, Trp or p-$NH_2$-Phe; $R_2$ is Tyr of Phe; $R_3$ is Gly or a D-amino acid residue which may optionally be substituted; $R_4$ is Leu, Ile or Nle; $R_5$ is a group of the formula: Gly-NH-$R_6$ wherein $R_6$ is a hydrogen or an optionally substitued alkyl group or a group of the formula: NH-$R_{6'}$ wherein $R_{6'}$ is a hydrogen, an alkyl group which may optionally be substituted with amino, hydroxy or ureido, in combination with a nonpeptide compound having luteinizing hormone releasing hormone antagonizing activity, (i) of the formula:

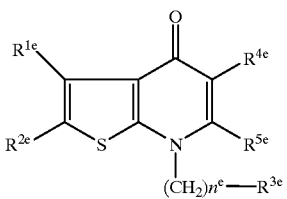

wherein $R^{1e}$ and $R^{2e}$ are independently a hydrogen atom, or a group bonded through a carbon atom, a nitrogen atom, an oxygen atom or a sulfur atom; $R^{3e}$ is an optionally substituted homo- or hetero-cyclic ring; $R^{4e}$ is a hydrogen atom, a group bonded through a carbon atom, a nitrogen atom, an oxygen atom or a sulfur atom, or an optionally substituted heterocyclic group; $R^{5e}$ is a hydrogen atom or a group bonded through a carbon atom; and n is an integer of 0 to 3, or a salt thereof, or (ii) of the formula:

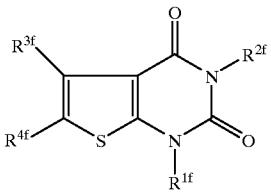

wherein $R^{1f}$ is (1) a hydrogen atom, (2) a group bonded through a carbon atom or (3) a group of the formula:

—(CH$_2$)n—R$^{1f}$ wherein R$^{1f}$ is a group bonded through a carbon atom or an optionally substituted homo- or heterocyclic group and n is an integer of 0 to 3; R$^{2f}$ is a hydrogen atom or a group bonded through a carbon atom; and R$^{3f}$ and R$^{4f}$ are independently a group bonded through a carbon atom, or a salt thereof.

2. The method as claimed in claim 1, wherein the compound having luteinizing hormone releasing hormone activity is selected from the group consisting of leuprorelin, gonadorelin, buserelin, triptorelin, goserelin, nafarelin, histrelin, deslorelin, meterelin, and recirelin.

3. The method as claimed in claim 1, wherein the nonpeptide compound having luteinizing hormone releasing hormone antagonizing activity is of the formula

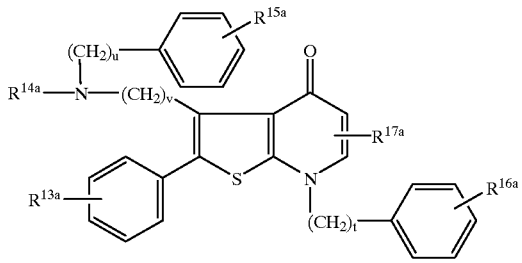

wherein R$^{13a}$ stands for 1 to 5 substituents and independently stands for a hydrogen atom, an alkyl group, an alkoxy group, a halogen atom or an alkanoylamino group; R$^{14a}$ stands for a hydrogen atom or an alkyl group; R$^{15a}$ stands for 1 to 5 substituents and independently stands for a hydrogen atom, a halogen atom, an alkyl group, an alkoxy group or an alkylthio group; R$^{16a}$ stands for 1 to 5 substituents and independently stands for a hydrogen atom, an alkyl group, a halogen atom or an alkoxy group; R$^{17a}$ stands for one or two substituents and independently stands for an optionally esterified or amidated carboxyl group, an alkylcarbonyl group, an arylcarbonyl group or an optionally substituted alkyl group; and each of v, t and u denote an integer, of 0 to 3.

4. The method as claimed in claim 1, wherein the nonpeptide compound having luteinizing hormone releasing hormone antagonizing activity is of the formula:

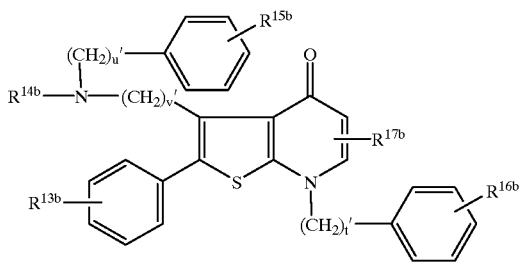

wherein R$^{13b}$ stands for 1 to 3 substituents and independently stands for a hydrogen atom, a C$_{1-6}$ alkoxy group or a C$_{1-8}$ alkanoylamino group, R$^{14b}$ stands for a hydrogen atom or a C$_{1-6}$ alkyl group, R$^{15b}$ stands for 1 to 3 substituents and independently stands for a hydrogen atom or a halogen atom, R$^{16b}$ stands for 1 to 3 substituents and independently stands for a hydrogen atom, a halogen atom or a C$_{1-6}$ alkoxy group, R$^{17b}$ stands for 1 to 2 substituents and independently stands for a carboxyl group which may optionally be esterified or amidated or a C$_{1-6}$ alkylcarbonyl group, and each of v', t' and u' denote an integer of 1 to 3.

5. The method as claimed in claim 1, wherein 0.1–10 mg/kg/day of the nonpeptide compound having luteinizing hormone releasing hormone antagonizing activity, is administered subcutaneously or orally for 1 day to 3 weeks, or the same dose of a sustained release dosage form is administered and, then, the compound having luteinizing hormone releasing hormone activity is administered.

6. The method as claimed in claim 5, wherein 0.001–0.03 mg/kg/day of the compound having luteinizing hormone releasing hormone activity in a sustained release subcutaneous dosage form is administered.

7. The method as claimed in claim 1, wherein the nonpeptide compound having luteinizing hormone-releasing-hormone antagonizing activity is 4,7-dihydro-3-(N-methyl-N-benzylaminomethyl)-7-(2-methoxybenzyl)-2-(4-methoxyphenyl)-4-oxo-thieno [2,3-b]pyridine-5-carboxylic acid ethyl ester or its salt.

8. The method as claimed in claim 1, wherein the nonpeptide compound having luteinizing hormone releasing hormone antagonizing activity is 2-(4-acetylaminophenyl)-4,7-dihydro-3-(N-methyl-N-benzylaminomethyl)-7-(2-methoxybenzyl)-4-oxo-thieno[2,3-b]pyridine-5-carboxylic acid ethyl ester or its salt.

9. The method as claimed in claim 1, wherein the nonpeptide compound having luteinizing hormone releasing hormone antagonizing activity is 5-n-butyryl-4,7-dihydro-3-(N-methyl-N-benzylaminomethyl)-7-(2-fluorobenzyl)-2-(4-methoxyphenyl)-4-oxo-thieno[2,3-b]pyridine or its salt.

10. The method as claimed in claim 1, wherein the nonpeptide compound having luteinizing hormone releasing hormone antagonizing activity is 5-benzoyl-4,7-dihydro-3-(N-methyl-N-benzylaminomethyl)-7-(2-fluorobenzyl)-2-(4-methoxyphenyl)-4-oxo-thieno[2,3-b]pyridine or its salt.

11. The method as claimed in claim 1, wherein the nonpeptide compound having luteinizing hormone releasing hormone antagonizing activity is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b] pyridine or its salt.

12. The method as claimed in claim 11, wherein the nonpeptide compound having luteinizing hormone releasing hormone antagonizing activity is 7-(2,6-difluorobenzyl)-4,7-dihydro-3-(N-methyl-N-benzylaminomethyl)-5-isobutyryl-2-(4-propionylaminophenyl)-4-oxo-thieno[2,3-b]pyridine or its salt.

13. The method as claimed in claim 1, wherein the nonpeptide compound having luteinizing hormone releasing hormone antagonizing activity is 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine or its salt.

14. The method as claimed in claim 1, wherein the nonpeptide compound having luteinizing hormone releasing hormone antagonizing activity is 3-(N-benzyl-N-methylaminomethyl)-4,7-dihydro-2-(4-allyloxyphenyl)-5-isobutyryl-7-(2,6-difluorobenzyl)-4-oxothieno[2,3-b] pyridine or its salt.

15. The method as claimed in claim 1, wherein the nonpeptide compound having luteinizing hormone releasing hormone antagonizing activity is isopropyl[3-(N-benzyl-N-methylaminomethyl)-2-(4-isobutyrylaminophenyl)-4-oxo-7-(2,6-difluorobenzyl)thieno[2,3-b]pyridine-5-carboxylatel or its salt.

16. The methhod as claimed in claim 1, wherein the nonpeptide compound having luteinizing hormone releasing hormone antagonizing activity is isopropyl[3-(N-benzyl-N-methylaminomethyl)-2-(4-isobutyrylaminophenyl)-4-oxo-7-(2,6-difluorobenzyl)-6-methylthieno[2,3-b]pyridine-5-carboxylate] or its salt.

17. The method as claimed in claim 1, wherein the nonpeptide compound having luteinizing hormone releasing hormone antagonizing activity is isopropyl[3-(N-benzyl-N-methylaminomethyl)-2-(4-allyloxyphenyl)-4-oxo-6-methyl-7-(2,6-difluorobenzyl)thieno[2,3-b]pyridine-5-carboxylate] or its salt.

18. The method as claimed in claim 1, wherein the compound having luteinizing hormone releasing hormone activity is in a controlled release dosage form.

19. The method as claimed in claim 18, wherein the controlled release dosage form is micro-capsules.

20. The method as claimed in claim 18, wherein the controlled release dosage form is a transnasal drug delivery system or an implant.

21. A pharmaceutical kit for treating a sex hormone-dependent disease, which comprises a compound having luteinizing hormone releasing hormone activity, of the formula:

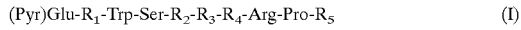

(Pyr)Glu-$R_1$-Trp-Ser-$R_2$-$R_3$-$R_4$-Arg-Pro-$R_5$     (I)

wherein $R_1$ is His, Tyr, Trp or p-$NH_2$-Phe; $R_2$ is Tyr of Phe; $R_3$ is Gly or a D-amino acid residue which may optionally be substituted; $R_4$ is Leu, Ile or Nle; $R_5$ is a group of the formula: Gly-NH-$R_6$ wherein $R_6$ is a hydrogen or an optionally substitued alkyl group or a group of the formula: NH-$R_{6'}$ wherein $R_{6'}$ is a hydrogen, an alkyl group which may optionally be substituted with amino, hydroxy or ureido, in combination with a nonpeptide compound having luteinizing hormone releasing hormone antagonizing activity, (i) of the formula:

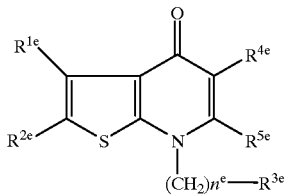

(X)

wherein $R^{1e}$ and $R^{2e}$ are independently a hydrogen atom, or a group bonded through a carbon atom, a nitrogen atom, an oxygen atom or a sulfur atom; $R^{3e}$ is an optionally substituted homo- or hetero-cyclic ring; $R^{4e}$ is a hydrogen atom, a group bonded through a carbon atom, a nitrogen atom, an oxygen atom or a sulfur atom, or an optionally substituted heterocyclic group; $R^{5e}$ is a hydrogen atom or a group bonded through a carbon atom; and n is an integer of 0 to 3, or a salt thereof, or (ii) of the formula:

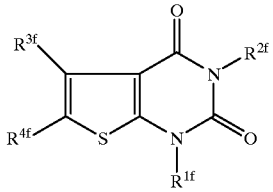

(XX)

wherein $R^{1f}$ is (1) a hydrogen atom, (2) a group bonded through a carbon atom or (3) a group of the formula: —$(CH_2)n$—$R^{1f'}$ wherein $R^{1f'}$ is a group bonded through a carbon atom or an optionally substituted homo- or heterocyclic group and n is an integer of 0 to 3; $R^{2f}$ is a hydrogen atom or a group bonded through a carbon atom; and $R^{3f}$ and $R^{4f}$ are independently a group bonded through a carbon atom, or a salt thereof.

22. The pharmaceutical kit as claimed in claim 21 comprising a compound having luteinizing hormone releasing hormone activity in a non-oral dosage form in combination with a nonpeptide compound having luteinizing hormone releasing hormone antagonizing activity in an oral dosage form.

* * * * *